United States Patent
Sung et al.

(10) Patent No.: US 9,119,778 B2
(45) Date of Patent: Sep. 1, 2015

(54) DRY POWDER FORMULATIONS AND METHODS FOR TREATING PULMONARY DISEASES

(71) Applicant: Pulmatrix, Inc., Lexington, MA (US)

(72) Inventors: Jean C. Sung, Cambridge, MA (US); Michael M. Lipp, Framingham, MA (US)

(73) Assignee: Pulmatrix Operating Company, Inc., Lexington, MA (US)

( * ) Notice: Subject to any disclaimer, the term of this patent is extended or adjusted under 35 U.S.C. 154(b) by 0 days.

(21) Appl. No.: 14/667,857

(22) Filed: Mar. 25, 2015

(65) Prior Publication Data

US 2015/0196486 A1   Jul. 16, 2015

Related U.S. Application Data

(63) Continuation of application No. 14/456,445, filed on Aug. 11, 2014, now abandoned, which is a continuation of application No. 13/259,635, filed as application No. PCT/US2010/028961 on Mar. 26, 2010, now abandoned.

(60) Provisional application No. 61/305,819, filed on Feb. 18, 2010, provisional application No. 61/298,092, filed on Jan. 25, 2010, provisional application No. 61/267,747, filed on Dec. 8, 2009, provisional application No. 61/255,764, filed on Oct. 28, 2009, provisional application No. 61/163,763, filed on Mar. 26, 2009, provisional application No. 61/163,767, filed on Mar. 26, 2009, provisional application No. 61/163,772, filed on Mar. 26, 2009.

(51) Int. Cl.
| | |
|---|---|
| *A61K 9/14* | (2006.01) |
| *A61P 31/00* | (2006.01) |
| *A61P 11/00* | (2006.01) |
| *A61K 33/14* | (2006.01) |
| *A61K 31/19* | (2006.01) |
| *A61K 9/00* | (2006.01) |
| *A61M 15/00* | (2006.01) |
| *A61K 47/18* | (2006.01) |
| *A61K 31/194* | (2006.01) |

(52) U.S. Cl.
CPC ............ *A61K 9/0075* (2013.01); *A61K 9/14* (2013.01); *A61K 31/19* (2013.01); *A61K 31/194* (2013.01); *A61K 33/14* (2013.01); *A61K 47/183* (2013.01); *A61M 15/003* (2014.02); *A61M 15/0045* (2013.01); *A61M 2202/064* (2013.01)

(58) Field of Classification Search
None
See application file for complete search history.

(56) References Cited

U.S. PATENT DOCUMENTS

| | | | |
|---|---|---|---|
| 4,233,405 A | 11/1980 | Neubeck | |
| 4,637,815 A | 1/1987 | Lemole | |
| 5,466,680 A | 11/1995 | Rudy | |
| 5,612,053 A | 3/1997 | Baichwal et al. | |
| 5,785,049 A | 7/1998 | Smith et al. | |
| 5,817,028 A | 10/1998 | Anderson | |
| 5,855,913 A | 1/1999 | Hanes et al. | |
| 5,985,309 A | 11/1999 | Edwards et al. | |
| 6,165,463 A | 12/2000 | Platz et al. | |
| RE37,053 E | 2/2001 | Hanes et al. | |
| 6,214,536 B1 | 4/2001 | Boucher, Jr. | |
| 6,254,854 B1 | 7/2001 | Edwards et al. | |
| 6,475,523 B1 | 11/2002 | Staniforth | |
| 6,582,728 B1 | 6/2003 | Platz et al. | |
| 6,613,308 B2 | 9/2003 | Bartus et al. | |
| 6,732,732 B2 | 5/2004 | Edwards et al. | |
| 6,749,835 B1 | 6/2004 | Lipp et al. | |
| 7,008,644 B2 | 3/2006 | Batycky et al. | |
| 7,112,572 B2 | 9/2006 | Deadman et al. | |
| 7,182,961 B2 | 2/2007 | Batycky et al. | |
| 7,192,919 B2 | 3/2007 | Tzannis et al. | |
| 7,306,787 B2 | 12/2007 | Tarara et al. | |
| 7,384,649 B2 | 6/2008 | Batycky et al. | |
| 7,556,798 B2 | 7/2009 | Edwards et al. | |
| 7,575,761 B2 | 8/2009 | Bennett et al. | |
| 7,838,532 B2 | 11/2010 | Surber et al. | |
| 7,879,358 B2 | 2/2011 | Jackson et al. | |
| 2001/0038858 A1 | 11/2001 | Roser et al. | |
| 2003/0129141 A1 | 7/2003 | Plaz et al. | |
| 2003/0186894 A1 | 10/2003 | Kuo et al. | |
| 2003/0232019 A1 | 12/2003 | Basu et al. | |
| 2004/0047810 A1 | 3/2004 | Staniforth et al. | |
| 2004/0105821 A1 | 6/2004 | Bernstein et al. | |

(Continued)

FOREIGN PATENT DOCUMENTS

| | | |
|---|---|---|
| CN | 1240349 | 1/2000 |
| CN | 101106975 | 1/2000 |

(Continued)

OTHER PUBLICATIONS

Adi, et al., "Agglomerate strength and dispersion of pharmaceutical powders", Journal of Aerosol Science, 42 285-294, 2011.

(Continued)

Primary Examiner — Robert A Wax
Assistant Examiner — Randeep Singh
(74) Attorney, Agent, or Firm — McDermott Will & Emery LLP

(57) ABSTRACT

The present invention is directed toward respirable dry particles for delivery of divalent metal cation salts and/or monovalent cation salts to the respiratory tract and methods for treating a subject having a respiratory disease and/or infection.

13 Claims, 52 Drawing Sheets

(56) References Cited

U.S. PATENT DOCUMENTS

| | | |
|---|---|---|
| 2005/0054682 A1 | 3/2005 | Phillips |
| 2005/0211244 A1 | 9/2005 | Nilsson et al. |
| 2005/0255049 A1 | 11/2005 | Slowey et al. |
| 2005/0276845 A1 | 12/2005 | Roser et al. |
| 2005/0281740 A1 | 12/2005 | Gong et al. |
| 2006/0142208 A1 | 6/2006 | Boucher, Jr. |
| 2006/0147520 A1 | 7/2006 | Ruegg |
| 2006/0276483 A1 | 12/2006 | Surber et al. |
| 2007/0270502 A1 | 11/2007 | Edwards et al. |
| 2007/0292454 A1 | 12/2007 | Bell et al. |
| 2008/0190424 A1 | 8/2008 | Lucking et al. |
| 2009/0208999 A1 | 8/2009 | Groenendaal et al. |
| 2009/0232744 A1 | 9/2009 | Keller et al. |
| 2010/0159007 A1 | 6/2010 | Staniforth |
| 2010/0285142 A1 | 11/2010 | Staniforth et al. |
| 2011/0192397 A1 | 8/2011 | Saskar et al. |
| 2011/0236492 A1 | 9/2011 | Morton |
| 2012/0070417 A1 | 3/2012 | Batycky |
| 2012/0107414 A1 | 5/2012 | Lipp |
| 2013/0004542 A1 | 1/2013 | Martyn |

FOREIGN PATENT DOCUMENTS

| | | |
|---|---|---|
| CN | 1446877 | 10/2003 |
| CN | 101237853 | 3/2007 |
| EP | 0681833 | 4/1995 |
| EP | 1466610 | 10/2004 |
| JP | 2004-503482 | 2/2004 |
| JP | 2004-532217 | 10/2004 |
| JP | 2005-511628 | 4/2005 |
| NZ | 328476 | 5/1999 |
| NZ | 605168 | 8/1999 |
| NZ | 530123 | 1/2007 |
| WO | 96/31221 | 10/1996 |
| WO | 97/36574 | 10/1997 |
| WO | 97/44013 | 11/1997 |
| WO | 98/16205 | 4/1998 |
| WO | 0113892 | 1/2001 |
| WO | 0176610 | 10/2001 |
| WO | 01/85136 | 11/2001 |
| WO | 01/95874 | 12/2001 |
| WO | 02/083079 | 10/2002 |
| WO | 03/043585 | 5/2003 |
| WO | 03035028 | 5/2003 |
| WO | 2004/002551 | 1/2004 |
| WO | 2004096204 | 11/2004 |
| WO | 2005/004852 | 1/2005 |
| WO | 2005/041921 | 5/2005 |
| WO | 2005/041922 | 5/2005 |
| WO | 2005084638 | 9/2005 |
| WO | 2005094869 | 10/2005 |
| WO | 2006/125153 | 11/2006 |
| WO | 2010/111680 | 9/2010 |
| WO | 2010111640 | 9/2010 |
| WO | 2010111641 | 9/2010 |
| WO | 2010111644 | 9/2010 |
| WO | 2010111650 | 9/2010 |

OTHER PUBLICATIONS

Chiou, et al. "A novel production method for inhalable cyclosporine a powders by confined liquid impinging jet precipitation," Journal of Aerosol Science, 39 500-509, 2008.

Crowder, et al., "2001: An Odyssey in Inhaler Formulation and Design," Pharmaceutical Technology, 99-113. Jul. 2001.

Ghorioi, et al., "Dispersion of fine and ultrafine powders through surface modification and rapid expansion," 85:11-24, 2013.

Jaffari, et al., "Rapid characterisation of the inherent dispersibility of respirable powders using dry dispersion laser diffraction," International Journal of Pharmaceuticals, 447:124-131, 2013.

Kaye, et al., "Simultaneously Manufactured Nano-In-Micro (SIMANIM) Particles for Dry-Powder Modified-Release Delivery of Antibodies," Pharmaceutics, Preformulations and Drug Delivery, 98:11:4055-4068, 2009.
Edwards, et al., "Novel Inhalants for Control and Protection Against Airborne Infections," Proceedings of Respiratory Drug Delivery 2006, Apr. 23, 2006.
Shur et al, "Cospray-Dried Unfractionated Heparin with L-Leucine as a Dry Power Inhaler Mucolytic for Cystic Fibrosis Therapy," J. Pharmaceutical Science, 97:4857-4868 (2008).
Broadhead et al., "The Spray Drying of Pharma uticals," Drug Development and Industrial Pharmacy, 18 (11&12):1169-1206(1992).
Oneda et al., "The Effect of Formulation Variables on the Dissolution and Physical Properties of Spray-Dried Micropsheres Containing Organic Salts," Powder Technology, 130 377-384 (2003).
Modler et al., "Calcium as an Adjuvant for Spray-Drying Acid Whey," Journal of Dairy Science, 61:294-299 (1978).
Geller et al, Development of a DPI Tobramycin Formulation Using Pulmosphere Technology, Journal of Aerosol Medicine and Pulmonary Drug Delivery, 24:175-182 (2011).
Problemy Tuberkuleza, 58(1):40-41 (1980).
Chan et al., "Spray Dried Powders and Powder Blends of Recombinant Human Deoxyribonuclease (rhDNase) for Aerosol Delivery," Pharmaceutical Research, 14(4):431-437 (1997).
International Search Report from Corresponding PCT Application No. PCT/US2010/028961.
Seville et al., "Spray-Dried Powders for Pulmonary Drug Delivery." Crit. Rev. in Therapeutic Drug Carrier Systems, 24 (4):307-360 (2007).
Vehring. "Pharmaceutical Particle Engineering via Spray Drying," Pharmaceutical Research, 25(5):999-1022 (2008).
Rabbini et al., "The Influence of Formulation Components on the Aerosolisation Properties of Spray Dried Powders," Journal of Controlled Release, 110:130-140 (2005).

FIG. 1A

Feedstock Formulations I, II, III, & XIV
Table of Properties

| Formulation | Lot | Spray Dryer | Solids conc (g/L) | Liquid feed static mixing | Inlet temp (°C) | Outlet temp (°C) | Atomizer gas (kg/hr) | Process gas (kg/hr) | Liquid feed (mL/min) | Product collection | Yield (%) |
|---|---|---|---|---|---|---|---|---|---|---|---|
| I (Citrate) Leucine: CaCl2: Na3Cit 10.0: 35.1: 54.9 | I-A | Niro | 10 | Yes | 282 | 98 | 14.5 Air press (mm) | 85 Aspirator | 70 | Cartridge filter | 75% |
| | I-B | Büchi | 5 | No | 220 | 108 | 40 | 90% | 6.7 | Cyclone (high performance) | 83% |
| | I-C | Büchi | 5 | No | 220 | 95 | 40 | 90% | 7 | Cyclone (high performance) | 81% |
| II (Lactate) Leucine: CaLact: NaCl 10.0: 58.6: 31.4 | II-A | Niro | 10 | Yes | 282 | 98 | 14.5 Air press (mm) | 85 Aspirator | 70 | Cartridge filter | 63% |
| | II-B | Büchi | 5 | No | 220 | 91-109 | 40 | 90% | 5.2 | Cyclone (high performance) | 73% |
| | II-C | Büchi | 5 | No | 220 | 100 | 40 | 90% | 6 | Cyclone (high performance) | 69% |
| III (Sulfate) Leucine: CaCl2: Na2SO4 10.0: 39.6: 50.4 | III-A | Niro | 10 | Yes | 282 | 98 | 14.5 Air press (mm) | 85 Aspirator | 70 | Cartridge filter | 74% |
| | III-B | Büchi | 5 | No | 220 | 83 | 30 | 80% | 9.3 | Cyclone (high performance) | 73% |
| | III-C | Büchi | 5 | No | 220 | 92 | 40 | 90% | 7 | Cyclone (high performance) | 76% |
| Placebo Leucine 100 | Placebo-A | Niro | 15 | Yes | 282 | 98 | 14.5 Air press (mm) | 85 Aspirator | 70 | Cartridge filter | 63% |
| | Placebo-B | Büchi | 5 | No | 220 | 82 | 40 | 90% | 7 | Cyclone (high performance) | 66% |

FIG. 1A (Continued)

| | | | | | | | Air press (mm) | Aspirator | | |
|---|---|---|---|---|---|---|---|---|---|---|
| XIV (Lactate with maltodextrin) Maltodextrin: CaLact: NaCl 10.0: 58.6: 31.4 | XIV-A | Büchi | 5 | No | 220 | 90-98 | 40 | 90% | 5.2 | Cyclone (high performance) | 72% |
| | XIV-B | Büchi | 5 | No | 220 | 100 | 40 | 90% | 5.2 | Cyclone (high performance) | 77% |
| | XIV-C | Büchi | 5 | No | 220 | 100-106 | 40 | 90% | 5.6 | Cyclone (high performance) | 78% |

FIG. 1B

Feedstock Formulations I, II, III, & XIV
Table of Properties (Cont.)

| Formulation | Lot | HPLC Ca²⁺ Content (%) | | | Na⁺ Content (%) | Density Tap density (g/cc) | Bulk density (g/cc) | Karl Fischer Water content (%) | |
|---|---|---|---|---|---|---|---|---|---|
| | | Theoretical | Ave | StDev | Theoretical | Ave | Ave | Ave | StDev |
| I (Citrate) *Leucine: CaCl2: Na3Cit* 10.0: 35.1: 54.9 | I-A | 12.7 | 12.5 | 0.1 | 14.7 | 0.34 | 0.19 | | |
| | I-B | | | | | | | | |
| | I-C | | | | | | | | |
| II (Lactate) *Leucine: CaLact: NaCl* 10.0: 58.6: 31.4 | II-A | 10.8 | 11.3 | 0.1 | 12.3 | 0.72 | 0.31 | | |
| | II-B | | | | | | | 6.6% | |
| | II-C | | | | | | | | |
| III (Sulfate) *Leucine: CaCl2: Na2SO4* 10.0: 39.6: 50.4 | III-A | 14.3 | 13.6 | 0.2 | 16.4 | 0.39 | 0.18 | | |
| | III-B | | | | | | | | |
| | III-C | | | | | | | | |
| Placebo *Leucine* 100 | Placebo-A | 0.0 | 0.0 | 0.0 | 0.0 | 0.04 | 0.034 | | |
| | Placebo-B | | | | | | | | |

FIG. 1B (Continued)

| XIV (Lactate with maltodextrin) Maltodextrin: CaLact: NaCl 10.0: 58.6: 31.4 | | | | | | | | |
|---|---|---|---|---|---|---|---|---|
| XIV-A | 14.3 | | | 16.4 | 0.75 | 0.43 | 6.0% | |
| XIV-B | 14.3 | | | 16.4 | | | 6.7% | 0.43 |
| XIV-C | 14.3 | 10.74 | 0.02 | 16.4 | | | 2.8% | 0.02 |

FIG. 1C

Feedstock Formulations I, II, III, & XIV
Table of Properties (cont.)   ACI-2, Gravimetric

| Formulation | Lot | FPF_TD <3.4 um | | FPF_TD <5.6 um | | % Mass collected | |
|---|---|---|---|---|---|---|---|
| | | Ave | StDev | Ave | StDev | Ave | StDev |
| I (Citrate) Leucine: CaCl2: Na3Cit 10.0: 35.1: 54.9 | I-A | 45.7% | 0.9% | 61.6% | 1.3% | 66.3% | 1.3% |
| | I-B | 33.3% | | 49.2% | | 61.2% | |
| | I-C | 52.1% | | 64.8% | | 67.7% | |
| II (Lactate) Leucine: CaL

FIG. 1D

Feedstock Formulations I, II, III, & XIV
Table of Properties (cont.) ACI-8, Gravimetric

| Formulation | Lot | MMAD (um) | | GSD | | FPF_TD <3.4um | | FPF_TD <5.6um | | FPF_TD <5.0um (%) | | Grav. Recov. | FPF_RD <5.0um (%) | |
|---|---|---|---|---|---|---|---|---|---|---|---|---|---|---|
| | | Ave | StDev | Ave | StDev | Ave | StDev | Ave | StDev | Ave | StDev | | Ave | StDev |
| I (Citrate) Leucine: CaCl2: Na3Cit 10.0: 35.1: 54.9 | I-A | 2.72 | 0.06 | 2.09 | 0.01 | 41.7% | 1.6% | 56.2% | 1.6% | 53.9% | 1.8% | 65.0% | 82.9% | 1.2% |
| | I-B | | | | | | | | | | | | | |
| | I-C | | | | | | | | | | | | | |
| II (Lactate) Leucine: CaLact: NaCl 10.0: 58.6: 31.4 | II-A | 2.89 | 0.05 | 2.04 | 0.01 | 39.7% | 2.0% | 55.3% | 9.9% | 52.4% | 0.9% | 64.9% | 80.8% | 0.8% |
| | II-B | | | | | | | | | | | | | |
| | II-C | | | | | | | | | | | | | |
| III (Sulfate) Leucine: CaCl2: Na2SO4 10.0: 39.6: 50.4 | III-A | 2.59 | 0.08 | 2.98 | 0.10 | 51.5% | 1.6% | 68.7% | 7.7% | 65.8% | 0.8% | 49.6% | 83.4% | 1.0% |
| | III-B | | | | | | | | | | | | | |
| | III-C | | | | | | | | | | | | | |
| Placebo Leucine 100 | Placebo-A | 4.29 | 0.12 | 1.84 | 0.02 | 17.4% | 1.6% | 32.5% | 2.2% | 29.1% | 2.4% | 49.6% | 58.7% | 1.5% |
| | Placebo-B | | | | | | | | | | | | | |

FIG. 1E

Feedstock Formulations I, II, III, & XIV
Table of Properties (cont.) ACI-8, Chemical

| Formulation | Lot | MMAD (um) | | GSD | | FPF_TD <5.0um (%) | | Anal. | FPF_RD <5.0um (%) | |
|---|---|---|---|---|---|---|---|---|---|---|
| | | Ave | StDev | Ave | StDev | Ave | StDev | Recov. | Ave | StDev |
| I (Citrate) *Leucine: CaCl2: Na3Cit* *10.0: 35.1: 54.9* | I-A | 3.37 | 0.02 | 2.76 | 0.02 | 51.9% | 2.0% | 79.5% | 65.3% | 1.2% |
| | I-B | | | | | | | | | |
| | I-C | | | | | | | | | |
| II (Lactate) *Leucine: CaLact: NaCl* *10.0: 58.6: 31.4* | II-A | 3.57 | 0.13 | 2.61 | 0.05 | 53.1% | 1.9% | 84.2% | 63.1% | 1.8% |
| | II-B | | | | | | | | | |
| | II-C | | | | | | | | | |
| III (Sulfate) *Leucine: CaCl2: Na2SO4* *10.0: 39.6: 50.4* | III-A | 2.79 | 0.14 | 3.33 | 0.19 | 54.9% | 2.7% | 72.4% | 75.9% | 1.6% |
| | III-B | | | | | | | | | |
| | III-C | | | | | | | | | |

FIG. 1F
Feedstock Formulations I, II, III, & XIV
Table of Properties (cont.)

Spraytec | | | | | | | HELOS/RODOS | | | | | |

| Formulation | Lot | Dv50 (um) | | GSD | | V < 5.0um (%) | | Bar | x50/dg (um) | | GSD | | 1/4 bar | 0.5/4 bar |
|---|---|---|---|---|---|---|---|---|---|---|---|---|---|---|
| | | Ave | StDev | Ave | StDev | Ave | StDev | | Ave | StDev | Ave | StDev | | |
| I (Citrate) Leucine: CaCl2: Na3Cit 10.0: 35.1: 54.9 | I-A | 3.07 | 0.29 | 3.19 | 0.28 | 69.80 | 4.74 | 0.5 bar | 2.62 | 0.04 | 1.93 | 0.02 | 1.17 | 1.19 |
| | | | | | | | | 1.0 bar | 2.57 | 0.04 | 1.88 | 0.03 | | |
| | | | | | | | | 2.0 bar | 2.49 | 0.03 | 1.84 | 0.00 | | |
| | | | | | | | | 4.0 bar | 2.20 | 0.03 | 1.82 | 0.04 | | |
| | I-B | 6.97 | | 3.29 | | 40.46 | | 1.0 bar | 2.88 | | 2.11 | | 1.21 | |
| | I-C | 3.02 | | 3.71 | | 72.91 | | | | | | | | |
| II (Lactate) Leucine: CaLact: NaCl 10.0: 58.6: 31.4 | II-A | 1.78 | 0.23 | 3.57 | 0.18 | 83.13 | 1.39 | 0.5 bar | 1.57 | 0.02 | 2.51 | 0.02 | 1.08 | 1.12 |
| | | | | | | | | 1.0 bar | 1.51 | 0.02 | 2.51 | 0.02 | | |
| | | | | | | | | 2.0 bar | 1.47 | 0.02 | 2.53 | 0.01 | | |
| | | | | | | | | 4.0 bar | 1.40 | 0.03 | 2.51 | 0.03 | | |
| | II-B | 2.85 | | 3.16 | | 69.51 | | 1.0 bar | 2.04 | | 2.17 | | 1.09 | |
| | II-C | 1.86 | | 3.61 | | 85.33 | | | | | | | | |
| III (Sulfate) Leucine: CaCl2: Na2SO4 10.0: 39.6: 50.4 | III-A | 3.05 | 0.10 | 3.73 | 0.18 | 67.62 | 0.94 | 0.5 bar | 2.59 | 0.14 | 2.32 | 0.40 | 1.42 | 1.47 |
| | | | | | | | | 1.0 bar | 2.50 | 0.10 | 2.24 | 0.36 | | |
| | | | | | | | | 2.0 bar | 2.17 | 0.07 | 2.08 | 0.17 | | |
| | | | | | | | | 4.0 bar | 1.76 | 0.06 | 1.86 | 0.08 | | |
| | III-B | 4.61 | | 3.27 | | | | 1.0 bar | 3.26 | | 2.13 | | 1.02 | |
| | III-C | 2.93 | | 3.23 | | 68.12 | | | | | | | | |

FIG. 1F (Continued)

| | | | | | | | | | | | | | | |
|---|---|---|---|---|---|---|---|---|---|---|---|---|---|---|
| Placebo Leucine 100 | Placebo-A | 21.77 | 3.66 | 3.25 | 0.05 | 12.07 | 1.60 | 0.5 bar | 7.68 | 0.34 | 2.09 | 0.07 | 1.37 | 1.62 |
| | | | | | | | | 1.0 bar | 6.47 | 0.17 | 2.07 | 0.05 | | |
| | | | | | | | | 2.0 bar | 5.69 | 0.11 | 2.09 | 0.04 | | |
| | | | | | | | | 4.0 bar | 4.74 | 0.20 | 2.10 | 0.03 | | |
| | Placebo-B | 7.52 | | 3.41 | | 37.21 | | | | | | | | |
| XIV (Lactate with maltodextrin) Maltodextrin: CaLact: NaCl 10.0: 58.6: 31.4 | XIV-A | 1.59 | 0.25 | 2.90 | 0.11 | 87.16 | 1.23 | 0.5 bar | 1.45 | | 1.88 | | 1.00 | 1.04 |
| | | | | | | | | 1.0 bar | 1.40 | 0.01 | 1.87 | 0.01 | | |
| | | | | | | | | 2.0 bar | 1.42 | 0.02 | 1.88 | 0.01 | | |
| | | | | | | | | 4.0 bar | 1.39 | 0.01 | 1.87 | 0.01 | | |
| | XIV-B | 1.60 | 0.25 | 2.29 | 0.15 | 90.18 | 4.81 | 0.5 bar | 1.31 | | 1.85 | | 1.02 | 1.04 |
| | | | | | | | | 1.0 bar | 1.28 | | 1.84 | | | |
| | | | | | | | | 2.0 bar | 1.28 | | 1.84 | | | |
| | | | | | | | | 4.0 bar | 1.26 | | 1.83 | | | |
| | XIV-C | 1.69 | 0.07 | 2.69 | 0.22 | 88.88 | 0.75 | 0.5 bar | 1.30 | | 1.84 | | 0.98 | 1.02 |
| | | | | | | | | 1.0 bar | 1.24 | | 1.81 | | | |
| | | | | | | | | 2.0 bar | 1.25 | | 1.82 | | | |
| | | | | | | | | 4.0 bar | 1.27 | | 1.83 | | | |

Scanning electron Microscopy (SEM) images of representative sample of Formulation I Scanning electron Microscopy (SEM) images of representative sample of Formulation II

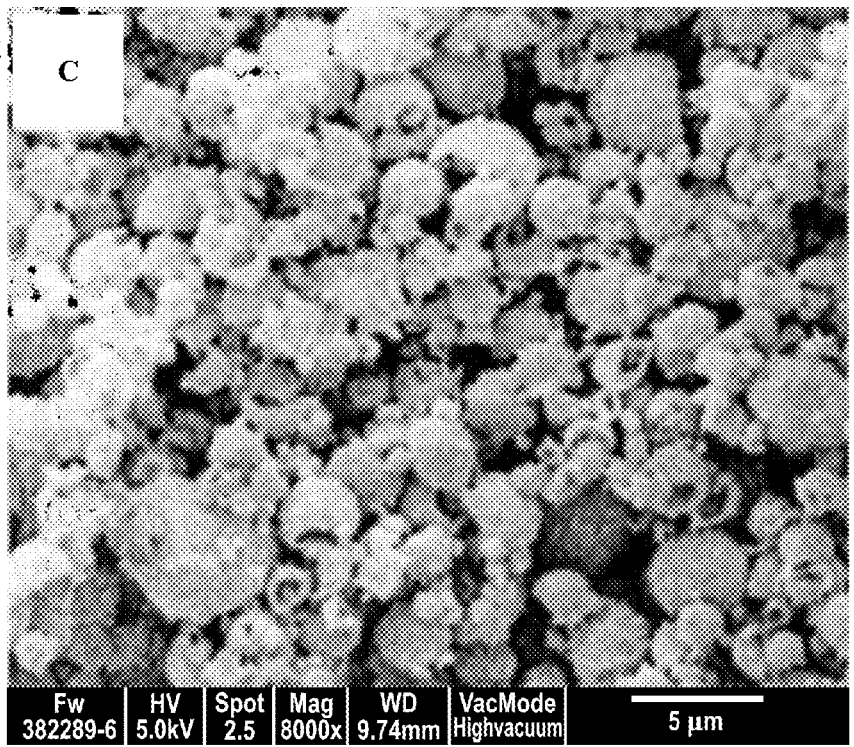
FIG. 5C Scanning electron Microscopy (SEM) images of representative sample of Formulation III
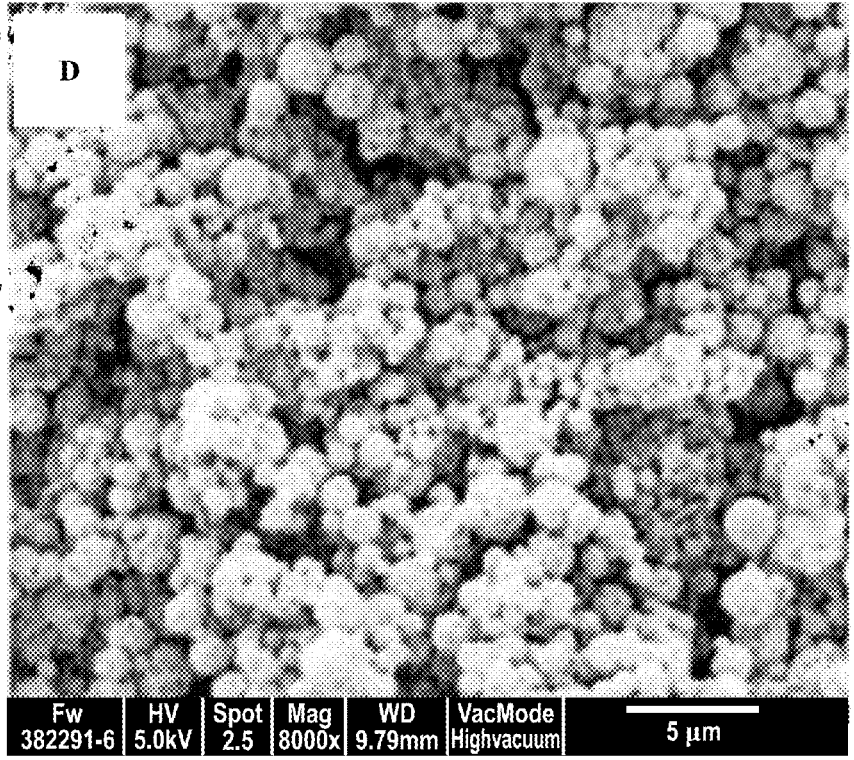
FIG. 5D Scanning electron Microscopy (SEM) images of representative sample of Formulation XIV FIG. 6A Feedstock Formulations 1-9
Table of Properties

| Formulation | Counterion | Excipient | Formulation | Ratio | Ca2+ % | Na % | Ca:Na Ratio | x50(μm) @ 1 bar | GSD @ 1 bar | 1/4 bar |
|---|---|---|---|---|---|---|---|---|---|---|
| 1 (II-B) | Lactate | 10% Leucine | leu:CaLact:NaCl | 10: 58.6: 31.4 | 10.8% | 12.3% | 1:2 | 2.04 | 2.17 | 1.09 |
| 2 | Lactate | 50% Leucine | leu:CaLact:NaCl | 50: 48.4: 1.6 | 8.9% | 0.6% | 8:1 | | | |
| 3 | Lactate | 10% Leucine | leu:CaLact:NaCl | 10: 66.6: 23.4 | 12.2% | 9.2% | 1:1.3 | 3.39 | 2.25 | 0.95 |
| 4 (I-B) | Citrate | 10% Leucine | leu:CaCl2:Na3Cit | 10: 35.1: 54.9 | 12.7% | 14.7% | 1:2 | 2.88 | 2.11 | 1.21 |
| 5 | Citrate | 67% Leucine | leu:CaCl2:Na3Cit | 67.1: 30: 2.9 | 10.8% | 0.8% | 8:1 | | | |
| 6 | Citrate | None | CaCl2:Na3Cit | 39:61 | 16.3% | 0.4% | 1:2 | | | |
| 7 (III-B) | Sulfate | 10% Leucine | leu:CaCl2:Na2SO4 | 10: 39.6: 50.4 | 14.3% | 8.2% | 1:2 | 3.26 | 2.13 | 1.02 |
| 8 | Sulfate | 68% Leucine | leu:CaCl2:Na2SO4 | 67.6: 30: 2.4 | 10.8% | 0.4% | 8:1 | | | |
| 9 | Sulfate | None | CaCl2:Na2SO4 | 44: 56 | 15.9% | 9.1% | 1:2 | | | |

| Formulation | Spraytec dV50 (μm) | Spraytec GSD | water % |
|---|---|---|---|
| 1 (II-B) | 2.85 | 3.16 | 6.58% |
| 2 | 6.14 | 2.71 | |
| 3 | 4.82 | 3.10 | 5.21% |
| 4 (I-B) | 6.97 | 3.29 | |
| 5 | 8.39 | 3.08 | 7.21% |
| 6 | 6.38 | 3.41 | |
| 7 (III-B) | 4.61 | 3.27 | |
| 8 | 21.23 | 3.01 | 6.53% |
| 9 | 8.20 | 3.55

FIG. 6B

Feedstock Formulations 1-9
Table of Properties

| Formulation | Powder weight μm | Emitted Dose % | FPF_TD <3.4 um % | FPF_TD <5.6 um % | % Mass collected | yield % | Tapped density (g/cc) |
|---|---|---|---|---|---|---|---|
| 1 (II-B) | 25.86 | 100.00% | 35.55% | 55.42% | 61.12% | 73.26% | 0.89 |
| 2 | 15.10 | 98.86% | 24.93% | 48.92% | 62.69% | 34.06% | 0.46 |
| 3 | 30.03 | 99.85% | 18.00% | 37.52% | 58.12% | 85.11% | 0.74 |
| 4 (I-B) | 25.84 | 99.45% | 33.25% | 49.17% | 61.16% | 82.72% | 0.26 |
| 5 | 25.16 | 99.68% | 11.47% | 27.47% | 47.73% | n/a | 0.42 |
| 6 | 25.34 | 100.00% | 9.47% | 20.19% | 36.09% | 83.53% | 0.32 |
| 7 (III-B) | 23.15 | 99.38% | 47.37% | 62.00% | 72.27% | 72.57% | 0.42 |
| 8 | 25.10 | 98.05% | 13.15% | 25.24% | 47.68% | n/a | 0.22 |
| 9 | 25.32 | 100.00% | 8.62% | 19.42% | 38.54% | 54.91% | 0.49 |

FIG. 7

1. Salt aerosol
2. Bacteria/Virus

MUCUS — 1800μm

Collection buffer

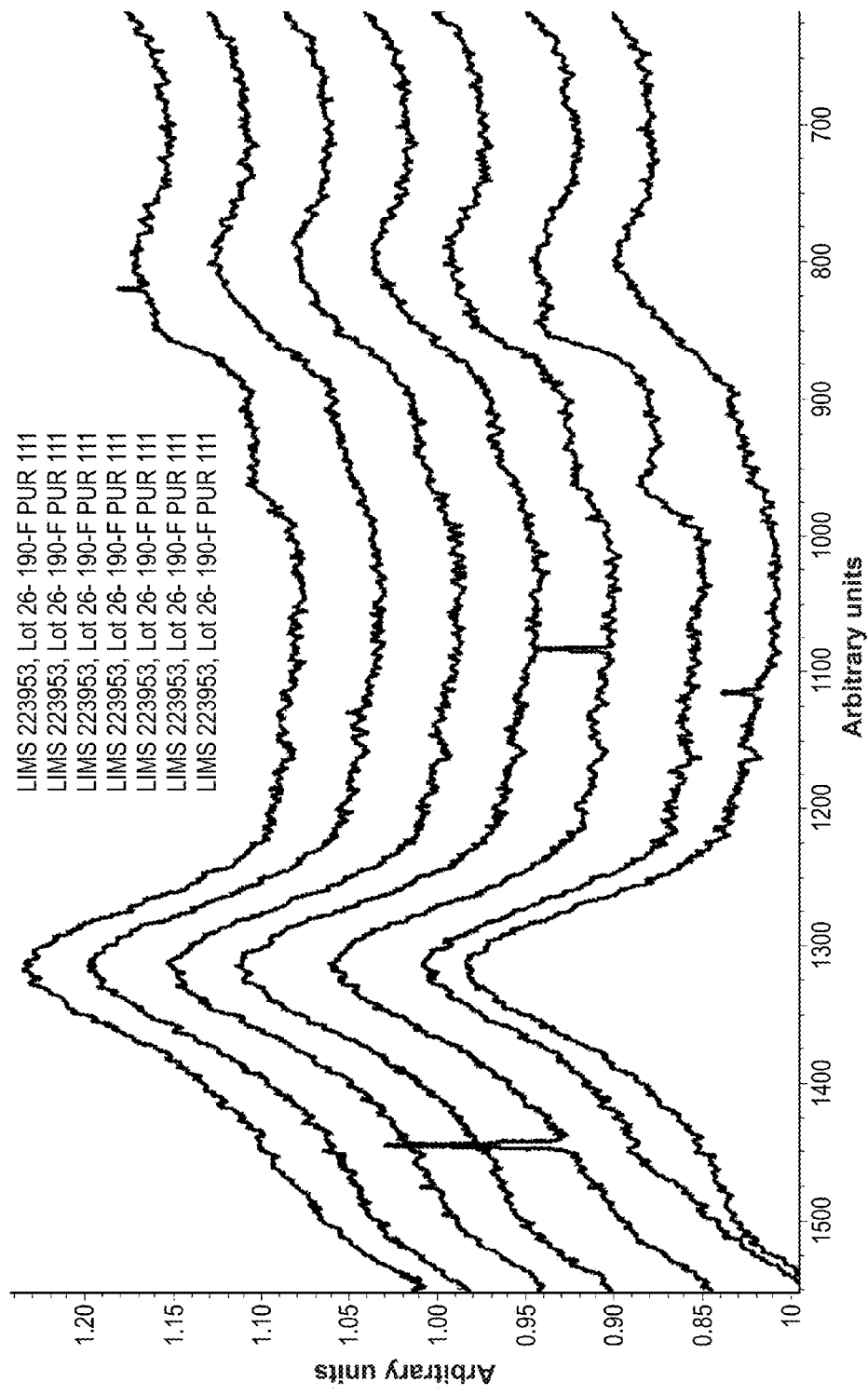

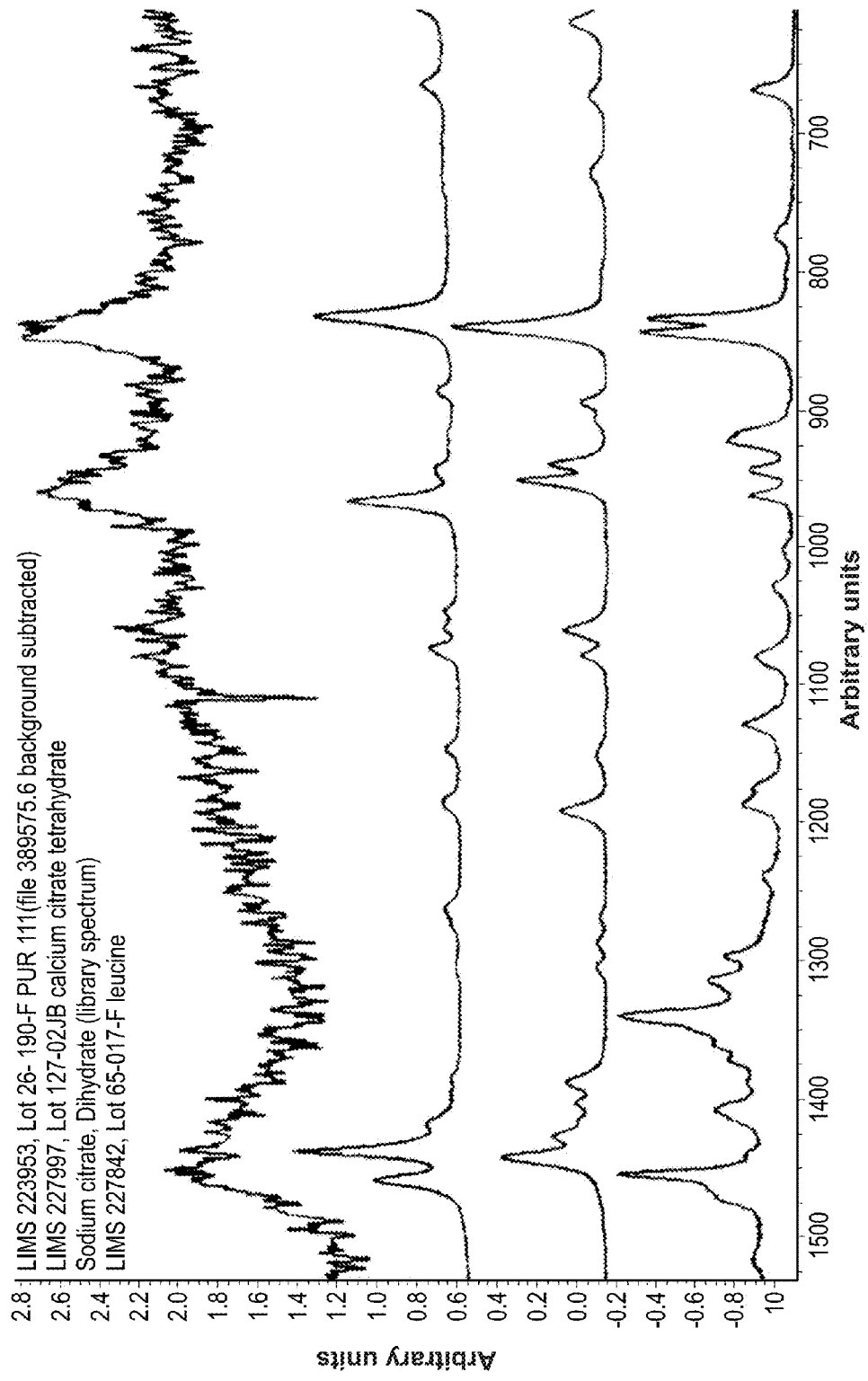

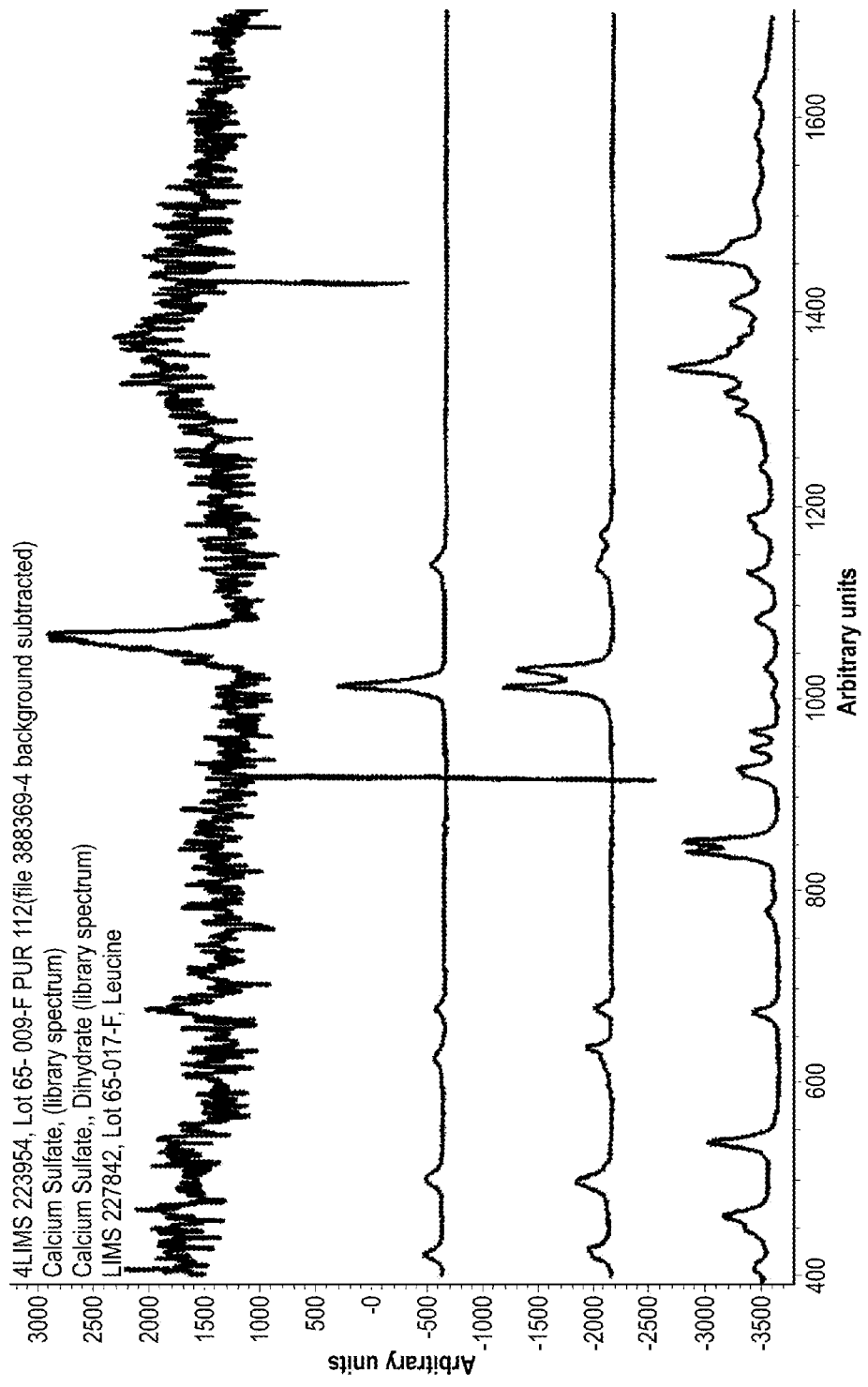

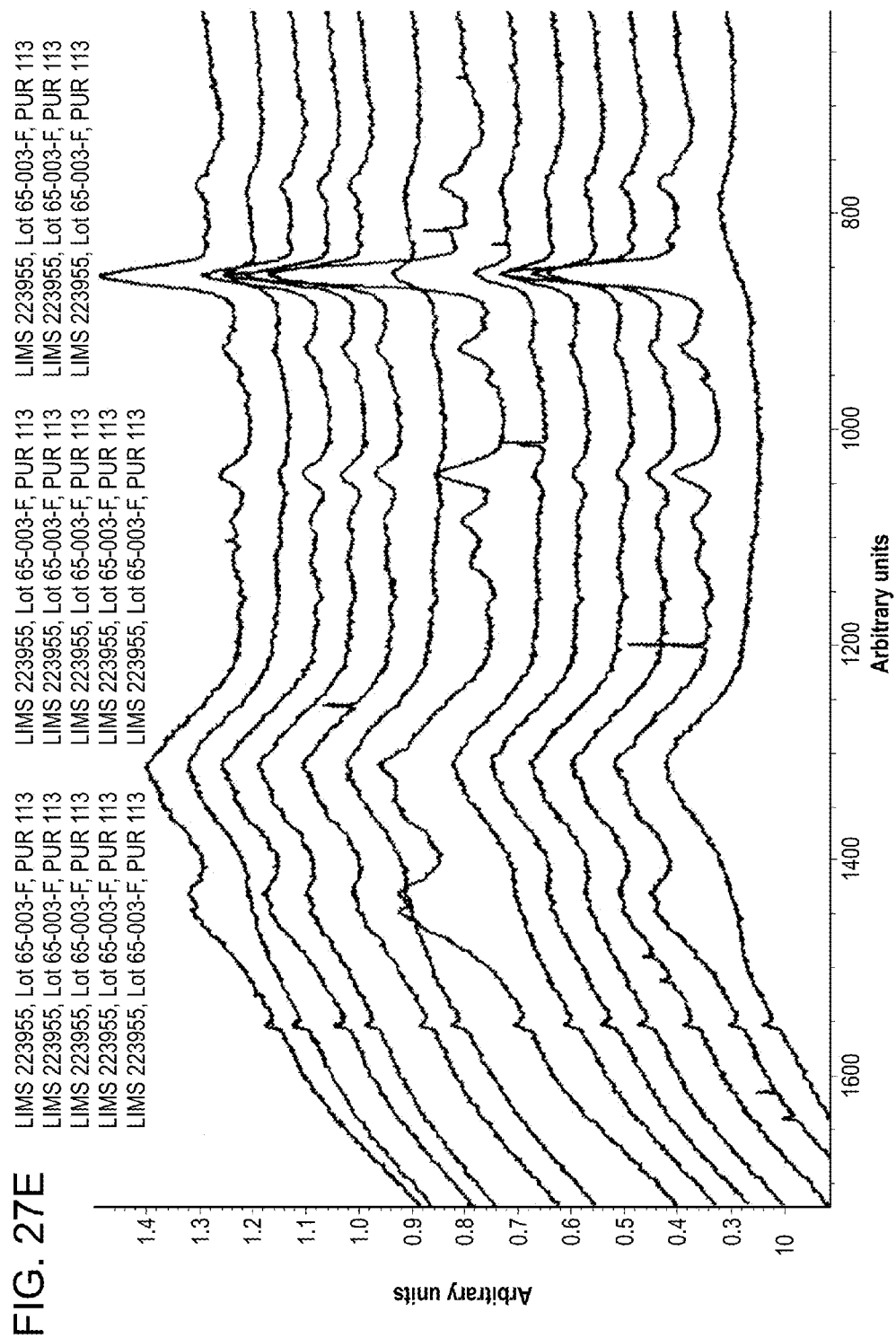

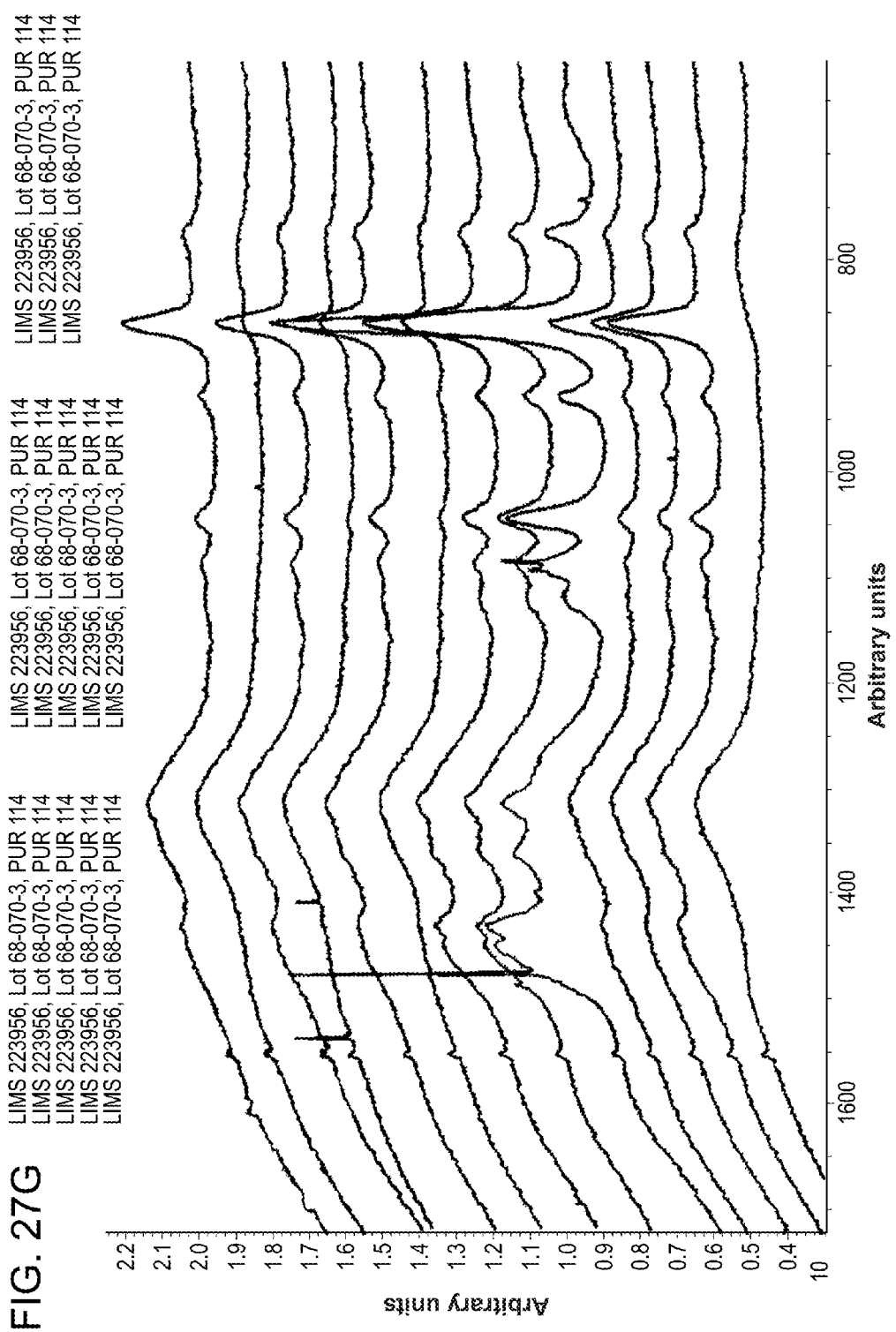

FIG. 37

| Powder formulations | | | Table 27 | | | |
|---|---|---|---|---|---|---|
| Formulation # | Formulation composition | | | | | |
| | Excipient | Excipient (wt %) | Calcium salt | Calcium salt (wt %) | Sodium salt | Sodium salt (wt %) |
| 1 | Leucine | 50.0 | Calcium chloride | 29.5 | Sodium chloride | 20.5 |
| 2 | Leucine | 50.0 | Calcium acetate | 33.8 | Sodium chloride | 16.2 |
| 3 | Leucine | 50.0 | Calcium lactate | 37.0 | Sodium chloride | 13.0 |
| 4 | Leucine | 50.0 | Calcium chloride | 22.0 | Sodium sulfate | 28.0 |
| 5 | Leucine | 50.0 | Calcium chloride | 19.5 | Sodium citrate | 30.5 |
| 6 | Leucine | 10.0 | Calcium lactate | 66.6 | Sodium chloride | 23.4 |
| 7 | Leucine | 10.0 | Calcium chloride | 39.6 | Sodium sulfate | 50.4 |
| 8 | Leucine | 10.0 | Calcium chloride | 35.1 | Sodium citrate | 54.9 |
| 9 | n.a. | n.a. | Calcium lactate | 74.0 | Sodium chloride | 26.0 |
| 10 | n.a. | n.a. | Calcium chloride | 44.0 | Sodium sulfate | 56.0 |
| 11 | n.a. | n.a. | Calcium chloride | 39.0 | Sodium citrate | 61.0 |
| 12 | Leucine | 10.0 | Calcium lactate | 58.6 | Sodium chloride | 31.4 |
| 13 | Maltodextrin | 10.0 | Calcium lactate | 58.6 | Sodium chloride | 31.4 |
| 14 | Mannitol | 10.0 | Calcium lactate | 58.6 | Sodium chloride | 31.4 |
| 15 | Lactose | 10.0 | Calcium lactate | 58.6 | Sodium chloride | 31.4 |
| 16 | Half leucine and half maltodextrin (wt basis) | 10.0 | Calcium lactate | 58.6 | Sodium chloride | 31.4 |
| 17 | Half leucine and half maltodextrin (wt basis) | 20.0 | Calcium lactate | 52.1 | Sodium chloride | 27.9 |
| 18 | Leucine | 20.0 | Calcium lactate | 52.1 | Sodium chloride | 27.9 |
| 19 | Leucine | 12.0 | Calcium lactate | 57.3 | Sodium chloride | 30.7 |
| 20 | Leucine | 8.0 | Calcium lactate | 59.9 | Sodium chloride | 32.1 | n.a. not applicable

DRY POWDER FORMULATIONS AND METHODS FOR TREATING PULMONARY DISEASES

RELATED APPLICATIONS

This application is a continuation of U.S. patent application Ser. No. 14/456,445 filed on Aug. 11, 2014, which is a continuation of Ser. No. 13/259,635, filed on Nov. 21, 2011, which is the U.S. National Stage of International Application No. PCT/US2010/028961, filed Mar. 26, 2010, published in English, and claims the benefit of U.S. Provisional Application No. 61/305,819, filed on Feb. 18, 2010, U.S. Provisional Application No. 61/298,092, filed on Jan. 25, 2010, U.S. Provisional Application No. 61/267,747, filed on Dec. 8, 2009, U.S. Provisional Application No. 61/255,764, filed on Oct. 28, 2009, U.S. Provisional Application No. 61/163,772, filed on Mar. 26, 2009, U.S. Provisional Application No. 61/163,767, filed on Mar. 26, 2009 and U.S. Provisional Application No. 61/163,763, filed on Mar. 26, 2009. The entire contents of each of the foregoing applications are incorporated herein by reference.

BACKGROUND OF THE INVENTION

Pulmonary delivery of therapeutic agents can offer several advantages over other modes of delivery. These advantages include rapid onset, the convenience of patient self-administration, the potential for reduced drug side-effects, ease of delivery by inhalation, the elimination of needles, and the like. Inhalation therapy is capable of providing a drug delivery system that is easy to use in an inpatient or outpatient setting, results in very rapid onset of drug action, and produces minimal side effects.

Metered dose inhalers (MDIs) are used to deliver therapeutic agents to the respiratory tract. MDIs are generally suitable for administering therapeutic agents that can be formulated as solid respirable dry particles in a volatile liquid under pressure. Opening of a valve releases the suspension at relatively high velocity. The liquid then volatilizes, leaving behind a fast-moving aerosol of dry particles that contain the therapeutic agent. MDIs are reliable for drug delivery only to mid-sized airways for the treatment of respiratory ailments. However, it is the small-sized airways (i.e., bronchioles and alveoli) that are often the site of manifestation of pulmonary diseases such as asthma and infections.

Liquid aerosol delivery is one of the oldest forms of pulmonary drug delivery. Typically, liquid aerosols are created by an air jet nebulizer, which releases compressed air from a small orifice at high velocity, resulting in low pressure at the exit region due to the Bernoulli effect. See, e.g., U.S. Pat. No. 5,511,726. The low pressure is used to draw the fluid to be aerosolized out of a second tube. This fluid breaks into small droplets as it accelerates in the air stream. Disadvantages of this standard nebulizer design include relatively large primary liquid aerosol droplet size often requiring impaction of the primary droplet onto a baffle to generate secondary splash droplets of respirable sizes, lack of liquid aerosol droplet size uniformity, significant recirculation of the bulk drug solution, and low densities of small respirable liquid aerosol droplets in the inhaled air.

Ultrasonic nebulizers use flat or concave piezoelectric disks submerged below a liquid reservoir to resonate the surface of the liquid reservoir, forming a liquid cone which sheds aerosol particles from its surface (U.S. 2006/0249144 and U.S. Pat. No. 5,551,416). Since no airflow is required in the aerosolization process, high aerosol concentrations can be achieved, however the piezoelectric components are relatively expensive to produce and are inefficient at aerosolizing suspensions, requiring active drug to be dissolved at low concentrations in water or saline solutions. Newer liquid aerosol technologies involve generating smaller and more uniform liquid respirable dry particles by passing the liquid to be aerosolized through micron-sized holes. See, e.g., U.S. Pat. Nos. 6,131,570; 5,724,957; and 6,098,620. Disadvantages of this technique include relatively expensive piezoelectric and fine mesh components as well as fouling of the holes from residual salts and from solid suspensions.

Dry powder inhalation has historically relied on lactose blending to allow for the dosing of particles that are small enough to be inhaled, but aren't dispersible enough on their own. This process is known to be inefficient and to not work for some drugs. Several groups have tried to improve on these shortcomings by developing dry powder inhaler (DPI) formulations that are respirable and dispersible and thus do not require lactose blending. Dry powder formulations for inhalation therapy are described in U.S. Pat. No. 5,993,805 to Sutton et al.; U.S. Pat. No. 6,921,6527 to Platz et al.; WO 0000176 to Robinson et al.; WO 9916419 to Tarara et al.; WO 0000215 to Bot et al; U.S. Pat. No. 5,855,913 to Hanes et al.; and U.S. Pat. Nos. 6,136,295 and 5,874,064 to Edwards et al.

Broad clinical application of dry powder inhalation delivery has been limited by difficulties in generating dry powders of appropriate particle size, particle density, and dispersibility, in keeping the dry powder stored in a dry state, and in developing a convenient, hand-held device that effectively disperses the respirable dry particles to be inhaled in air. In addition, the particle size of dry powders for inhalation delivery is inherently limited by the fact that smaller respirable dry particles are harder to disperse in air. Dry powder formulations, while offering advantages over cumbersome liquid dosage forms and propellant-driven formulations, are prone to aggregation and low flowability which considerably diminish dispersibility and the efficiency of dry powder-based inhalation therapies. For example, interparticular Van der Waals interactions and capillary condensation effects are known to contribute to aggregation of dry particles. Hickey, A. et al., "Factors Influencing the Dispersion of Dry Powders as Aerosols", Pharmaceutical Technology, August, 1994.

To overcome interparticle adhesive forces, Batycky et al. in U.S. Pat. No. 7,182,961 teach production of so called "aerodynamically light respirable particles," which have a volume median geometric diameter (VMGD) of greater than 5 microns (μm) as measured using a laser diffraction instrument such as HELOS (manufactured by Sympatec, Princeton, N.J.). See Batycky et al., column 7, lines 42-65. Another approach to improve dispersibility of respirable particles of average particle size of less than 10 μm, involves the addition of a water soluble polypeptide or addition of suitable excipients (including amino acid excipients such as leucine) in an amount of 50% to 99.9% by weight of the total composition. Eljamal et al., U.S. Pat. No. 6,582,729, column 4, lines 12-19 and column 5, line 55 to column 6, line 31. However, this approach reduces the amount of active agent that can be delivered using a fixed amount of powder. Therefore, an increased amount of dry powder is required to achieve the intended therapeutic results, for example, multiple inhalations and/or frequent administration may be required. Still other approaches involve the use of devices that apply mechanical forces, such as pressure from compressed gasses, to the small particles to disrupt interparticular adhesion during or just prior to administration. See, e.g., U.S. Pat. No. 7,601,336 to Lewis et al., U.S. Pat. No. 6,737,044 to Dickinson et al., U.S. Pat. No. 6,546,928 to Ashurst et al., or U.S. Pat. Applications 20090208582 to Johnston et al.

A further limitation that is shared by each of the above methods is that the aerosols produced typically include substantial quantities of inert carriers, solvents, emulsifiers, propellants, and other non-drug material. In general, the large quantities of non-drug material are required for effective formation of respirable dry particles small enough for alveolar delivery (e.g. less than 5 microns and preferably less than 3 microns). However, these amounts of non-drug material also serve to reduce the purity and amount of active drug substance that can be delivered. Thus, these methods remain substantially incapable of introducing large active drug dosages accurately to a patient for systemic delivery.

Therefore, there remains a need for the formation of small particle size aerosols that are highly dispersible. In addition, methods that produce aerosols comprising greater quantities of drug and lesser quantities of non-drug material are needed. Finally, a method that allows a patient to administer a unit dosage rapidly with one or two, small volume breaths is needed.

SUMMARY OF THE INVENTION

The invention relates to respirable dry powders comprised of dry particles that contain one or more divalent metal cations, such as calcium ($Ca^{2+}$), as an active ingredient, and to dry powders that contain the respirable particles. The invention also relates to respirable dry particles that contain one or more monovalent cations (such as Na+) and to dry powders that contain the respirable particles. The active ingredient (e.g., calcium ion) is generally present in the dry powders and dry particles in the form of one or more salts, which can independently be crystalline, amorphous or a combination of crystalline and amorphous. The dry powders and dry particles can optionally include additional monovalent salts (e.g. sodium salts), therapeutically active agents or pharmaceutically acceptable excipients. In one aspect, the respirable dry particles may be small and highly dispersible. In another aspect, the respirable dry particles may be large or small, e.g., a geometric diameter (VMGD) between 0.5 microns and 30 microns. Optionally, the MMAD of the particles may be between 0.5 and 10 microns, more preferably between 1 and 5 microns.

In some aspects, the respirable dry powders have a volume median geometric diameter (VMGD) of about 10 microns or less and a dispersibility ratio [ratio of VMGD measured at dispersion pressure of 1 bar to VMGD measured at 4 bar] (¼ bar) of less than about 2 as measured by laser diffraction (RODOS/HELOS system), and contain a calcium salt; that provides divalent metal cation in an amount of about 5% or more by weight of the dry powder. The respirable dry powders can further comprise a monovalent salt that provides monovalent cation, such as $Na^+$, in an amount of about 6% or more by weight of the powders.

The respirable dry powders can have a Fine Particle Fraction (FPF) of less than 5.6 microns of at least 45%, FPF of less than 3.4 microns of at least 30%, and/or FPF of less than 5.0 microns of at least 45%. Alternatively or in addition, the respirable dry powders can have a mass median aerodynamic diameter (MMAD) of about 5 microns or less. The molecular weight ratio of divalent metal cation to the divalent metal cation salt contained in the respirable dry particle can be greater than about 0.1 and/or greater than about 0.16.

The respirable dry powder compositions can include a pharmaceutically acceptable excipient, such as leucine, maltodextrin or mannitol, which can be present in an amount of about 50% or less by weight, preferably in an amount of about 20% or less by weight.

The divalent metal cation salt present in the respirable dry powders can be a beryllium salt, a magnesium salt, a calcium salt, a strontium salt, a barium salt, a radium salt and a ferrous salt. For example, the divalent metal cation salt can be a calcium salt, such as calcium lactate, calcium sulfate, calcium citrate, calcium chloride or any combination thereof. The monovalent salt that is optionally present in the respirable dry particle can be a sodium salt, a lithium salt a potassium salt or any combination thereof.

In certain aspects, the respirable dry powder contains a divalent metal cation salt and a monovalent salt, and contains an amorphous divalent metal cation phase and a crystalline monovalent salt phase. The glass transition temperature of the amorphous phase can be least about 120° C. These respirable dry particles can optionally contain an excipient, such as leucine, maltodextrin and mannitol, which can be amorphous, crystalline or a mixture of forms. The respirable dry particle can have a heat of solution between about −10 kcal/mol and 10 kcal/mol.

Preferably, the divalent metal cation salt is a calcium salt, and the monovalent salt is a sodium salt. The calcium salt can be calcium citrate, calcium lactate, calcium sulfate, calcium chloride or any combination thereof, and the sodium salt can be sodium chloride.

In other aspects, the respirable dry powder contains a divalent metal salt that provides a cation in an amount of about 5% or more by weight of the dry powder, the respirable dry powder have a Hausner Ratio of greater than 1.5 and a ¼ bar or 0.5/4 bar of 2 or less.

The invention also relates to a respirable dry powder that contains respirable dry particles that contain calcium citrate or calcium sulfate, and that are made using a process that includes a) providing a first liquid feed stock comprising an aqueous solution of calcium chloride, and a second liquid feed stock comprising an aqueous solution of sodium sulfate or sodium citrate; b) mixing the first liquid feed stock and the second liquid feed stock to produce a mixture in which an anion exchange reaction occurs to produce a saturated or supersaturated solution comprising calcium sulfate and sodium chloride, or calcium citrate and sodium chloride; and c) spray drying the saturated or supersaturated solution produced in b) to produce respirable dry particles. Mixing in b) can be batch mixing or static mixing.

The invention also relates to methods for treating a respiratory disease, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of the respirable dry particles or dry powder. The invention also relates to methods for the treatment or prevention of acute exacerbations of chronic pulmonary diseases, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of the respirable dry particles or dry powder.

The invention also relates to methods for treating, preventing and/or reducing contagion of an infectious disease of the respiratory tract, comprising administering to the respiratory tract of a subject in need thereof an effective amount of the respirable dry particles or dry powder.

The invention also relates to a respirable dry powder or dry particle, as described herein, for use in therapy (e.g., treatment, prophylaxis, or diagnosis). The invention also relates to the use of a respirable dry particle or dry powder, as described herein, for use in treatment, prevention or reducing contagion as described herein, and in the manufacture of a medicament for the treatment, prophylaxis or diagnosis of a respiratory disease and/or infection as described herein.

BRIEF DESCRIPTION OF THE DRAWINGS

FIGS. 1A-1F is a table that shows properties for dry powders prepared from feedstock Formulations I, II, III and XIV described in Examples 1-3 and 14. FIG. 1A includes spray drying parameters used for spray drying the powders. FIG. 1B shows the HPLC results for percent calcium ion content of the powders, density results including tap and bulk densities, and Karl Fischer results for percent water content in the powders. FIG. 1C shows fine particle fraction (FPF) data and percent mass of powders collected using a two-stage (ACI-2) Andersen Cascade Impactor. FIG. 1D shows fine particle fraction (FPF) data and percent mass of powders collected using an eight-stage (ACI-8) Andersen Cascade Impactor. FIG. 1E shows data for mass median aerodynamic diameter (MMAD) and FPF (based on total dose and recovered dose). FIG. 1F shows data for volume median geometric diameter (DV50), geometric standard deviation (GSD) and percent volume less than 5.0 microns (V<5.0 μm) as measured by Spraytec instrument and geometric or volume particle size distribution (which is also referred to as VMGD, x50/dg or x50), GSD and ¼ bar and 0.5/4 bar information as measured by HELOS with RODOS attachment instrument.

FIG. 5A-D are electron micrographs of Formulation I (FIG. 5A); Formulation II (FIG. 5B); Formulation III (FIG. 5C); and Formulation XIV (FIG. 5D)

FIGS. 6A-6B is a table that shows properties for dry powders prepared by feedstock Formulations 6.1-6.9. Formulation 6.1 in FIG. 5 corresponds to Formulation II-B in Example 2. Formulation 6.4 in FIG. 5 corresponds to Formulation I-B in Example 1. Formulation 6.7 in FIG. 5 corresponds to Formulation III-B in Example 3. Abbreviations in the table heading are described elsewhere in the specification. In FIG. 5, all powders were made using a Büchi spray dryer.

FIG. 7 is a schematic of the pass-through model.

FIG. 11A shows the changes in body temperature of ferrets treated with a calcium citrate powder compared to the control animals. FIG. 11B shows the changes in body temperature of ferrets treated with a calcium sulfate powder compared to the control animals. FIG. 11C shows the changes in body temperature of ferrets treated with a calcium lactate powder compared to the control animals. FIG. 11D shows the change in body temperature from baseline for each animal using area under the curve for the duration of the study (d0-d10). Data depict the mean±SEM for each group (p=0.09 for the leucine control and lactate group by Student t-test).

FIGS. 27A-H are RAMAN spectra. FIG. 27A shows RAMAN spectra for six particles from the Formulation I sample, and are shown overlaid. FIG. 27B shows spectrum 389575-6 is background subtracted and overlaid with the Raman spectra of calcium citrate tetrahydrate, sodium citrate, and leucine. FIG. 27C shows RAMAN spectra for eight particles from the Formulation III sample, and are shown overlaid. FIG. 27D shows spectrum 388369-4 is background subtracted and overlaid with Raman spectra of calcium sulfate, calcium sulfate dihydrate, sodium sulfate anhydrous, and leucine. FIG. 27E shows RAMAN spectra for twelve particles from the Formulation II sample, and are shown overlaid. FIG. 27F shows spectra 389576-7 and 389576-12 are background subtracted and overlaid with the Raman spectra of calcium lactate pentahydrate, and leucine. FIG. 27G shows RAMAN spectra for twelve particles from the Formulation XIV sample, and are shown overlaid. FIG. 27H, spectrum 389577-9 is background subtracted and overlaid with the Raman spectra of calcium lactate pentahydrate.

Figure 2:
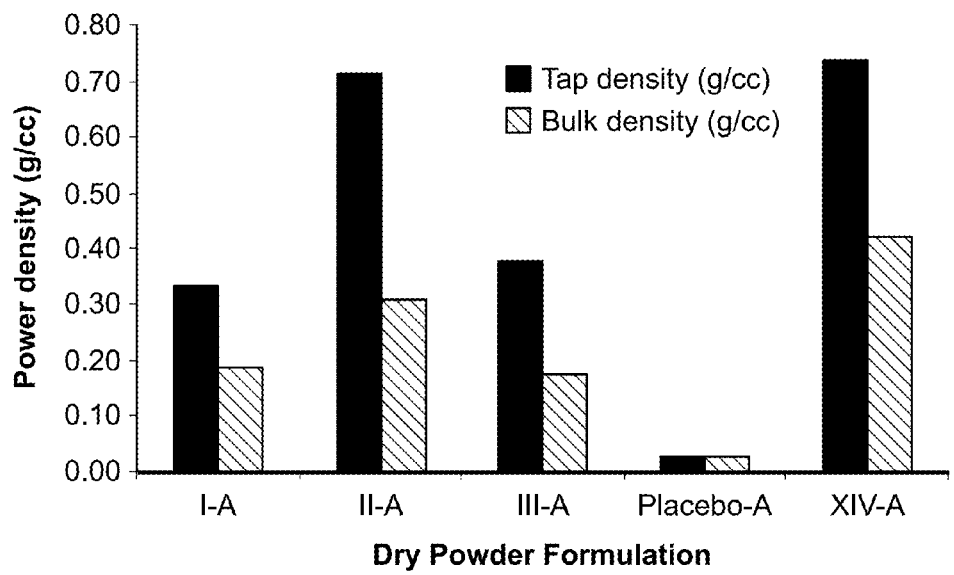
FIG. 2 is a graph that shows a comparison between the average tap and bulk densities for particles prepared from feedstock Formulations I, II and III and a placebo.
Figure 3:
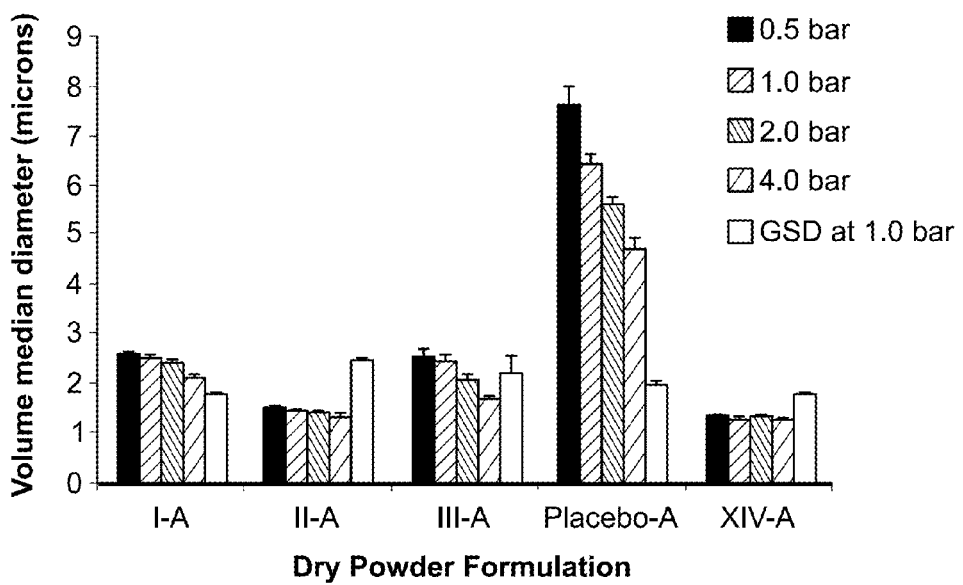
FIG. 3 is a graph that shows a comparison between the particles (prepared from feedstock Formulations I-III and a placebo) at different dispersion (regulator) pressures for measured volume median geometric diameter (×50) using a laser diffraction instrument (HELOS with RODOS).
Figure 4:
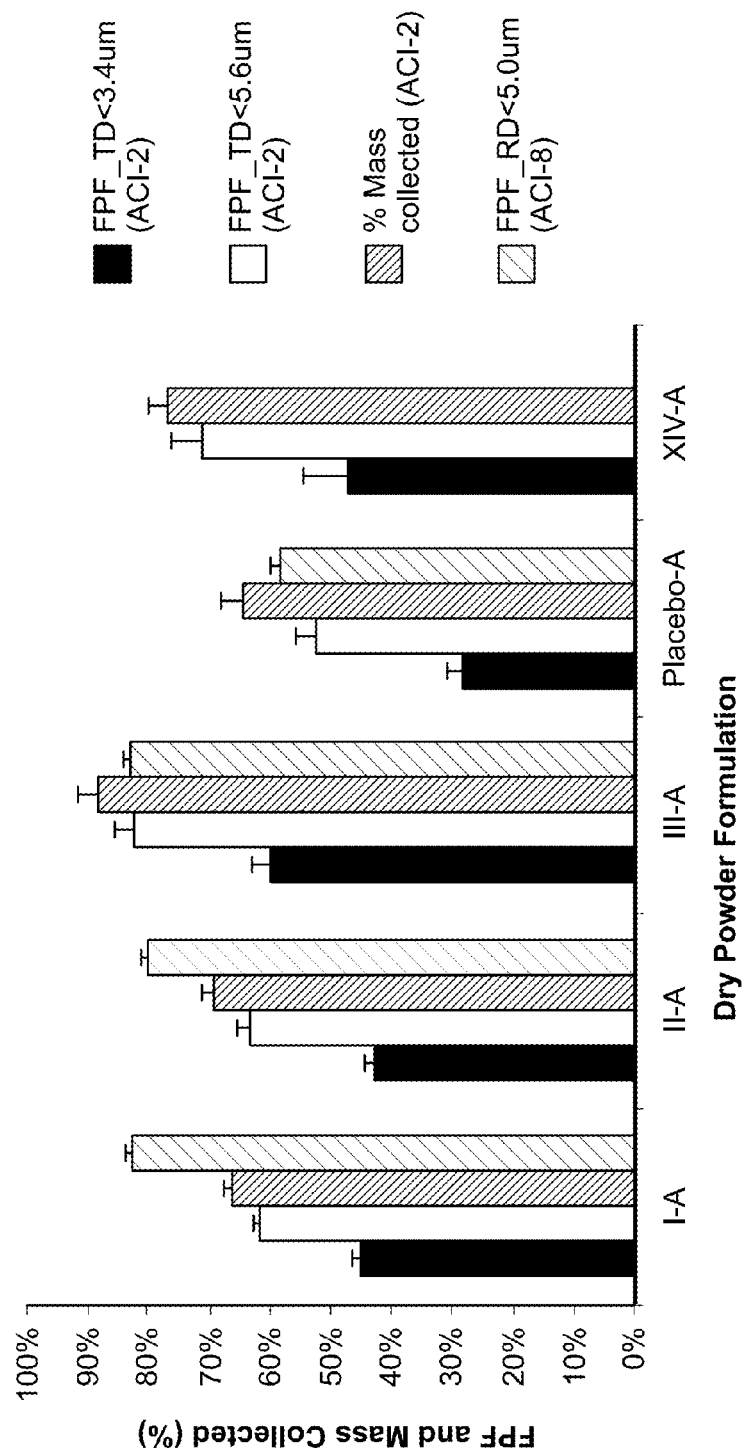
FIG. 4 is a graph that shows a comparison between the particles prepared from feedstock Formulations I (identified as PUR111 (Citrate)), II (identified as PUR113 (Lactate)) and III (identified as PUR112 (Sulfate)) and a placebo for average FPF obtained by an ACI-2 and ACI-8.

Respirable dry powders that contain small particles and that are dispersible in air, and preferably dense (e.g., dense in active ingredient) are a departure from the conventional wisdom. It is well known that the propensity for particles to aggregate or agglomerate increases as particle size decreases. See, e.g., Hickey, A. et al., "Factors Influencing the Dispersion of Dry Powders as Aerosols", Pharmaceutical Technology, August, 1994.

As described herein, the invention provides respirable dry powders that contain respirable particles that are small and dispersible in air without additional energy sources beyond the subject's inhalation. Thus, the respirable dry powders and respirable dry particles can be used therapeutically, without including large amounts of non-active components (e.g., excipients) in the particles or powders, or by using devices that apply mechanical forces to disrupt aggregated or agglomerated particles during or just prior to administration.

The respirable dry powders and respirable particles of the invention are also generally, dense in active ingredient(s), i.e., divalent metal cations (e.g., calcium containing salt(s)). For example, as described herein, when an excipient is included in the respirable dry powder or particles, the excipient is a minor component (e.g., about 50% or less, by weight, preferably about 20% or less by weight, about 12% or less by weight, about 10% or less by weight, about 8% or less by weight or less by weight). Thus, in one aspect, the respirable particles are not only small and highly dispersible, but can contain a large amount of divalent metal cation, for example, calcium ($Ca^{2+}$). Accordingly, a smaller amount of powder will need to be administered in order to deliver the desired dose of divalent metal cation (e.g., calcium). For example, the desired dose of calcium may be delivered with one or two inhalations from a capsule-type or blister-type inhaler.

DEFINITIONS

The term "dry powder" as used herein refers to a composition contains finely dispersed respirable dry particles that are capable of being dispersed in an inhalation device and subsequently inhaled by a subject. Such dry powder or dry particle may contain up to about 15% water or other solvent, or be substantially free of water or other solvent, or be anhydrous.

The term "dry particles" as used herein refers to respirable particles that may contain up to about 15% water or other solvent, or be substantially free of water or other solvent, or be anhydrous.

The term "respirable" as used herein refers to dry particles or dry powders that are suitable for delivery to the respiratory tract (e.g., pulmonary delivery) in a subject by inhalation. Respirable dry powders or dry particles have a mass median aerodynamic diameter (MMAD) of less than about 10 microns, preferably about 5 microns or less.

As used herein, the terms "administration" or "administering" of respirable dry particles refers to introducing respirable dry particles to the respiratory tract of a subject.

As used herein, the term "respiratory tract" includes the upper respiratory tract (e.g., nasal passages, nasal cavity, throat, pharynx), respiratory airways (e.g., larynx, tranchea, bronchi, bronchioles) and lungs (e.g., respiratory bronchioles, alveolar ducts, alveolar sacs, alveoli).

The term "dispersible" is a term of art that describes the characteristic of a dry powder or dry particles to be dispelled into a respirable aerosol. Dispersibility of a dry powder or dry particles is expressed herein as the quotient of the volume median geometric diameter (VMGD) measured at a dispersion (i.e., regulator) pressure of 1 bar divided by the VMGD measured at a dispersion (i.e., regulator) pressure of 4 bar, or VMGD at 0.5 bar divided by the VMGD at 4 bar as measured by HELOS/RODOS. These quotients are referred to herein as "¼ bar," and "0.5/4 bar," respectively, and dispersibility correlates with a low quotient. For example, ¼ bar refers to the VMGD of respirable dry particles or powders emitted from the orifice of a RODOS dry powder disperser (or equivalent technique) at about 1 bar, as measured by a HELOS or other laser diffraction system, divided the VMGD of the same respirable dry particles or powders measured at 4 bar by HELOS/RODOS. Thus, a highly dispersible dry powder or dry particles will have a ¼ bar or 0.5/4 bar ratio that is close to 1.0. Highly dispersible powders have a low tendency to agglomerate, aggregate or clump together and/or, if agglomerated, aggregated or clumped together, are easily dispersed or de-agglomerated as they emit from an inhaler and are breathed in by the subject. Dispersibility can also be assessed by measuring the size emitted from an inhaler as a function of flowrate.

The terms "FPF (<5.6)," "FPF (<5.6 microns)," and "fine particle fraction of less than 5.6 microns" as used herein, refer to the fraction of a sample of dry particles that have an aerodynamic diameter of less than 5.6 microns. For example, FPF (<5.6) can be determined by dividing the mass of respirable dry particles deposited on the stage one and on the collection filter of a two-stage collapsed Andersen Cascade Impactor (ACI) by the mass of respirable dry particles weighed into a capsule for delivery to the instrument. This parameter may also be identified as "FPF_TD(<5.6)," where TD means total dose. A similar measurement can be conducted using an eight-stage ACI. The eight-stage ACI cutoffs are different at the standard 60 L/min flowrate, but the FPF_TD(<5.6) can be extrapolated from the eight-stage complete data set. The eight-stage ACI result can also be calculated by the USP method of using the dose collected in the ACI instead of what was in the capsule to determine FPF.

The terms "FPF (<3.4)," "FPF (<3.4 microns)," and "fine particle fraction of less than 3.4 microns" as used herein, refer to the fraction of a mass of respirable dry particles that have an aerodynamic diameter of less than 3.4 microns. For example, FPF (<3.4) can be determined by dividing the mass of respirable dry particles deposited on the collection filter of a two-stage collapsed ACI by the total mass of respirable dry particles weighed into a capsule for delivery to the instrument. This parameter may also be identified as "FPF_TD(<3.4)," where TD means total dose. A similar measurement can be conducted using an eight-stage ACI. The eight-stage ACI result can also be calculated by the USP method of using the dose collected in the ACI instead of what was in the capsule to determine FPF.

The terms "FPF (<5.0)," "FPF (<5.0 microns)," and "fine particle fraction of less than 5.0 microns" as used herein, refer to the fraction of a mass of respirable dry particles that have an aerodynamic diameter of less than 5.0 microns. For example, FPF (<5.0) can be determined by using an eight-stage ACI at the standard 60 L/min flowrate by extrapolating from the eight-stage complete data set. This parameter may also be identified as "FPF_TD(<5.0)," where TD means total dose.

As used herein, the term "emitted dose" or "ED" refers to an indication of the delivery of a drug formulation from a suitable inhaler device after a firing or dispersion event. More specifically, for dry powder formulations, the ED is a measure of the percentage of powder that is drawn out of a unit dose package and that exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-measured parameter, and can be determined using the method of USP Section 601 Aerosols, Metered-Dose Inhalers and Dry Powder Inhalers, Delivered-Dose Uniformity, Sampling the Delivered Dose from Dry Powder Inhalers, United States Pharmacopia convention, Rockville, Md., 13$^{th}$ Revision, 222-225, 2007. This method utilizes an in vitro device set up to mimic patient dosing.

The term "effective amount," as used herein, refers to the amount of agent needed to achieve the desired effect, such as an amount that is sufficient to increase surface and/or bulk viscoelasticy of the respiratory tract mucus (e.g., airway lining fluid), increase gelation of the respiratory tract mucus (e.g., at the surface and/or bulk gelation), increase surface tension of the respiratory tract mucus, increasing elasticity of the respiratory tract mucus (e.g., surface elasticity and/or bulk elasticity), increase surface viscosity of the respiratory tract mucus (e.g., surface viscosity and/or bulk viscosity), reduce the amount of exhaled particles, reduce pathogen (e.g., bacteria, virus) burden, reduce symptoms (e.g., fever, coughing, sneezing, nasal discharge, diarrhea and the like), reduce occurrence of infection, reduce viral replication, or improve or prevent deterioration of respiratory function (e.g., improve forced expiratory volume in 1 second FEV1 and/or forced expiratory volume in 1 second FEV1 as a proportion of forced vital capacity FEV1/FVC, reduce bronchoconstriction). The actual effective amount for a particular use can vary according to the particular dry powder or dry particle, the mode of administration, and the age, weight, general health of the subject, and severity of the symptoms or condition being treated. Suitable amounts of dry powders and dry particles to be administered, and dosage schedules, for a particular patient can be determined by a clinician of ordinary skill based on these and other considerations.

The term "pharmaceutically acceptable excipient" as used herein means that the excipient can be taken into the lungs with no significant adverse toxicological effects on the lungs. Such excipient are generally regarded as safe (GRAS) by the U.S. Food and Drug Administration.

Dry Powders and Dry Particles

The invention relates to respirable dry powders and dry particles that contain one or more divalent metal cations, such as beryllium (Be$^{2+}$), magnesium, (Mg$^{2+}$), calcium (Ca$^{2+}$), strontium (Sr$^{2+}$), barium (Ba$^{2+}$), radium (Ra$^{2+}$), or iron (ferrous ion, Fe$^{2+}$), as an active ingredient. The active divalent metal cation (e.g., calcium) is generally present in the dry powders and dry particles in the form of a salt, which can be crystalline or amorphous. The dry powders and dry particles can optionally include additional salts (e.g. monovalent salts, such as sodium salts, potassium salts, and lithium salts.), therapeutically active agents or pharmaceutically acceptable excipients.

In some aspects, the respirable dry powder and dry particles contain one or more salts of a group IIA element (i.e., one or more beryllium salts, magnesium salts, calcium salts, barium salts, radium salts or any combination of the forgoing). In more particular aspects, the respirable dry powder and dry particles contain one or more calcium salts, magnesium salts or any combination of the forgoing. In particular embodiments, the respirable dry powder and dry particles contain one or more calcium salts. In other particular embodiments, respirable dry powder and dry particles contain one or more magnesium salts.

Suitable beryllium salts include, for example, beryllium phosphate, beryllium acetate, beryllium tartrate, beryllium citrate, beryllium gluconate, beryllium maleate, beryllium succinate, sodium beryllium malate, beryllium alpha brom camphor sulfonate, beryllium acetylacetonate, beryllium formate or any combination thereof.

Suitable magnesium salts include, for example, magnesium fluoride, magnesium chloride, magnesium bromide, magnesium iodide, magnesium phosphate, magnesium sulfate, magnesium sulfite, magnesium carbonate, magnesium oxide, magnesium nitrate, magnesium borate, magnesium acetate, magnesium citrate, magnesium gluconate, magnesium maleate, magnesium succinate, magnesium malate, magnesium taurate, magnesium orotate, magnesium glycinate, magnesium naphthenate, magnesium acetylacetonate, magnesium formate, magnesium hydroxide, magnesium stearate, magnesium hexafluorsilicate, magnesium salicylate or any combination thereof.

Suitable calcium salts include, for example, calcium chloride, calcium sulfate, calcium lactate, calcium citrate, calcium carbonate, calcium acetate, calcium phosphate, calcium alginite, calcium stearate, calcium sorbate, calcium gluconate and the like.

Suitable strontium salts include, for example, strontium chloride, strontium phosphate, strontium sulfate, strontium carbonate, strontium oxide, strontium nitrate, strontium acetate, strontium tartrate, strontium citrate, strontium gluconate, strontium maleate, strontium succinate, strontium malate, strontium aspartate in either L and/or D-form, strontium fumarate, strontium glutamate in either L- and/or D-form, strontium glutarate, strontium lactate, strontium L-threonate, strontium malonate, strontium ranelate (organic metal chelate), strontium ascorbate, strontium butyrate, strontium clodronate, strontium ibandronate, strontium salicylate, strontium acetyl salicylate or any combination thereof.

Suitable barium salts include, for example, barium hydroxide, barium fluoride, barium chloride, barium bromide, barium iodide, barium sulfate, barium sulfide (S), barium carbonate, barium peroxide, barium oxide, barium nitrate, barium acetate, barium tartrate, barium citrate, barium gluconate, barium maleate, barium succinate, barium malate, barium glutamate, barium oxalate, barium malonate, barium naphthenate, barium acetylacetonate, barium formate, barium benzoate, barium p-t-butylbenzoate, barium adipate, barium pimelate, barium suberate, barium azelate, barium sebacate, barium phthalate, barium isophthalate, barium terephthalate, barium anthranilate, barium mandelate, barium salicylate, barium titanate or any combination thereof.

Suitable radium salts included, for example, radium fluoride, radium chloride, radium bromide, radium iodide, radium oxide, radium nitride or any combination thereof.

Suitable iron (ferrous) salts include, for example, ferrous sulfate, ferrous oxides, ferrous acetate, ferrous citrate, ferrous ammonium citrate, ferrous ferrous gluconate, ferrous oxalate, ferrous fumarate, ferrous maleate, ferrous malate, ferrous lactate, ferrous ascorbate, ferrous erythrobate, ferrous glycerate, ferrous pyruvate or any combination thereof.

In one aspect, the dry particles of the invention are small, and preferably divalent metal cation (e.g., calcium) dense, and are dispersible. The size of the dry particles can be expressed in a variety of ways that are conventional in the art, such as, fine particle fraction (FPF), volumetric median geometric diameter (VMGD), or mass median aerodynamic diameter (MMAD). Generally, the dry particles of the invention have a VMGD as measured by HELOS/RODOS at 1.0 bar of about 10 µm or less (e.g., about 0.1 µm to about 10 µm). Preferably, the dry particles of the invention have an VMGD of about 9 µm or less (e.g., about 0.1 µm to about 9 µm), about 8 µm or less (e.g., about 0.1 µm to about 8 µm), about 7 µm or less (e.g., about 0.1 µm to about 7 µm), about 6 µm or less (e.g., about 0.1 µm to about 6 µm), about 5 µm or less (e.g., less than 5 µm, about 0.1 µm to about 5 µm), about 4 µm or less (e.g., 0.1 µm to about 4 µm), about 3 µm or less (e.g., 0.1 µm to about 3 µm), about 2 µm or less (e.g., 0.1 µm to about 2 µm), about 1 µm or less (e.g., 0.1 µm to about 1 µm), about 1 µm to about 6 µm, about 1 µm to about 5 µm, about 1 µm to about 4 µm, about 1 µm to about 3 µm, or about 1 µm to about 2 µm as measured by HELOS/RODOS at 1.0 bar.

In another aspect, the dry particles of the invention are large, and preferably calcium dense, and are dispersible. Generally, the dry particles of the invention have a VMGD as measured by HELOS/RODOS at 1.0 bar of about 30 µm or less (e.g., about 5 µm to about 30 µm). Preferably, the dry particles of the invention have an VMGD of about 25 µm or less (e.g., about 5 µm to about 25 µm), about 20 µm or less (e.g., about 5 µm to about 20 µm), about 15 µm or less (e.g., about 5 µm to about 15 µm), about 12 µm or less (e.g., about 5 µm to about 12 µm), about 10 µm or less (e.g., about 5 µm to about 10 µm), or about 8 µm or less (e.g., 6 µm to about 8 µm) as measured by HELOS/RODOS at 1.0 bar.

In addition, whether the particles are small or large, the dry particles of the invention are dispersible, and have ¼ bar and/or 0.5/4 bar of about 2.2 or less (e.g., about 1.0 to about 2.2) or about 2.0 or less (e.g., about 1.0 to about 2.0). Preferably, the dry particles of the invention have ¼ bar and/or 0.5/4 bar of about 1.9 or less (e.g., about 1.0 to about 1.9), about 1.8 or less (e.g., about 1.0 to about 1.8), about 1.7 or less (e.g., about 1.0 to about 1.7), about 1.6 or less (e.g., about 1.0 to about 1.6), about 1.5 or less (e.g., about 1.0 to about 1.5), about 1.4 or less (e.g., about 1.0 to about 1.4), about 1.3 or less (e.g., less than 1.3, about 1.0 to about 1.3), about 1.2 or less (e.g., 1.0 to about 1.2), about 1.1 or less (e.g., 1.0 to about 1.1 μm) or the dry particles of the invention have ¼ bar of about 1.0.

Alternatively or in addition, the respirable dry particles of the invention can have an MMAD of about 10 microns or less, such as an MMAD of about 0.5 micron to about 10 microns. Preferably, the dry particles of the invention have an MMAD of about 5 microns or less (e.g. about 0.5 micron to about 5 microns, preferably about 1 micron to about 5 microns), about 4 microns or less (e.g., about 1 micron to about 4 microns), about 3.8 microns or less (e.g. about 1 micron to about 3.8 microns), about 3.5 microns or less (e.g. about 1 micron to about 3.5 microns), about 3.2 microns or less (e.g. about 1 micron to about 3.2 microns), about 3 microns or less (e.g. about 1 micron to about 3.0 microns), about 2.8 microns or less (e.g. about 1 micron to about 2.8 microns), about 2.2 microns or less (e.g. about 1 micron to about 2.2 microns), about 2.0 microns or less (e.g. about 1 micron to about 2.0 microns) or about 1.8 microns or less (e.g. about 1 micron to about 1.8 microns).

Alternatively or in addition, the respirable dry powders and dry particles of the invention can have an FPF of less than about 5.6 microns (FPF<5.6 μm) of at least about 20%, at least about 30%, at least about 40%, preferably at least about 45%, at least about 50%, at least about 55%, at least about 60%, at least about 65%, or at least about 70%.

Alternatively or in addition, the dry powders and dry particles of the invention have a FPF of less than 5.0 microns (FPF_TD<5.0 μm) of at least about 20%, at least about 30%, at least about 45%, preferably at least about 40%, at least about 45%, at least about 50%, at least about 60%, at least about 65% or at least about 70%. Alternatively or in addition, the dry powders and dry particles of the invention have a FPF of less than 5.0 microns of the emitted dose (FPF_ED<5.0 μm) of at least about 45%, preferably at least about 50%, at least about 60%, at least about 65%, at least about 70%, at least about 75%, at least about 80%, or at least about 85%. Alternatively or in addition, the dry powders and dry particles of the invention can have an FPF of less than about 3.4 microns (FPF<3.4 μm) of at least about 20%, preferably at least about 25%, at least about 30%, at least about 35%, at least about 40%, at least about 45%, at least about 50%, or at least about 55%.

Alternatively or in addition, the respirable dry powders and dry particles of the invention have a tap density of about 0.1 $g/cm^3$ to about 1.0 $g/cm^3$. For example, the small and dispersible dry particles have a tap density of about 0.1 $g/cm^3$ to about 0.9 $g/cm^3$, about 0.2 $g/cm^3$ to about 0.9 $g/cm^3$, about 0.2 $g/cm^3$ to about 0.9 $g/cm^3$, about 0.3 $g/cm^3$ to about 0.9 $g/cm^3$, about 0.4 $g/cm^3$ to about 0.9 $g/cm^3$, about 0.5 $g/cm^3$ to about 0.9 $g/cm^3$, or about 0.5 $g/cm^3$ to about 0.8 $g/cm^3$, greater than about 0.4 g/cc, greater than about 0.5 g/cc, greater than about 0.6 g/cc, greater than about 0.7 g/cc, about 0.1 $g/cm^3$ to about 0.8 $g/cm^3$, about 0.1 $g/cm^3$ to about 0.7 $g/cm^3$, about 0.1 $g/cm^3$ to about 0.6 $g/cm^3$, about 0.1 $g/cm^3$ to about 0.5 $g/cm^3$, about 0.1 $g/cm^3$ to about 0.4 $g/cm^3$, about 0.1 $g/cm^3$ to about 0.3 $g/cm^3$, less than 0.3 $g/cm^3$. In a preferred embodiment, tap density is greater than about 0.4 g/cc. In another preferred embodiment, tap density is greater than about 0.5 g/cc. Alternatively, tap density is less than about 0.4 g/cc.

Alternatively or in addition, the respirable dry powders and dry particles of the invention can have a water or solvent content of less than about 15% by weight of the respirable dry particle. For example, the respirable dry particles of the invention can have a water or solvent content of less than about 15% by weight, less than about 13% by weight, less than about 11.5% by weight, less than about 10% by weight, less than about 9% by weight, less than about 8% by weight, less than about 7% by weight, less than about 6% by weight, less than about 5% by weight, less than about 4% by weight, less than about 3% by weight, less than about 2% by weight, less than about 1% by weight or be anhydrous. The respirable dry particles of the invention can have a water or solvent content of less than about 6% and greater than about 1%, less than about 5.5% and greater than about 1.5%, less than about 5% and greater than about 2%, about 2%, about 2.5%, about 3%, about 3.5%, about 4%, about 4.5% about 5%.

As described herein, the respirable dry particles of the invention contain one or more divalent metal cations (e.g., calcium ($Ca^{2+}$)) as an active ingredient which is generally present in the form of a salt (e.g., crystalline and/or amorphous). Suitable calcium salts that can be present in the respirable dry particles of the invention include, for example, calcium chloride, calcium sulfate, calcium lactate, calcium citrate, calcium carbonate, calcium acetate, calcium phosphate, calcium alginite, calcium stearate, calcium sorbate, calcium gluconate and the like. In certain preferred aspects, the dry powder or dry particles of the invention do not contain calcium phosphate, calcium carbonate, calcium alginate, calcium stearate or calcium gluconate. In another preferred aspect, the dry powder or dry particles of the invention include calcium citrate, calcium lactate, calcium chloride, calcium sulfate, or any combination of these salts. In another preferred aspect, the dry powder or dry particles include calcium citrate, calcium lactate, or any combination of the these salts. If desired, the respirable dry particles of the invention contain a divalent metal cation salt (e.g., a calcium salt) and further contain one or more additional salts, such as one or more non-toxic salts of the elements sodium, potassium, magnesium, calcium, aluminum, silicon, scandium, titanium, vanadium, chromium, cobalt, nickel, copper, manganese, zinc, tin, silver and the like. Preferably, the dry particles contain at least one calcium salt and at least one monovalent cation salt (e.g., a sodium salt).

Suitable sodium salts that can be present in the respirable dry particles of the invention include, for example, sodium chloride, sodium citrate, sodium sulfate, sodium lactate, sodium acetate, sodium bicarbonate, sodium carbonate, sodium stearate, sodium ascorbate, sodium benzoate, sodium biphosphate, sodium phosphate, sodium bisulfite, sodium borate, sodium gluconate, sodium metasilicate and the like. In a preferred aspect, the dry powders and dry particles include sodium chloride, sodium citrate, sodium lactate, sodium sulfate, or any combination of these salts.

Suitable lithium salts include, for example, lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate or and combination thereof.

Suitable potassium salts include, for example, potassium chloride, potassium bromide, potassium iodide, potassium bicarbonate, potassium nitrite, potassium persulfate, potassium sulfite, potassium bisulfite, potassium phosphate, potassium acetate, potassium citrate, potassium glutamate, dipotassium guanylate, potassium gluconate, potassium malate, potassium ascorbate, potassium sorbate, potassium succinate, potassium sodium tartrate and any combination thereof.

Preferred divalent metal salts (e.g., calcium salts) have one, preferably two or more of the following characteristics: (i) can be processed into a respirable dry particle, (ii) possess sufficient physicochemical stability in dry powder form to facilitate the production of a powder that is dispersible and physically stable over a range of conditions, including upon exposure to elevated humidity, (iii) undergo rapid dissolution upon deposition in the lungs, for example, half of the mass of the cation of the divalent metal can dissolved in less than 30 minutes, less than 15 minutes, less than 5 minutes, less than 2 minutes, less than 1 minute, or less than 30 seconds, and (iv) do not possess properties that can result in poor tolerability or adverse events, such as a significant exothermic or endothermic heat of solution ($\Delta H$). for example, a $\Delta H$ lower than of about −10 kcal/mol or greater than about 10 kcal/mol. Rather, a preferred $\Delta H$ is between about −9 kcal/mol and about 9 kcal/mol, between about −8 kcal/mol and about 8 kcal/mol, between about −7 kcal/mol and about 7 kcal/mol, between about −6 kcal/mol and about 6 kcal/mol, between about −5 kcal/mol and about 5 kcal/mol, between about −4 kcal/mol and about 4 kcal/mol, between about −3 kcal/mol and about 3 kcal/mol, between about −2 kcal/mol and about 2 kcal/mol, between about −1 kcal/mol and about 1 kcal/mol, or about 0 kcal/mol Regarding the dissolution rate upon deposition of the dry powder or particles in the lungs, an alternative to rapid dissolution of the particles in the lungs, the divalent metal salt undergoes sustained dissolution upon deposition. The period of sustained dissolution, in one aspect, is on the time scale of minutes, for example half of the cation of the divalent metal salt can be released from the particle in greater than about 30 minutes or greater than about 45 minutes. In another aspect, the period of sustained dissolution is over a time scale of hours, for example half of the divalent metal salt can be released in greater than about 1 hour, greater than 1.5 hours, greater than about 2 hours, greater than about 4 hours, greater than about 8 hours, or greater than about 12 hours. In a further aspect, the sustain dissolution is over a period of one day or two days.

Suitable divalent metal cation salts (e.g., calcium salts) can have desired solubility characteristics. In general, highly or moderately soluble divalent metal cation salts (e.g., calcium salts) are preferred. For example, suitable divalent metal cation salts (e.g., calcium salts) that are contained in the respirable dry particles and dry powders can have a solubility in distilled water at room temperature (20-30° C.) and 1 bar of at least about 0.4 g/L, at least about 0.85 g/L, at least about 0.90 g/L, at least about 0.95 g/L, at least about 1.0 g/L, at least about 2.0 g/L, at least about 5.0 g/L, at least about 6.0 g/L, at least about 10.0 g/L, at least about 20 g/L, at least about 50 g/L, at least about 90 g/L, at least about 120 g/L, at least about 500 g/L, at least about 700 g/L or at least about 1000 g/L. Preferably, the divalent metal cation salt has a solubility greater than about 0.90 g/L, greater than about 2.0 g/L, or greater than about 90 g/L.

Dry particles and dry powders of the invention can be prepared, if desired, that contain divalent metal cation salts (e.g., calcium salts) that are not highly soluble in water. As described herein, such dry particles and dry powders can be prepared using a feed stock of a different, more soluble salt, and permitting anion exchange to produce the desired divalent metal cation salts (e.g., calcium salt) prior to or concurrently with spray drying.

Dry powder and particles of the invention may contain a high percentage of active ingredient (e.g., divalent metal cation (e.g., calcium)) in the composition, and be divalent metal cation dense. The dry particles may contain 3% or more, 5% or more, 10% or more, 15% or more, 20% ore more, 25% or more, 30% or more, 35% or more, 40% or more, 50% or more, 60% or more, 70% or more, 75% or more, 80% or more, 85% or more, 90% or more, or 95% or more active ingredient.

It is advantageous when the divalent metal cation salt (e.g., calcium salt) dissociates to provide two or more moles of divalent metal cation (e.g., $Ca^{2+}$) per mole of salt. Such salts can be used to produce respirable dry powders and dry particles that are dense in divalent metal cation (e.g., calcium). For example, one mole of calcium citrate provides three moles of $Ca^{2+}$ upon dissolution. It is also generally preferred that the divalent metal cation salt (e.g., calcium salt) is a salt with a low molecular weight and/or contain low molecular weight anions. Low molecular weight divalent metal cation salts, such as calcium salts that contain calcium ions and low molecular weight anions, are divalent cation dense (e.g., $Ca^{2+}$) dense relative to high molecular salts and salts that contain high molecular weight anions. It is generally preferred that the divalent metal cation salt (e.g., calcium salt) has a molecular weight of less than about 1000 g/mol, less than about 950 g/mol, less than about 900 g/mol, less than about 850 g/mol, less than about 800 g/mol, less than about 750 g/mol, less than about 700 g/mol, less than about 650 g/mol, less than about 600 g/mol, less than about 550 g/mol, less than about 510 g/mol, less than about 500 g/mol, less than about 450 g/mol, less than about 400 g/mol, less than about 350 g/mol, less than about 300 g/mol, less than about 250 g/mol, less than about 200 g/mol, less than about 150 g/mol, less than about 125 g/mol, or less than about 100 g/mol. In addition or alternatively, it is generally preferred that the divalent metal cation (e.g., calcium ion) contributes a substantial portion of the weight to the overall weight of the divalent metal cation salt. It is generally preferred that the divalent metal cation (e.g., calcium ion) contribute at least 10% of the weight of the overall salt, at least 16%, at least 20%, at least 24.5%, at least 26%, at least 31%, at least 35%, or at least 38% of the weight of the overall divalent metal cation salt (e.g., calcium salt).

Alternatively or in addition, the respirable dry particles of the invention can include a suitable divalent metal cation salt (e.g., calcium salt) that provides divalent metal cation ($Ca^{2+}$), wherein the weight ratio of divalent metal cation (e.g., calcium ion) to the overall weight of said salt is between about 0.1 to about 0.5. For example, the weight ratio of divalent methal cation (e.g, calcium ion) to the overall weight of said salt is between about 0.15 to about 0.5, between about 0.18 to about 0.5, between about 0.2 to about 5, between about 0.25 to about 0.5, between about 0.27 to about 0.5, between about 0.3 to about 5, between about 0.35 to about 0.5, between about 0.37 to about 0.5, or between about 0.4 to about 0.5.

Alternatively or in addition, the respirable dry particles of the invention can contain a divalent metal cation salt (e.g., calcium salt) which provides divalent cation (e.g., $Ca^{2+}$) in an amount of at least about 5% by weight of the respirable dry particles. For example, the respirable dry particles of the invention can include a divalent metal cation salt (e.g., calcium salt) which provides divalent cation (e.g., $Ca^{2+}$) in an amount of at least about 7% by weight, at least about 10% by weight, at least about 11% by weight, at least about 12% by weight, at least about 13% by weight, at least about 14% by weight, at least about 15% by weight, at least about 17% by weight, at least about 20% by weight, at least about 25% by weight, at least about 30% by weight, at least about 35% by weight, at least about 40% by weight, at least about 45% by weight, at least about 50% by weight, at least about 55% by weight, at least about 60% by weight, at least about 65% by weight or at least about 70% by weight of the respirable dry particles.

Alternatively or in addition, the respirable dry particles of the invention can contain a divalent metal cation salt which provides divalent metal cation (e.g., $Ca^{2+}$, $Be^{2+}$, $Mg^{2+}$, $Sr^{2+}$, $Ba^{2+}$, $Fe^{2+}$) in an amount of at least about 5% by weight of the respirable dry particles and also contain a monovalent salt (e.g, sodium salt, lithium salt, potassium salt) which provides monovalent cation (e.g, $Na^+$, $Li^+$, $K^+$) in an amount of at least about 3% by weight of the respirable dry particles. For example, the respirable dry particles of the invention can include a divalent metal cation salt (e.g., calcium salt) which provides divalent cation (e.g., $Ca^{2+}$) in an amount of at least about 7% by weight, at least about 10% by weight, at least about 11% by weight, at least about 12% by weight, at least about 13% by weight, at least about 14% by weight, at least about 15% by weight, at least about 17% by weight, at least about 20% by weight, at least about 25% by weight, at least about 30% by weight, at least about 35% by weight, at least about 40% by weight, at least about 45% by weight, at least about 50% by weight, at least about 55% by weight, at least about 60% by weight, at least about 65% by weight or at least about 70% by weight of the respirable dry particles; and further contain a monovalent salt sodium salt which provides monovalent anion ($Na^+$) in an amount of at least about 3%, at least about 4%, at least about 5%, at least about 6%, at least about 7%, at least about 8%, at least about 9%, at least about 10%, at least about 11%, at least about 12%, at least about 14%, at least about 16%, at least about 18%, at least about 20%, at least about 22%, at least about 25%, at least about 27%, at least about 29%, at least about 32%, at least about 35%, at least about 40%, at least about 45%, at least about 50% or at least about 55% by weight of the respirable dry particles.

Alternatively or in addition, the respirable dry particles of the invention contain a divalent metal cation salt and a monovalent cation salt, where the divalent cation, as a component of one or more salts, is present in an amount of at least 5% by weight of dry particle, and the weight ratio of divalent cation to monovalent cation is about 50:1 (i.e., about 50 to about 1) to about 0.1:1 (i.e., about 0.1 to about 1). The weight ratio of divalent metal cation to monovalent cation, is based on the amount of divalent metal cation and monovalent cation that are contained in the divalent metal cation salt and monovalent salts, respectively, that are contained in the dry particle. In particular examples, the weight ratio of divalent metal cation to monovalent cation is about 0.2:1, about 0.3:1, about 0.4:1, about 0.5:1, about 0.6:1, about 0.7:1, about 0.8:1, about 0.86:1, about 0.92:1, about 1:1; about 1.3:1, about 2:1, about 5:1, about 10:1, about 15:1, about 20:1, about 25:1, about 30:1, about 35:1, about 40:1, about 45:1, or about 50:1, about 20:1 to about 0.1:1, about 15:1 to about 0.1:1, about 10:1 to about 0.1:1, or about 5:1 to about 0.1:1.

Alternatively or in addition, the respirable dry particles of the invention can contain a divalent metal cation salt and a monovalent cation salt, in which the divalent metal cation salt and the monovalent cation salt contain chloride, lactate, citrate or sulfate as the counter ion, and the ratio of divalent metal cation (e.g., $Ca^{2+}$, $Be^{2+}$, $Mg^{2+}$, $Sr^{2+}$, $Ba^{2+}$, $Fe^{2+}$) to monovalent cation (e.g, $Na^+$, $Li^+$, $K^+$) mole:mole is about 50:1 (i.e., about 50 to about 1) to about 0.1:1 (i.e., about 0.1 to about 1). The mole ratio of divalent metal cation to monovalent cation, is based on the amount of divalent metal cation and monovalent cation that are contained in the divalent metal cation salt and monovalent cation salt, respectively, that are contained in the dry particle. Preferably, divalent metal cation, as a component of one or more divalent metal cation salts, is present in an amount of at least 5% by weight of the respirable dry particle. In particular examples, divalent metal cation and monovalent cation are present in the respirable dry particles in a mole ratio of about 8.0:1, about 7.5:1, about 7.0:1, about 6.5:1, about 6.0:1, about 5.5:1, about 5.0:1, about 4.5:1, about 4.0:1, about 3.5:1, about 3.0:1, about 2.5:1, about 2.0:1, about 1.5:1, about 1.0:1, about 0.77:1, about 0.65:1, about 0.55:1, about 0.45:1, about 0.35:1, about 0.25:1, or about 0.2:1, about 8.0:1 to about 0.55:1, about 7.0:1 to about 0.55:1, about 6.0:1 to about 0.55:1, about 5.0:1 to about 0.55:1, about 4.0:1 to about 0.55:1, about 3.0:1 to about 0.55:1, about 2.0:1 to about 0.55:1, or about 1.0:1 to about 0.55:1.

Preferred respirable dry particles contain at least one calcium salt selected from the group consisting of calcium lactate, calcium citrate, calcium sulfate, and calcium chloride, and also contain sodium chloride.

Calcium citrate, calcium sulfate and calcium lactate possess sufficient aqueous solubility to allow for their processing into respirable dry powders via spray-drying and to facilitate their dissolution upon deposition in the lungs, yet possess a low enough hygroscopicity to allow for the production of dry powders with high calcium salt loads that are relatively physically stable upon exposure to normal and elevated humidity. Calcium citrate, calcium sulfate and calcium lactate also have a significantly lower heat of solution than calcium chloride, which is beneficial for administration to the respiratory tract, and citrate, sulfate and lactate ions are safe and acceptable for inclusion in pharmaceutical compositions.

Accordingly, in addition to any combination of the features and properties described herein, the respirable dry particles of the invention can contain one or more salts in a total amount of at least about 51% by weight of the respirable dry particles; wherein each of the one or more salts independently consists of a cation selected from the group consisting of calcium and sodium and an anion selected from the group consisting of lactate ($C_3H_5O_3^-$), chloride ($Cl^-$) citrate ($C_6H_5O_7^{3-}$) and sulfate ($SO_4^{2-}$), with the proviso that at least one of the salts is a calcium salt. For example, the respirable dry particles of the invention can include one or more of the salts in a total amount of at least about 55%, at least about 60%, at least about 65%, at least about 70%, at least about 75%, at least about 80%, at least about 85%, at least about 90%, at least about 91%, at least about 92%, or at least about 95% by weight of the respirable dry particles.

Alternatively or in addition, the respirable dry particles of the invention can contain a calcium salt and a sodium salt, where the calcium cation, as a component of one or more calcium salts, is present in an amount of at least 5% by weight of the dry particle, and the weight ratio of calcium ion to sodium ion is about 50:1 (i.e., about 50 to about 1) to about 0.1:1 (i.e., about 0.1 to about 1). The weight ratio of calcium ion to sodium ion, is based on the amount of calcium ion and sodium ion that are contained in the calcium salt and sodium salts, respectively, that are contained in the dry particle. In particular examples, the weight ratio of calcium ion to sodium ion is about 0.2:1, about 0.3:1, about 0.4:1, about 0.5:1, about 0.6:1, about 0.7:1, about 0.8:1, about 0.86:1, about 0.92:1, about 1:1; about 1.3:1, about 2:1, about 5:1, about 10:1, about 15:1, about 20:1, about 25:1, about 30:1, about 35:1, about 40:1, about 45:1, or about 50:1, about 20:1 to about 0.1:1, about 15:1 to about 0.1:1, about 10:1 to about 0.1:1, or about 5:1 to about 0.1:1.

Alternatively or in addition, the respirable dry particles of the invention can contain a calcium salt and a sodium salt, in which the calcium salt and the sodium salt contain chloride, lactate, citrate or sulfate as the counter ion, and the ratio of calcium to sodium mole:mole is about 50:1 (i.e., about 50 to about 1) to about 0.1:1 (i.e., about 0.1 to about 1). The mole ratio of calcium to sodium, is based on the amount of calcium and sodium that are contained in the calcium salt and sodium salt, respectively, that are contained in the dry particle. Preferably, calcium, as a component of one or more calcium salts, is present in an amount of at least 5% by weight of the respirable dry particle. In particular examples, calcium and sodium are present in the respirable dry particles in a mole ratio of about 8.0:1, about 7.5:1, about 7.0:1, about 6.5:1, about 6.0:1, about 5.5:1, about 5.0:1, about 4.5:1, about 4.0:1, about 3.5:1, about 3.0:1, about 2.5:1, about 2.0:1, about 1.5:1, about 1.0:1, about 0.77:1, about 0.65:1, about 0.55:1, about 0.45:1, about 0.35:1, about 0.25:1, or about 0.2:1, about 8.0:1 to about 0.55:1, about 7.0:1 to about 0.55:1, about 6.0:1 to about 0.55:1, about 5.0:1 to about 0.55:1, about 4.0:1 to about 0.55:1, about 3.0:1 to about 0.55:1, about 2.0:1 to about 0.55:1, or about 1.0:1 to about 0.55:1.

If desired, the respirable dry particles described herein can include a physiologically or pharmaceutically acceptable carrier or excipient. For example, a pharmaceutically-acceptable excipient includes any of the standard carbohydrate, sugar alcohol, and amino acid carriers that are known in the art to be useful excipients for inhalation therapy, either alone or in any desired combination. These excipients are generally relatively free-flowing particulates, do not thicken or polymerize upon contact with water, are toxicologically innocuous when inhaled as a dispersed powder and do not significantly interact with the active agent in a manner that adversely affects the desired physiological action of the salts of the invention. Carbohydrate excipients that are useful in this regard include the mono- and polysaccharides. Representative monosaccharides include carbohydrate excipients such as dextrose (anhydrous and the monohydrate; also referred to as glucose and glucose monohydrate), galactose, mannitol, D-mannose, sorbose and the like. Representative disaccharides include lactose, maltose, sucrose, trehalose and the like. Representative trisaccharides include raffinose and the like. Other carbohydrate excipients include maltodextrin and cyclodextrins, such as 2-hydroxypropyl-beta-cyclodextrin can be used as desired. Representative sugar alcohols include mannitol, sorbitol and the like.

Suitable amino acid excipients include any of the naturally occurring amino acids that form a powder under standard pharmaceutical processing techniques and include the non-polar (hydrophobic) amino acids and polar (uncharged, positively charged and negatively charged) amino acids, such amino acids are of pharmaceutical grade and are generally regarded as safe (GRAS) by the U.S. Food and Drug Administration. Representative examples of non-polar amino acids include alanine, isoleucine, leucine, methionine, phenylalanine, proline, tryptophan and valine. Representative examples of polar, uncharged amino acids include cystine, glycine, glutamine, serine, threonine, and tyrosine. Representative examples of polar, positively charged amino acids include arginine, histidine and lysine. Representative examples of negatively charged amino acids include aspartic acid and glutamic acid. These amino acids are generally available from commercial sources that provide pharmaceutical-grade products such as the Aldrich Chemical Company, Inc., Milwaukee, Wis. or Sigma Chemical Company, St. Louis, Mo.

Preferred amino acid excipients, such as the hydrophobic amino acid leucine, can be present in the dry particles of the invention in an amount of about 50% or less by weight of respirable dry particles. For example, the respirable dry particles of the invention can contain the amino acid leucine in an amount of about 5% to about 30% by weight, about 10% to about 20% by weight, about 5% to about 20% by weight, about 45% or less by weight, about 40% or less by weight, about 35% or less by weight, about 30% or less by weight, about 25% or less by weight, about 20% or less by weight, about 18% or less by weight, about 16% or less by weight, about 15% or less by weight, about 14% or less by weight, about 13% or less by weight, about 12% or less by weight, about 11% or less by weight, about 10% or less by weight, about 9% or less by weight, about 8% or less by weight, about 7% or less by weight, about 6% or less by weight, about 5% or less by weight, about 4% or less by weight, about 3% or less by weight, about 2% or less by weight, or about 1% or less by weight.

Preferred carbohydrate excipients, such as maltodextrin and mannitol, can be present in the dry particles of the invention in an amount of about 50% or less by weight of respirable dry particles. For example, the respirable dry particles of the invention can contain maltodextrin in an amount of about 45% or less by weight, about 40% or less by weight, about 35% or less by weight, about 30% or less by weight, about 25% or less by weight, about 20% or less by weight, about 18% or less by weight, about 16% or less by weight, about 15% or less by weight, about 14% or less by weight, about 13% or less by weight, about 12% or less by weight, about 11% or less by weight, about 10% or less by weight, about 9% or less by weight, about 8% or less by weight, about 7% or less by weight, about 6% or less by weight, about 5% or less by weight, about 4% or less by weight, about 3% or less by weight, about 2% or less by weight, or about 1% or less by weight. In some preferred aspects, the dry particles contain an excipient selected from leucine, maltodextrin, mannitol and any combination thereof. In particular embodiments, the excipient is leucine, maltodextrin, or mannitol.

In particular embodiments, the respirable dry particles of the invention can contain (a) a calcium salt selected from calcium lactate, calcium citrate or calcium sulfate in an amount of at least about 30%, at least about 40%, at least about 45% by weight, or at least about 50% by weight of dry particle; and (b) a sodium salt, such as sodium chloride, in an amount of at least about 25% or at least about 30% by weight of dry particle, and have any of the properties or features described herein. If desired, an excipient, such as leucine, maltodextrin, mannitol or any combination thereof, can be present an amount of about 50% or less or about 20% or less by weight of the dry particle. For example, the respirable dry particles of the invention can include (a) a calcium salt in an amount of about 30% to about 65%, about 40% to about 65%, or about 45% to about 65% by weight of dry particle; (b) a sodium salt, such as sodium chloride, in an amount of about 25% to about 60%, or about 30% to about 60% by weight of dry particle; (c) an excipient, such as leucine, maltodextrin, mannitol or any combination thereof, in an amount of about 20% or less by weight of dry particle, or more preferably about 10% or less by weight of dry particle, and (d) have any of the properties or features, such as ¼ bar, 0.5/4 bar, VMGD, MMAD, FPF described herein.

In some aspects, the respirable dry particles comprise a divalent metal ion salt and a monovalent salt and are characterized by the crystalline and amorphous content of the particles. For example, the respirable dry particles can comprise a mixture of amorphous and crystalline content, such as an amorphous divalent metal ion salt-rich phase and a crystalline monovalent salt phase. Respirable dry particles of this type provide several advantages. For example as described herein, the crystalline phase (e.g. crystalline sodium chloride) can contribute to the stability of the dry particle in the dry state and to the dispersibility characteristics, whereas the amorphous phase (e.g., amorphous calcium salt) can facilitate rapid water uptake and dissolution of the particle upon deposition in the respiratory tract. It is particularly advantageous when salts with relatively high aqueous solubilities (such as sodium chloride) that are present in the dry particles are in a crystalline state and when salts with relatively low aqueous solubilities (such as calcium citrate) are present in the dry particles in an amorphous state.

The amorphous phase is also characterized by a high glass transition temperature ($T_g$), such as a $T_g$ of at least 100° C., at least 110° C., 120° C., at least 125° C., at least 130° C., at least 135° C., at least 140° C., between 120° C. and 200° C., between 125° C. and 200° C., between 130° C. and 200° C., between 120° C. and 190° C., between 125° C. and 190° C., between 130° C. and 190° C., between 120° C. and 180° C., between 125° C. and 180° C., or between 130° C. and 180° C.

In some embodiments, the respirable dry particles contain divalent metal cation salt-rich amorphous phase and a monovalent salt crystalline phase and the ratio of amorphous phase to crystalline phase (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5. In other embodiments, the respirable dry particles contain divalent metal cation salt-rich amorphous phase and a monovalent salt crystalline phase and the ratio of amorphous phase to particle by weight (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5. In other embodiments, the respirable dry particles contain divalent metal cation salt-rich amorphous phase and a monovalent salt crystalline phase and the ratio of crystalline phase to particle by weight (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5.

In some embodiments, the respirable dry particles comprises a calcium salt, such as calcium citrate, calcium sulfate, calcium lactate, calcium chloride or any combination thereof, and a sodium salt, such as sodium chloride, sodium citrate, sodium sulfate, sodium lactate, or any combination thereof, wherein the respirable dry particle contains an calcium salt-rich amorphous phase, and a crystalline sodium salt phase. In particular embodiments, the calcium salt-rich amorphous phase includes calcium citrate and at least some calcium chloride, calcium lactate and at least some calcium chloride, or calcium sulfate and at least some calcium chloride. In some embodiments, the respirable dry particles contain calcium salt-rich amorphous phase and a sodium salt crystalline phase and the ratio of amorphous phase to crystalline phase (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5. In other embodiments, the respirable dry particles contain calcium salt-rich amorphous phase and a sodium salt crystalline phase and the ratio of amorphous phase to particle by weight (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5. In other embodiments, the respirable dry particles contain calcium salt-rich amorphous phase and a sodium salt crystalline phase and the ratio of crystalline phase to particle by weight (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5.

Preferrably, the respirable dry particles have a ¼ bar or 0.5/4 bar of 2 or less, as described herein. For example, a ¼ bar or 0.5/4 of 1.9 or less, 1.8 or less, 1.7 or less, 1.6 or less, 1.5 or less, 1.4 or less, 1.3 or less, 1.2 or less, 1.1 or less or about 1.0. Alternatively or in addition, the respirable dry particles have an MMAD of about 5 microns or less. Alternatively or in addition, the respirable dry particles can have a VMGD between about 0.5 microns and about 5 microns, or a VMGD between about 5 microns and about 20 microns. Alternatively or in addition, the respirable dry particles can have a heat of solution that not is greater than about −10 kcal/mol (e.g., between −10 kcal/mol and 10 kcal/mol).

As described herein, the respirable dry particles can further comprise an excipient, such as leucine, maltodextrin or mannitol. The excipient can be crystalline or amorphous or present in a combination of these forms. In some embodiments, the excipient is amorphous or predominately amorphous.

As described herein, RAMAN spectra of respirable dry powders that contained an excipient (i.e., leucine, maltodextrin) did not include peaks assigned to the excipients. This indicates that the excipients were not concentrated at the surface of the particles, and that the excipients are either evenly distributed throughout the particle or not exposed to the surface of the particle. Leucine excipients, in particular, have been reported to improve dispersibility when concentrated on the surface of particles. See, e.g., US2003/0186894. Accordingly, it does not appear that leucine is acting as a dispersion enhancer in this way. Thus, in the respirable dry particles of the invention that contain an excipient (e.g., leucine), the excipient can be distributed within the particle but not on the particle surface, or distributed throughout the particle (e.g., homogenously distributed). For example, in some particular embodiments, a resperable dry particle of the invention does not produce a characteristic peak indicative of the presence of an excipient (e.g., leucine) under RAMAN spectroscopy. In more particular embodiments, a dry respirable powder that contains leucine does not produce a characteristic leucine peak (e.g., at 1340 $cm^{-1}$) under RAMAN spectroscopy.

As described herein, some powders of the invention have poor flow properties. Yet, surprisingly, these powders are highly dispersible. This is surprising because flow properties and dispersibility are both known to be negatively effected by particle agglomeration or aggregation. Thus, it was unexpected that particles that have poor flow characteristics would be highly dispersible.

In addition to any of the features and properties described herein, in any combination, the respirable dry particles can have poor flow properties yet have good dispersibility. For example, the respirable dry particles can have a Hausner Ratio that is greater than 1.35 (e.g, 1.4 or greater, 1.5 or greater, 1.6 or greater, 1.7 or greater, 1.8 or greater, 1.9 or greater, 2.0 or greater) and also have a ¼ bar or 0.5 bar that is 2 or less, 1.9 or less, 1.8 or less, 1.7 or less, 1.6 or less, 1.5 or less, 1.4 or less, 1.3 or less, 1.2 or less, 1.1 or less or about 1.0.

In addition to any of the features and properties described herein, in any combination, the respirable dry particles can have a heat of solution that is not highly exothermic. Preferably, the heat of solution is determined using the ionic liquid of a simulated lung fluid (e.g. as described in Moss, O. R. 1979. Simulants of lung interstitial fluid. Health Phys. 36, 447-448; or in Sun, G. 2001. Oxidative interactions of synthetic lung epithelial lining fluid with metal-containing particulate matter. Am J Physiol Lung Cell Mol Physiol. 281, L807-L815) at pH 7.4 and 37° C. in an isothermal calorimeter. For example, the respirable dry particles can have a heat of solution that is less exothermic than the heat of solution of calcium chloride dihydratedihydrate, e.g., have a heat of solution that is greater than about −10 kcal/mol, greater than about −9 kcal/mol, greater than about −8 kcal/mol, greater than about −7 kcal/mol, greater than about −6 kcal/mol, greater than about −5 kcal/mol, greater than about −4 kcal/mol, greater than about −3 kcal/mol, greater than about −2 kcal/mol, greater than about −1 kcal/mol or about −10 kcal/mol to about 10 kcal/mol.

If desired, the salt formulation can include one or more additional agents, such as mucoactive or mucolytic agents, surfactants, antibiotics, antivirals, antihistamines, cough suppressants, bronchodilators, anti-inflammatory agents, steroids, vaccines, adjuvants, expectorants, macromolecules, therapeutics that are helpful for chronic maintenance of CF.

Examples of suitable mucoactive or mucolytic agents include MUC5AC and MUC5B mucins, DNA-ase, N-acetylcysteine (NAC), cysteine, nacystelyn, dornase alfa, gelsolin, heparin, heparin sulfate, P2Y2 agonists (e.g. UTP, INS365), hypertonic saline, and mannitol.

Suitable surfactants include L-alpha-phosphatidylcholine dipalmitoyl ("DPPC"), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC), fatty alcohols, polyoxyethylene-9-lauryl ether, surface active fatty, acids, sorbitan trioleate (Span 85), glycocholate, surfactin, poloxomers, sorbitan fatty acid esters, tyloxapol, phospholipids, and alkylated sugars.

If desired, the salt formulation can contain an antibiotic. For example, salt formulations for treating bacterial pneumonia or VAT, can further comprise an antibiotic, such as a macrolide (e.g., azithromycin, clarithromycin and erythromycin), a tetracycline (e.g., doxycycline, tigecycline), a fluoroquinolone (e.g., gemifloxacin, levofloxacin, ciprofloxacin and mocifloxacin), a cephalosporin (e.g., ceftriaxone, defotaxime, ceftazidime, cefepime), a penicillin (e.g., amoxicillin, amoxicillin with clavulanate, ampicillin, piperacillin, and ticarcillin) optionally with a β-lactamase inhibitor (e.g., sulbactam, tazobactam and clavulanic acid), such as ampicillin-sulbactam, piperacillin-tazobactam and ticarcillin with clavulanate, an aminoglycoside (e.g., amikacin, arbekacin, gentamicin, kanamycin, neomycin, netilmicin, paromomycin, rhodostreptomycin, streptomycin, tobramycin, and apramycin), a penem or carbapenem (e.g. doripenem, ertapenem, imipenem and meropenem), a monobactam (e.g., aztreonam), an oxazolidinone (e.g., linezolid), vancomycin, glycopeptide antibiotics (e.g. telavancin), tuberculosis-mycobacterium antibiotics and the like.

If desired, the salt formulation can contain an agent for treating infections with mycobacteria, such as *Mycobacterium tuberculosis*. Suitable agents for treating infections with mycobacteria (e.g., *M. tuberculosis*) include an aminoglycoside (e.g. capreomycin, kanamycin, streptomycin), a fluoroquinolone (e.g. ciprofloxacin, levofloxacin, moxifloxacin), isozianid and isozianid analogs (e.g. ethionamide), aminosalicylate, cycloserine, diarylquinoline, ethambutol, pyrazinamide, protionamide, rifampin, and the like.

If desired, the salt formulation can contain a suitable antiviral agent, such as oseltamivir, zanamavir, amantidine, rimantadine, ribavirin, gancyclovir, valgancyclovir, foscavir, Cytogam® (Cytomegalovirus Immune Globulin), pleconaril, rupintrivir, palivizumab, motavizumab, cytarabine, docosanol, denotivir, cidofovir, and acyclovir. The salt formulation can contain a suitable anti-influenza agent, such as zanamivir, oseltamivir, amantadine, or rimantadine.

Suitable antihistamines include clemastine, asalastine, loratadine, fexofenadine and the like.

Suitable cough suppressants include benzonatate, benproperine, clobutinal, diphenhydramine, dextromethorphan, dibunate, fedrilate, glaucine, oxalamine, piperidione, opiods such as codeine and the like.

Suitable brochodilators include short-acting $beta_2$ agonists, long-acting $beta_2$ agonists (LABA), long-acting muscarinic anagonists (LAMA), combinations of LABAs and LAMAs, methylxanthines, and the like. Suitable short-active beta2 agonists include albuterol, epinephrine, pirbuterol, levalbuterol, metaproteronol, maxair, and the like. Suitable LABAs include salmeterol, formoterol and isomers (e.g. arformoterol), clenbuterol, tulobuterol, vilanterol (Revolair™), indacaterol, and the like. Examples of LAMAs include tiotroprium, glycopyrrolate, aclidinium, ipratropium and the like. Examples of combinations of LABAs and LAMAs include indacaterol with glycopyrrolate, indacaterol with tiotropium, and the like. Examples of methylxanthine include theophylline, and the like.

Suitable anti-inflammatory agents include leukotriene inhibitors, PDE4 inhibitors, other anti-inflammatory agents, and the like. Suitable leukotriene inhibitors include montelukast (cystinyl leukotriene inhibitors), masilukast, zafirleukast (leukotriene D4 and E4 receptor inhibitors), zileuton (5-lipoxygenase inhibitors), and the like. Suitable PDE4 inhibitors include cilomilast, roflumilast, and the like. Other anti-inflammatory agents include omalizumab (anti IgE immunoglobulin), IL-13 and IL-13 receptor inhibitors (such as AMG-317, MILR1444A, CAT-354, QAX576, IMA-638, Anrukinzumab, IMA-026, MK-6105, DOM-0910 and the like), IL-4 and IL-4 receptor inhibitors (such as Pitrakinra, AER-003, AIR-645, APG-201, DOM-0919 and the like) IL-1 inhibitors such as canakinumab, CRTh2 receptor antagonists such as AZD1981 (from AstraZeneca), neutrophil elastase inhibitor such as AZD9668 (from AstraZeneca), P38 kinase inhibitor such as losmapimed, and the like.

Suitable steroids include corticosteroids, combinations of corticosteroids and LABAs, combinations of corticosteroids and LAMAs, and the like. Suitable corticosteroids include budesonide, fluticasone, flunisolide, triamcinolone, beclomethasone, mometasone, ciclesonide, dexamethasone, and the like. Combinations of corticosteroids and LABAs include salmeterol with fluticasone, formoterol with budesonide, formoterol with fluticasone, formoterol with mometasone, indacaterol with mometasone, and the like.

Suitable expectorants include guaifenesin, guaiacolculfonate, ammonium chloride, potassium iodide, tyloxapol, antimony pentasulfide and the like.

Suitable vaccines such as nasally inhaled influenza vaccines and the like.

Suitable macromolecules include proteins and large peptides, polysaccharides and oligosaccharides, and DNA and RNA nucleic acid molecules and their analogs having therapeutic, prophylactic or diagnostic activities. Proteins can include antibodies such as monoclonal antibodies. Nucleic acid molecules include genes, antisense molecules such as siRNAs that bind to complementary DNA, RNA, or ribosomes to inhibit transcription or translation.

Selected macromolecule drugs for systemic applications: Calcitonin, Erythropoietin (EPO), Factor IX, Granulocyte Colony Stimulating Factor (G-CSF), Granulocyte Macrophage Colony, Stimulating Factor (GM-CSF), Growth Hormone, Insulin, Interferon Alpha, Interferon Beta, Interferon Gamma, Luteinizing Hormone Releasing Hormone (LHRH), follicle stimulating hormone (FSH), Ciliary Neurotrophic Factor, Growth Hormone Releasing Factor (GRF), Insulin-Like Growth Factor, Insulinotropin, Interleukin-1 Receptor Antagonist, Interleukin-3, Interleukin-4, Interleukin-6, Macrophage Colony Stimulating Factor (M-CSF), Thymosin Alpha 1, IIb/IIIa Inhibitor, Alpha-1 Antitrypsin, Anti-RSV Antibody, palivizumab, motavizumab, and ALN-RSV, Cystic Fibrosis Transmembrane Regulator (CFTR) Gene, Deoxyribonuclease (DNase), Heparin, Bactericidal/Permeability Increasing Protein (BPI), Anti-Cytomegalovirus (CMV) Antibody, Interleukin-1 Receptor Antagonist, and the like.

Selected therapeutics that are helpful for chronic maintenance of CF include antibiotics/macrolide antibiotics, bronchodilators, inhaled LABAs, and agents to promote airway secretion clearance. Suitable examples of antibiotics/macrolide antibiotics include tobramycin, azithromycin, ciprofloxacin, colistin, and the like. Suitable examples of bronchodilators include inhaled short-acting beta$_2$ agonists such as albuterol, and the like. Suitable examples of inhaled LABAs include salmeterol, formoterol, and the like. Suitable examples of agents to promote airway secretion clearance include dornase alfa, hypertonic saline, and the like.

It is generally preferred that the respirable dry particles and dry powders do not contain salts, excipients, or other active ingredients that have a molecular weight of greater than about 1 kilodalton (1000 dalton, Da). For example, the respirable particles of the invention preferably do not contain a protein, a polypeptide, oligopeptides, nucleic acid or an oligonucleotide with a molecular weight of greater than 1 KDa, great than about 900 Da, greater than about 800 Da, greater than about 700 Da, or greater than about 600 Da.

Because the respirable dry powders and respirable dry particles described herein contain salts, they may be hygroscopic. Accordingly it is desirable to store or maintain the respirable dry powders and respirable dry particles under conditions to prevent hydration of the powders. For example, if it is desirable to prevent hydration, the relative humidity of the storage environment should be less than 75%, less than 60%, less than 50%, less than 40%, less than 30%, less than 25%, less than 20%, less than 15%, less than 10%, or less than 5% humidity. The respirable dry powders and respirable dry particles can be packaged (e.g., in sealed capsules, blisters, vials) under these conditions.

The invention also relates to respirable dry powders or respirable dry particles produced by preparing a feedstock solution, emulsion or suspension and spray drying the feedstock according to the methods described herein. The feedstock can be prepared using (a) a calcium salt, such as calcium lactate or calcium chloride, in an amount of at least about 25% by weight (e.g., of total solutes used for preparing the feedstock) and (b) a sodium salt, such as sodium citrate, sodium chloride or sodium sulfate, in an amount of at least about 1% by weight (e.g., of total solutes used for preparing the feedstock). If desired, one or more excipient, such as leucine can be added to the feedstock in an amount of about 74% or less by weight (e.g., of total solutes used for preparing the feedstock). For example, the calcium salt used for preparing the feedstock can be in an amount of at least about 30%, at least about 35%, at least about 40%, at least about 50%, at least about 60% or at least about 70% by weight of total solutes used for preparing the feedstock. The sodium salt used for preparing the feedstock, for example, can be in an amount of at least about 2%, at least about 3%, at least about 4%, at least about 5%, at least about 6%, at least about 7%, at least about 8%, at least about 9%, at least about 10%, at least about 20%, at least about 25%, at least about 30%, at least about 40%, at least about 50%, at least about 55% or at least about 65% by weight of total solutes used for preparing the feedstock. The excipient added to the feedstock, for example, can be in an amount about 50% or less, about 30% or less, about 20% or less, about 10% or less, about 9% or less, about 8% or less, about 7% or less, about 6% or less, about 5% or less, about 4% or less, about 3% or less, about 2% or less, about 1% or less by weight of total solutes used for preparing the feedstock.

In an embodiment, the respirable dry powders or respirable dry particles of the invention can be obtained by (1) preparing a feedstock comprising (a) a dry solute containing in percent by weight of the total dry solute about 10.0% leucine, about 35.1% calcium chloride and about 54.9% sodium citrate and (a) one or more suitable solvents for dissolution of the solute and formation of the feedstock, and (2) spray drying the feedstock. In another embodiment, the respirable dry powders or respirable dry particles of the invention can be obtained by (1) preparing a feedstock comprising (a) a dry solute containing in percent by weight of the total dry solute about 10.0% leucine, about 58.6% calcium lactate and about 31.4% sodium chloride and (a) one or more suitable solvents for dissolution of the solute and formation of the feedstock, and (2) spray drying the feedstock. In another embodiment, the respirable dry powders or respirable dry particles of the invention can be obtained by (1) preparing a feedstock comprising (a) a dry solute containing in percent by weight of the total dry solute about 10.0% leucine, about 39.6% calcium chloride and about 50.44% sodium sulfate and (b) one or more suitable solvents for dissolution of the solute and formation of the feedstock and (2) spray drying the feedstock. In another embodiment, the respirable dry powders or respirable dry particles of the invention can be obtained by (1) preparing a feedstock comprising (a) a dry solute containing in percent by weight of the total dry solute about 10.0% maltodextrin, about 58.6% calcium lactate and about 31.4% sodium chloride and (a) one or more suitable solvents for dissolution of the solute and formation of the feedstock, and (2) spray drying the feedstock. As described herein, various methods (e.g., static mixing, bulk mixing) can be used for mixing the solutes and solvents to prepare feedstocks, which are known in the art. If desired, other suitable methods of mixing may be used. For example, additional components that cause or facilitate the mixing can be included in the feedstock. For example, carbon dioxide produces fizzing or effervescence and thus can serve to promote physical mixing of the solute and solvents. Various salts of carbonate or bicarbonate can promote the same effect that carbon dioxide produces and, therefore, can be used in preparation of the feedstocks of the invention.

In preferred embodiments, the respirable dry powders or respirable dry particles of the invention possess aerosol characteristics that permit effective delivery of the respirable dry particles to the respiratory system without the use of propellants.

In an embodiment, the respirable dry powders or respirable dry particles of the invention can be produced through an ion exchange reaction. In certain embodiments of the invention, two saturated or sub-saturated solutions are fed into a static mixer in order to obtain a saturated or supersaturated solution post-static mixing. Preferably, the post-mixed solution is supersaturated. The two solutions may be aqueous or organic, but are preferably substantially aqueous. The post-static mixing solution is then fed into the atomizing unit of a spray dryer. In a preferable embodiment, the post-static mixing solution is immediately fed into the atomizer unit. Some examples of an atomizer unit include a two-fluid nozzle, a rotary atomizer, or a pressure nozzle. Preferably, the atomizer unit is a two-fluid nozzle. In one embodiment, the two-fluid nozzle is an internally mixing nozzle, meaning that the gas impinges on the liquid feed before exiting to most outward orifice. In another embodiment, the two-fluid nozzle is an externally mixing nozzle, meaning that the gas impinges on the liquid feed after exiting the most outward orifice.

The dry particles of the invention can be blended with an active ingredient or co-formulated with an active ingredient to maintain characteristic high dispersibility of the dry particles and dry powders of the invention.

In one aspect, salts of divalent cations (e.g., calcium, magnesium) can be co-formulated with a non-calcium active agent, to make small, highly dispersible powders or large, porous particles. Optionally, these particles may include a monovalent cationic salt (e.g., sodium, potassium), and also optionally an excipient (e.g., leucine, maltodextrin, mannitol, lactose). The components can be mixed (e.g., mixed as one solution, static mixed as two solutions) together in a single particle before spray drying.

In another aspect, the dry particles of the invention are large, porous, and are dispersible. The size of the dry particles can be expressed in a variety of ways. The particles may have VMGD between 5 to 30 μm, or between 5 and 20 μm, with a tap density of less than 0.5 g/cc, preferably less than 0.4 g/cc.

Methods for Preparing Dry Powders and Dry Particles

The respirable dry particles and dry powders can be prepared using any suitable method. Many suitable methods for preparing respirable dry powders and particles are conventional in the art, and include single and double emulsion solvent evaporation, spray drying, milling (e.g., jet milling), blending, solvent extraction, solvent evaporation, phase separation, simple and complex coacervation, interfacial polymerization, suitable methods that involve the use of supercritical carbon dioxide ($CO_2$), and other suitable methods. Respirable dry particles can be made using methods for making microspheres or microcapsules known in the art. These methods can be employed under conditions that result in the formation of respirable dry particles with desired aerodynamic properties (e.g., aerodynamic diameter and geometric diameter). If desired, respirable dry particles with desired properties, such as size and density, can be selected using suitable methods, such as sieving.

The respirable dry particles are preferably spray dried. Suitable spray-drying techniques are described, for example, by K. Masters in "Spray Drying Handbook", John Wiley & Sons, New York (1984). Generally, during spray-drying, heat from a hot gas such as heated air or nitrogen is used to evaporate a solvent from droplets formed by atomizing a continuous liquid feed. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. For example, a rotary atomizer having a 4- or 24-vaned wheel may be used. Examples of suitable spray dryers that can be outfitted with either a rotary atomizer or a nozzle, include, Mobile Minor Spray Dryer or the Model PSD-1, both manufactured by Niro, Inc. (Denmark). Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 100° C. to about 300° C., and preferably is about 220° C. to about 285° C. The spray dryer outlet temperature will vary depending upon such factors as the feed temperature and the properties of the materials being dried. Generally, the outlet temperature is about 50° C. to about 150° C., preferably about 90° C. to about 120° C., or about 98° C. to about 108° C. If desired, the respirable dry particles that are produced can be fractionated by volumetric size, for example, using a sieve, or fractioned by aerodynamic size, for example, using a cyclone, and/or further separated according to density using techniques known to those of skill in the art.

To prepare the respirable dry particles of the invention, generally, a solution, emulsions or suspension that contains the desired components of the dry powder (i.e., a feed stock) is prepared and spray dried under suitable conditions. Preferably, the dissolved or suspended solids concentration in the feed stock is at least about 1 g/L, at least about 2 g/L, at least about 5 g/L, at least about 10 g/L, at least about 15 g/L, at least about 20 g/L, at least about 30 g/L, at least about 40 g/L, at least about 50 g/L, at least about 60 g/L, at least about 70 g/L, at least about 80 g/L, at least about 90 g/L, or at least about 100 g/L. The feed stock can be provided by preparing a single solution or suspension by dissolving or suspending suitable components (e.g., salts, excipients, other active ingredients) in a suitable solvent. The solvent, emulsion or suspension can be prepared using any suitable methods, such as bulk mixing of dry and/or liquid components or static mixing of liquid components to form a combination. For example, a hydrophillic component (e.g., an aqueous solution) and a hydrophobic component (e.g., an organic solution) can be combined using a static mixer to form a combination. The combination can then be atomized to produce droplets, which are dried to form respirable dry particles. Preferably, the atomizing step is performed immediately after the components are combined in the static mixer.

In one example, respirable dry particles that contain calcium citrate, sodium chloride and leucine are prepared by spray drying. A first phase is prepared that comprises an aqueous solution of sodium citrate and leucine. A second phase is prepared that comprises calcium chloride in an appropriate solvent. One or both solutions may be separately heated as needed to assure solubility of their components. The first and second phases are then combined in a static mixer to form a combination. The combination is spray dried to form respirable dry particles.

The feed stock, or components of the feed stock, can be prepared using any suitable solvent, such as an organic solvent, an aqueous solvent or mixtures thereof. Suitable organic solvents that can be employed include but are not limited to alcohols such as, for example, ethanol, methanol, propanol, isopropanol, butanols, and others. Other organic solvents include but are not limited to perfluorocarbons, dichloromethane, chloroform, ether, ethyl acetate, methyl tert-butyl ether and others. Co-solvents that can be employed include an aqueous solvent and an organic solvent, such as, but not limited to, the organic solvents as described above. Aqueous solvents include water and buffered solutions.

The feed stock or components of the feed stock can have any desired pH, viscosity or other properties. If desired, a pH buffer can be added to the solvent or co-solvent or to the formed mixture. Generally, the pH of the mixture ranges from about 3 to about 8.

Respirable dry particles and dry powders can be fabricated and then separated, for example, by filtration or centrifugation by means of a cyclone, to provide a particle sample with a preselected size distribution. For example, greater than about 30%, greater than about 40%, greater than about 50%, greater than about 60%, greater than about 70%, greater than about 80%, or greater than about 90% of the respirable dry particles in a sample can have a diameter within a selected range. The selected range within which a certain percentage of the respirable dry particles fall can be, for example, any of the size ranges described herein, such as between about 0.1 to about 3 microns VMGD.

The diameter of the respirable dry particles, for example, their VMGD, can be measured using an electrical zone sensing instrument such as a Multisizer lie, (Coulter Electronic, Luton, Beds, England), or a laser diffraction instrument such as a HELOS system (Sympatec, Princeton, N.J.). Other instruments for measuring particle geometric diameter are well known in the art. The diameter of respirable dry particles in a sample will range depending upon factors such as particle composition and methods of synthesis. The distribution of size of respirable dry particles in a sample can be selected to permit optimal deposition within targeted sites within the respiratory system.

Experimentally, aerodynamic diameter can be determined using time of flight (TOF) measurements. For example, an instrument such as the Model 3225 Aerosizer DSP Particle Size Analyzer (Amherst Process Instrument, Inc., Amherst, Mass.) can be used to measure aerodynamic diameter. The Aerosizer measures the time taken for individual respirable dry particles to pass between two fixed laser beams.

Aerodynamic diameter also can be experimentally determined directly using conventional gravitational settling methods, in which the time required for a sample of respirable dry particles to settle a certain distance is measured. Indirect methods for measuring the mass median aerodynamic diameter include the Andersen Cascade Impactor and the multistage liquid impinger (MSLI) methods. The methods and instruments for measuring particle aerodynamic diameter are well known in the art.

Tap density is a measure of the envelope mass density characterizing a particle. The envelope mass density of a particle of a statistically isotropic shape is defined as the mass of the particle divided by the minimum sphere envelope volume within which it can be enclosed. Features which can contribute to low tap density include irregular surface texture and porous structure. Tap density can be measured by using instruments known to those skilled in the art such as the Dual Platform Microprocessor Controlled Tap Density Tester (Vankel, N.C.), a GeoPyc™ instrument (Micrometrics Instrument Corp., Norcross, Ga.), or SOTAX Tap Density Tester model TD2 (SOTAX Corp., Horsham, Pa.). Tap density can be determined using the method of USP Bulk Density and Tapped Density, United States Pharmacopia convention, Rockville, Md., $10^{th}$ Supplement, 4950-4951, 1999.

Fine particle fraction can be used as one way to characterize the aerosol performance of a dispersed powder. Fine particle fraction describes the size distribution of airborne respirable dry particles. Gravimetric analysis, using a Cascade impactor, is one method of measuring the size distribution, or fine particle fraction, of airborne respirable dry particles. The Andersen Cascade Impactor (ACI) is an eight-stage impactor that can separate aerosols into nine distinct fractions based on aerodynamic size. The size cutoffs of each stage are dependent upon the flow rate at which the ACI is operated. The ACI is made up of multiple stages consisting of a series of nozzles (i.e., a jet plate) and an impaction surface (i.e., an impaction disc). At each stage an aerosol stream passes through the nozzles and impinges upon the surface. Respirable dry particles in the aerosol stream with a large enough inertia will impact upon the plate. Smaller respirable dry particles that do not have enough inertia to impact on the plate will remain in the aerosol stream and be carried to the next stage. Each successive stage of the ACI has a higher aerosol velocity in the nozzles so that smaller respirable dry particles can be collected at each successive stage.

If desired, a two-stage collapsed ACI can also be used to measure fine particle fraction. The two-stage collapsed ACI consists of only the top two stages of the eight-stage ACI and allows for the collection of two separate powder fractions. Specifically, a two-stage collapsed ACI is calibrated so that the fraction of powder that is collected on stage one is composed of respirable dry particles that have an aerodynamic diameter of less than 5.6 microns and greater than 3.4 microns. The fraction of powder passing stage one and depositing on a collection filter is thus composed of respirable dry particles having an aerodynamic diameter of less than 3.4 microns. The airflow at such a calibration is approximately 60 L/min.

The FPF(<5.6) has been demonstrated to correlate to the fraction of the powder that is able to make it into the lung of the patient, while the FPF(<3.4) has been demonstrated to correlate to the fraction of the powder that reaches the deep lung of a patient. These correlations provide a quantitative indicator that can be used for particle optimization.

An ACI can be used to approximate the emitted dose, which herein is called gravimetric recovered dose and analytical recovered dose. "Gravimetric recovered dose" is defined as the ratio of the powder weighed on all stage filters of the ACI to the nominal dose. "Analytical recovered dose" is defined as the ratio of the powder recovered from rinsing all stages, all stage filters, and the induction port of the ACI to the nominal dose. The FPF_TD(<5.0) is the ratio of the interpolated amount of powder depositing below 5.0 μm on the ACI to the nominal dose. The FPF_RD(<5.0) is the ratio of the interpolated amount of powder depositing below 5.0 μm on the ACI to either the gravimetric recovered dose or the analytical recovered dose.

Another way to approximate emitted dose is to determine how much powder leaves its container, e.g. capture or blister, upon actuation of a dry powder inhaler (DPI). This takes into account the percentage leaving the capsule, but does not take into account any powder depositing on the DPI. The emitted dose is the ratio of the weight of the capsule with the dose before inhaler actuation to the weight of the capsule after inhaler actuation. This measurement can also be called the capsule emitted powder mass (CEPM)

A Multi-Stage Liquid Impinger (MSLI) is another device that can be used to measure fine particle fraction. The Multi-stage liquid Impinger operates on the same principles as the ACI, although instead of eight stages, MSLI has five. Additionally, each MSLI stage consists of an ethanol-wetted glass frit instead of a solid plate. The wetted stage is used to prevent particle bounce and re-entrainment, which can occur when using the ACI.

The invention also relates to a method for producing a respirable dry powder comprising respirable dry particles that contain calcium citrate or calcium sulfate. The method comprises a) providing a first liquid feed stock comprising an aqueous solution of calcium chloride, and a second liquid feed stock comprising an aqueous solution of sodium sulfate or sodium citrate; b) mixing the first liquid feed stock and the second liquid feed stock to produce a mixture in which an anion exchange reaction occurs to produce a saturated or supersaturated solution comprising calcium sulfate and sodium chloride, or calcium citrate and sodium chloride; and c) spray drying the saturated or supersaturated solution produced in b) to produce respirable dry particles. The first liquid feed stock and the second liquid feed stock can be batch mixed or preferably, static mixed. In some embodiments, the resulting mixture is spray dried, and atomized within 60 minutes, within 30 minutes, within 15 minutes, within 10 minutes, within 5 minutes, within 4 minutes, within 3 minutes, within 2 minutes, within 1 minute, within 45 seconds, within 30 seconds, within 15 seconds, within 5 seconds of mixing, preferably static mixing.

The invention also relates to a respirable dry powder or respirable dry particles produced using any of the methods described herein.

The respirable dry particles of the invention can also be characterized by the chemical stability of the salts or the excipients that the respirable dry particles comprise. The chemical stability of the constituent salts can affect important characteristics of the respirable particles including shelf-life, proper storage conditions, acceptable environments for administration, biological compatibility, and effectiveness of the salts. Chemical stability can be assessed using techniques well known in the art. One example of a technique that can be used to assess chemical stability is reverse phase high performance liquid chromatography (RP-HPLC). Respirable dry particles of the invention include salts that are generally stable over a long period time.

If desired, the respirable dry particles and dry powders described herein can be further processed to increase stability. An important characteristic of pharmaceutical dry powders is whether they are stable at different temperature and humidity conditions. Unstable powders will absorb moisture from the environment and agglomerate, thus altering particle size distribution of the powder.

Excipients, such as maltodextrin, may be used to create more stable particles and powders. The maltodextrin may act as an amporphous phase stabilizer and inhibit the components from converting from an amorphous to crystalline state. Alternatively, a post-processing step to help the particles through the crystallization process in a controlled way (e.g., on the baghouse at elevated humidity) can be employed with the resultant powder potentially being further processed to restore their dispersibility if agglomerates formed during the crystallization process, such as by passing the particles through a cyclone to break apart the agglomerates. Another possible approach is to optimize around process conditions that lead to manufacturing particles that are more crystalline and therefore more stable. Another approach is to use different excipients, or different levels of current excipients to attempt to manufacture more stable forms of the salts.

The respirable dry particles and dry powders described herein are suitable for inhalation therapies. The respirable dry particles may be fabricated with the appropriate material, surface roughness, diameter and tap density for localized delivery to selected regions of the respiratory system such as the deep lung or upper or central airways. For example, higher density or larger respirable dry particles may be used for upper airway delivery, or a mixture of varying size respirable dry particles in a sample, provided with the same or a different formulation, may be administered to target different regions of the lung in one administration.

In order to relate the dispersion of powder at different inhalation flow rates, volumes, and from inhalers of different resistances, the energy required to perform the inhalation maneuver can be calculated. Inhalation energy can be calculated from the equation $E=R^2Q^2V$ where E is the inhalation energy in Joules, R is the inhaler resistance in $kPa^{1/2}/LPM$, Q is the steady flow rate in L/min and V is the inhaled air volume in L.

Healthy adult populations are predicted to be able to achieve inhalation energies ranging from 2.9 to 22 Joules by using values of peak inspiratory flow rate (PIFR) measured by Clarke et al. (Journal of Aerosol Med, 6(2), p. 99-110, 1993) for the flow rate Q from two inhaler resistances of 0.02 and 0.055 kPa½/LPM, with a inhalation volume of 2 L based on both FDA guidance documents for dry powder inhalers and on the work of Tiddens et al. (Journal of Aerosol Med, 19, (4), p. 456-465, 2006) who found adults averaging 2.2 L inhaled volume through a variety of DPIs.

Mild, moderate and severe adult COPD patients are predicted to be able to achieve inhalation energies of 5.1 to 21 Joules, 5.2 to 19 Joules, and 2.3 to 18 Joules respectively. This is again based on using measured PIFR values for the flow rate Q in the equation for inhalation energy. The PIFR achievable for each group is a function of the inhaler resistance that is being inhaled through. The work of Broeders et al. (Eur Respir J, 18, p. 780-783, 2001) was used to predict maximum and minimum achievable PIFR through 2 dry powder inhalers of resistances 0.021 and 0.032 kPa½/LPM for each.

Similarly, adult asthmatic patients are predicted to be able to achieve inhalation energies of 7.4 to 21 Joules based on the same assumptions as the COPD population and PIFR data from Broeders et al.

Healthy adults, adult COPD patients, and asthmatic adults, for example, should be capable of providing sufficient inhalation energy to empty and disperse the dry powder formulations of the invention. For example, a 25 mg dose of Formulation III was found to require only 0.16 Joules to empty 80% of the fill weight in a single inhalation well deagglomerated as illustrated by a Dv50 within 1 micrometer of that at much higher inhalation energies. All the adult patient populations listed above were calculated to be able to achieve greater than 2 Joules, more than an order of magnitude more inhalational energy than required.

An advantage of the invention is the production of powders that disperse well across a wide range of flowrates and are relatively flowrate independent. The dry particles and powders of the invention enable the use of a simple, passive DPI for a wide patient population.

Methods

The respirable dry powders and respirable dry particles of the present invention are for administration to the respiratory tract. The dry powders and dry particles of the invention can be administered to a subject in need thereof for the treatment of respiratory (e.g., pulmonary) diseases, such as asthma, airway hyperresponsiveness, seasonal allergic allergy, bronchiectasis, chronic bronchitis, emphysema, chronic obstructive pulmonary disease, cystic fibrosis and the like, and for the treatment and/or prevention of acute exacerbations of these chronic diseases, such as exacerbations caused by viral infections (e.g., influenza virus, parainfluenza virus, respiratory syncytial virus, rhinovirus, adenovirus, metapneumovirus, coxsackie virus, echo virus, corona virus, herpes virus, cytomegalovirus, and the like), bacterial infections (e.g., *Streptococcus pneumoniae*, which is commonly referred to as pneumococcus, *Staphylococcus aureus, Burkholderis* ssp., *Streptococcus agalactiae, Haemophilus influenzae, Haemophilus parainfluenzae Klebsiella pneumoniae, Escherichia coli, Pseudomonas aeruginosa, Moraxella catarrhalis, Chlamydophila pneumoniae, Mycoplasma pneumoniae, Legionella pneumophila, Serratia marcescens, Mycobacterium tuberculosis, Bordetella pertussis*, and the like), fungal infections (e.g., *Histoplasma capsulatum, Cryptococcus neoformans, Pneumocystis jiroveci, Coccidioides immitis*, and the like) or parasitic infections (e.g., *Toxoplasma gondii, Strongyloides stercoralis*, and the like), or environmental allergens and irritants (e.g., aeroallergens, including pollen and cat dander, airborne particulates, and the like).

The dry powders and dry particles of the invention can be administered to a subject in need thereof for the treatment and/or prevention and/or reducing contagion of infectious diseases of the respiratory tract, such as pneumonia (including community-acquired pneumonia, nosocomial pneumonia (hospital-acquired pneumonia, HAP; health-care associated pneumonia, HCAP), ventilator-associated pneumonia (VAP)), ventilator-associated tracheobronchitis (VAT), bronchitis, croup (e.g., postintubation croup, and infectious croup), tuberculosis, influenza, common cold, and viral infections (e.g., influenza virus, parainfluenza virus, respiratory syncytial virus, rhinovirus, adenovirus, metapneumovirus, coxsackie virus, echo virus, corona virus, herpes virus, cytomegalovirus, and the like), bacterial infections (e.g., *Streptococcus pneumoniae*, which is commonly referred to as pneumococcus, *Staphylococcus aureus, Streptococcus agalactiae, Haemophilus influenzae, Haemophilus parainfluenzae Klebsiella pneumoniae, Escherichia coli, Pseudomonas aeruginosa, Moraxella catarrhalis, Chlamydophila pneumoniae, Mycoplasma pneumoniae, Legionella pneumophila, Serratia marcescens, Mycobacterium tuberculosis, Bordetella pertussis*, and the like), fungal infections (e.g., *Histoplasma capsulatum, Cryptococcus neoformans, Pneumocystis jiroveci, Coccidioides immitis*, and the like) or parasitic infections (e.g., *Toxoplasma gondii, Strongyloides stercoralis*, and the like), or environmental allergens and irritants (e.g., aeroallergens, airborne particulates, and the like).

The respirable dry particles and dry powder can be administered to alter the biophysical and/or biological properties of the mucosal lining of the respiratory tract (e.g, the airway lining fluid) and underlying tissue (e.g., respiratory tract epithelium). These properties include, for example, gelation at the mucus surface, surface tension of the mucosal lining, surface elasticity and/or viscosity of the mucosal lining, bulk elasticity and/or viscosity of the mucosal lining. Without wishing to be bound by a particular theory, it is believed that the benefits produced by the respirable dry particles or dry powder and the methods described herein (e.g., therapeutic and prophylactic benefits), result from an increase in the amount of calcium cation ($Ca^{2+}$ provided by the calcium salts in the respirable dry particles or dry powder) in the respiratory tract (e.g., lung mucus or airway lining fluid) after administration of the respirable dry particles or dry powder.

The respirable dry powders and dry particles can be administered to increase the rate of mucociliary clearance. Clearance of microbes and inhaled particles is an important function of airways to prevent respiratory infection and exposure to or systemic absorption of potentially noxious agents. This is performed as an integrated function by epithelial, mucus-secreting, and immunologic response cells present at the airway surface. It prominently includes the cilia at the epithelial cell airway surface, whose function is to beat synchronously to transport the overlying liquid mucus blanket proximally (toward the mouth), where it exits the airway and is swallowed or expectorated.

The respirable dry powders and dry particles can be administered to assist in all of these functions. By increasing surface viscoelasticity, the respirable dry powders and dry particles retain microbes and particulates at the surface of the airway mucus blanket, where they do not gain systemic exposure to the host. Hypertonic dry powders and dry particles induce water/liquid transport out of the airway epithelial cells, making the peri-ciliary liquid layer less viscous and rendering ciliary beating more effective in moving and clearing the overlying mucus blanket. Dry particles and dry powders that contain calcium salts as the pharmacologically active agent, also cause an increase in both ciliary beat frequency and the force or vigor of ciliary contractions, with resultant increase in clearance velocity of the overlying mucus stream.

Mucociliary clearance is measured by a well-established technique that measures the function and speed of clearance quantitatively using safe, inhaled radioisotope preparation (e.g., Technitium ($^{99m}Tc$)) in solution. The radioisotope is measured quantitatively by external scintigraphy. Serial measurements over several hours allow for the assessment of velocity of clearance and effect of a drug vs. baseline/control value.

In some aspects, the invention is a method for treating a pulmonary diseases, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of respirable dry particles or dry powder, as described herein.

In other aspects, the invention is a method for the treatment or prevention of acute exacerbations of a chronic pulmonary disease, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of respirable dry particles or dry powder, as described herein.

In other aspects, the invention is a method for treating, preventing and/or reducing contagion of an infectious disease of the respiratory tract, comprising administering to the respiratory tract of a subject in need thereof an effective amount of respirable dry particles or dry powder, as described herein.

The respirable dry particles and dry powders can be administered to the respiratory tract of a subject in need thereof using any suitable method, such as instillation techniques, and/or an inhalation device, such as a dry powder inhaler (DPI) or metered dose inhaler (MDI). A number of DPIs are available, such as, the inhalers disclosed is U.S. Pat. Nos. 4,995,385 and 4,069,819, Spinhaler® (Fisons, Loughborough, U.K.), Rotahalers®, Diskhaler® and Diskus® (GlaxoSmithKline, Research Triangle Technology Park, N.C.), FlowCapss® (Hovione, Loures, Portugal), Inhalators® (Boehringer-Ingelheim, Germany), Aerolizer® (Novartis, Switzerland), and others known to those skilled in the art.

Generally, inhalation devices (e.g., DPIs) are able to deliver a maximum amount of dry powder or dry particles in a single inhalation, which is related to the capacity of the blisters, capsules (e.g. size 000, 00, 0E, 0, 1, 2, 3, and 4, with respective volumetric capacities of 1.37 ml, 950 µl, 770 µl, 680 µl, 480 µl, 360 µl, 270 µl, and 200 µl) or other means that contain the dry particles or dry powders within the inhaler. Accordingly, delivery of a desired dose or effective amount may require two or more inhalations. Preferably, each dose that is administered to a subject in need thereof contains an effective amount of respirable dry particles or dry powder and is administered using no more than about 4 inhalations. For example, each dose of respirable dry particles or dry powder can be administered in a single inhalation or 2, 3, or 4 inhalations. The respirable dry particles and dry powders, are preferably administered in a single, breath-activated step using a breath-activated DPI. When this type of device is used, the energy of the subject's inhalation both disperses the respirable dry particles and draws them into the respiratory tract.

The respirable dry particles or dry powders can be delivered by inhalation to a desired area within the respiratory tract, as desired. It is well-known that particles with an aerodynamic diameter of about 1 micron to about 3 microns, can be delivered to the deep lung. Larger aerodynamic diameters, for example, from about 3 microns to about 5 microns can be delivered to the central and upper airways.

It is believed that when some dry powders that contain divalent metal salts as active ingredients are administered, there is a possibility that at least some of the respirable dry powder will deposit in the oral cavity and produce an unpleasant "salty mouth" sensation. It is envisioned that this sensation could lead patients to not comply with therapeutic instructions or to discontinue therapy. An advantage of the respirable dry powders of this invention is that they are small and highly dispersible, and therefore, deposition in the oral cavity is reduced and the occurrence of an unpleasant salty mouth sensation is reduced or prevented.

For dry powder inhalers, oral cavity deposition is dominated by inertial impaction and so characterized by the aerosol's Stokes number (DeHaan et al. Journal of Aerosol Science, 35 (3), 309-331, 2003). For equivalent inhaler geometry, breathing pattern and oral cavity geometry, the Stokes number, and so the oral cavity deposition, is primarily affected by the aerodynamic size of the inhaled powder. Hence, factors which contribute to oral deposition of a powder include the size distribution of the individual particles and the dispersibility of the powder. If the MMAD of the individual particles is too large, e.g. above 5 um, then an increasing percentage of powder will deposit in the oral cavity. Likewise, if a powder has poor dispersibility, it is an indication that the particles will leave the dry powder inhaler and enter the oral cavity as agglomerates. Agglomerated powder will perform aerodynamically like an individual particle as large as the agglomerate, therefore even if the individual particles are small (e.g., MMAD of 5 microns or less), the size distribution of the inhaled powder may have an MMAD of greater than 5 µm, leading to enhanced oral cavity deposition.

Therefore, it is desirable to have a powder in which the particles are small (e.g., MMAD of 5 microns or less, e.g. between 1 to 5 microns), and are highly dispersible (e.g. ¼ bar or alternatively, 0.5/4 bar of 2.0, and preferably less than 1.5). More preferably, the respirable dry powder is comprised of respirable dry particles with an MMAD between 1 to 4 microns or 1 to 3 microns, and have a ¼ bar less than 1.4, or less than 1.3, and more preferably less than 1.2.

The absolute geometric diameter of the particles measured at 1 bar using the HELOS system is not critical provided that the particle's envelope density is sufficient such that the MMAD is in one of the ranges listed above, wherein MMAD is VMGD times the square root of the envelope density (MMAD=VMGD*sqrt(envelope density)). If it is desired to deliver a high unit dose of salt using a fixed volume dosing container, then, particles of higher envelop density are desired. High envelope density allows for more mass of powder to be contained within the fixed volume dosing container. Preferable envelope densities are greater than 0.1 g/cc, greater than 0.25 g/cc, greater than 0.4 g/cc, greater than 0.5 g/cc, and greater than 0.6 g/cc.

The respirable dry powders and particles of the invention can be employed in compositions suitable for drug delivery via the respiratory system. For example, such compositions can include blends of the respirable dry particles of the invention and one or more other dry particles or powders, such as dry particles or powders that contain another active agent, or that consist of or consist essentially of one or more pharmaceutically acceptable excipients.

Respirable dry powders and dry particles suitable for use in the methods of the invention can travel through the upper airways (i.e., the oropharynx and larynx), the lower airways, which include the trachea followed by bifurcations into the bronchi and bronchioli, and through the terminal bronchioli which in turn divide into respiratory bronchioli leading then to the ultimate respiratory zone, the alveoli or the deep lung. In one embodiment of the invention, most of the mass of respirable dry powders or particles deposit in the deep lung. In another embodiment of the invention, delivery is primarily to the central airways. In another embodiment, delivery is to the upper airways.

The respirable dry particles or dry powders of the invention can be delivered by inhalation at various parts of the breathing cycle (e.g., laminar flow at mid-breath). An advantage of the high dispersibility of the dry powders and dry particles of the invention is the ability to target deposition in the respiratory tract. For example, breath controlled delivery of nebulized solutions is a recent development in liquid aerosol delivery (Dalby et al. in Inhalation Aerosols, edited by Hickey 2007, p. 437). In this case, nebulized droplets are released only during certain portions of the breathing cycle. For deep lung delivery, droplets are released in the beginning of the inhalation cycle, while for central airway deposition, they they are released later in the inhalation.

The highly dispersible powders of this invention provide advantages for targeting the timing of drug delivery in the breathing cycle and also location in the human lung. Because the respirable dry powders of the invention can be dispersed rapidly, such as within a fraction of a typical inhalation maneuver, the timing of the powder dispersal can be controlled to deliver an aerosol at specific times within the inhalation.

With a highly dispersible powder, the complete dose of aerosol can be dispersed at the beginning portion of the inhalation. While the patient's inhalation flow rate ramps up to the peak inspiratory flow rate, a highly dispersible powder will begin to disperse already at the beginning of the ramp up and could completely disperse a dose in the first portion of the inhalation. Since the air that is inhaled at the beginning of the inhalation will ventilate deepest into the lungs, dispersing the most aerosol into the first part of the inhalation is preferable for deep lung deposition. Similarly, for central deposition, dispersing the aerosol at a high concentration into the air which will ventilate the central airways can be achieved by rapid dispersion of the dose near the mid to end of the inhalation. This can be accomplished by a number of mechanical and other means such as a switch operated by time, pressure or flow rate which diverts the patient's inhaled air to the powder to be dispersed only after the switch conditions are met.

Aerosol dosage, formulations and delivery systems may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6: 273-313 (1990); and in Moren, "Aerosol Dosage Forms and Formulations," in Aerosols in Medicine, Principles, Diagnosis and Therapy, Moren, et al., Eds., Esevier, Amsterdam (1985).

As described herein, it is believed that the therapeutic and prophylactic effects of the respirable dry particles and dry powders are the result of an increased amount of calcium in the respiratory tract (e.g., lung) following administration of respirable dry particles and dry powders. Accordingly, since the amount of calcium provided can vary depending upon the particular salt selected, dosing can be based on the desired amount of calcium to be delivered to the lung. For example, one mole of calcium chloride ($CaCl_2$) dissociates to provide one mole of $Ca^{2+}$, but one mole of calcium citrate can provide three moles of $Ca^{2+}$.

Generally, an effective amount of a pharmaceutical formulation will deliver a dose of about 0.001 mg $Ca^{+2}$/kg body weight/dose to about 2 mg $Ca^{+2}$/kg body weight/dose, about 0.002 mg $Ca^{+2}$/kg body weight/dose to about 2 mg $Ca^{+2}$/kg body weight/dose, about 0.005 mg $Ca^{+2}$/kg body weight/dose to about 2 mg $Ca^{+2}$/kg body weight/dose, about 0.01 mg $Ca^{+2}$/kg body weight/dose to about 2 mg $Ca^{+2}$/kg body weight/dose, about 0.01 mg $Ca^{+2}$/kg body weight/dose to about 60 mg $Ca^{+2}$/kg body weight/dose, about 0.01 mg $Ca^{+2}$/kg body weight/dose to about 50 mg $Ca^{+2}$/kg body weight/dose, about 0.01 mg $Ca^{+2}$/kg body weight/dose to about 40 mg $Ca^{+2}$/kg body weight/dose, about 0.01 mg $Ca^{+2}$/kg body weight/dose to about 30 mg $Ca^{+2}$/kg body weight/dose, about 0.01 mg $Ca^{+2}$/kg body weight/dose to about 20 mg $Ca^{+2}$/kg body weight/dose, about 0.01 mg $Ca^{+2}$/kg body weight/dose to about 10 mg $Ca^{+2}$/kg body weight/dose, about 0.01 mg $Ca^{+2}$/kg body weight/dose to about 5 mg $Ca^{+2}$/kg body weight/dose, about 0.01 mg $Ca^{+2}$/kg body weight/dose to about 2 mg $Ca^{+2}$/kg body weight/dose, about 0.02 mg $Ca^{+2}$/kg body weight/dose to about 2 mg $Ca^{+2}$/kg body weight/dose, about 0.03 mg $Ca^{+2}$/kg body weight/dose to about 2 mg $Ca^{+2}$/kg body weight/dose, about 0.04 mg $Ca^{+2}$/kg body weight/dose to about 2 mg $Ca^{+2}$/kg body weight/dose, about 0.05 mg $Ca^{+2}$/kg body weight/dose to about 2 mg $Ca^{+2}$/kg body weight/dose, about 0.1 mg $Ca^{+2}$/kg body weight/dose to about 2 mg $Ca^{+2}$/kg body weight/dose, about 0.1 mg $Ca^{+2}$/kg body weight/dose to about 1 mg $Ca^{+2}$/kg body weight/dose, about 0.1 mg $Ca^{+2}$/kg body weight/dose to about 0.5 mg $Ca^{+2}$/kg body weight/dose, about 0.2 mg $Ca^{+2}$/kg body weight/dose to about 0.5 mg $Ca^{+2}$/kg body weight/dose, about 0.18 mg $Ca^{+2}$/kg body weight/dose, about 0.001 mg $Ca^{+2}$/kg body weight/dose, about 0.005 mg $Ca^{+2}$/kg body weight/dose, about 0.01 mg $Ca^{+2}$/kg body weight/dose, about 0.02 mg $Ca^{+2}$/kg body weight/dose, or about 0.5 mg $Ca^{+2}$/kg body weight/dose.

In some embodiments the amount of calcium delivered to the respiratory tract (e.g., lungs, respiratory airway) is about 0.001 mg $Ca^{+2}$/kg body weight/dose to about 2 mg $Ca^{+2}$/kg body weight/dose, about 0.002 mg $Ca^{+2}$/kg body weight/dose to about 2 mg $Ca^{+2}$/kg body weight/dose, about 0.005 mg $Ca^{+2}$/kg body weight/dose to about 2 mg $Ca^{+2}$/kg body weight/dose, about 0.01 mg $Ca^{+2}$/kg body weight/dose to about 2 mg $Ca^{+2}$/kg body weight/dose, about 0.01 mg $Ca^{+2}$/kg body weight/dose to about 60 mg $Ca^{+2}$/kg body weight/dose, about 0.01 mg $Ca^{+2}$/kg body weight/dose to about 50 mg $Ca^{+2}$/kg body weight/dose, about 0.01 mg $Ca^{+2}$/kg body weight/dose to about 40 mg $Ca^{+2}$/kg body weight/dose, about 0.01 mg $Ca^{+2}$/kg body weight/dose to about 30 mg $Ca^{+2}$/kg body weight/dose, about 0.01 mg $Ca^{+2}$/kg body weight/dose to about 20 mg $Ca^{+2}$/kg body weight/dose, about 0.01 mg $Ca^{+2}$/kg body weight/dose to about 10 mg $Ca^{+2}$/kg body weight/dose, about 0.01 mg $Ca^{+2}$/kg body weight/dose to about 5 mg $Ca^{+2}$/kg body weight/dose, about 0.01 mg $Ca^{+2}$/kg body weight/dose to about 2 mg $Ca^{+2}$/kg body weight/dose, about 0.02 mg $Ca^{+2}$/kg body weight/dose to about 2 mg $Ca^{+2}$/kg body weight/dose, about 0.03 mg $Ca^{+2}$/kg body weight/dose to about 2 mg $Ca^{+2}$/kg body weight/dose, about 0.04 mg $Ca^{+2}$/kg body weight/dose to about 2 mg $Ca^{+2}$/kg body weight/dose, about 0.05 mg $Ca^{+2}$/kg body weight/dose to about 2 mg $Ca^{+2}$/kg body weight/dose, about 0.1 mg $Ca^{+2}$/kg body weight/dose to about 2 mg $Ca^{+2}$/kg body weight/dose, about 0.1 mg $Ca^{+2}$/kg body weight/dose to about 1 mg $Ca^{+2}$/kg body weight/dose, about 0.1 mg $Ca^{+2}$/kg body weight/dose to about 0.5 mg $Ca^{+2}$/kg body weight/dose, about 0.2 mg $Ca^{+2}$/kg body weight/dose to about 0.5 mg $Ca^{+2}$/kg body weight/dose, about 0.18 mg $Ca^{+2}$/kg body weight/dose, about 0.001 mg $Ca^{+2}$/kg body weight/dose, about 0.005 mg $Ca^{+2}$/kg body weight/dose, about 0.01 mg $Ca^{+2}$/kg body weight/dose, about 0.02 mg $Ca^{+2}$/kg body weight/dose, or about 0.5 mg $Ca^{+2}$/kg body weight/dose.

In other embodiments the amount of calcium delivered to the upper respiratory tract (e.g., nasal cavity) is of about 0.001 mg $Ca^{+2}$/kg body weight/dose to about 2 mg $Ca^{+2}$/kg body weight/dose, about 0.002 mg $Ca^{+2}$/kg body weight/dose to about 2 mg $Ca^{+2}$/kg body weight/dose, about 0.005 mg $Ca^{+2}$/kg body weight/dose to about 2 mg $Ca^{+2}$/kg body weight/dose, about 0.01 mg $Ca^{+2}$/kg body weight/dose to about 2 mg $Ca^{+2}$/kg body weight/dose, about 0.01 mg $Ca^{+2}$/kg body weight/dose to about 60 mg $Ca^{+2}$/kg body weight/dose, about 0.01 mg $Ca^{+2}$/kg body weight/dose to about 50 mg $Ca^{+2}$/kg body weight/dose, about 0.01 mg $Ca^{+2}$/kg body weight/dose to about 40 mg $Ca^{+2}$/kg body weight/dose, about 0.01 mg $Ca^{+2}$/kg body weight/dose to about 30 mg $Ca^{+2}$/kg body weight/dose, about 0.01 mg $Ca^{+2}$/kg body weight/dose to about 20 mg $Ca^{+2}$/kg body weight/dose, about 0.01 mg $Ca^{+2}$/kg body weight/dose to about 10 mg $Ca^{+2}$/kg body weight/ dose, about 0.01 mg $Ca^{+2}$/kg body weight/dose to about 5 mg $Ca^{+2}$/kg body weight/dose, about 0.01 mg $Ca^{+2}$/kg body weight/dose to about 2 mg $Ca^{+2}$/kg body weight/dose, about 0.02 mg $Ca^{+2}$/kg body weight/dose to about 2 mg $Ca^{+2}$/kg body weight/dose, about 0.03 mg $Ca^{+2}$/kg body weight/dose to about 2 mg $Ca^{+2}$/kg body weight/dose, about 0.04 mg $Ca^{+2}$/kg body weight/dose to about 2 mg $Ca^{+2}$/kg body weight/dose, about 0.05 mg $Ca^{+2}$/kg body weight/dose to about 2 mg $Ca^{+2}$/kg body weight/dose, about 0.1 mg $Ca^{+2}$/kg body weight/dose to about 2 mg $Ca^{+2}$/kg body weight/dose, about 0.1 mg $Ca^{+2}$/kg body weight/dose to about 1 mg $Ca^{+2}$/kg body weight/dose, about 0.1 mg $Ca^{+2}$/kg body weight/dose to about 0.5 mg $Ca^{+2}$/kg body weight/dose, about 0.2 mg $Ca^{+2}$/kg body weight/dose to about 0.5 mg $Ca^{+2}$/kg body weight/dose, about 0.18 mg $Ca^{+2}$/kg body weight/dose, about 0.001 mg $Ca^{+2}$/kg body In addition, when the respirable dry particles and dry powders include a sodium salt, the respirable dry particles and dry powders can be administered in an amount sufficient to deliver a dose of about 0.001 mg $Na^{+}$/kg body weight/dose to about 10 mg $Na^{+}$/kg body weight/dose, or about 0.01 mg $Na^{+}$/kg body weight/dose to about 10 mg $Na^{+}$/kg body weight/dose, or about 0.1 mg $Na^{+}$/kg body weight/dose to about 10 mg $Na^{+}$/kg body weight/dose, or about 1.0 mg $Na^{+}$/kg body weight/dose to about 10 mg $Na^{+}$/kg body weight/dose, or about 0.001 mg $Na^{+}$/kg body weight/dose to about 1 mg $Na^{+}$/kg body weight/dose, or about 0.01 mg $Na^{+}$/kg body weight/dose to about 1 mg $Na^{+}$/kg body weight/dose, or about 0.1 mg $Na^{+}$/kg body weight/dose to about 1 mg $Na^{+}$/kg body weight/dose, about 0.2 to about 0.8 mg $Na^{+}$/kg body weight/dose, about 0.3 to about 0.7 mg $Na^{+}$/kg body weight/dose, or about 0.4 to about 0.6 mg $Na^{+}$/kg body weight/dose.

In some embodiments the amount of sodium delivered to the respiratory tract (e.g., lungs, respiratory airway) is about 0.001 mg/kg body weight/dose to about 10 mg/kg body weight/dose, or about 0.01 mg/kg body weight/dose to about 10 mg/kg body weight/dose, or about 0.1 mg/kg body weight/dose to about 10 mg/kg body weight/dose, or about 1 mg/kg body weight/dose to about 10 mg/kg body weight/dose, or about 0.001 mg/kg body weight/dose to about 1 mg/kg body weight/dose, or about 0.01 mg/kg body weight/dose to about 1 mg/kg body weight/dose, or about 0.1 mg/kg body weight/dose to about 1 mg/kg body weight/dose, or about 0.2 to about 0.8 mg/kg body weight/dose, or about 0.3 to about 0.7 mg/kg body weight/dose, or about 0.4 to about 0.6 mg/kg body weight/dose.

In other embodiments the amount of sodium delivered to the upper respiratory tract (e.g., nasal cavity) is about 0.001 mg/kg body weight/dose to about 10 mg/kg body weight/dose, or about 0.01 mg/kg body weight/dose to about 10 mg/kg body weight/dose, or about 0.1 mg/kg body weight/dose to about 10 mg/kg body weight/dose, or about 1 mg/kg body weight/dose to about 10 mg/kg body weight/dose, or about 0.001 mg/kg body weight/dose to about 1 mg/kg body weight/dose, or about 0.01 mg/kg body weight/dose to about 1 mg/kg body weight/dose, or about 0.1 mg/kg body weight/dose to about 1 mg/kg body weight/dose, or about 0.2 to about 0.8 mg/kg body weight/dose, or about 0.3 to about 0.7 mg/kg body weight/dose, or about 0.4 to about 0.6 mg/kg body weight/dose.

Suitable intervals between doses that provide the desired therapeutic effect can be determined based on the severity of the condition (e.g., infection), overall well being of the subject and the subject's tolerance to respirable dry particles and dry powders and other considerations. Based on these and other considerations, a clinician can determine appropriate intervals between doses. Generally, respirable dry particles and dry powders are administered once, twice or three times a day, as needed.

If desired or indicated, the respirable dry particles and dry powders described herein can be administered with one or more other therapeutic agents. The other therapeutic agents can be administered by any suitable route, such as orally, parenterally (e.g., intravenous, intraarterial, intramuscular, or subcutaneous injection), topically, by inhalation (e.g., intrabronchial, intranasal or oral inhalation, intranasal drops), rectally, vaginally, and the like. The respirable dry particles and dry powders can be administered before, substantially concurrently with, or subsequent to administration of the other therapeutic agent. Preferably, the respirable dry particles and dry powders and the other therapeutic agent are administered so as to provide substantial overlap of their pharmacologic activities.

Another advantage provided by the respirable dry powders and respirable dry particles described herein, is that dosing efficiency can be increased as a result of hygroscopic growth of particles inside the lungs, due to particle moisture growth. The propensity of the partially amorphous, high salt compositions of the invention to take up water at elevated humidities can also be advantageous with respect to their deposition profiles in vivo. Due to their rapid water uptake at high humidities, these powder formulations can undergo hygroscopic growth do the absorbance of water from the humid air in the respiratory tract as they transit into the lungs. This can result in an increase in their effective aerodynamic diameters during transit into the lungs, which will further facilitate their deposition in the airways.

EXEMPLIFICATION

Materials used in the following Examples and their sources are listed below. Calcium chloride dihydrate, calcium lactate pentahydrate, sodium chloride, L-leucine, maltodextrin, mannitol, lactose and trehalose were obtained from Sigma-Aldrich Co. (St. Louis, Mo.) or Spectrum Chemicals (Gardena, Calif.); sodium sulfate from EMD Chemicals (Gibbstown, N.J.), Sigma-Aldrich Co. (St. Louis, Mo.) or Spectrum Chemicals (Gardena, Calif.); and sodium citrate dihydrate from J. T. Baker (Phillipsburg, N.J.), Mallinckrodt Baker (Phillipsburg, N.J.) or Spectrum Chemicals (Gardena, Calif.). Ultrapure water was from a water purification system (Millipore Corp., Billerica, Mass.).

Methods:

Geometric or Volume Diameter.

Volume median diameter (×50), which may also be referred to as volume median geometric diameter (VMGD), was determined using a laser diffraction technique. The equipment consisted of a HELOS diffractometer and a RODOS dry powder disperser (Sympatec, Inc., Princeton, N.J.). The RODOS disperser applies a shear force to a sample of particles, controlled by the regulator pressure (typically set at 1.0 bar with orifice ring pressure set at 7 mbar) of the incoming compressed dry air. The pressure settings may be varied to vary the amount of energy used to disperse the powder. For example, the regulator pressure may be varied from 0.2 bar to 4.0 bar; and the orifice ring pressure may be varied from 5.00 mbar to 115.00 mbar. Powder sample is dispensed from a microspatula into the RODOS funnel. The dispersed particles travel through a laser beam where the resulting diffracted light pattern produced is collected, typically using an R2 lens, by a series of detectors. The ensemble diffraction pattern is then translated into a volume-based particle size distribution using the Fraunhofer diffraction model, on the basis that smaller particles diffract light at larger angles. Using this method geometric standard deviation (GSD) for the volume mean geometric diameter was also determined.

Fine Particle Fraction.

The aerodynamic properties of the powders dispersed from an inhaler device were assessed with a Mk-II 1 ACFM Andersen Cascade Impactor (Copley Scientific Limited, Nottingham, UK). The instrument was run in controlled environmental conditions of 18 to 25° C. and relative humidity (RH) between 20 and 40%. The instrument consists of eight stages that separate aerosol particles based on inertial impaction. At each stage, the aerosol stream passes through a set of nozzles and impinges on a corresponding impaction plate. Particles having small enough inertia will continue with the aerosol stream to the next stage, while the remaining particles will impact upon the plate. At each successive stage, the aerosol passes through nozzles at a higher velocity and aerodynamically smaller particles are collected on the plate. After the aerosol passes through the final stage, a filter collects the smallest particles that remain. Gravimetric and/or chemical analyses can then be performed to determine the particle size distribution. A short stack cascade impactor is also utilized to allow for reduced labor time to evaluate two aerodynamic particle size cut-points. With this collapsed cascade impactor, stages are eliminated except those required to establish fine and coarse particle fractions.

The impaction techniques utilized allowed for the collection of two or eight separate powder fractions. The capsules (HPMC, Size 3; Shionogi Qualicaps, Madrid, Spain) were approximately half-filled with powder and placed in a hand-held, breath-activated dry powder inhaler (DPI) device, the high resistance RS-01 DPI (Plastiape, Osnago, Italy). The capsule was punctured and the powder was drawn through the cascade impactor operated at a flow rate of 60.0 L/min for 2.0 s. At this flowrate, the calibrated cut-off diameters for the eight stages are 8.6, 6.5, 4.4, 3.3, 2.0, 1.1, 0.5 and 0.3 microns and for the two stages used with the short stack cascade impactor, the cut-off diameters are 5.6 microns and 3.4 microns. The fractions were collected by placing filters in the apparatus and determining the amount of powder that impinged on them by gravimetric measurements or chemical measurements on an HPLC, as labeled in the tables. The fine particle fraction of the total dose of powder (FPF_TD) less than or equal to an effective cut-off aerodynamic diameter was calculated by dividing the powder mass recovered from the desired stages of the impactor by the total particle mass in the capsule. Results are reported as the fine particle fraction of less than 5.6 microns (FPF<5.6 microns) and the fine particle fraction of less than 3.4 microns (FPF<3.4 microns). The fine particle fraction can alternatively be calculated relative to the recovered or emitted dose of powder by dividing the powder mass recovered from the desired stages of the impactor by the total powder mass recovered.

Aerodynamic Diameter.

Mass median aerodynamic diameter (MMAD) was determined using the information obtained by the Andersen Cascade Impactor. The cumulative mass under the stage cut-off diameter is calculated for each stage and normalized by the recovered dose of powder. The MMAD of the powder is then calculated by linear interpolation of the stage cut-off diameters that bracket the 50th percentile.

Emitted Dose.

A measure of the emission properties of the powders was determined by using the information obtained from the Andersen Cascade Impactor tests. The filled capsule weight was recorded at the beginning of the run and the final capsule weight was recorded after the completion of the run. The difference in weight represented the amount of powder emitted from the capsule (CEPM or capsule emitted powder mass). The emitted dose was calculated by dividing the amount of powder emitted from the capsule by the total initial particle mass in the capsule.

Tap Density.

Two methods were utilized to measure tap density. (1) A modified method requiring smaller powder quantities was initially used, following USP <616> with the substitution of a 1.5 cc microcentrifuge tube (Eppendorf AG, Hamburg, Germany) to hold the powder. (2) USP <616> was used, utilizing a 100 cc graduated cylinder. Instruments for measuring tap density, known to those skilled in the art, include but are not limited to the Dual Platform Microprocessor Controlled Tap Density Tester (Vankel, Cary, N.C.) or a GeoPyc instrument (Micrometrics Instrument Corp., Norcross, Ga.). Tap density is a standard measure of the envelope mass density. The envelope mass density of an isotropic particle is defined as the mass of the particle divided by the minimum spherical envelope volume within which it can be enclosed.

Scanning Electron Microscopy (SEM).

SEM was performed using a FEI Quanta 200 scanning electron microscope (Hillsboro, Oreg.) equipped with an Everhart Thornley (ET) detector. Images were collected and analysed using xTm (v. 2.01) and XT Docu (v. 3.2) software, respectively. The magnification was verified using a NIST traceable standard. Each sample was prepared for analysis by placing a small amount on a carbon adhesive tab supported on an aluminum mount. Each sample was then sputter coated with Au/Pd using a Cressington 108 auto Sputter Coater at approximately 20 mA and 0.13 mbar (Ar) for 75 seconds. The data acquisition parameters are displayed in the information bar at the bottom of each image. The magnification reported on each image was calculated upon the initial data acquisition. The scale bar reported in the lower portion of each image is accurate upon resizing and should be used when making size determinations.

Liquid Feedstock Preparation for Spray Drying.

Spray drying homogenous particles requires that the ingredients of interest be solubilized in solution or suspended in a uniform and stable suspension. Certain calcium salts, such as calcium chloride, calcium acetate and calcium lactate, are sufficiently water-soluble to prepare suitable spray drying solutions. However, other calcium salts, such as calcium sulfate, calcium citrate and calcium carbonate, have a low solubility in water. The solubility in water of exemplary calcium salts are listed in Table 1. As a result of these low solubilities, formulation feedstock development work was necessary to prepare solutions or suspensions that could be spray dried. These solutions or suspensions included combinations of salts in an appropriate solvent, typically water but also ethanol and water mixtures or other solvents as described earlier in the specification.

TABLE 1

Calcium Salts' Solubility in Water
Calcium Salt Solubility in Water (at 20-30° C., 1 bar)

| Salt | Water solubility (g/L) |
|---|---|
| Calcium chloride | 1368[1,2] |
| Calcium acetate | 347[1] |
| Calcium lactate | 105[1] |
| Calcium gluconate | 33.23[3] |
| Calcium sulfate | 2.98[1] |
| Calcium citrate | 0.96[1] |

TABLE 1-continued Calcium Salts' Solubility in Water
Calcium Salt Solubility in Water (at 20-30° C., 1 bar)

| Salt | Water solubility (g/L) |
|---|---|
| Calcium phosphate dibasic | 0.2[1] |
| Calcium carbonate | Pract. Insol.[2] |
| Calcium stearate | Pract. Insol.[2] |
| Calcium alginate | Not applicable |
| Sodium Carbonate | 505[1] |
| Sodium Chloride | 360[1] |
| Sodium Citrate | 910[1] |
| Sodium Sulfate | 194[1] |

[1]Perry, Robert H., Don W. Green, and James O. Maloney. *Perry's Chemical Engineers' Handbook*. 7th ed. New York: McGraw-Hill, 1997. Print.
[2]Solubility at 60° C.
[3]O'Neil, Maryadele J. *The Merck Index: an Encyclopedia of Chemicals, Drugs, and Biologicals*. 14th ed. Whitehouse Station, N.J.: Merck, 2006. Print.

As mentioned previously, calcium chloride has high water solubility. Sodium salts, such as sodium sulfate, sodium citrate and sodium carbonate, are also very soluble in water. As will be discussed further in the following examples, calcium chloride and sodium salts (the "starting materials") are combined in solution or suspension to obtain stable calcium salts in final dry powder form. When combining the calcium chloride and sodium salt in solution, the calcium and the anion contributed from the sodium salt may react in a precipitation reaction to produce the desired calcium salt (i.e., $CaCl_2 + 2NaXX \rightarrow CaXX + 2NaCl$). In this case, the maximum solids concentration that maintained a clear solution or a stable suspension were used for spray drying. Certain calcium salts were soluble enough to be dissolved in water and then spray dried alone. The same concept may be applied to, for example, magnesium salts by using magnesium chloride, potassium salts using potassium chloride, and sodium salts.

The starting materials may be provided in molar amounts where the full precipitation reaction may proceed to completion, termed 'reaction to completion.' The weight percent of calcium ion in exemplary calcium salts are further listed in Table 2.

TABLE 2

Weight Percent of $Ca^{2+}$ in Salt Molecules
Weight % of Calcium ion in Salt Molecule

| Salt | Formula | MW | Weight % of $Ca^{2+}$ in molecule |
|---|---|---|---|
| Calcium carbonate | $CaCO_3$ | 100.09 | 40.0 |
| Calcium chloride | $CaCl_2$ | 110.98 | 36.0 |
| Calcium phosphate dibasic | $CaHPO_4$ | 136.06 | 29.4 |
| Calcium sulfate | $CaSO_4$ | 136.14 | 29.4 |
| Calcium acetate | $Ca(C_2H_3O_2)_2$ | 158.17 | 25.3 |
| Calcium citrate | $Ca_3(C_6H_5O_7)_2$ | 498.46 | 24.1 |
| Calcium lactate | $Ca(C_3H_5O_3)_2$ | 218.218 | 18.3 |
| Calcium sorbate | $CaC_{12}H_{14}O_4$ | 262.33 | 15.2 |
| Calcium gluconate | $CaC_{12}H_{22}O_{14}$ | 430.373 | 9.3 |
| Calcium stearate | $CaC_{36}H_{70}O_4$ | 607.02 | 6.6 |
| Calcium alginate | $[Ca(C_6H_7O_6)_2]_n$ | NA | NA |

Alternatively, excess calcium chloride may be added for an incomplete reaction, or 'reaction not to completion,' where a given amount of calcium chloride is present in the final powder form. While calcium chloride is hygroscopic, its high water solubility may be beneficial to have in small amounts in the final product to increase the solubility of the final product, to be able to tailor the dissolution profile, and to increase the relative calcium ion ratio to sodium or other cations present in the formulation. For ease of formulation development, the required molar ratios of calcium chloride and sodium salt were converted to mass ratios of calcium chloride and sodium salt. An example is for calcium citrate (i.e., calcium chloride+sodium citrate), where the precipitation reaction proceeds forward as follows:

$$3CaCl_2 + 2Na_3C_6H_5O_7 \rightarrow Ca_3(C_6H_5O_7)_2 + 6NaCl$$

This reaction results in a 1:2 molar ratio of Ca:Na ions. For the reaction to proceed to completion, 3 moles of calcium chloride and 2 moles of sodium citrate are required. To convert to mass in grams and a weight ratio, the moles of salts are multiplied by the molecular weight of the salts in grams per mole:

For calcium chloride: 3 mol $CaCl_2 \times 111$ g/mol=333 g $CaCl_2$ 2 mol $Na_3C_6H_5O_7 \times 258$ g/mol=516 g $Na_3C_6H_5O_7$ For sodium citrate:

Therefore, a 1:1.55 or 39:61 weight ratio of $CaCl_2$:$Na_3C_6H_5O_7$ is required for a complete reaction. These ratios were solubilized and spray dried to produce 'pure salt' formulations. In addition, dry powders were produced with an additional excipient, such as leucine or lactose. The ratio of calcium to sodium salt remained the same so as to produce a 'reaction to completion.' For example, for a formulation of 50% (w/w) leucine, the remainder is composed of salts, such as calcium citrate (i.e., $CaCl_2$:$Na_3C_6H_5O_7$) where the 39:61, $CaCl_2$:$Na_3C_6H_5O_7$ weight ratio is maintained. Thus, for that reaction: 50% (w/w) leucine, 19.5% (w/w) $CaCl_2$ and 30.5% (w/w) $Na_3C_6H_5O_7$ will be added. For a spray drying process, the salts and other excipients will be dissolved or suspended in a solvent (i.e., water). The solids concentration (w/v) can be chosen depending on the solubility of the different components. For the citrate formulation, a concentration of 5 mg/mL was appropriate, given the limited solubility of calcium citrate: 0.95 mg/mL. Therefore, 5 g of solids (i.e., 2.5 g leucine, 0.975 g calcium chloride and 1.525 g of sodium citrate) were dissolved in 1 L of ultrapure water.

In addition, when preparing spray drying solutions, the water weight of the hydrated starting material must be accounted for. The ratios used for formulations were based on the molecular weight of the anhydrous salts. For certain salts, hydrated forms are more readily available than the anhydrous form. This required an adjustment in the ratios originally calculated, using a multiplier to correlate the molecular weight of the anhydrous salt with the molecular weight of the hydrate. An example of this calculation is included below.

For the example above, calcium chloride anhydrous molecular weight is 110.98 g/mol and the dihydrate molecular weight is 147.01 g/mol. Sodium citrate anhydrous molecular weight is 258.07 g/mol and the dihydrate molecular weight is 294.10 g/mol.

The multiplier is analogous to the ratio of the dihydrate to anhydrous molecular weight, e.g., 1.32 for calcium chloride and 1.14 for sodium citrate. Therefore, adjusting for the dihydrate forms results in: 2.5 g leucine, 1.287 g (i.e., 0.975 g×1.32) calcium chloride dihydrate and 1.738 g (i.e., 1.525 g×1.14) of sodium citrate dihydrate were dissolved and spray dried.

Spray Drying Using Niro Spray Dryer.

Dry powders were produced by spray drying utilizing a Niro Mobile Minor spray dryer (GEA Process Engineering Inc., Columbia, Md.) with powder collection from a cyclone, a product filter or both. Atomization of the liquid feed was performed using a co-current two-fluid nozzle either from Niro (GEA Process Engineering Inc., Columbia, Md.) or a Spraying Systems (Carol Stream, Ill.) two-fluid nozzle with gas cap 67147 and fluid cap 2850SS, although other two-fluid nozzle setups are also possible. Additional atomization techniques include rotary atomization or a pressure nozzle. The liquid feed was fed using gear pumps (Cole-Panner Instrument Company, Vernon Hills, Ill.) directly into the two-fluid nozzle or into a static mixer (Charles Ross & Son Company, Hauppauge, N.Y.) immediately before introduction into the two-fluid nozzle. An additional liquid feed technique includes feeding from a pressurized vessel. Nitrogen or air may be used as the drying gas, provided that moisture in the air is at least partially removed before its use. Pressurized nitrogen or air can be used as the atomization gas feed to the two-fluid nozzle. The process gas inlet temperature can range from 100° C. to 300° C. and outlet temperature from 50° C. to 120° C. with a liquid feedstock rate of 20 mL/min to 100 mL/min. The gas supplying the two-fluid atomizer can vary depending on nozzle selection and for the Niro co-current two-fluid nozzle can range from 8 kg/hr to 15 kg/hr and be set a pressures ranging from 0.5 bar to 2.0 bar or for the Spraying Systems two-fluid nozzle with gas cap 67147 and fluid cap 2850SS can range from 40 to 100 g/min. The atomizing gas rate can be set to achieve a certain gas to liquid mass ratio, which directly affects the droplet size created. The pressure inside the drying drum can range from +3 "WC to −6 "WC. Spray dried powders can be collected in a container at the outlet of the cyclone, onto a cartridge or baghouse filter, or from both a cyclone and a cartridge or baghouse filter.

Spray Drying Using Büchi Spray Dryer.

Dry powders were prepared by spray drying on a Büchi B-290 Mini Spray Dryer (BÜCHI Labortechnik AG, Flawil, Switzerland) with powder collection from either a standard or High Performance cyclone. The system used the Büchi B-296 dehumidifier to ensure stable temperature and humidity of the air used to spray dry. Furthermore, when the relative humidity in the room exceeded 30% RH, an external LG dehumidifier (model 49007903, LG Electronics, Englewood Cliffs, N.J.) was run constantly. Atomization of the liquid feed utilized a Büchi two-fluid nozzle with a 1.5 mm diameter. Inlet temperature of the process gas can range from 100° C. to 220° C. and outlet temperature from 80° C. to 120° C. with a liquid feedstock flowrate of 3 mL/min to 10 mL/min. The two-fluid atomizing gas ranges from 25 mm to 45 mm (300 LPH to 530 LPH) and the aspirator rate from 70% to 100% (28 $m^3$/hr to 38 $m^3$/hr).

Table 3 provides feedstock formulations used in preparation of some dry powders described herein.

TABLE 3

Feedstock Formulations

| Formulation | Composition (w/w) |
|---|---|
| I | 10.0% leucine, 35.1% calcium chloride, 54.9% sodium citrate |
| II | 10.0% leucine, 58.6% calcium lactate, 31.4% sodium chloride |
| III | 10.0% leucine, 39.6% calcium chloride, 50.4% sodium sulfate |
| XIV | 10.0% maltodextrin, 58.6% calcium lactate, 31.4% sodium chloride |

Table 4 provides expected final dry powder compositions. These compositions are based on the expectation that the ion exchange reaction described above goes to completion for Formulations I and III. Without wishing to be bound by any particular theory, the evaporation of the droplet that occurs during spray drying is expected to drive the least soluble salt to precipitate first, which is the calcium citrate and calcium sulfate in formulations I and III, respectively.

TABLE 4

Dry Powder Products of Spray Drying

| Formulation | Composition (w/w) |
|---|---|
| I | 10.0% leucine, 52.8% calcium citrate, 37.2% sodium chloride |
| II | 10.0% leucine, 58.6% calcium lactate, 31.4% sodium chloride |
| III | 10.0% leucine, 48.4% calcium sulfate, 41.6% sodium chloride |
| XIV | 10.0% maltodextrin, 58.6% calcium lactate, 31.4% sodium chloride |

Description of Placebo:

A Placebo formulation comprising 100 weight percent leucine was produced by spray drying. An aqueous phase was prepared for a batch process by dissolving leucine in ultrapure water with constant agitation until the materials were completely dissolved in the water at room temperature. For a static mixing process, the ultrapure water was divided in half and half of the total required leucine was dissolved in each volume of water. The solutions were then spray dried using a Niro or a Büchi spray dryer. For the Placebo formulation, two batches (A and B) of feedstock were prepared and spray dried. The total solids concentration for Batch A was 15 g/L and for Batch B was 5 g/L. The process conditions used for spray drying Batch A (Placebo-A) on the Niro Mobile Minor spray dryer were similar to the conditions used to spray dry Formulation I-A in Example 1. The process conditions used for spray drying Batch B (Placebo-B) were similar to the conditions used to spray dry Formulation I-C in Example 1, with the exception that the outlet temperature was about 82° C. for Formulation Placebo-B. Additional information relating to process conditions and properties of the Formulation Placebo-A and Placebo-B powders and/or particles prepared in this example are provided in the Tables or graphs shown in FIGS. 1A-1F and 2-4.

EXAMPLE 1

This example describes the preparation of dry powders using feedstock of Formulation I: 10.0 weight percent leucine, 35.1 weight percent calcium chloride and 54.9 weight percent sodium citrate.

An aqueous phase was prepared for a batch process by dissolving leucine in ultrapure water, then sodium citrate dihydrate, and finally calcium chloride dihydrate. The solution or suspension was kept agitated throughout the process until the materials were completely dissolved in the water at room temperature. For a static mixing process, the sodium salt and calcium salt were kept in separate solutions. The ultrapure water was divided in half and half of the total required leucine was dissolved in each volume of water. The sodium citrate dihydrate was dissolved in one aqueous phase and the calcium chloride dihydrate dissolved in the second aqueous phase. The solutions or suspensions were kept agitated throughout the process until the materials were completely dissolved in the water at room temperature. The solutions or suspensions were then spray dried using a Niro or a Büchi spray dryer. For each formulation, three batches (A, B & C) of feedstock were prepared and spray dried. Details on the liquid feedstock preparations for each of the three batches are shown in Table 5, where the total solids concentration is reported as the total of the dissolved anhydrous material weights. Batch A particles were prepared using batch A feedstock on a Niro spray dryer. Batch B and C particles were prepared using the corresponding feedstocks on a Büchi spray dryer.

TABLE 5

Summary of liquid feedstock preparations of four batches of particles for Formulation I.

| Formulation: | I-A | I-B | I-C | I-D |
|---|---|---|---|---|
| Liquid feedstock mixing | Static mixed | Batch mixed | Batch mixed | Static mixed |
| Total solids concentration | 10 g/L | 5 g/L | 5 g/L | 15 g/L |
| Total solids | 380 g | 6.25 g | 10.50 g | 570 g |
| Total volume water | 38.0 L | 1.25 L | 2.1 L | 38 L |
| Amount leucine in 1 L | 1.00 g | 0.50 g | 1.05 g | 1.5 g |
| Amount sodium citrate dihydrate in 1 L | 6.26 g | 3.13 g | 3.13 g | 9.39 g |
| Amount calcium chloride dihydrate in 1 L | 4.65 g | 2.32 g | 2.32 g | 6.98 g |

Batch A (I-A) dry powders were produced by spray drying on the Niro Mobile Minor spray dryer (GEA Process Engineering Inc., Columbia, Md.) with powder collection from a product cartridge filter. Atomization of the liquid feed used a co-current two-fluid nozzle from Niro (GEA Process Engineering Inc., Columbia, Md.) with 1.0 mm insert. The liquid feed was fed using gear pumps (Cole-Panner Instrument Company, Vernon Hills, Ill.) into a static mixer (Charles Ross & Son Company, Hauppauge, N.Y.) immediately before introduction into the two-fluid nozzle. Nitrogen was used as the drying gas. The process gas inlet temperature was set to 282° C., with the outlet temperature reading about 98° C. The gas supplying the two-fluid atomizer was set at a flowrate of 14.5 kg/hr and a pressure of 2 psi, the process gas flowrate was set at 85 kg/hr and a pressure of 25 psi, and the pressure inside the drying drum was at −2 "WC. The liquid feed stock total flowrate was 70 mL/min, with each stream being fed at 35 mL/min Spray dried powders were collected from a product collection cartridge filter.

Batch B (I-B) and Batch C (I-C) dry powders were prepared by spray drying on a Büchi B-290 Mini Spray Dryer (BÜCHI Labortechnik AG, Flawil, Switzerland) with a Büchi two-fluid nozzle with a 1.5 mm diameter and powder collection from a High Performance cyclone. The system used the Büchi B-296 dehumidifier to ensure stable temperature and humidity of the air used to spray dry. Inlet temperature of the process gas was set at 220° C. with a liquid feedstock flowrate of 6.7 mL/min for Formulation I-B and 7 mL/min for Formulation I-C. The outlet temperature was about 108° C. for Formulation I-B and about 95° C. for Formulation I-C. The two-fluid atomizing gas was at 40 mm and the aspirator rate at 90%.

Batch D (I-D) dry powders were produced by spray drying on the Niro Mobile Minor spray dryer (GEA Process Engineering Inc., Columbia, Md.) with powder collection from a product filter membrane. Atomization of the liquid feed used a two-fluid nozzle from Spraying Systems (Carol Stream, Ill.) with gas cap 67147 and fluid cap 2850SS. The liquid feed was fed using gear pumps (Cole-Panner Instrument Company, Vernon Hills, Ill.) into a static mixer (Charles Ross & Son Company, Hauppauge, N.Y.) immediately before introduction into the two-fluid nozzle. Nitrogen was used as the drying gas. The process gas inlet temperature was set to approximately 265° C., with the outlet temperature reading about 99° C. The gas supplying the two-fluid atomizer was set at a flowrate of 80 g/min, the process gas flowrate was set at 80 kg/hr and the pressure inside the drying drum was at −2 "WC. The liquid feed stock total flowrate was 66 mL/min, with each stream being fed at 33 mL/min Spray dried powders were collected from a product collection filter membrane.

Some of the physical properties of the particles obtained in four separate batches (Formulation I-A, I-B, I-C and I-D) are summarized in Table 6. In addition to the data provided in Table 5, further data related to the dry powders prepared from feedstock formulation I-A is summarized as follows. The fine particle fraction (FPF) as measured by a full 8-stage Andersen Cascade Impactor with gravimetric analysis was on average 56.2% for FPF less than 5.6 microns and 41.7% for FPF less than 3.4 microns. The aerodynamic diameter was also measured with a full-stage ACI with gravimetric analysis. The average value for the mass median aerodynamic diameter (MMAD) was 2.72 microns. The volume size was determined by laser diffraction on the HELOS/RODOS sizing equipment and the average value for the volume median diameter (×50) at a pressure of 1 bar was 2.57 microns. In addition, the powder displayed relatively flowrate independent behavior as can be seen from the ratio of ×50 measured at 0.5 bar to ×50 measured at 4.0 bar, which was 1.19. The value for ¼ bar for these particles was 1.17.

Additional properties of the dry powders prepared from feedstock Formulation I-D are summarized as follows. The fine particle fraction (FPF) as measured by a full 8-stage Andersen Cascade Impactor with gravimetric analysis was on average 58.8% for FPF less than 5.6 microns and 46.7% for FPF less than 3.4 microns. The aerodynamic diameter was also measured with a full-stage ACI with gravimetric analysis. The average value for the mass median aerodynamic diameter (MMAD) was 2.38 microns. The volume size was determined by laser diffraction on the HELOS/RODOS sizing equipment and the average value for the volume median diameter (×50) at a pressure of 1 bar was 2.45 microns. In addition, the powder displayed relatively flowrate independent behavior as can be seen from the ratio of ×50 measured at 0.5 bar to ×50 measured at 4.0 bar, which was 1.12. The value for ¼ bar for these particles was 1.09.

TABLE 6

Summary of ACI-2 data for the four batches of particles for Formulation I

| Formulation: | I-A | I-B | I-C | I-D |
|---|---|---|---|---|
| FPF less than 5.6 µm on ACI-2 (%) | 61.6 | 49.2 | 64.8 | 67.2 |
| FPF less than 3.4 µm on ACI-2 (%) | 45.7 | 33.3 | 52.1 | 54.8 |

Figure 5A:
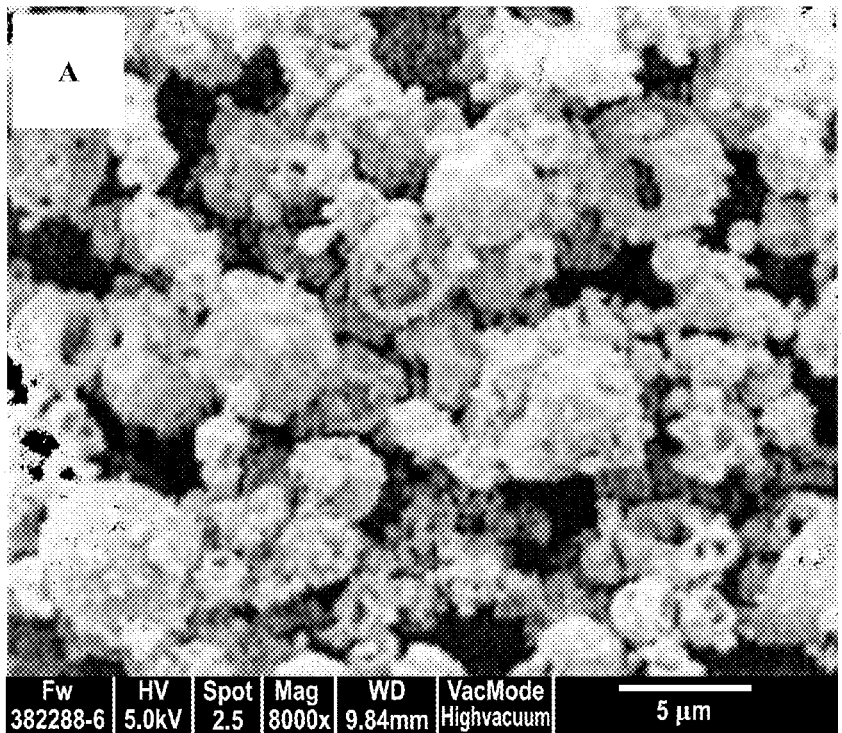
Figure 5B:
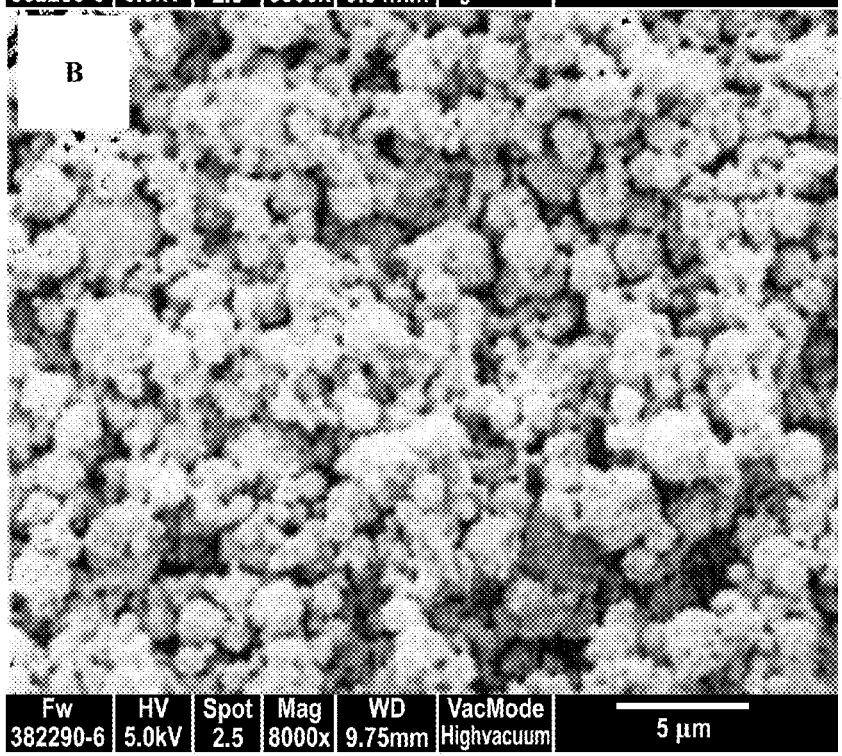

Additional information relating to properties of the Formulation I-A powder and/or particles prepared in this example are provided in the Tables or graphs shown in FIGS. 1A-1F and 2-4. In FIG. 1D, GSD refers to geometric standard deviation. In FIG. 1F, Dv50 refers to volume median geometric diameter (VMGD) as measured by Spraytec instrument; V refers to volume. SEM was performed as described above (FIG. 5A).

EXAMPLE 2

This example describes the preparation of dry powders using feedstock of Formulation II: 10.0 weight percent leucine, 58.6 weight percent calcium lactate and 31.4 weight percent sodium chloride.

An aqueous phase was prepared for a batch process by dissolving leucine in ultrapure water, then sodium chloride, and finally calcium lactate pentahydrate. The solution was kept agitated throughout the process until the materials were completely dissolved in the water at room temperature. For the calcium lactate formulation, four batches (A, B, C and D) of feedstock were prepared and spray dried. Details on the liquid feedstock preparations for each of the four batches are shown in Table 7, where the total solids concentration is reported as the total of the dissolved anhydrous material weights. Batch A and D particles were prepared using batch A and D feedstock, respectively on a Niro spray dryer. The process conditions used for spray drying Batch A (II-A) were similar to the conditions used to spray dry Formulation I-A in Example 1 and those for Batch D (II-D) were similar to the conditions used to spray dry Formulation 1-D in Example 1. Batch B and C particles were prepared using the corresponding feedstocks on a Büchi Mini spray dryer with process conditions similar to those used to spray dry for Formulations I-B and I-C in Example 1, with the exception of the following process conditions. The liquid feedstock flowrate was set at 5.2 mL/min for Formulation II-B and 6 mL/min for Formulation II-C. The outlet temperature was about 91° C. to 109° C. for Formulation II-B and about 100° C. for Formulation II-C.

TABLE 7

Summary of liquid feedstock preparations of four batches of particles for Formulation II.

| Formulation: | II-A | II-B | II-C | II-D |
|---|---|---|---|---|
| Liquid feedstock mixing | Static mixed | Batch mixed | Batch mixed | Static mixed |
| Total solids concentration | 10 g/L | 5 g/L | 5 g/L | 15 g/L |
| Total solids | 400 g | 10.0 g | 9.20 g | 570 g |
| Total volume water | 40.0 L | 2.00 L | 1.84 L | 38 L |
| Amount leucine in 1 L | 1.00 g | 0.50 g | 0.50 g | 1.5 g |
| Amount sodium chloride in 1 L | 3.14 g | 1.57 g | 1.57 g | 4.71 g |
| Amount calcium lactate pentahydrate in 1 L | 8.28 g | 4.13 g | 4.13 g | 12.42 g |

Some of the physical properties of the particles obtained in four separate batches (Formulation II-A, II-B, II-C and II-D) are summarized in Table 8. In addition to the data provided in Table 8, further data about the dry particles prepared by feedstock formulation II-A is summarized as follows. The fine particle fraction (FPF) as measured by a full 8-stage Andersen Cascade Impactor with gravimetric analysis was on average 55.3% for FPF less than 5.6 microns and 39.7% for FPF less than 3.4 microns. The aerodynamic diameter was also measured with a full-stage ACI with gravimetric analysis. The average value for the mass median aerodynamic diameter (MMAD) was 2.89 microns. The volume size was determined by laser diffraction on the HELOS/RODOS sizing equipment and the average value for the volume median diameter (×50) at a pressure of 1 bar was 1.51 microns. In addition, the powder displayed relatively flowrate independent behavior as can be seen from the ratio of ×50 measured at 0.5 bar to ×50 measured at 4.0 bar, which was 1.12. The value for ¼ bar for these particles was 1.08.

Additional properties of the dry powders prepared by feedstock formulation II-D are summarized as follows. The fine particle fraction (FPF) as measured by a full 8-stage Andersen Cascade Impactor with gravimetric analysis was on average 62.2% for FPF less than 5.6 microns and 45.3% for FPF less than 3.4 microns. The aerodynamic diameter was also measured with a full-stage ACI with gravimetric analysis. The average value for the mass median aerodynamic diameter (MMAD) was 2.72 microns. The volume size was determined by laser diffraction on the HELOS/RODOS sizing equipment and the average value for the volume median diameter (×50) at a pressure of 1 bar was 1.47 microns. In addition, the powder displayed relatively flowrate independent behavior as can be seen from the ratio of ×50 measured at 0.5 bar to ×50 measured at 4.0 bar, which was 1.08. The value for ¼ bar for these particles was 1.03.

TABLE 8

Summary of ACI-2 data for the four batches of particles for Formulation II.

| Formulation: | II-A | II-B | II-C | II-D |
|---|---|---|---|---|
| FPF less than 5.6 μm on ACI-2 (%) | 63.5 | 55.4 | 56.5 | 71.4 |
| FPF less than 3.4 μm on ACI-2 (%) | 43.4 | 35.5 | 34.7 | 49.7 |

Additional information relating to properties of the Formulation II powders and/or particles prepared in this example are provided in the Tables or graphs shown in FIGS. 1A-1F and 2-4. SEM was performed as described above (FIG. 5B).

EXAMPLE 3

This example describes the preparation of dry powders using feedstock of Formulation III: 10 weight percent leucine, 39.6 weight percent calcium chloride and 50.4 weight percent sodium sulfate.

An aqueous phase was prepared for a batch process by dissolving leucine in ultrapure water, then sodium sulfate, and finally calcium chloride dihydrate. The solution or suspension was kept agitated throughout the process until the materials were completely dissolved in the water at room temperature. For a static mixing process, the sodium salt and calcium salt were kept in separate solutions. The ultrapure water was divided in half and half of the total required leucine was dissolved in each volume of water. The sodium sulfate was dissolved in one aqueous phase and the calcium chloride dihydrate dissolved in the second aqueous phase. The solutions or suspensions were kept agitated throughout the process until the materials were completely dissolved in the water at room temperature. The solutions or suspensions were then spray dried using a Niro or a Büchi spray dryer. For each formulation, four batches (A, B, C and D) of feedstock were prepared and spray dried. Details on the liquid feedstock preparations for each of the four batches are shown in Table 9, where the total solids concentration is reported as the total of the dissolved anhydrous material weights. Batch A and D particles were prepared using batch A and D feedstock, respectively on a Niro spray dryer. Batch B and C particles were prepared using the corresponding feedstocks on a Büchi spray dryer. The process conditions used for spray drying Batch A (III-A) were similar to the conditions used to spray dry Formulation I-A in Example 1 and the process conditions used for spray drying Batch D (III-D) were similar to the conditions used to spray dry Formulation I-D in Example 1. Batch B and C particles were prepared using the corresponding feedstocks on a Büchi Mini spray dryer with process conditions similar to those used to spray dry Formulations I-B and I-C in Example 1, with the exception of the following process conditions. The liquid feedstock flowrate was set at 8.3 mL/min for Formulation III-B and 7 mL/min for Formulation III-C. The outlet temperature was about 83° C. for Formulation III-B and about 92° C. for Formulation III-C. The aspirator was set at 80% for Formulation III-B.

TABLE 9

Summary of liquid feedstock preparations of four batches of particles for Formulation III.

| Formulation: | III-A | III-B | III-C | III-D |
|---|---|---|---|---|
| Liquid feedstock mixing | Static mixed | Batch mixed | Batch mixed | Static mixed |
| Total solids concentration | 10 g/L | 5 g/L | 5 g/L | 15 g/L |
| Total solids | 400 g | 2.5 g | 9.5 g | 185 g |
| Total volume water | 40 L | 0.5 L | 1.9 L | 37 L |
| Amount leucine in 1 L | 1.00 g | 0.5 g | 0.5 g | 0.5 g |
| Amount sodium sulfate in 1 L | 5.04 g | 2.52 g | 2.52 g | 2.52 g |
| Amount calcium chloride dihydrate in 1 L | 5.25 g | 2.61 g | 2.61 g | 2.61 g |

The physical properties of the particles obtained in four separate batches (Formulation III-A, III-B, III-C and III-D) are summarized in Table 10. In addition to the data provided in Table 10, further data about the dry powders prepared from feedstock formulation III-A is summarized as follows. The fine particle fraction (FPF) as measured by a full 8-stage Andersen Cascade Impactor with gravimetric analysis was on average 68.7% for FPF less than 5.6 microns and 51.5% for FPF less than 3.4 microns. The aerodynamic diameter was also measured with a full-stage ACI with gravimetric analysis. The average value for the mass median aerodynamic diameter (MMAD) was 2.59 microns. The volume size was determined by laser diffraction on the HELOS/RODOS sizing equipment and the average value for the volume median diameter (×50) at a pressure of 1 bar was 2.50 microns. In addition, the powder displayed relatively flowrate independent behavior as can be seen from the ratio of ×50 measured at 0.5 bar to ×50 measured at 4.0 bar, which was 1.47. The value for ¼ bar for these particles was 1.42.

Additional properties of the dry powders prepared by feedstock formulation III-D are summarized as follows. The fine particle fraction (FPF) as measured by a full 8-stage Andersen Cascade Impactor with gravimetric analysis was on average 77.9% for FPF less than 5.6 microns and 68.3% for FPF less than 3.4 microns. The aerodynamic diameter was also measured with a full-stage ACI with gravimetric analysis. The average value for the mass median aerodynamic diameter (MMAD) was 2.17 microns. The volume size was determined by laser diffraction on the HELOS/RODOS sizing equipment and the average value for the volume median diameter (×50) at a pressure of 1 bar was 1.90 microns. In addition, the powder displayed relatively flowrate independent behavior as can be seen from the ratio of ×50 measured at 0.5 bar to ×50 measured at 4.0 bar, which was 1.17. The value for ¼ bar for these particles was 1.63.

TABLE 10

Summary of ACI_2 data for the four batches of particles for Formulation III.

| Formulation: | III-A | III-B | III-C | III-D |
|---|---|---|---|---|
| FPF less than 5.6 μm on ACI-2 (%) | 82.7 | 62.0 | 69.0 | 82.8 |
| FPF less than 3.4 μm on ACI-2 (%) | 60.1 | 47.4 | 53.2 | 70.9 |

Additional information relating to properties of the Formulation III powders and/or particles prepared in this example is provided in the Tables or graphs shown in FIGS. 1A-1F and 2-4. SEM was performed as described above (FIG. 5C)

EXAMPLE 4

This example describes the dose emission of powders of formulation batches I-B, II-B, and III-B from dry powder inhaler at room and elevated conditions.

Method: Spray dried powders of the three different formulations (I-B, II-B, and III-B) were filled into size 2 HPMC capsules (Quali-V, Qualicaps, Whitsett, N.C.) to approximately half full (13-30 mg depending on powder). Capsules were punctured prior to loading into one of four capsule DPIs in order to ensure adequate hole openings in the capsule. The capsules were loaded horizontally into the inhalers which were then connected to the custom chamber. Each dry powder inhaler had a pressure transducer connected to it to monitor the flow rate through the inhaler during the test. When the test was begun, an airflow of 45 L/min was drawn through each inhaler for 3 short bursts of 0.3 seconds each, separated by 1 minute. During each burst, the air drawn through the inhaler caused the capsule to spin and emit the powder in it into one of 4 sub-chambers which had one row of 3 tissue culture wells forming the floor of the sub-chamber. The aerosol cloud was allowed to settle for one minute before the next subsequent burst for a total of 3 bursts and a total air volume of 0.68 L being drawn through the inhaler. The duration and total airflow rate was controlled with a flow controller (TPK-2000, MSP Corporation, Shoreview, Minn.) and recorded with an air mass flow meter (model#3063, TSI Inc., Shoreview, Minn.). Individual inhaler airflow rates were monitored with pressure sensors (model #ASCX01DN, Honeywell International Inc., Morristown, N.J.) which had been previously calibrated and whose signal was converted to flow rate via a custom Lab-view code. In one case, the custom chamber was located on the lab bench at room conditions, while in another 2 cases it was located in a stability chamber (Darwin Chambers Company, St. Louis, Mo.) set to 37° C. and 90% RH. For the first case in the stability chamber, the capsules were punctured and loaded into inhalers at room conditions, the door of the chamber was opened, the inhalers attached and the flow rate was actuated ~30 seconds after the capsules entered the chamber. In the second case, the capsules were first placed unpunctured in the stability chamber for 3 minutes, then removed from the chamber, punctured and loaded at room conditions, attached in the chamber and actuated within 30 seconds of the second entry into the chamber. Following each test, the capsules were removed from the inhalers and weighed and used to calculate the percentage of powder emitted from the capsule. For each of the 3 sets of conditions, two 12 well tissue culture plates (each plate required 4 capsules in 4 inhalers delivering powder to 3 wells each) were exposed to powder for each of the powder formulations tested, giving a total of 8 capsule emissions for each powder at each temperature and humidity setting.

As shown in Table 11 below, for all three powder batches (I-B, II-B, and III-B) the average amount of powder emitted from the capsule is greater than 99% based on the weight change of the capsule.

TABLE 11

Emitted Dose Percent

| Powder Batch | Emitted Dose % |
| --- | --- |
| I-B | 99.45 |
| II-B | 100.0 |
| III-B | 99.38 | pressure of 1 bar were 2.57 microns, 1.51 microns, 2.50 microns, and 6.47 microns, respectively. Values for pressure values at 0.5 bar, 2.0 bar, and 4.0 bar can be seen in Table 12. In addition, the powder displayed relatively flowrate independent behavior as can be seen from the ratio of ×50 measured at 0.5 bar to ×50 measured at 4.0 bar as shown in Table 12. The values are 1.19, 1.12, 1.47, and 1.62, respectively. The table also includes values for the ratio of 1.0 bar to 4.0 bar, for the sake of comparison to other art, since this is another measure of flowrate dependency.

TABLE 12

Dispersion and Density Properties of Formulations I-A, II-A, III-A

| | Density Tap | ACI-8, Gravimetric | | | Spraytec | HELOS/RODOS | | | |
|---|---|---|---|---|---|---|---|---|---|
| Formulation | density (g/cc) Ave | MMAD (um) Ave | FPF_TD <3.4 um Ave | FPF_TD <5.6 um Ave | Dv50 (um) Ave | Regulator pressure (bar) | x50 (µm) Ave | 0.5 bar/ 4 bar | 1 bar/ 4 bar |
| Formulation I-A | 0.29 | 2.72 | 41.7% | 56.2% | 3.07 | 0.5 | 2.62 | 1.19 | 1.17 |
| | | | | | | 1.0 | 2.57 | | |
| | | | | | | 2.0 | 2.49 | | |
| | | | | | | 4.0 | 2.20 | | |
| Formulation II-A | 0.69 | 2.89 | 39.7% | 55.3% | 1.78 | 0.5 | 1.57 | 1.12 | 1.08 |
| | | | | | | 1.0 | 1.51 | | |
| | | | | | | 2.0 | 1.47 | | |
| | | | | | | 4.0 | 1.40 | | |
| Formulation III-A | 0.34 | 2.59 | 51.5% | 68.7% | 3.05 | 0.5 | 2.59 | 1.47 | 1.42 |
| | | | | | | 1.0 | 2.50 | | |
| | | | | | | 2.0 | 2.17 | | |
| | | | | | | 4.0 | 1.76 | | |
| Placebo (100% leucine) | 0.04 | 4.29 | 17.4% | 32.5% | 21.77 | 0.5 | 7.68 | 1.62 | 1.37 |
| | | | | | | 1.0 | 6.47 | | |
| | | | | | | 2.0 | 5.69 | | |
| | | | | | | 4.0 | 4.74 | | |

EXAMPLE 5

This example describes the dispersion properties and density properties of formulations I-A, II-A, III-A, and Leucine formulation for placebo as summarized in Table 12. All the data found in Table 12 can also be found in FIGS. 1A through 1E. As evidenced by the results shown in Table 12, all formulations are highly dispersible, meaning that their measured volume sizes are relatively independent of pressure on the HELOS/RODOS. As shown in Table 12, the ratio of the volume median sizes obtained at low dispersion pressures (0.5 bar or 1.0 bar) and at a high dispersion pressure (4.0 bar) can be used as an indicator of dispersibility. These values are referred to as the 0.5 bar/4.0 bar ratio or the 1.0 bar/4.0 bar ratio.

The tap density was determined by the modified USP<616> method using a 1.5 cc microcentrifuge tube and the average value for tap density at 1,000 taps were 0.29, 0.69, 0.34, and 0.04 g/cc, respectively. The MMAD, as measured by a full-stage (eight-stage) Andersen Cascade Impactor (ACI), were 2.72, 2.89, 2.59, and 4.29 um, respectively. The FPF below 3.4 um, as measured on a full-stage ACI, were 41.7%, 39.7%, 51.5%, and 17.4%, respectively, and below 5.6 um were 56.2%, 55.3%, 68.7%, and 32.5%, respectively. The volume size was determined by laser diffraction and the average values for the volume median diameter (×50) at a

EXAMPLE 6

This example describes the preparation of dry powders using feedstock Formulations 6.1-6.9 as listed in Table 13 below.

TABLE 13

| Feedstock Formulations 6.1-6.9 | |
|---|---|
| Formulation | Composition and Weight % (w/w) |
| 6.1 | 10.0% leucine, 58.6% calcium lactate, 31.4% sodium chloride |
| 6.2 | 50.0% leucine, 48.4% calcium lactate, 1.6% sodium chloride |
| 6.3 | 10.0% leucine, 66.6% calcium lactate, 23.4% sodium chloride |
| 6.4 | 10.0% leucine, 35.1% calcium chloride, 54.9% sodium citrate |
| 6.5 | 67.1% leucine, 30.0% calcium chloride, 2.9% sodium citrate |
| 6.6 | 39.0% calcium chloride, 61.0% sodium citrate |
| 6.7 | 10.0% leucine, 39.6% calcium chloride, 50.4% sodium sulfate |
| 6.8 | 67.6% leucine, 30.0% calcium chloride, 2.4% sodium sulfate |
| 6.9 | 44.0% calcium chloride, 56.0% sodium sulfate |

The general mode of preparation of the dry powders in this example is similar to what was described for the powders in the above examples with the exception that all of the dry powders in this example were spray dried using a Büchi B-290 spray dryer with High Performance cyclone. Formulations 6.1, 6.4, and 6.7 in this Example correspond to Formulations II-B, I-B, and III-B in the Examples above, respectively.

The physical properties of the powders and/or particles obtained in this example are summarized in the Tables shown in FIGS. 6A and 6B.

Formulations 6.1-6.9 in Table 13 correspond to Formulations 6.1-6.9 in FIGS. 6A and 6B, respectively. In FIG. 6A, x50 and Dv50 refer to volume median diameter or volume median geometric diameter (VMGD); and GSD refers to geometric standard deviation. In FIG. 6B, yield % refers to percentage of the weight of the recovered product in the collection jar attached to the High Performance cyclone divided by the weight of the solutes in the feedstock. All other abbreviations are described elsewhere in the application.

EXAMPLE 7

This example describes the dose emission of powders prepared by feedstock Formulations 6.1-6.9 from a dry powder inhaler at room and elevated conditions. Some of this data is also presented above, in Example 4.

Method: Spray dried powders of the nine feedstock formulations 6.1-6.9 were separately filled into size 2 HPMC capsules (Quali-V, Qualicaps, Whitsett, N.C.) to approximately half full (13-30 mg depending on powder). Capsules were punctured prior to loading into one of four capsule based DPIs in order to ensure adequate hole openings in the capsule. The capsules were loaded horizontally into the inhalers which were then connected to the custom chamber. Each dry powder inhaler had a pressure transducer connected to it to monitor the flow rate through the inhaler during the test. When the test was begun, an airflow of 45 L/min was drawn through each inhaler for 3 short bursts of 0.3 seconds each, separated by 1 minute. During each burst, the air drawn through the inhaler caused the capsule to spin and emit the powder in it into one of 4 sub-chambers which had one row of 3 tissue culture wells forming the floor of the sub-chamber. The aerosol cloud was allowed to settle for one minute before the next subsequent burst for a total of 3 bursts and a total air volume of 0.68 L being drawn through the inhaler. The duration and total airflow rate was controlled with a flow controller (TPK-2000, MSP Corporation, Shoreview, Minn.) and recorded with an air mass flow meter (model#3063, TSI Inc., Shoreview, Minn.). Individual inhaler airflow rates were monitored with pressure sensors (model #ASCX01DN, Honeywell International Inc., Morristown, N.J.) which had been previously calibrated and whose signal was converted to flow rate via a custom Lab-view code. In one case, the custom chamber was located on the lab bench at room conditions, while in another 2 cases it was located in a stability chamber (Darwin Chambers Company, St. Louis, Mo.) set to 37° C. and 90% RH. For the first case in the stability chamber, the capsules were punctured and loaded into inhalers at room conditions, the door of the chamber was opened, the inhalers attached and the flow rate was actuated ~30 seconds after the capsules entered the chamber. In the second case, the capsules were first placed unpunctured in the stability chamber for 3 minutes, then removed from the chamber, punctured and loaded at room conditions, attached in the chamber and actuated within 30 seconds of the second entry into the chamber. Following each test, the capsules were removed from the inhalers and weighed and used to calculate the percentage of powder emitted from the capsule. For each of the 3 sets of conditions, two 12 well tissue culture plates (each plate required 4 capsules in 4 inhalers delivering powder to 3 wells each) were exposed to powder for each of the powder formulations tested, giving a total of 8 capsule emissions for each powder at each temperature and humidity setting.

As shown in Table 14 below, for all nine powder batches (obtained using feedstock Formulations 6.1-6.9) the average amount of powder emitted from the capsule is greater than 98% based on the weight change of the capsule.

TABLE 14

Emitted Dose Percent

| Formulation | Emitted Dose (%) |
|---|---|
| 6.1 | 100.00% |
| 6.2 | 98.86% |
| 6.3 | 99.85% |
| 6.4 | 99.45% |
| 6.5 | 99.68% |
| 6.6 | 100.00% |
| 6.7 | 99.38% |
| 6.8 | 98.05% |
| 6.9 | 100.00% |

EXAMPLE 8

This example describes the results of a short-term stability study that was conducted for the dry powders prepared by feedstock formulations 6.1, 6.4 and 6.7.

An important characteristic of pharmaceutical dry powders is stability at different temperature and humidity conditions. One property that may lead to an unstable powder is the powder's tendency to absorb moisture from the environment, which then will likely lead to agglomeration of the particles, thus altering the apparent particle size of the powder at similar dispersion conditions. Spray dried powders were held at a range of conditions for a periods of one week to three or more months and periodically tested for particle size distribution. Storage conditions included closed capsules in vials at 25° C. and 60% RH, closed capsules in vials at 40° C. and 75% RH, closed capsules at room temperature and 40% RH, open capsules at 30° C. and 65% RH and open capsules at 30° C. and 75% RH. Size 3 HPMC capsules (Quali-V, Qualicaps, Whitsett, N.C.) were half filled with each dry powder. One sample was tested immediately in the Spraytec (Malvern Instruments Inc., Westborough, Mass.), a laser diffraction spray particle sizing system where dry powders can be dispersed from an inhaler using the inhaler cell setup. Approximately 16 capsules were filled with each powder prepared using feedstock solutions 6.1, 6.4 and 6.7. Capsules were kept in the lab at controlled humidity and temperature conditions (~23-28% RH), and also in the outside lab at varying temperature and relative humidity (~40-75% RH). Capsules kept at storage conditions of 25° C. and 60% RH, 40° C. and 75% RH, 30° C. and 65% RH and 30° C. and 75% RH were held in stability chambers (Darwin Chambers Company, St. Louis, Mo.) set at those conditions. At specific time points (ranging from 30 min to 3 months), one to three capsules from each condition were tested on the Spraytec for geometric particle size distribution and the ACI-2 for aerodynamic particle size properties.

Generally, the powders that were in closed capsules in vials remained stable for a long period of time, longer than three months. Powders that were in open capsules with no vials showed agglomeration after exposure to higher humidity conditions. The stability data are summarized in Table 15 below.

TABLE 15

Short-term Stability Data

| | | | closed capsules in vials | | closed capsules, no vials | | open capsules, no vials | | | |
|---|---|---|---|---|---|---|---|---|---|---|
| | | | | | | | Spraytec | ACI-2 | Spraytec | ACI-2 |
| Formulation | Counterion | Excipient | 25 C./60% RH | 40 C./75% RH | Spraytec 40% RH | ACI-2 40% RH | 30 C./65% RH | 30 C./65% RH | 30 C./75% RH | 30 C./75% RH |
| 6.1 | Lactate | 10% Leucine | >3 months | 0.5-1 month | >8 days | 4-6 days | >30 min | >30 min | >30 min | >30 min |
| 6.4 | Citrate | 10% Leucine | >3 months | 1-3 months | >7 days | N/A | >30 min | >30 min | <30 min | >30 min |
| 6.7 | Sulfate | 10% | >3 months | 1-3 months | 2-7 days | N/A | >30 min | >30 min | >30 min | >30 min |

EXAMPLE 9

This example describes a Bacterial Pass-Through Assay performed using dry powders prepared using feedstock formulations A-E.

Method: To test the effect of aerosolized dry powder formulations on bacterial movement across mucus, a pass-through model was used. In this model, 200 µL of 4% sodium alginate (Sigma-Aldrich, St. Louis, Mo.) was added to the apical surface of a 12 mm Costar Transwell membrane (Corning, Lowell, Mass.; 3.0 µm pore size) and subsequently exposed to dry powder formulations. Dry powders were aerosolized into the chamber using a dry powder insufflator (Penn-Century, Inc., Philadelphia, Pa.) and allowed to settle by gravity over a 5 minute period. Following this exposure, 10 µL of *Klebsiella pneumoniae* (~$10^7$ CFU/mL in saline) was added to the apical surface of the mimetic. At various time points after the addition of bacteria, aliquots of the basolateral buffer were removed and the number of bacteria in each aliquot was determined by serially diluting and plating on blood agar plates. A schematic of this method is shown in FIG. 7. The concentration of salt that was delivered to each Transwell was quantified by HPLC. For this purpose, empty wells of the 12 well cell culture plate that were next to each Transwell and were exposed to the same dose of formulation were rinsed with sterile water and diluted 1:1 with acetic acid to solubilize the calcium salts in each powder.

The effect of calcium containing powders on *K. pneumoniae* movement through sodium alginate mucus mimetic was tested. Dry powder formulations comprising calcium salts with different solubility profiles, together with leucine and sodium chloride, were screened for activity. Table 16 (below) lists the feedstock formulations of the powders that were tested. A 50.0% (w/w) leucine loading in the composition was necessary, as opposed to the 10.0% (w/w) leucine loading in the formulations described in the examples above, due to dosing and detection limitations in the pass through model. The calcium and sodium molar ratio was chosen for each formulation to target a 1:1 molar ratio, while not needing to go too low on the relative weights of any particular salt. Therefore, the lactate, citrate, and acetate formulations used were not in a 1:1 molar ratio in order to keep the weights of the sodium chloride and the calcium chloride in those formulations, respectively, above about 10% by weight.

TABLE 16

Feedstock Formulations

| Formulation | Composition (w/w) | Ca:Na mole ratio |
|---|---|---|
| A | 50.0% leucine, 22.0% calcium chloride, 28.0% sodium sulfate | 1.0:2.0 |
| B | 50.0% leucine, 25.5% calcium chloride, 24.5% sodium carbonate | 1.0:2.0 |
| C | 50.0% leucine, 19.5% calcium chloride, 30.5% sodium citrate | 1.0:2.0 |
| D | 50.0% leucine, 37.0% calcium lactate, 13.0% sodium chloride | 1.0:1.3 |
| E | 50.0% leucine, 33.75% calcium acetate, 16.25% sodium chloride | 1.0:1.8 |

Figure 8A:
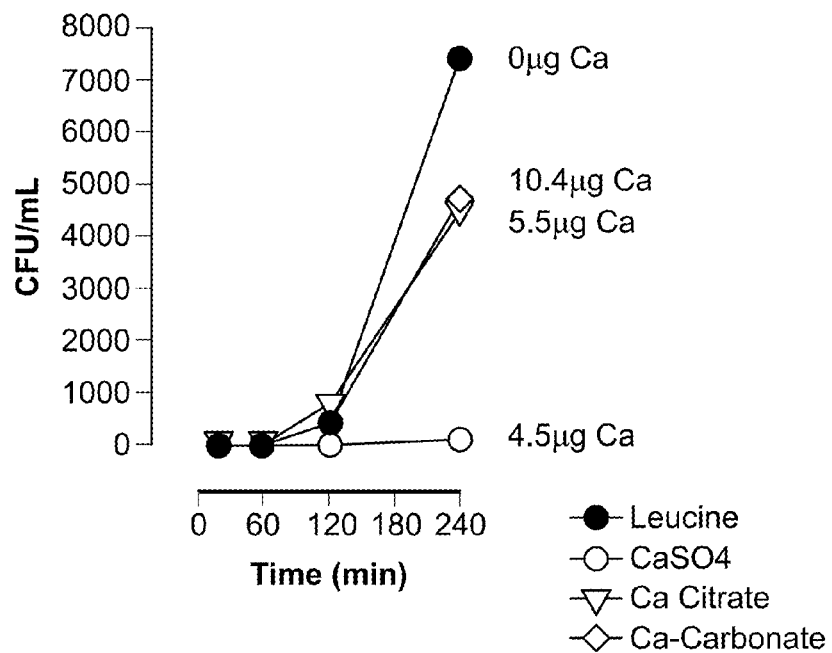
FIG. 8A is a graph showing the results of the bacterial pass-through model with exposure to dry powders. A calcium sulfate-containing powder (4.5 ug Ca/cm$^2$ delivered dose) reduced bacterial movement through sodium alginate mimetic. iii.
Figure 8B:
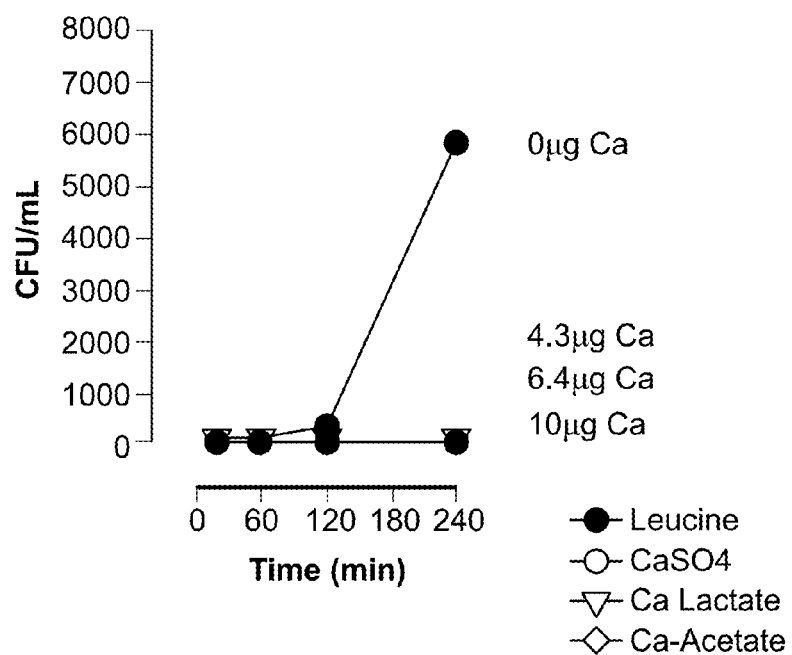
FIG. 8B is a graph showing the results of the bacterial pass-through model with exposure to dry powders. The calcium salt dry powders, prepared from the feedstock formulations A-E, tested contained 0 ug, 4.3 ug, 6.4 ug or 10 ug of calcium. Calcium sulfate (4.3 ug Ca/cm$^2$ delivered dose), calcium acetate (10 ug Ca/cm$^2$ delivered dose) and calcium lactate (6.4 ug Ca/cm$^2$ delivered dose) containing powders reduced bacterial movement through sodium alginate mimetic.

The results for this test are shown in FIGS. 8A and 8B. The two different figures represent two different sets of experiments, run at the same conditions. The leucine control and sulfate data allow for relative comparison between the two sets of experiments. The powders containing the anions sulfate, lactate, and acetate, i.e., the dry powders prepared from feedstock formulations A, D, and E, respectively, reduced the movement of bacteria across the mimetic, whereas the powders containing the anions carbonate and citrate, i.e., dry powders prepared from feedstock formulations B and C, exhibited no effect. These finding correlated with the known solubility of the calcium salts in water, suggesting that the possible failure of carbonate and citrate salts to inhibit the movement of *K. pneumoniae* could be related to the solubility of these powders at the surface of the sodium alginate mimetic. This conclusion is also based on the plausible assumption that the ion exchange reaction described previously goes to completion during spray drying, and that the form of the calcium salt in Formulations A through E is calcium sulfate, calcium carbonate, calcium citrate, calcium lactate, and calcium acetate, respectively. The solubility of these salts from least soluble to most soluble: calcium carbonate<calcium citrate<calcium sulfate<calcium lactate<calcium acetate. (See Table 1 above.)

EXAMPLE 10

This example describes the performance of dry powders in reducing viral replication utilizing a viral replication model.

In this example, a series of dose response studies with different dry powder prepared from feedstock formulations consisting of different calcium salts are described. Dry powders were made with leucine, a calcium salt (lactate or chloride), and sodium salt (chloride, sulfate, citrate or carbonate). Feedstock formulations listed 10-1, 10-2 and 10-3 were spray dried on a Man B-290 mini spray dryer. The system used the Man B-296 dehumidifier to ensure stable temperature and humidity of the air used to spray dry. Feedstock Formulation 10-4 was spray dried on a Niro Mobile Minor Spray Dryer in an open cycle with nitrogen.

Four liquid feedstocks were prepared with the following components and ratios (weight percentage) as listed in Table 17.

TABLE 17

Feedstock Formulations

| Formulation | Feedstock Composition (w/w) | Lot Number | Ca:Na mole ratio |
|---|---|---|---|
| 10-1 | 50.0% leucine, 37.0% calcium lactate, 13.0% sodium chloride | 45.6.1 | 1.0:1.3 |
| 10-2 | 50.0% leucine, 22.0% calcium chloride, 28.0% sodium sulfate | 27.155.1 | 1.0:2.0 |
| 10-3 | 50.0% leucine, 19.5% calcium chloride, 30.5% sodium citrate | 27.156.1 | 1.0:2.0 |
| 10-4 | 50.0% leucine, 25.5% calcium chloride, 24.5% sodium carbonate | 26.019.1 | 1.0:2.0 |

A 50.0% (w/w) leucine loading in the composition was necessary, as opposed to the 10.0% (w/w) leucine loading in the formulations described in the examples above, due to dosing and detection limitations in the viral replication model. The calcium and sodium mole ratio was chosen for each formulation to target a 1:1 molar ratio, while not needing to go too low on the relative weights of any particular salt. Therefore, the lactate and citrate formulations used were not in a 1:1 mole ratio in order to keep the weights of the sodium chloride and the calcium chloride in those formulations, respectively, above about 10% by weight.

Formulations 10-1, 10-2 and 10-3 were spray dried with feedstock solids concentrations of 5 g/L, while the exact amount of salts and excipient dissolved in ultrapure water and its specific volume varied. The following process settings were used: inlet temperature of 220° C., liquid flow rate of approximately 10 mL/min, room conditions at 23.2-24.6° C. and 19-21% RH, and dehumidifier air at 3-5° C. and 30% RH. The outlet temperature, cyclone and aspirator rate varied. Formulation 10-1 was spray dried using a high performance cyclone with the aspirator at 80% and an outlet temperature of 93° C. Dry powder formulations 10-2 and 10-3 were made with the regular cyclone, an aspirator at 100% and an outlet temperature of 111-115° C. Formulation 10-4 was spray dried with a solids concentration of 2.7 g/L and the following process settings: inlet temperature of 140° C., outlet temperature of 75° C., liquid feedstock flowrate of 30 mL/min, process gas flowrate of 100 kg/hr, atomizer gas flowrate of 20 g/min and a spray drying drum chamber pressure of −2 "WC.

A cell culture model of Influenza infection was used to study the effects of Formulations 1 through 4. Calu-3 cells (American Type Culture Collection, Manasas, Va.) were cultured on permeable membranes (12 mm Transwells; 0.4 µm pore size, Corning Lowell, Mass.) until confluent (the membrane was fully covered with cells) and air-liquid interface (ALI) cultures were established by removing the apical media and culturing at 37° C./5% $CO_2$. Cells were cultured for >2 weeks at ALI before each experiment. Prior to each experiment the apical surface of each Transwell was washed 3× with PBS (Hyclone, Logan, Utah). Calu-3 cells were exposed to dry powders using a proprietary dry powder sedimentation chamber. In order to expose cells to equivalent doses of calcium, capsules were filled with different amounts of each powder. The high, medium, and low fill weights were calculated based on matching the amount of calcium delivered by each powder (4.23 mg, 1.06 mg, and 0.35 mg). For each dry powder condition tested, two capsules were weighed as empty, filled, and after exposure in order to determine emitted dose of the powder. Table 18 (below) shows the capsule fill weights before and after exposure and the concentration of calcium delivered to cells as determined by HPLC measurements. Immediately after exposure, the basolateral media (media on the bottom side of the Transwell) was replaced with fresh media. Triplicate wells were exposed to dry powders from each feedstock formulation in each test. A second cell culture plate was exposed to the same dry powders from the feedstock formulations to quantify the delivery of total salt or calcium to cells. One hour after exposure, cells were infected with 10 µL of Influenza A/WSN/33/1 (H1N1) or Influenza A/Panama/2007/99 (H3N2) at a multiplicity of infection of 0.1-0.01 (0.1-0.01 virions per cell). Four hours after aerosol treatment, the apical surfaces were washed to remove excess dry powders and unattached virus and cells were cultured for an additional 20 h at 37° C. plus 5% $CO_2$. Twenty-four hours after aerosol treatment, virus released onto the apical surface of infected cells was collected in culture media or PBS and the concentration of virus in the apical wash was quantified by $TCID_{50}$ (50% Tissue Culture Infectious Dose) assay. The $TCID_{50}$ assay is a standard endpoint dilution assay that is used to quantify how much of a virus is present in a sample.

TABLE 18

Dry powder, prepared from feedstock formulations 10-1 to 10-4, tested to evaluate their effect on Influenza A/WSN/33/1 infection in a cell culture model. Dry powder formulations were tested to evaluate their effect on Influenza A/WSN/33/1 infection in a cell culture model. To deliver an equivalent amount of calcium ion ($Ca^{+2}$), the desired fill weight was calculated for each dry powder formulation. Qualicap capsules were weighed empty, filled, and after exposure to determine the emitted dose. Triplicate wells were exposed to each capsule and after wells were washed. HPLC analysis of these samples determined the amount of $Ca^{+2}$ delivered to cells.

| Feedstock Formulation (for Dry Powders) | Intended Fill (mg) | Empty Capsule (mg) | Filled Capsule (mg) | Capsule after Exposure (mg) | Calcium ion concentration determined by HPLC (µg/cm²) |
|---|---|---|---|---|---|
| 10-2 (50.0% leucine, 22.0% calcium chloride, 28.0% sodium sulfate) | 53.18 | 31.7 | 83.0 | 31.9 | 20.5 ± 0.7[a] |
| | 13.29 | 32.5 | 45.9 | 33.9 | 5.8[b] |
| | 4.43 | 33.3 | 38.4 | 33.9 | 2.8[b] |
| 10-1 (50.0% leucine, 37.0% calcium lactate, 13.0% sodium chloride) | 62.17 | 64.972, 63.122* | 99.649, 98.881* | 64.994, 63.679* | 50.9 ± 1.1[a] |
| | 15.54 | 63.525 | 81.926 | 68.141 | 12.7 ± 1.7[a] |
| | 5.18 | 62.453 | 67.796 | 62.49 | 4.0[b] |

TABLE 18-continued

Dry powder, prepared from feedstock formulations 10-1 to 10-4, tested to evaluate their effect on Influenza A/WSN/33/1 infection in a cell culture model. Dry powder formulations were tested to evaluate their effect on Influenza A/WSN/33/1 infection in a cell culture model. To deliver an equivalent amount of calcium ion ($Ca^{+2}$), the desired fill weight was calculated for each dry powder formulation. Qualicap capsules were weighed empty, filled, and after exposure to determine the emitted dose. Triplicate wells were exposed to each capsule and after wells were washed. HPLC analysis of these samples determined the amount of $Ca^{+2}$ delivered to cells.

| Feedstock Formulation (for Dry Powders) | Intended Fill (mg) | Empty Capsule (mg) | Filled Capsule (mg) | Capsule after Exposure (mg) | Calcium ion concentration determined by HPLC ($\mu g/cm^2$) |
|---|---|---|---|---|---|
| 10-3 (50.0% leucine, 19.5% calcium chloride, 30.5% sodium citrate) | 60.0<br>14.99<br>5.00 | 64.4<br>64.0<br>63.5 | 123.6<br>78.5<br>70.3 | 81.994<br>65.388<br>63.829 | 20.5 ± 5.7[a]<br>7.6 ± 0.9[a]<br>3.6 ± 1.5[a] |
| 10-4 (50.0% leucine, 25.5% calcium chloride, 24.5% sodium carbonate) | 45.88<br>11.47<br>3.82 | 64.6<br>61.5<br>61.8 | 104.7<br>72.0<br>62.6 | 66.685<br>63.186<br>63.341 | 28.1 ± 7.3[a]<br>8.1 ± 2.6[a]<br>5.62 ± 2.7[a] |

*denotes the use of two capsules in order to achieve desired fill weight.
[a]denotes n = 3,
[b]denotes n = 1

EXAMPLE 10A

Dry powders, prepared from feedstock formulations 10-1 to 10-4, reduce Influenza A/WSN/33/1 (H1N1) infection in a dose-dependent manner.

To test the effect of dry powder formulations on Influenza infection in a cell culture model Calu-3 cells were exposed to four different dry powder formulations each consisting of 50% leucine, a calcium salt and sodium chloride. Viral infection was assessed by quantifying the amount of viral replication over a 24 h period. The specific powders tested are listed in Table 18 (above), and included carbonate, lactate, sulfate and citrate salts. In an attempt to expose cells to equivalent amounts of calcium of each of the four calcium containing powders, capsules were filled to appropriate fill weights prior to dosing. Cells exposed to no formulation (Air) were used as control cells.

Figure 9:
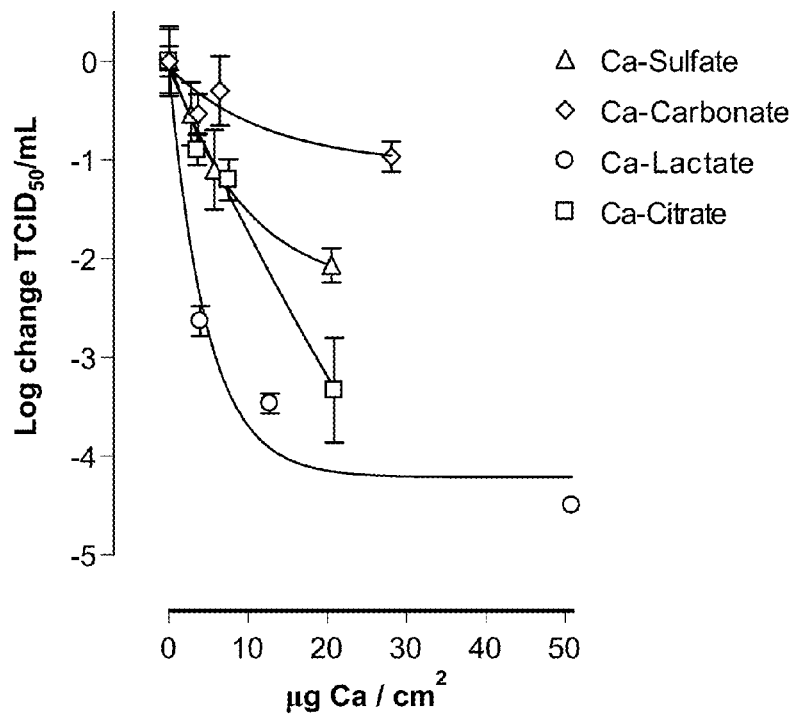
FIG. 9 is a graph that shows the effect of the respirable dry powders, prepared from feedstock formulations 10-1 to 10-4 in Example 10A, on Influenza A/WSN/33 (H1N1) infection in a dose-dependent manner.

As seen in FIG. 9, each powder exhibited a dose-responsive reduction in influenza infection; however, the magnitude of the effect was different among the four powders tested. At low calcium concentrations calcium lactate was most efficacious suggesting that it was the most potent of the powders tested. At higher concentrations of calcium, the calcium lactate and calcium citrate powders exhibited similar efficacy. Additional testing of the calcium citrate powder at even higher concentrations may demonstrate that it is the most efficacious powder. The calcium sulfate powder exhibited an intermediate effect and was comparable to calcium citrate at several concentrations. Calcium carbonate had only a minimal effect on viral replication even at the highest concentration (less than 10-fold). Of note, calcium carbonate is the least soluble of the powders tested.

As shown in FIG. 9, the dry powders prepared for this reduce Influenza infection in a dose-dependent manner. Calu-3 cells exposed to no formulation were used as a control and compared to Calu-3 cells exposed to dry powder formulations at different fill weights. The concentration of virus released by cells exposed to each aerosol formulation was quantified. Bars represent the mean and standard deviation of triplicate wells for each condition. Data were analyzed statistically by one way ANOVA and Tukey's multiple comparison post-test.

EXAMPLE 10B

Dry powder, prepared from feedstock formulations 10-1 to 10-4 in Table 19, reduce Influenza A/Panama/2007/99 (H3N2) infection in a dose-dependent manner.

To extend these studies, the same powders were tested with a second influenza strain [Influenza A/Panama/2007/99 (H3N2)]. Similar to Example 10A, Calu-3 cells were exposed to four different dry powder formulations each consisting of 50% leucine, a calcium salt and sodium chloride. Viral infection was assessed by quantifying the amount of viral replication over a 24 h period. The specific powders tested are listed in Table 19 (below) and included carbonate, lactate, sulfate and citrate salts. In an attempt to expose cells to equivalent amounts of calcium of each of the four calcium containing powders, capsules were filled to appropriate fill weights prior to dosing. Cells exposed to no formulation (Air) were used as control cells.

Figure 10:
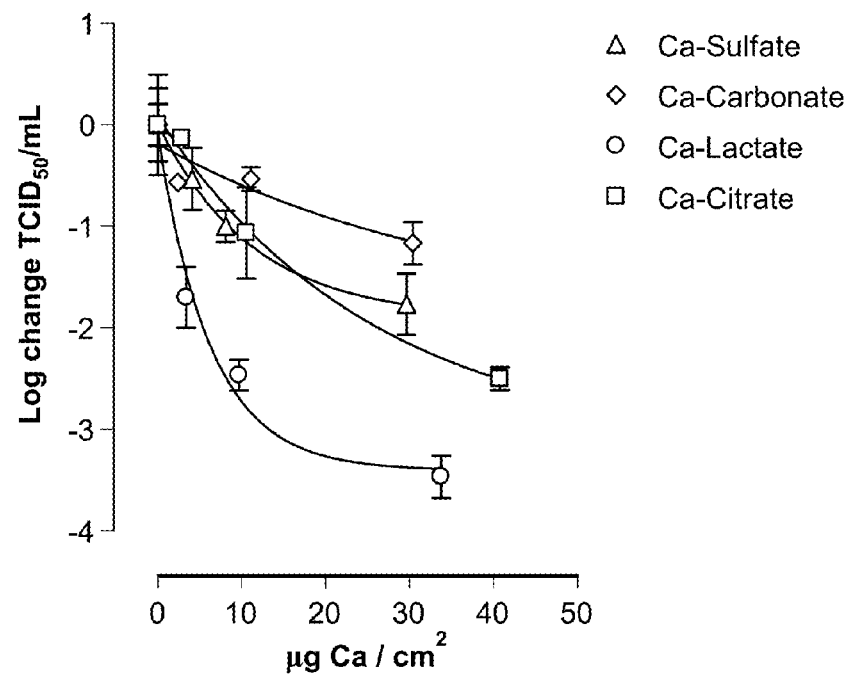
FIG. 10 is a graph that shows the effect of the respirable dry powders prepared for Example 10B on Influenza A/Panama/99/2007 (H3N2) infection in a dose-dependent manner.

As seen in FIG. 10, using this strain, similar efficacy was observed for each powder: calcium lactate was the most efficacious, calcium citrate and calcium sulfate exhibited intermediate efficacy and the calcium carbonate powder was only minimally efficacious. These data support the broad activity of Ca:Na dry powders against multiple influenza strains.

TABLE 19

Dry powders, prepared from feedstock formulations 10-1 to 10-4, tested to evaluate their effect on Influenza A/Panama/99/2007 (H3N2) infection in a cell culture model. To deliver an equivalent amount of $Ca^{+2}$, the desired fill weight was calculated for each dry powder formulation. Qualicap capsules were weighed empty, filled, and after exposure to determine the emitted dose. Triplicate wells were exposed to each capsule and after wells were washed. HPLC analysis of these samples determined the amount of $Ca^{+2}$ delivered to cells.

| Feedstock Formulation (for Dry Powders) | Desired Fill (mg) | Empty Capsule (mg) | Filled Capsule (mg) | Capsule after Exposure (mg) | Calcium ion concentration determined by HPLC ($\mu g/cm^2$ ± SD)[a] |
|---|---|---|---|---|---|
| 10-2 (50.0% leucine, 22.0% calcium chloride, 28.0% sodium sulfate) | 53.18<br>13.29<br>4.43 | 61.358<br>60.602<br>65.102 | 121.417<br>76.804<br>70.789 | 62.591<br>62.167<br>65.670 | 40.8 ± 5.0<br>10.5 ± 2.3<br>2.9 ± 0.6 |
| 10-1 (50.0% leucine, 37.0% calcium lactate, 13.0% sodium chloride) | 62.17<br>15.54<br>5.18 | 64.037<br>65.358<br>66.046 | 125.465<br>82.474<br>72.455 | 67.043<br>65.632<br>66.324 | 33.8 ± 3.5<br>9.7 ± 1.4<br>3.4 ± 0.9 |

TABLE 19-continued

Dry powders, prepared from feedstock formulations 10-1 to 10-4, tested to evaluate their effect on Influenza A/Panama/99/2007 (H3N2) infection in a cell culture model. To deliver an equivalent amount of $Ca^{+2}$, the desired fill weight was calculated for each dry powder formulation. Qualicap capsules were weighed empty, filled, and after exposure to determine the emitted dose. Triplicate wells were exposed to each capsule and after wells were washed. HPLC analysis of these samples determined the amount of $Ca^{+2}$ delivered to cells.

| Feedstock Formulation (for Dry Powders) | Desired Fill (mg) | Empty Capsule (mg) | Filled Capsule (mg) | Capsule after Exposure (mg) | Calcium ion concentration determined by HPLC ($\mu g/cm^2 \pm SD$)[a] |
|---|---|---|---|---|---|
| 10-3 (50.0% leucine, 19.5% calcium chloride, 30.5% sodium citrate) | 60.0 | 62.581 | 108.035 | 63.841 | 29.6 ± 10.1 |
|  | 14.99 | 63.393 | 75.770 | 64.085 | 8.1 ± 1.4 |
|  | 5.00 | 65.910 | 70.062 | 66.204 | 4.1 ± 0.8 |
| 10-4 (50.0% leucine, 25.5% calcium chloride, 24.5% sodium carbonate) | 45.88 | 64.506 | 115.876 | 65.004 | 30.4 ± 11.9 |
|  | 11.47 | 64.319 | 77.627 | 65.080 | 11.1 ± 4.3 |
|  | 3.82 | 66.495 | 71.398 | 66.698 | 2.4 ± 1.0 |

As shown in FIG. 10, the dry powders prepared for this Example reduce Influenza A/Panama/99/2007 (H3N2) infection in a dose-dependent manner. Calu-3 cells exposed to no formulation (0 μg $Ca^{2+}/cm^2$) were used as a control and compared to Calu-3 cells exposed to dry powder formulations at different fill weights and therefore different concentrations of calcium. The concentration of calcium delivered to cells in each experiment for each fill weight was determined using HPLC measurements of calcium in washes from empty plates exposed to each condition. The concentration of virus released by cells exposed to each aerosol formulation 24 h after dosing was quantified by $TCID_{50}$ assay. Each data point represents the mean and standard deviation of triplicate wells for each condition.

EXAMPLE 11

In Vivo Influenza Model

This example demonstrates that dry powder formulations comprised of calcium salts and sodium chloride reduce the severity of influenza infection in ferrets. The formulations tested are shown in Table 20. Control ferrets were exposed to a powder comprised of 100% leucine under the same exposure conditions. In preliminary in vitro studies, this control powder had no effect on viral replication. Calcium powders and control (Formulation I lot: 26-190-F, Formulation III lot: 65-009-F, Formulation II lot: 65-003-F and Leucine lot: 65-017-F) were aerosolized with a Palas Rotating Brush Generator 1000 solid particle disperser (RBG, Palas GmbH, Karlsruhe, Germany). Ferrets (n=8 per group) were exposed to ~0.2 mg Ca/kg and the severity of infection was evaluated over time. Each formulation was dispersed in a nose-only exposure system 1 hour before infection, 4 hours after infection and then BID for 4 days (d1-4). The study was terminated on day 10. Body temperatures were determined twice a day beginning on day 0 of the study. Ferrets infected with influenza typically show increases in body temperature within 2 days of infection, drop body weight over the course of the study and show clinical signs of infection such as lethargy and sneezing. These changes coincide with an increase in influenza viral titers shed from the nasal cavity and increases in nasal inflammation.

TABLE 20

Formulations tested for efficacy in ferrets

| Formulation | Composition |
|---|---|
| Formulation I | 10.0% leucine, 35.1% calcium chloride, 54.9% sodium citrate (Active with 12.7% calcium ion) |
| Formulation II | 10.0% leucine, 39.6% calcium chloride, 50.4% sodium sulfate (Active with 14.3% calcium ion) |
| Formulation III | 10.0% leucine, 58.6% calcium lactate, 31.4% sodium chloride (Active with 10.8% calcium ion) |

Figure 11A:
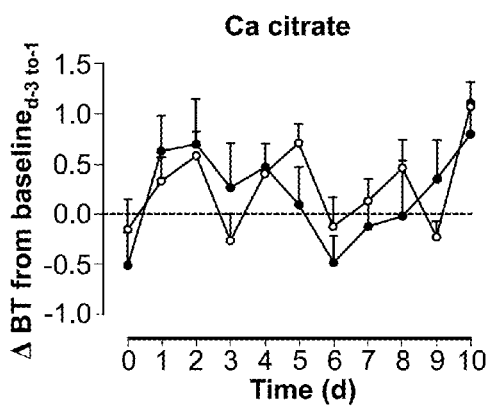
FIGS. 11A-D are graphs showing that dry powder formulations comprised of calcium salts and sodium chloride reduce the severity of influenza in ferrets.
Figure 11B:
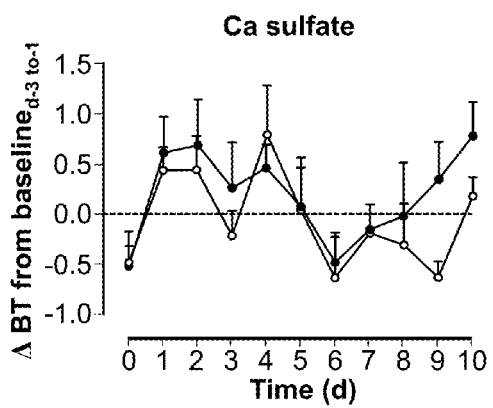
Figure 11C:
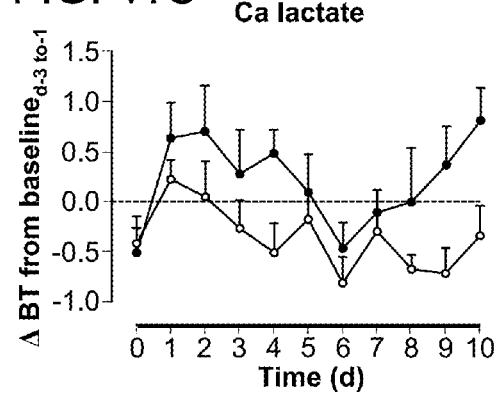
Figure 11D:
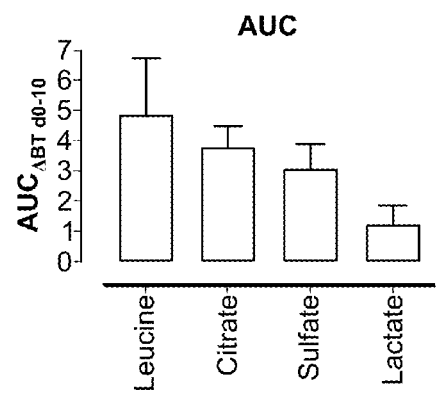

On study day −4, ferrets were implanted with a microchip subcutaneously in the right rear flank and another in the shoulder for redundancy. The transponder chip (IPTT-300 Implantable Programmable Temperature and Identification Transponder; Bio Medic Data Systems, Inc, Seaford, Del. 19973) allows for ferret identification and provides subcutaneous body temperature data throughout the study using a BMDS electronic proximity reader wand (WRS-6007; Biomedic Data Systems Inc, Seaford, Del.). Subcutaneous body temperatures taken on day −3 to −1 were used as baseline temperatures and used to calculate the change from baseline for each animal over the course of the study. Treatment with a dry powder formulation comprised of leucine (excipient), Ca-lactate (Formulation III), and NaCl had a significant impact on body temperature increases (FIG. 11C). The mean body temperature changes in this group remained at or below baseline measurements for the course of the study and the area under the curve (AUC) measurements were approximately 5-fold lower than the control (FIG. 11D). The two other powders tested exhibited less pronounced efficacy that was limited to differences from the control on specific days of the study. In particular, both the Ca citrate and Ca sulfate treated groups had lower body temperatures than the control animals on day 3 of the study (FIGS. 11A and 11B, respectively) and the Ca sulfate group had lower body temperatures over the final three days of the study.

EXAMPLE 12

This example demonstrates that dry powder formulations comprised of different excipients reduce influenza infection, but at higher doses than formulations comprised of leucine.

To assess the impact of the excipient on efficacy in vitro we tested two dry powder formulations (Table 21) that varied in excipient and compared their efficacy to Formulation III (containing leucine) using the influenza replication model. These formulations contained the same concentration of calcium lactate and sodium chloride and the same weight percentage of excipient (10%).

TABLE 21

Formulations used to evaluate efficacy against multiple influenza viruses and to test different excipients

| Lot # | Formulation | Composition | Ca:Na molar ratio | Manufacturing |
|---|---|---|---|---|
| 26-190-F | Formulation I | 10.0% leucine, 35.1% calcium chloride, 54.9% sodium citrate (Active with 12.7% calcium ion) | 1:2 | Niro |
| 65-003-F | Formulation II | 10.0% leucine, 39.6% calcium chloride, 50.4% sodium sulfate (Active with 14.3% calcium ion) | 1:2 | Niro |
| 65-009-F | Formulation III | 10.0% leucine, 58.6% calcium lactate, 31.4% sodium chloride (Active with 10.8% calcium ion) | 1:2 | Niro |
| 45.137.2 | N/A | 10.0% marmitol, 58.6% calcium lactate, 31.4% sodium chloride (Active with 10.8% calcium ion) | 1:2 | Büchi |
| 45.137.3 | Formulation XIV | 10.0% maltodextrin, 58.6% calcium lactate, 31.4% sodium chloride (Active with 10.8% calcium ion) | 1:2 | Büchi |

Figure 12:
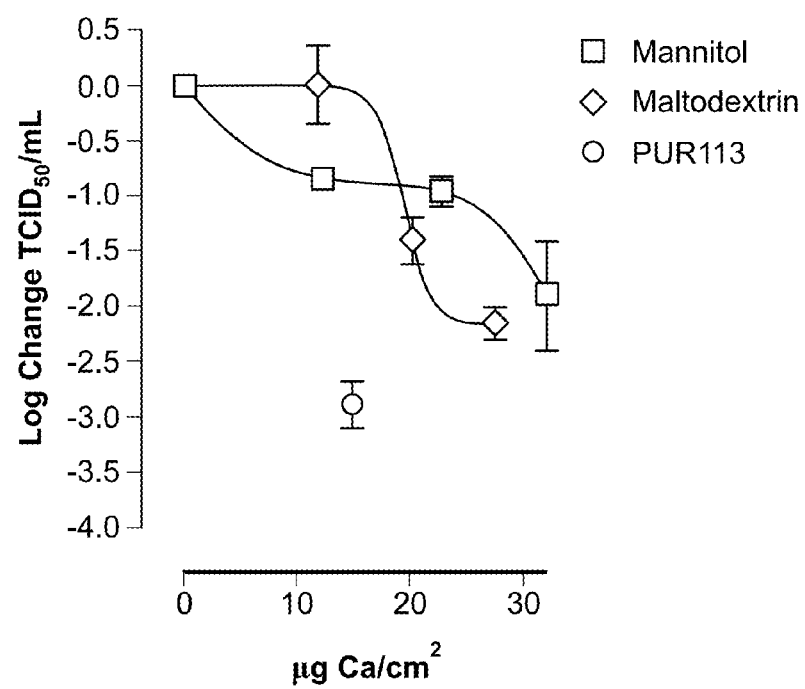
FIG. 12 is a graph showing dry powder formulations consisting of different excipients (mannitol, maltodextrin) with calcium lactate and sodium chloride reduced influenza titer at higher concentrations than the Formulation III powder alone.

Calu-3 cells exposed to no formulation were used as a control and compared to Calu-3 cells exposed to dry powder comprised of calcium lactate and sodium chloride with different excipients. Three different fill weights of the mannitol and maltodextrin powders were used to cover a dose range between 10 to 30 µg Ca2+/cm2. The concentration of virus released by cells exposed to each aerosol formulation was quantified (FIG. 12). Each data point represents the mean and standard deviation of duplicate wells for each concentration. Data were analyzed by one-way ANOVA and Tukey's multiple comparisons post-test. The data for the low dose of each powder is representative of two independent experiments.

Both the mannitol and maltodextrin containing formulations reduced influenza infection in a dose responsive manner, however, they were significantly less potent than the leucine containing powder. At a dose of 14.8 µg $Ca^{2+}/cm^2$, the leucine containing powder reduced influenza infection by $2.9 \pm 0.2$ $\log_{10}$ $TCID_{50}/mL$, whereas the mannitol powder at a comparable dose (12.2 µg $Ca^{2+}/cm^2$) reduced infection by $0.85 \pm 0.0$ $\log_{10}$ $TCID_{50}/mL$ and the maltodextrin powder (11.9 µg $Ca^{2+}/cm^2$) had no effect on replication (FIG. 12). Even at higher doses (>27 µg $Ca^{2+}/cm^2$), the maximal reduction for mannitol ($1.9 \pm 0.50$ log 10 $TCID_{50}/mL$) and maltodextrin ($2.2 \pm 0.14$ $\log_{10}$ $TCID_{50}/mL$) was less than that of the leucine powder. Of note, previous testing using powders comprised of 100% leucine found no effect of the excipient alone on viral replication. These data suggest that the nature of the excipient can impact the efficacy of calcium containing formulations.

EXAMPLE 13

This example demonstrates the efficacy of dry powder formulations comprising calcium salt, calcium lactate, calcium sulfate or calcium citrate powders with respect to treatment of influenza, parainfluenza or rhinovirus.

The Formulation I, Formulation II, and Formulation III powders were produced by spray drying utilizing a Mobile Minor spray dryer (Niro, GEA Process Engineering Inc., Columbia, Md.). All solutions had a solids concentration of 10 g/L and were prepared with the components listed in Table 22. Leucine and calcium salt were dissolved in DI water, and leucine and sodium salt were separately dissolved in DI water with the two solutions maintained in separate vessels. Atomization of the liquid feed was performed using a co-current two-fluid nozzle (Niro, GEA Process Engineering Inc., Columbia, Md.). The liquid feed was fed using gear pumps (Cole-Parmer Instrument Company, Vernon Hills, Ill.) into a static mixer (Charles Ross & Son Company, Hauppauge, N.Y.) immediately before introduction into the two-fluid nozzle. Nitrogen was used as the drying gas and dry compressed air as the atomization gas feed to the two-fluid nozzle. The process gas inlet temperature was 282° C. and outlet temperature was 98° C. with a liquid feedstock rate of 70 mL/min. The gas supplying the two-fluid atomizer was approximately 14.5 kg/hr. The pressure inside the drying chamber was at −2 "WC. Spray dried product was collected in a container from a filter device.

TABLE 22

Formulations used to evaluate efficacy against different respiratory viruses

| Lot # | Formulation | Composition | Ca:Na molar ratio | Manufacturing |
|---|---|---|---|---|
| 26-190-F | Formulation I | 10.0% leucine, 35.1% calcium chloride, 54.9% sodium citrate (Active with 12.7% calcium ion) | 1:2 | Niro |
| 65-003-F | Formulation III | 10.0% leucine, 39.6% calcium chloride, 50.4% sodium sulfate (Active with 14.3% calcium ion) | 1:2 | Niro |
| 65-009-F | Formulation II | 10.0% leucine, 58.6% calcium lactate, 31.4% sodium chloride (Active with 10.8% calcium ion) | 1:2 | Niro |

A cell culture model of Influenza A/Panama/2007/99, human parainfluenza type 3 (hPIV3) or Rhinovirus (Rv16) infection was used to evaluate the efficacy of dry powder formulations. This model has been described in detail previously (See, Example 10) and utilizes Calu-3 cells grown at air-liquid interface as a model of influenza infection of airway epithelial cells. Calu-3 cells were exposed to dry powders using a dry powder sedimentation chamber. The amount of calcium ion (Ca2+) delivered to each well was determined by HPLC using dry powder recovered from an empty well in the cell culture plate. The concentration of calcium deposited in each study is shown in Table 23.

TABLE 23

Calcium Deposition

| | Formulation I (µg Ca/cm$^2$) | | | Formulation III (µg Ca/cm$^2$) | | | Formulation II (µg Ca/cm$^2$) | | |
|---|---|---|---|---|---|---|---|---|---|
| | Low | Medium | High | Low | Medium | High | Low | Medium | High |
| Influenza | 12.74 | 17.12 | 28.85 | 11.37 | 15.84 | 27.73 | 10.93 | 16.01 | 26.61 |
| Parainfluenza | 10.58 | 16.19 | 25.04 | 12.26 | 15.71 | 25.32 | 11.03 | 16.81 | 26.33 |
| Rhinovirus | 11.63 | 16.25 | 24.11 | 10.86 | 15.01 | 23.89 | 11.49 | 15.22 | 24.69 |

One hour after exposure, cells were infected with 10 µL of Influenza A/Panama/99/2007 at a multiplicity of infection of 0.1-0.01 (0.1-0.01 virions per cell), human parainfluenza type 3 (hPIV3) at a multiplicity of infection of 0.1-0.01 (0.1-0.01 virions per cell), or 10 µL of rhinovirus (Rv16) at a multiplicity of infection of 0.1-0.01 (0.1-0.01 virions per cell). Four hours after dry powder treatment, the apical surfaces were washed to remove excess formulation and unattached virus, and cells were cultured for an additional 20 hours at 37° C. plus 5% $CO_2$. The next day (24 hours after infection) virus released onto the apical surface of infected cells was collected in culture media and the concentration of virus in the apical wash was quantified by $TCID_{50}$ (50% Tissue Culture Infectious Dose) assay. The $TCID_{50}$ assay is a standard endpoint dilution assay that is used to quantify how much of a given virus is present in a sample. For each of the three powders, Calu-3 cells were exposed to three different $Ca^{2+}$ doses and the replication of each virus was assessed.

Influenza

Figure 13A:
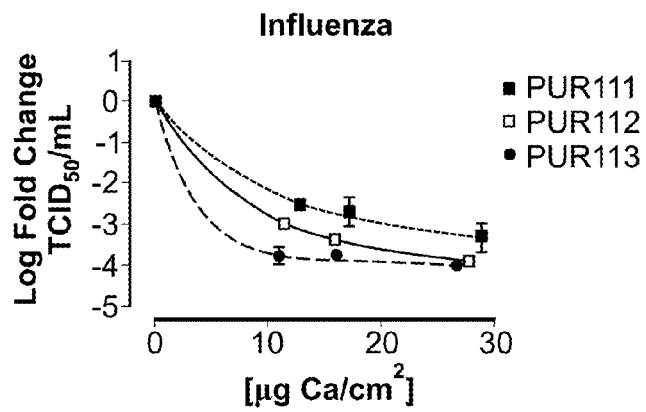
FIGS. 13A-C are graphs showing calcium dry powder formulations vary in efficacy against different viral pathogens. Calu-3 cells exposed to no formulation were used as a control and compared to Calu-3 cells exposed to Formulation I, Formulation II, and Formulation III. The concentration of virus released by cells exposed to each aerosol formulation was quantified. Symbols represent the mean and standard deviation of duplicate wells for each test.

In the influenza model, all three powders significantly reduce viral titer to comparable levels at the highest dose tested: Formulation I, Formulation III, and Formulation II reduced viral titer up to 3.25, 3.80, and 3.95 $\log_{10}$ $TCID_{50}$/mL, respectively (FIG. 13A). It is important to note that while at the highest dose tested these powders exhibited similar activity against influenza, at lower doses the data suggests the most efficacious powder was Formulation II (comprised of leucine, calcium lactate and sodium chloride). Formulation II reduced viral titers 3.70 and 3.75 $\log_{10}$ $TCID_{50}$/mL at low and medium doses, whereas low doses of Formulation I and Formulation III reduced viral titer 2.50 and 2.95 $\log_{10}$ $TCID_{50}$/mL, and mid doses of Formulation I and Formulation III reduced viral titers 2.65 and 3.30 $\log_{10}$ $TCID_{50}$/mL, respectively.

Parainfluenza

Figure 13B:
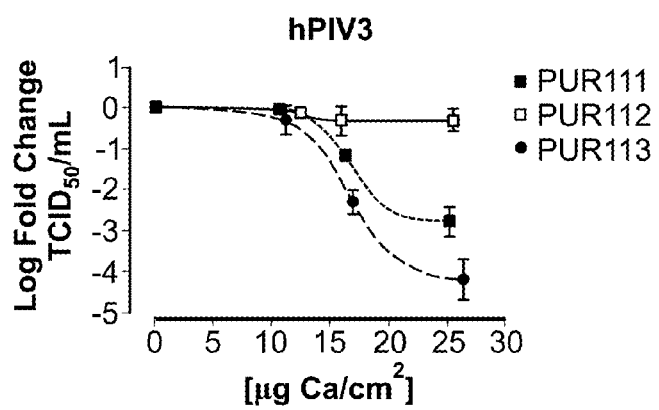

Formulation I, Formulation II, and Formulation III were tested over a similar dose range against parainfluenza. The parainfluenza titer in the Formulation III treated cell cultures was comparable to the control cells (FIG. 13B) at doses of calcium similar to those used in the influenza experiment, indicating that the calcium sulfate based formulation may exhibit activity only against specific pathogens. In contrast, Formulation I and Formulation II treatment resulted in a dose dependent reduction in parainfluenza infection. At high doses, Formulation I and Formulation II reduced infection by 2.70 and 4.10 $\log_{10}$ $TCID_{50}$/mL, respectively, compared to the control cells. Similarly, Formulation II exhibited greater efficacy than Formulation I at the middle dose tested, however, neither formulation reduced infection at the lowest dose tested (FIG. 13B; Table 25). Collectively, these data demonstrate that calcium based dry powder formulations effectively reduce the infectivity of parainfluenza. These effects are specific to certain calcium salts and the efficacious dose ranges differ significantly from that observed for influenza.

Rhinovirus

Figure 13C:
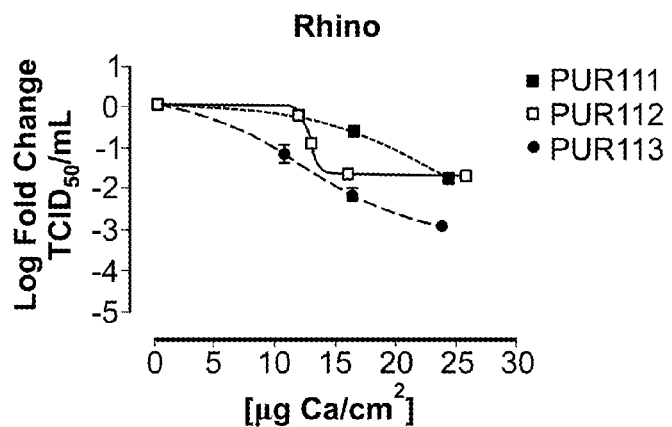

Influenza and parainfluenza are enveloped viruses. To test the broad spectrum activity of calcium dry powder formulations and extend these findings to nonenveloped viruses, the same powders were tested against rhinovirus. All three formulations reduced rhinovirus to some extent, with the Formulation II powder demonstrating the greatest activity (FIG. 13C). Formulation II treatment resulted in a significant, 2.80 $\log_{10}$ $TCID_{50}$/mL viral reduction at the highest dose tested. Low and medium doses of this powder reduced titer 1.15 and 2.10 $\log_{10}$ $TCID_{50}$/mL, respectively, compared to control cells. Formulation I and Formulation III treatment also reduced rhinovirus infection, albeit to a lesser extent than Formulation II. At the highest dose tested, Formulation I reduced infection by 1.70 $\log_{10}$ $TCID_{50}$/mL and Formulation III reduced infection 1.60 $\log_{10}$ $TCID_{50}$/mL. Together these results indicate that calcium based dry powder formulations can be broadly applied to diverse viral infections.

The above data suggests that by increasing the delivered dose of calcium dry powder formulations exhibit more activity than was previously observed at lower doses. Influenza infection was reduced by all three powders tested, although the calcium lactate based formulation (Formulation II) exhibited greater potency than the calcium sulfate (Formulation III) and calcium citrate (Formulation III) formulations. Additionally, across all three viral strains, Formulation II treatment resulted in the greatest reduction in viral titer. At higher doses Formulation I effectively reduced viral titer in all three viral strains, but the effect was much more pronounced with influenza and parainfluenza, suggesting a difference in mechanism that may be related to viral strain specificity. Formulation III treatment was active against parainfluenza, but exhibited better activity against both influenza and rhinovirus, suggesting that the specific calcium counterions may have some role in the optimal activity of the formulation.

EXAMPLE 14

Calcium Lactate, Sodium Chloride, Maltodextrin Dry Powder

This example describes the preparation of dry powders using feedstock of Formulation XIV: 10.0 weight percent maltodextrin, 58.6 weight percent calcium lactate and 31.4 weight percent sodium chloride.

An aqueous phase was prepared for a batch process by dissolving maltodextrin in ultrapure water, then calcium lactate pentahydrate, and finally sodium chloride. The solution was kept agitated throughout the process until the materials were completely dissolved in the water at room temperature. For the maltodextrin and calcium lactate formulation, three batches (A, B & C) of feedstock were prepared and spray dried. Details on the liquid feedstock preparations for each of the three batches are shown in Table 24, where the total solids concentration is reported as the total of the dissolved anhydrous material weights. The solutions or suspensions were then spray dried using a Büchi spray dryer. For each formulation, three batches (A, B & C) of feedstock were prepared and spray dried. Batch A, B and C particles were prepared using the corresponding feedstocks on a Büchi Mini spray dryer with process conditions similar to those used to spray dry for Formulations I-B and I-C in Example 1, with the exception of the following process conditions. The liquid feedstock flow rate was set at 5.2 mL/min for Formulation XIV-A and Formulation XIV-B and 5.6 mL/min for Formulation XIV-C. The outlet temperature was about 90° C. to 98° C. for Formulation XIV-A, about 100° C. to for Formulation XIV-B and about 100° C. 106° C. for Formulation XIV-C.

TABLE 24

Summary of liquid feedstock preparations of three batches of particles for Formulation XIV.

| Formulation: | XIV-A | XIV-B | XIV-C |
|---|---|---|---|
| Liquid feedstock mixing | Batch mixed | Batch mixed | Batch mixed |
| Total solids concentration | 5 g/L | 5 g/L | 5 g/L |
| Total solids | 5 g | 5 g | 20 g |
| Total volume water | 1.0 L | 1.0 L | 4.0 L |
| Amount leucine in 1 L | 0.5 g | 0.5 g | 0.5 g |
| Amount sodium chloride in 1 L | 1.55 g | 1.55 g | 1.55 g |
| Amount calcium lactate pentahydrate in 1 L | 4.13 g | 4.13 g | 4.13 g |

Some of the physical properties of the particles obtained in three separate batches (Formulation XIV-A, XIV-B, and XIV-C) are summarized in Table 25. In addition to the data provided in Table 25, further data about the dry particles prepared by feedstock formulation XIV-A is summarized as follows. The fine particle fraction (FPF) as measured by a collapsed 2-stage Andersen Cascade Impactor with gravimetric analysis was on average 71.3% for FPF less than 5.6 microns and 47.5% for FPF less than 3.4 microns. The volume size was determined by laser diffraction on the HELOS/RODOS sizing equipment and the average value for the volume median diameter (×50) at a pressure of 1 bar was 1.40 microns. In addition, the powder displayed flowrate independent behavior as can be seen from the ratio of ×50 measured at 0.5 bar to ×50 measured at 4.0 bar, which was 1.04. The value for ¼ bar for these particles was 1.00, demonstrating the that particles were highly dispersable.

TABLE 25

Summary of ACI-2 data for the three batches of particles for Formulation XIV.

| Formulation: | XIV-A | XIV-B | XIV-C |
|---|---|---|---|
| FPF less than 5.6 μm on ACI-2 (%) | 71.3 | 66.6 | 68.2 |
| FPF less than 3.4 μm on ACI-2 (%) | 47.5 | 44.8 | 48.7 |

Additional information relating to properties of the Formulation XIV powder and/or particles prepared in this example are provided in the Tables or graphs shown in FIGS. 1A-1F

EXAMPLE 15

Dispersibility

This example demonstrates the dispersibility of dry powder formulations comprising calcium lactate, calcium sulfate or calcium citrate powders when delivered from different dry powder inhalers over a range of inhalation maneuvers and relative to a traditional micronized drug product similarly dispersed.

The dispersibility of various powder formulations was investigated by measuring the geometric particle size and the percentage of powder emitted from capsules when inhaling on dry powder inhalers with flow rates representative of patient use. The particle size distribution and weight change of the filled capsules were measured for multiple powder formulations as a function of flow rate, inhaled volume and fill weight in 2 passive dry powder inhalers.

Powder formulations were filled into size 3 HPMC capsules (Capsugel V-Caps) by hand with the fill weight measured gravimetrically using an analytical balance (Mettler Toledo XS205). Fill weights of 25 and 35 mg were filled for Formulation I (lot #26-190-F), 25, 60 and 75 mg for Formulation II (Lot#69-191-1), 25 and 40 mg for Formulation III (Lot #65-009-F), 10 mg for a spray dried leucine powder (lot#65-017-F) and 25 mg of micronized albuterol sulfate (Cirrus lot#073-001-02-039A). Two capsule based passive dry powder inhalers (RS-01 Model 7, Low resistance Plastiape S.p.A. and RS-01 Model 7, High resistance Plastiape S.p.A.) were used which had specific resistances of 0.020 and 0.036 kPa½/LPM which span the typical range of dry powder inhaler resistance. Flow rate and inhaled volume were set using a timer controlled solenoid valve with flow control valve (TPK2000, Copley Scientific). Capsules were placed in the appropriate dry powder inhaler, punctured and the inhaler sealed to the inlet of the laser diffraction particle sizer (Spraytec, Malvern). The steady air flow rate through the system was initiated using the TPK2000 and the particle size distribution was measured via the Spraytec at 1 kHz for the durations at least 2 seconds and up to the total inhalation duration. Particle size distribution parameters calculated included the volume median diameter (Dv50) and the geometric standard deviation (GSD) and the fine particle fraction (FPF) of particles less than 5 micrometers in diameter. At the completion of the inhalation duration, the dry powder inhaler was opened, the capsule removed and re-weighed to calculate the mass of powder that had been emitted from the capsule during the inhalation duration. At each testing condition, 5 replicate capsules were measured and the results of Dv50, FPF and capsule emitted powder mass (CEPM) were averaged.

In order to relate the dispersion of powder at different flow rates, volumes, and from inhalers of different resistances, the energy required to perform the inhalation maneuver was calculated and the particle size and dose emission data plotted against the inhalation energy. Inhalation energy was calculated as $E=R^2Q^2V$ where E is the inhalation energy in Joules, R is the inhaler resistance in $kPa^{1/2}$/LPM, Q is the steady flow rate in L/min and V is the inhaled air volume in L.

FIG. 14 shows the dose emitted from a capsule for Formulation II powder at 3 different capsule fill weights, using both the high resistance and low resistance RS-01 dry powder inhalers. At each fill weight, steady inhalations ranged from a maximum energy condition of 9.2 Joules which was equivalent to a flow rate of 60 L/min through the high resistance inhaler (R=0.036 $kPa^{1/2}$/LPM) with a total volume of 2 L down to lower energies with reduced volumes down to 1 L, reduced flow rates down to 15 L/min and inhaler resistance down to R=0.020 $kPa^{1/2}$/LPM. As can be seen from FIG. 14, the entire mass of powder filled into the capsule empties out of the capsule in a single inhalation for all 3 fill weights of 25, 60 and 75 mg of Formulation II at the highest energy condition tested. For the 25 mg fill weight, greater than 80% of the fill weight empties on average for all inhalation conditions down to 0.16 Joules. At 60 mg, the capsule dose emission drops below 80% of the fill weight at 0.36 Joules. At a capsule fill weight of 75 mg, the capsule dose emission drops below 80% of the fill weight at 1.2 Joules.

Figure 14:
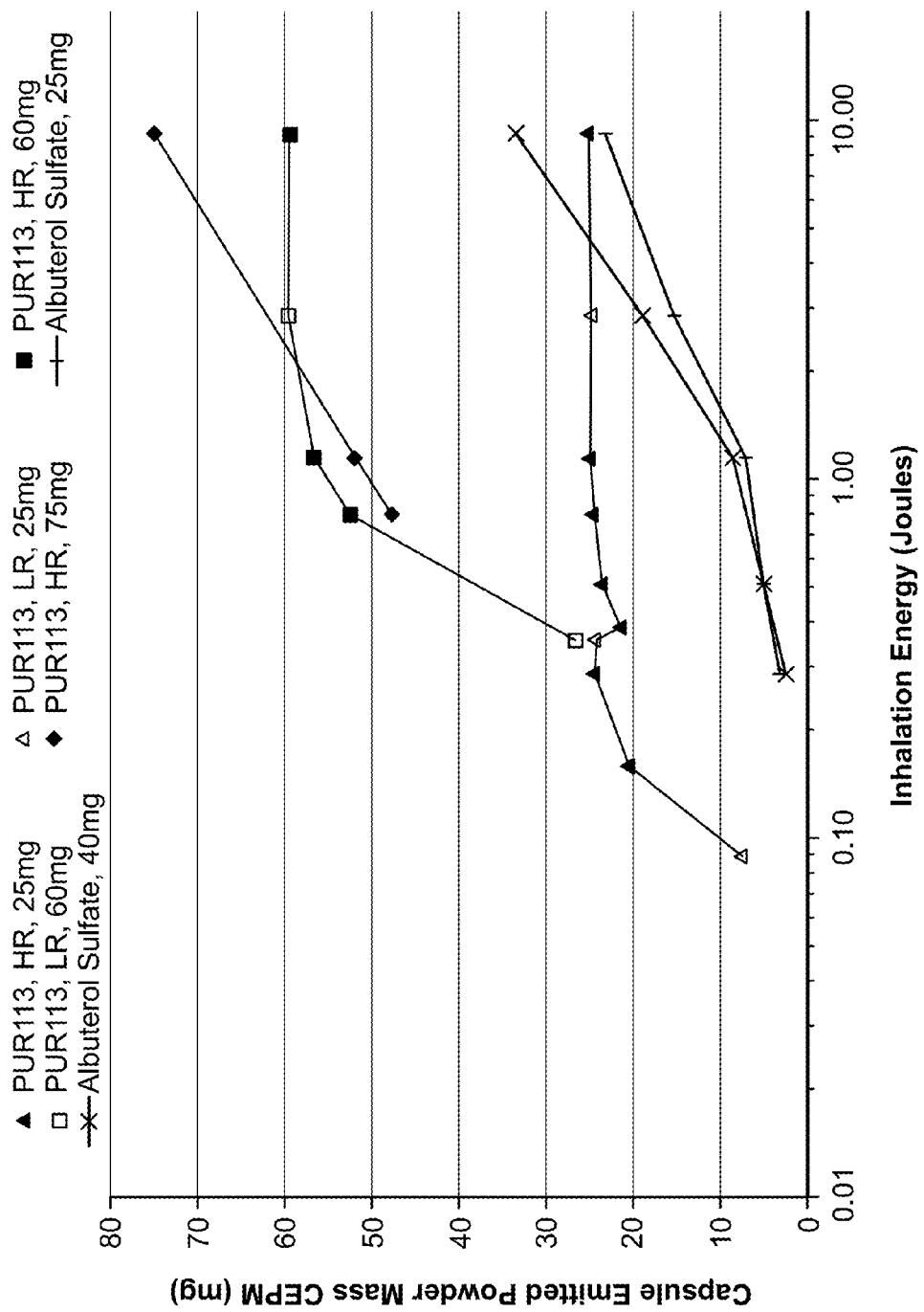
FIG. 14 is a graph showing the emitted dose of Formulation III powder at three different capsule fill weights (25 mg, 60 mg, 75 mg) at varying inhalation energies.

Also shown in FIG. 14 are 2 fill weights of 25 mg and 40 mg of a micronized albuterol sulfate drug formulation which was jet milled to an average particle size of 1.8 micrometers, hand filled into size 3 capsules and dispersed in the high resistance RS-01 inhaler. As can be seen for both the 25 and 40 mg fill weights, at an inhalation energy of 9.2 Joules (steady inhalation of 60 L/min for 2 L) the average CEPM is above 80% of the capsule fill weight (93% for the 25 mg fill weight and 84% for the 40 mg fill weight). However, at all measured lower energies, the CEPM drops to below 10 mg (<30% of capsule fill weight) for both fill weights and monotonically decreases with decreases in inhalation energy.

Figure 15:
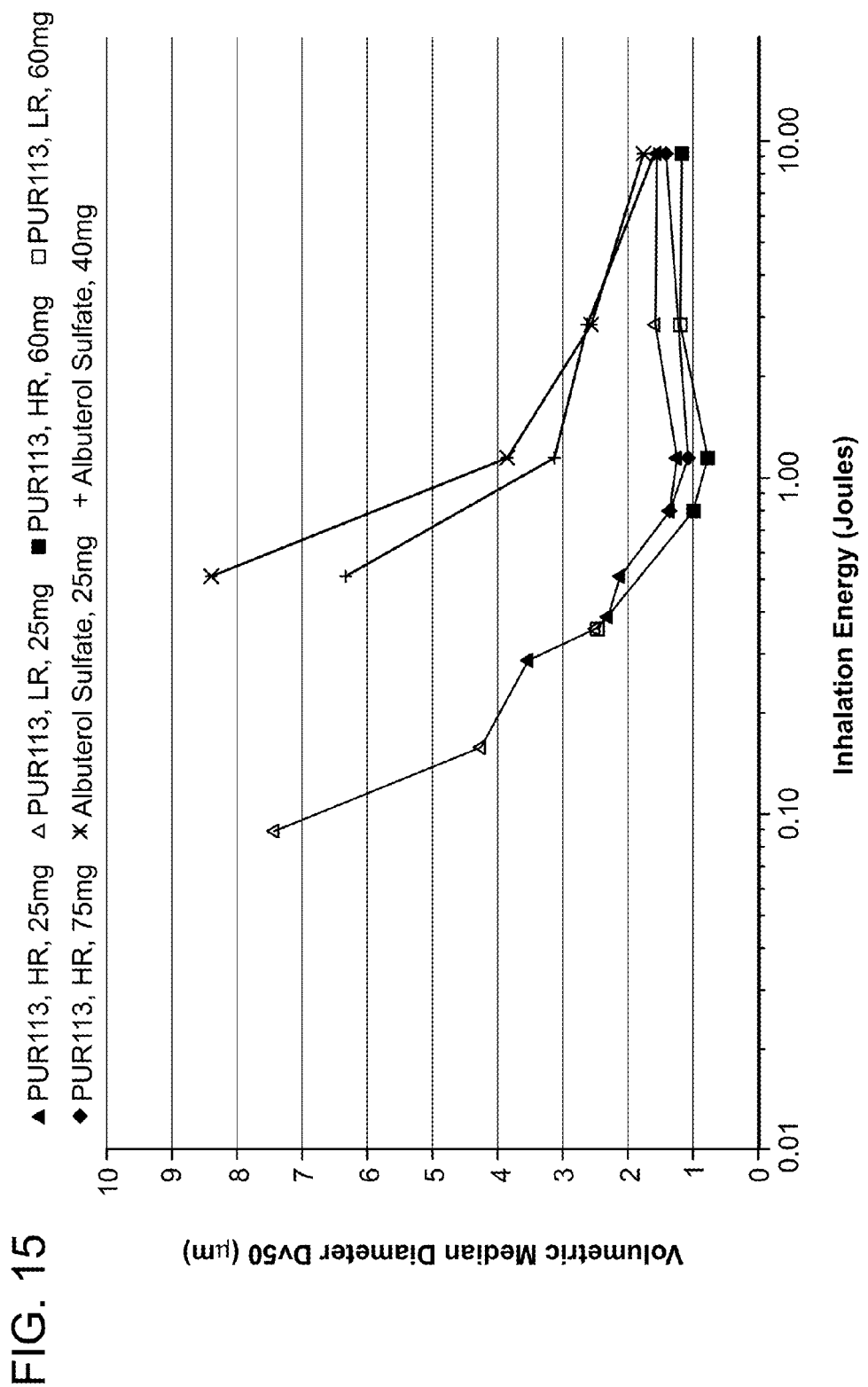
FIG. 15 is a graph showing the particle size distribution of calcium lactate (Formulation II) powders emitted from different inhalers, characterized by the volume median diameter (Dv50) and plotted against the inhalation energy applied. Consistent values of Dv50 at decreasing energy values indicate that the powder is well dispersed since additional energy does not result in additional deagglomeration of the emitted powder.

FIG. 15 shows the particle size distribution of the Formulation II powders that are emitted from the inhalers characterized by the volume median diameter (Dv50) and plotted against the inhalation energy applied. Consistent values of Dv50 at decreasing energy values indicate that the powder is well dispersed since additional energy does not result in additional deagglomeration of the emitted powder. The Dv50 values are consistent for all three fill weights of 75, 60 and 25 mg at all high energy values, with the Dv50 remaining below 2 micrometers down to 0.51 Joules for all 3 fill weights (FIG. 15). Taking into account that at the 60 and 75 mg fill weights, inhalations in the 0.5 to 1.2 Joule range did not fully emit the powder from the capsule (FIG. 14), it is clear that the powder which was emitted was still fully dispersed by the DPI (FIG. 15). In this range, the Dv50 is not significantly increased in size, which would be expected if the emitting powder contained a lot of agglomerates and was not well dispersed.

Also shown in the FIG. 15 are fill weights of 25 mg(×) and 40 mg(+) of a micronized albuterol sulfate drug formulation which was jet milled to an average particle size of 1.8 micrometers, hand filled into size 3 capsules and dispersed in the high resistance RS-01 inhaler. As can be seen for both the 25 and 40 mg fill weights, at an inhalation energy of 9.2 Joules (steady inhalation of 60 L/min for 2 L) the average Dv50 is below 2 micrometers (1.8 and 1.6 μm respectively) for both fill weights, demonstrating good dispersion and relatively few agglomerates. However, at all measured lower energies, the Dv50 increases to greater than 2 micrometers (3.9 and 3.1 μm respectively) and continues to monotonically increase with decreasing inhalation energy, demonstrating agglomeration and poor dispersion of the primary particles.

Additional powders were tested at all of the test conditions and average CEPM and Dv50 were determined (Table 26) These results demonstrate the ability of the powder formulations to be fully emptied and deagglomerated at inhalation energies down to approximately 0.5 Joules.

TABLE 26

Mean CEPM, Dv(50) and FPF as a function of fill weight, flowrate and duration for FORMUALTIONS I-III and placebo.

| Powder | DPI | Fill Weight (mg) | Flow Rate (LPM) | Duration (s) | Inhalation Energy, $E = R^2 Q^2 V$ (Joules) | Mean CEPM (mg) | Mean Dv(50) (μm) | Mean FPF, % <5 μm |
|---|---|---|---|---|---|---|---|---|
| Formulation I | RS.01.HR | 25 | 15 | 4 | 0.29 | 15.84 | 4.77 | 52.09 |
| Formulation I | RS.01.HR | 25 | 20 | 3 | 0.51 | 22.88 | 3.46 | 65.79 |
| Formulation I | RS.01.HR | 25 | 30 | 2 | 1.15 | 24.75 | 2.94 | 72.88 |
| Formulation I | RS.01.HR | 25 | 60 | 2 | 9.18 | 24.72 | 2.93 | 73.39 |
| Formulation I | RS.01.LR | 25 | 15 | 4 | 0.09 | 4.30 | 7.29 | 31.97 |
| Formulation I | RS.01.LR | 25 | 20 | 3 | 0.16 | 8.05 | 5.10 | 48.98 |
| Formulation I | RS.01.LR | 25 | 30 | 2 | 0.36 | 19.94 | 3.28 | 71.09 |
| Formulation I | RS.01.LR | 25 | 60 | 2 | 2.85 | 24.75 | 2.51 | 80.26 |
| Formulation I | RS.01.HR | 35 | 30 | 2 | 1.15 | 33.77 | 2.17 | 83.17 |
| Formulation I | RS.01.HR | 35 | 60 | 2 | 9.18 | 34.73 | 2.33 | 81.42 |
| Formulation I | RS.01.LR | 35 | 30 | 2 | 0.36 | 13.07 | 3.16 | 73.22 |
| Formulation I | RS.01.LR | 35 | 60 | 2 | 2.85 | 34.57 | 2.34 | 83.15 |
| Placebo | RS.01.HR | 10 | 15 | 4 | 0.29 | 3.87 | 25.71 | 6.22 |
| Placebo | RS.01.HR | 10 | 20 | 3 | 0.51 | 8.79 | 22.80 | 8.64 |
| Placebo | RS.01.HR | 10 | 30 | 2 | 1.15 | 9.42 | 22.95 | 11.83 |
| Placebo | RS.01.HR | 10 | 60 | 2 | 9.18 | 9.78 | 21.45 | 12.52 |
| Placebo | RS.01.LR | 10 | 15 | 4 | 0.09 | 1.87 | 40.36 | 3.17 |
| Placebo | RS.01.LR | 10 | 20 | 3 | 0.16 | 3.08 | 28.16 | 5.20 |
| Placebo | RS.01.LR | 10 | 30 | 2 | 0.36 | 7.01 | 18.62 | 9.39 |
| Placebo | RS.01.LR | 10 | 60 | 2 | 2.85 | 9.82 | 15.26 | 16.41 |
| Formulation III | RS.01.HR | 25 | 15 | 4 | 0.29 | 24.87 | 3.26 | 68.77 |
| Formulation III | RS.01.HR | 25 | 20 | 3 | 0.51 | 25.48 | 3.06 | 72.61 |
| Formulation III | RS.01.HR | 25 | 30 | 2 | 1.15 | 25.05 | 2.90 | 74.06 |
| Formulation III | RS.01.HR | 25 | 60 | 2 | 9.18 | 25.28 | 2.92 | 71.87 |
| Formulation III | RS.01.LR | 25 | 15 | 4 | 0.09 | 18.97 | 5.59 | 43.81 |
| Formulation III | RS.01.LR | 25 | 20 | 3 | 0.16 | 24.95 | 3.45 | 68.14 |
| Formulation III | RS.01.LR | 25 | 30 | 2 | 0.36 | 25.08 | 2.72 | 76.82 |
| Formulation III | RS.01.LR | 25 | 60 | 2 | 2.85 | 24.88 | 2.66 | 75.76 |
| Formulation III | RS.01.HR | 40 | 30 | 2 | 1.15 | 39.55 | 2.76 | 74.92 |
| Formulation III | RS.01.HR | 40 | 60 | 2 | 9.18 | 40.13 | 3.14 | 67.35 |
| Formulation III | RS.01.LR | 40 | 30 | 2 | 0.36 | 39.74 | 2.89 | 75.51 |
| Formulation III | RS.01.LR | 40 | 60 | 2 | 2.85 | 39.85 | 2.65 | 77.00 |
| Formulation II | RS.01.HR | 25 | 15 | 4 | 0.29 | 24.45 | 3.56 | 63.96 |
| Formulation II | RS.01.HR | 25 | 17.5 | 3.4 | 0.39 | 21.43 | 2.34 | 80.07 |
| Formulation II | RS.01.HR | 25 | 20 | 3 | 0.51 | 23.55 | 2.15 | 82.08 |
| Formulation II | RS.01.HR | 25 | 25 | 2.4 | 0.80 | 24.42 | 1.39 | 90.70 |
| Formulation II | RS.01.HR | 25 | 30 | 2 | 1.15 | 24.88 | 1.28 | 88.29 |
| Formulation II | RS.01.HR | 25 | 60 | 2 | 9.18 | 25.07 | 1.59 | 85.28 |
| Formulation II | RS.01.LR | 25 | 15 | 4 | 0.09 | 7.47 | 7.46 | 32.20 |

TABLE 26-continued

Mean CEPM, Dv(50) and FPF as a function of fill weight, flowrate and duration for FORMUALTIONS I-III and placebo.

| Powder | DPI | Fill Weight (mg) | Flow Rate (LPM) | Duration (s) | Inhalation Energy, $E = R^2Q^2V$ (Joules) | Mean CEPM (mg) | Mean Dv(50) (μm) | Mean FPF, % <5 μm |
|---|---|---|---|---|---|---|---|---|
| Formulation II | RS.01.LR | 25 | 20 | 3 | 0.16 | 20.39 | 4.29 | 57.09 |
| Formulation II | RS.01.LR | 25 | 30 | 2 | 0.36 | 24.23 | 2.52 | 78.85 |
| Formulation II | RS.01.LR | 25 | 60 | 2 | 2.85 | 24.81 | 1.61 | 89.78 |
| Formulation II | RS.01.HR | 60 | 25 | 2.4 | 0.80 | 52.42 | 0.99 | 90.45 |
| Formulation II | RS.01.HR | 60 | 30 | 2 | 1.15 | 56.50 | 0.78 | 92.70 |
| Formulation II | RS.01.HR | 60 | 60 | 2 | 9.18 | 59.42 | 1.19 | 90.64 |
| Formulation II | RS.01.LR | 60 | 30 | 2 | 0.36 | 26.62 | 2.48 | 80.08 |
| Formulation II | RS.01.LR | 60 | 60 | 2 | 2.85 | 59.51 | 1.19 | 90.64 |
| Formulation II | RS.01.HR | 75 | 25 | 2.4 | 0.80 | 47.63 | 1.36 | 89.83 |
| Formulation II | RS.01.HR | 75 | 30 | 2 | 1.15 | 51.84 | 1.07 | 92.59 |
| Formulation II | RS.01.HR | 75 | 60 | 2 | 9.18 | 74.90 | 1.41 | 85.20 |
| Micronized Albuterol 073-001-02-039A | RS.01.HR | 25 | 15 | 4 | 0.29 | 3.12 | 16.76 | 13.00 |
| Micronized Albuterol 073-001-02-039A | RS.01.HR | 25 | 20 | 3 | 0.51 | 5.00 | 8.40 | 32.10 |
| Micronized Albuterol 073-001-02-039A | RS.01.HR | 25 | 30 | 2 | 1.15 | 7.08 | 3.86 | 59.44 |
| Micronized Albuterol 073-001-02-039A | RS.01.LR | 25 | 60 | 2 | 2.85 | 15.28 | 2.57 | 75.01 |
| Micronized Albuterol 073-001-02-039A | RS.01.HR | 25 | 60 | 2 | 9.18 | 23.18 | 1.77 | 81.65 |
| Micronized Albuterol 073-001-02-039A | RS.01.HR | 40 | 15 | 4 | 0.29 | 2.43 | 17.63 | 10.73 |
| Micronized Albuterol 073-001-02-039A | RS.01.HR | 40 | 20 | 3 | 0.51 | 4.97 | 6.34 | 42.24 |
| Micronized Albuterol 073-001-02-039A | RS.01.HR | 40 | 30 | 2 | 1.15 | 8.55 | 3.13 | 67.18 |
| Micronized Albuterol 073-001-02-039A | RS.01.LR | 40 | 60 | 2 | 2.85 | 18.88 | 2.62 | 73.98 |
| Micronized Albuterol 073-001-02-039A | RS.01.HR | 40 | 60 | 2 | 9.18 | 33.40 | 1.60 | 84.30 |

EXAMPLE 16

Solid State Particle Analysis

A. X-Ray Powder Diffraction

Formulations I, II, III and XIV were analyzed for amorphous/crystalline content and polymorphic form using high resolution X-ray powder diffraction (XRPD) and differential scanning calorimetry (DSC). For XRPD, phase identification was performed to identify any crystalline phases observed in each XRPD pattern. XRPD patterns were collected using a PANalytical X'Pert Pro diffractometer (Almelo, The Netherlands). The specimen was analyzed using Cu radiation produced using an Optix long fine-focus source. An elliptically graded multilayer minor was used to focus the Cu Kα X-rays of the source through the specimen and onto the detector. The specimen was sandwiched between 3-micron thick films, analyzed in transmission geometry, and rotated to optimize orientation statistics. A beam-stop was used, along with helium purge in some cases, to minimize the background generated by air scattering. Soller slits were used for the incident and diffracted beams to minimize axial divergence. Diffraction patterns were collected using a scanning position-sensitive detector (X'Celerator) located 240 mm from the specimen. The data-acquisition parameters of each diffraction pattern are displayed above the image of each pattern in appendix C. Prior to the analysis a silicon specimen (NIST standard reference material 640c) was analyzed to verify the position of the silicon 111 peak. Calculated patterns for the potential crystalline components (including anhydrous and hydrated forms) were produced from either the Cambridge Structural Database or the International Center for Diffraction Data (ICDD) Database and compared to the experimental patterns. The crystalline components were qualitatively determined XRPD was also performed on powders that had been conditioned at 75% RH for a period of three to four hours in a Dynamic Vapor Sorption system in order to assess the propensity for recrystallization of said powders upon short-term exposure to elevated humidities.

Differential scanning calorimetry (DSC) was performed using a TA Instruments differential scanning calorimeter Q2000 (New Castle, Del.). The sample was placed into an aluminum DSC pan, and the weight accurately recorded. The data acquisition and processing parameters are displayed on each thermogram. Indium metal was used as the calibration standard. The glass transition temperature ($T_g$) is reported from the inflection point of the transition /or/ the half-height of the transition. Standard mode DSC experiments were initially conducted on the powders of interest in order to assess the overall thermal behavior of the powders. Cyclic mode DSC experiments were also performed in order to attempt to identify the occurrence of glass transitions occurring in these powders over temperature regions of interest identified in the standard DSC thermograms.

Figure 16:
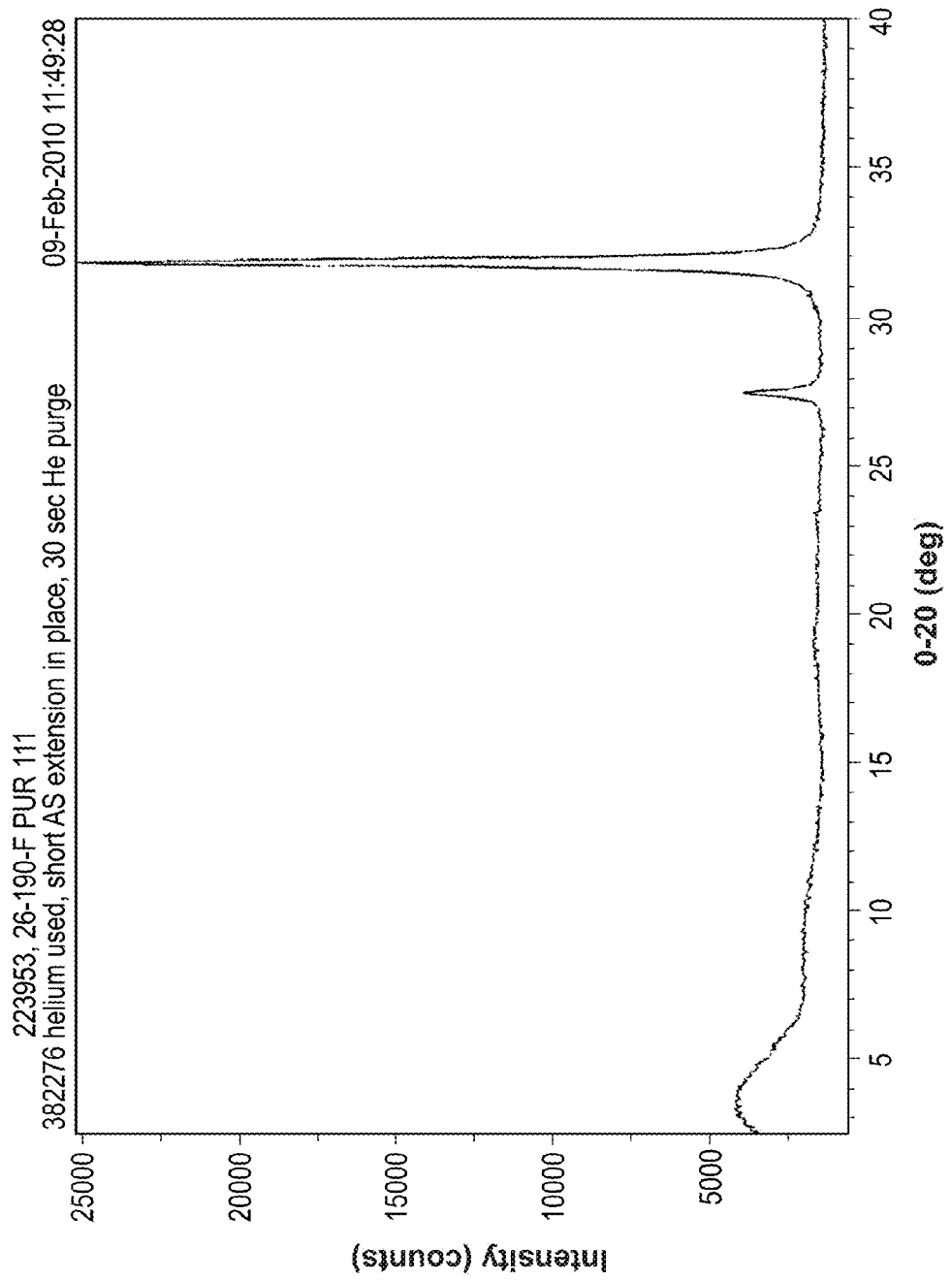
FIG. 16 shows a high resolution XRPD pattern of Formulation I powder. This pattern shows that Formulation I powder consists of a combination of crystalline sodium chloride and a poorly crystalline or amorphous calcium citrate and potentially calcium chloride-rich phase.
Figure 17:
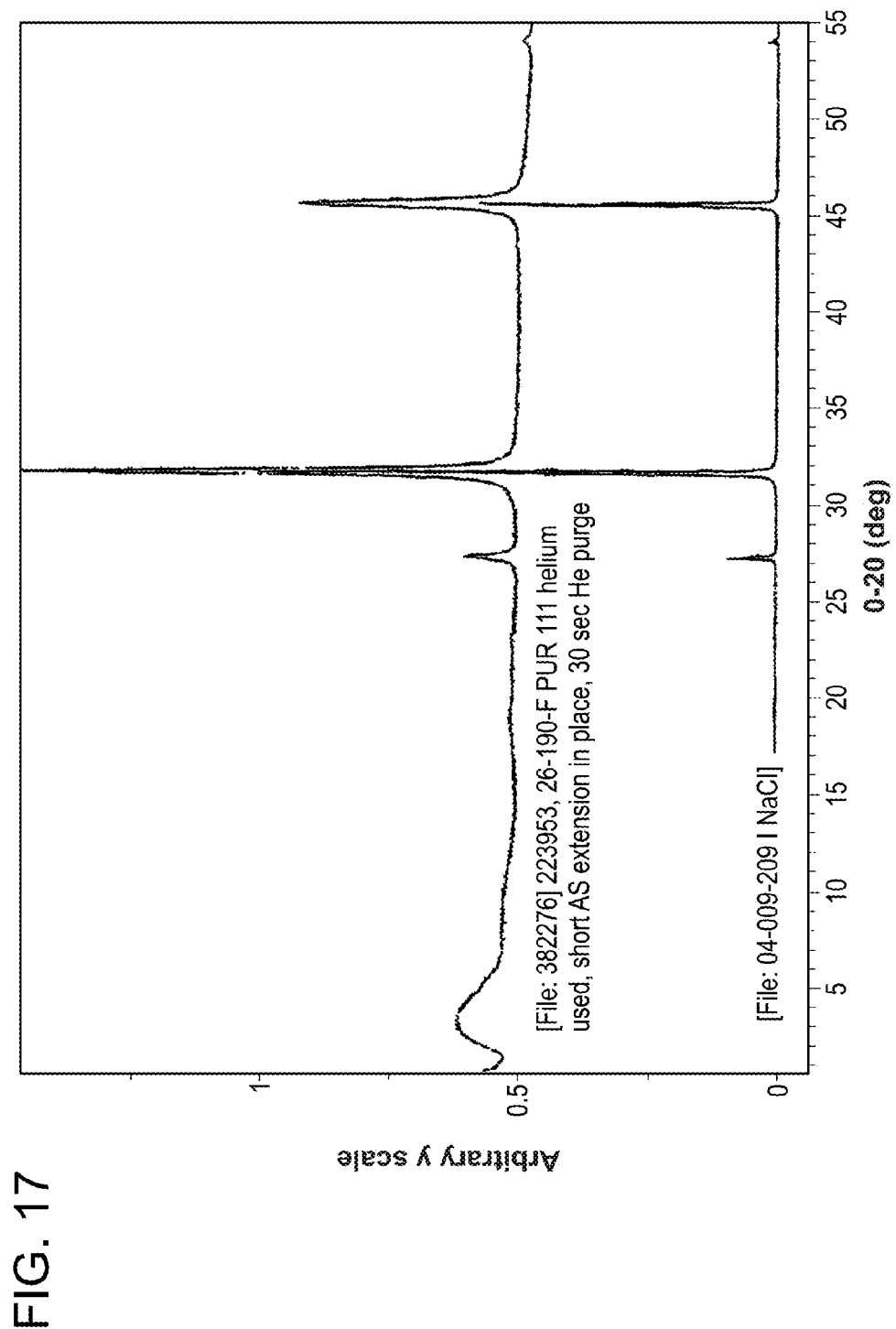
FIG. 17 shows a comparison of XRPD patterns for Formulation I powder with crystalline reflections from NaCl.
Figure 18:
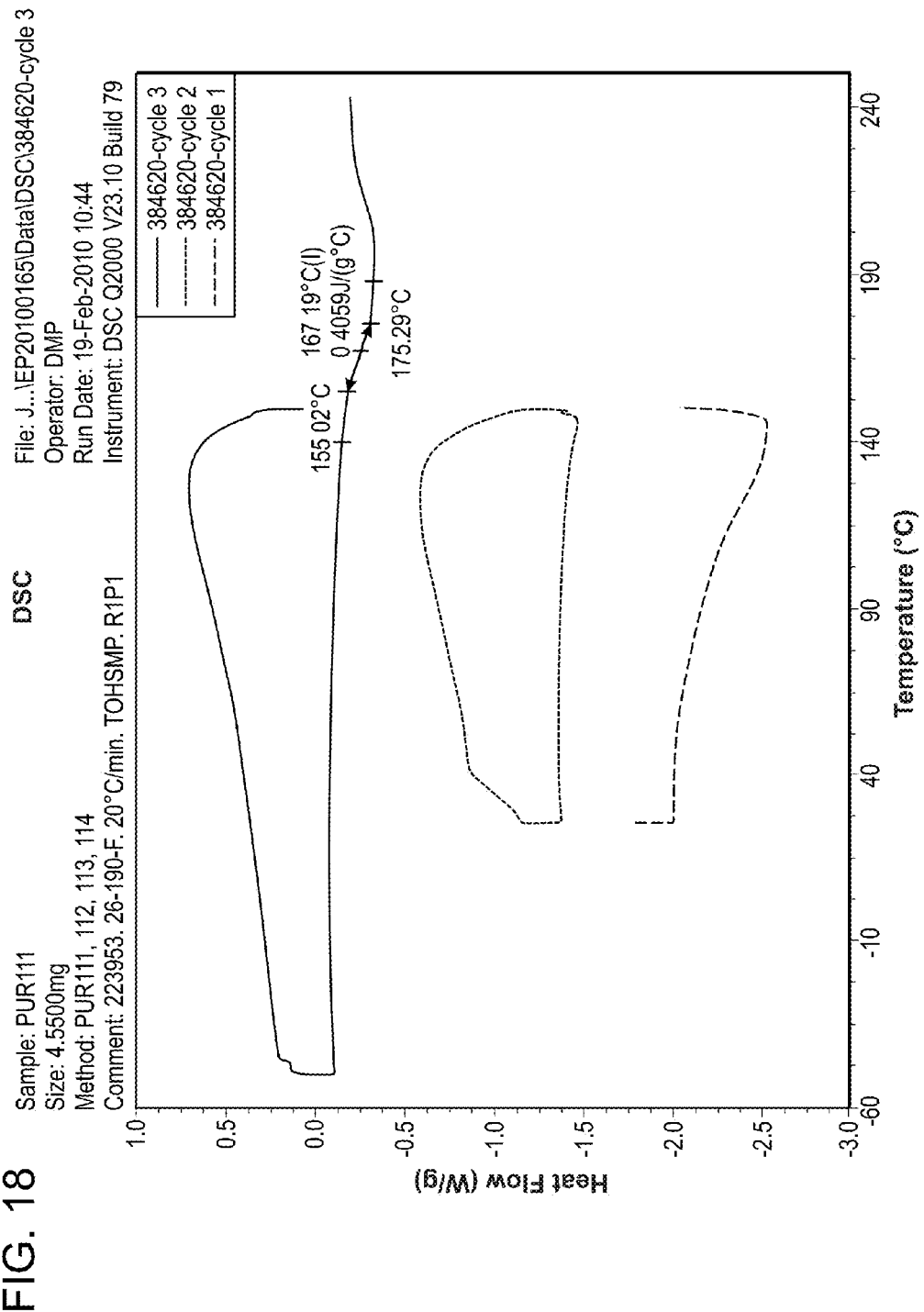
FIG. 18 shows an overlay of temperature cycling DSC thermogram of Formulation I. A glass transition temperature of approximately 167° C. was observed via cyclic DSC for the amorphous calcium-rich phase.

Surprisingly, high calcium and sodium salt content powders were produced that possessed a mixture of amorphous and crystalline content that possessed optimized properties with respect to their dispersibility and stability in the dry state and their dissolution and water absorption properties in the hydrated state. As shown in FIGS. 16 and 17, the Formulation I powder was observed via XRPD to consist of a combination of crystalline sodium chloride and a poorly crystalline or amorphous calcium citrate and potentially calcium chloride-rich phase (as evidenced by a lack of observance of any characteristic peaks for any calcium salt forms in this powder as well as the absence of any characteristic peaks for leucine). As shown in FIG. 18, a glass transition temperature of approximately 167° C. was observed via cyclic DSC for the amorphous calcium-rich phase, indicating that this amorphous phase should be relatively stable to crystalline conversion at standard conditions (25° C., 30% RH). The presence of crystalline sodium chloride in this powder in the dry state may enhance the dispersibility and stability of said powder. The presence of the calcium salt in a poorly crystalline or amorphous form in the Formulation I powder may also facilitate the rapid water uptake and dissolution properties of the Formulation I formulation upon deposition in the lungs (i.e., crystalline sodium chloride is readily soluble, whereas calcium citrate is poorly soluble).

Figure 19:
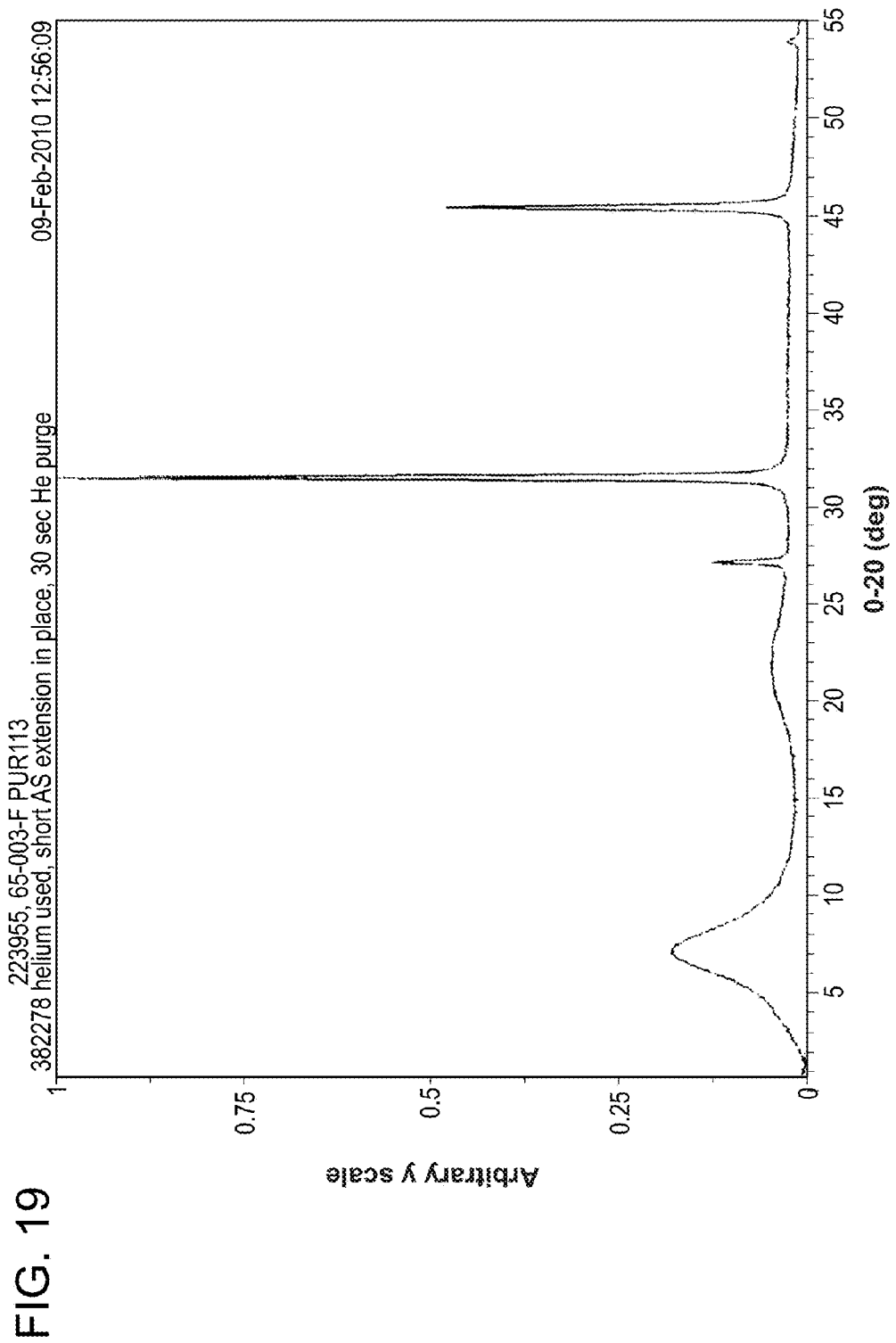
FIG. 19 shows a high resolution XRPD pattern of Formulation III powder. This pattern shows that Formulation II powder consists of a combination of crystalline sodium chloride and a poorly crystalline or amorphous calcium lactate and potentially calcium chloride-rich phase.
Figure 20:
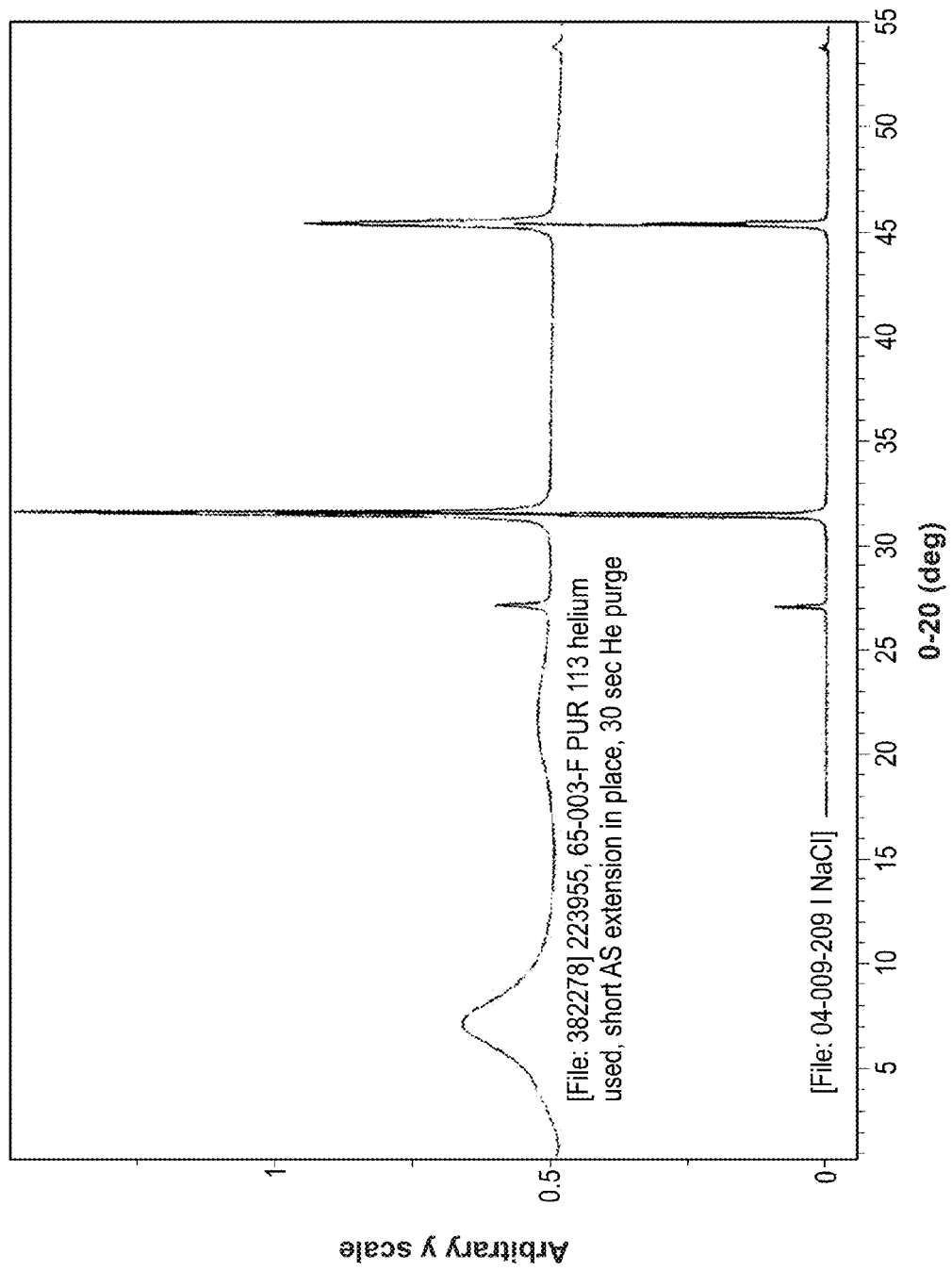
FIG. 20 shows a comparison of XRPD patterns for Formulation III powder with crystalline reflection from NaCl.
Figure 21:
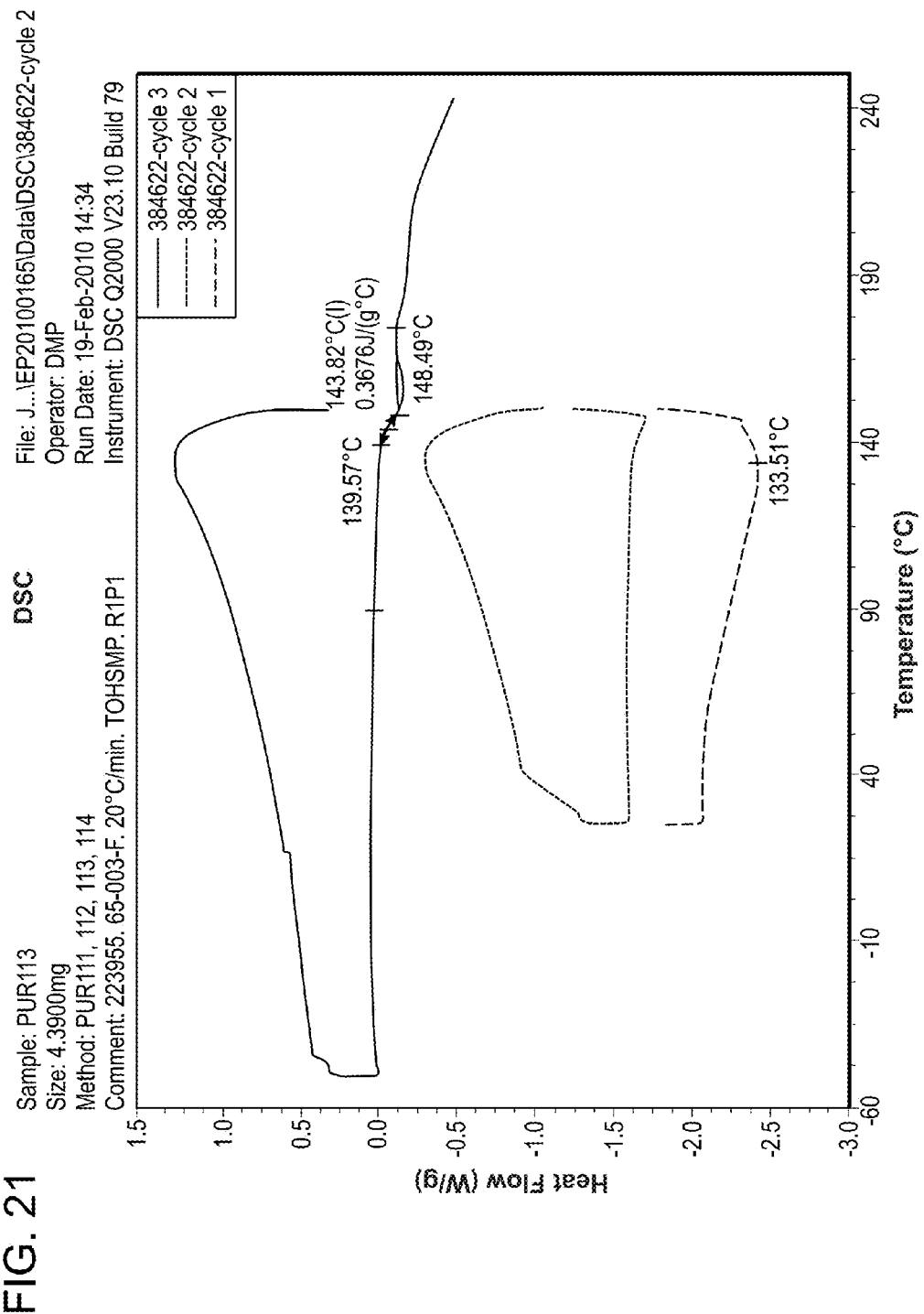
FIG. 21 shows an overlay of temperature cycling DSC thermogram of Formulation III. A glass transition temperature of approximately 144° C. was observed via cyclic DSC for the amorphous calcium-rich phase.
Figure 22:
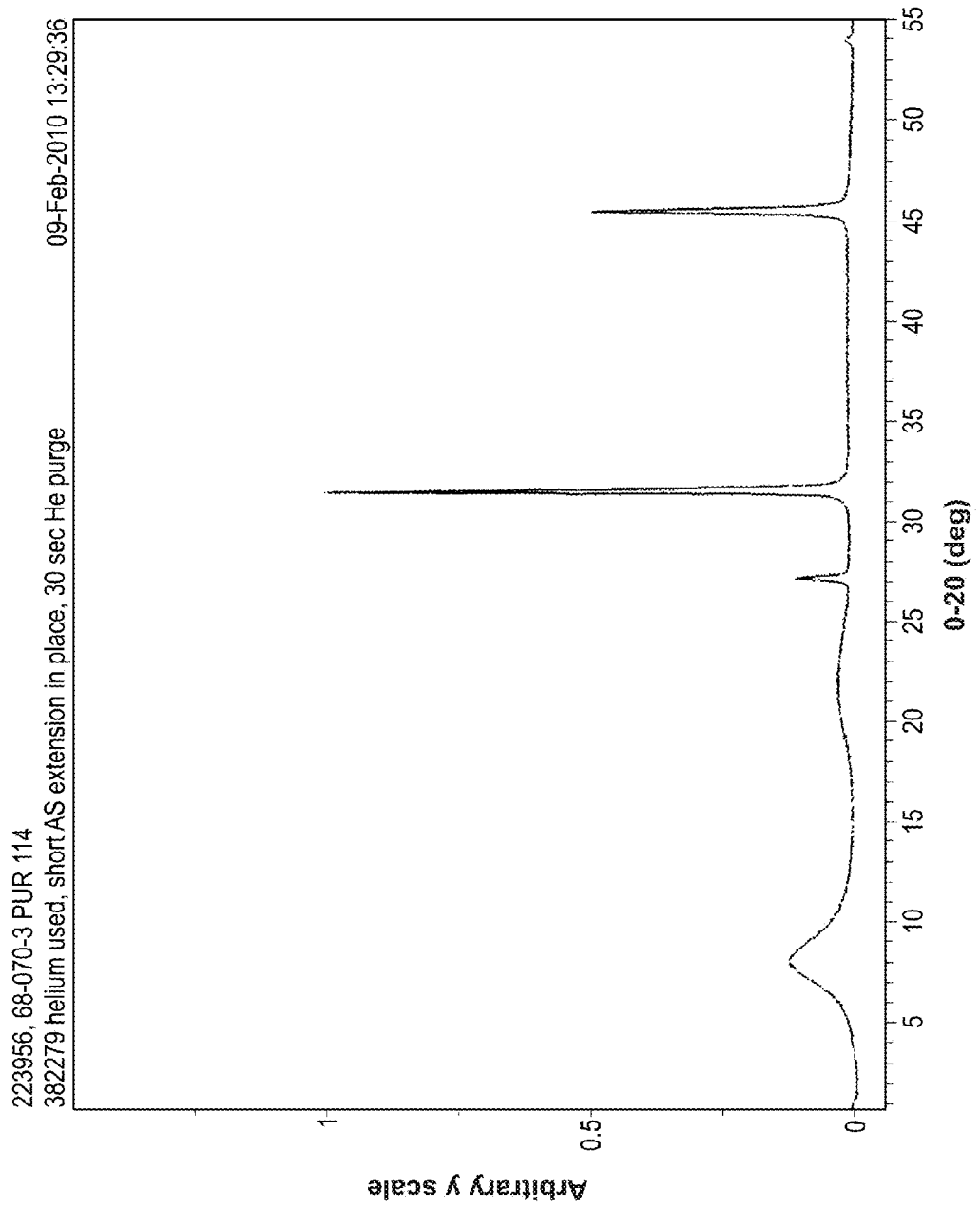
FIG. 22 shows a high resolution XRPD pattern of Formulation XIV powder.
Figure 23:
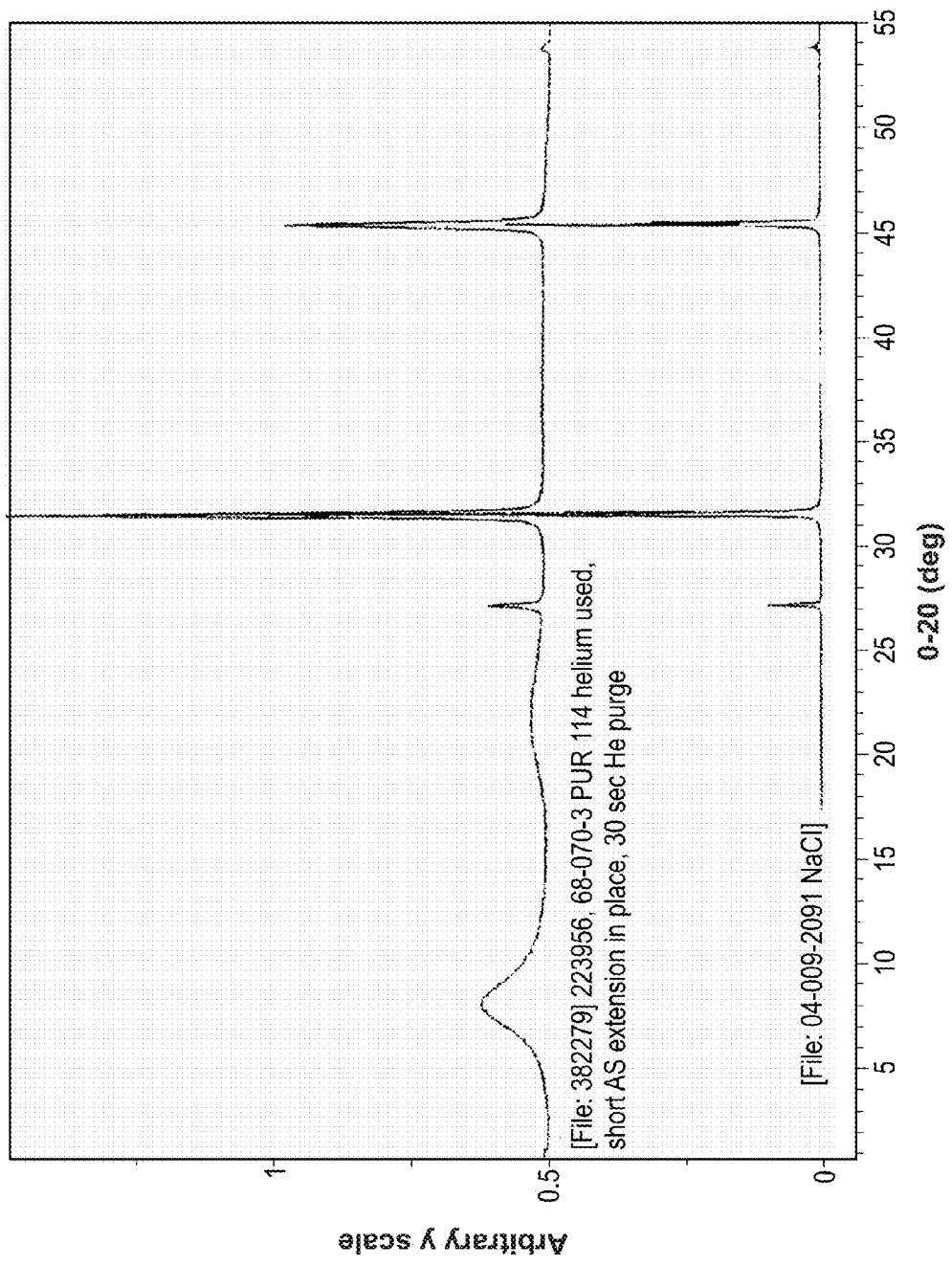
FIG. 23 shows a comparison of XRPD patterns for Formulation XIV powder with crystalline reflection from NaCl.
Figure 24:
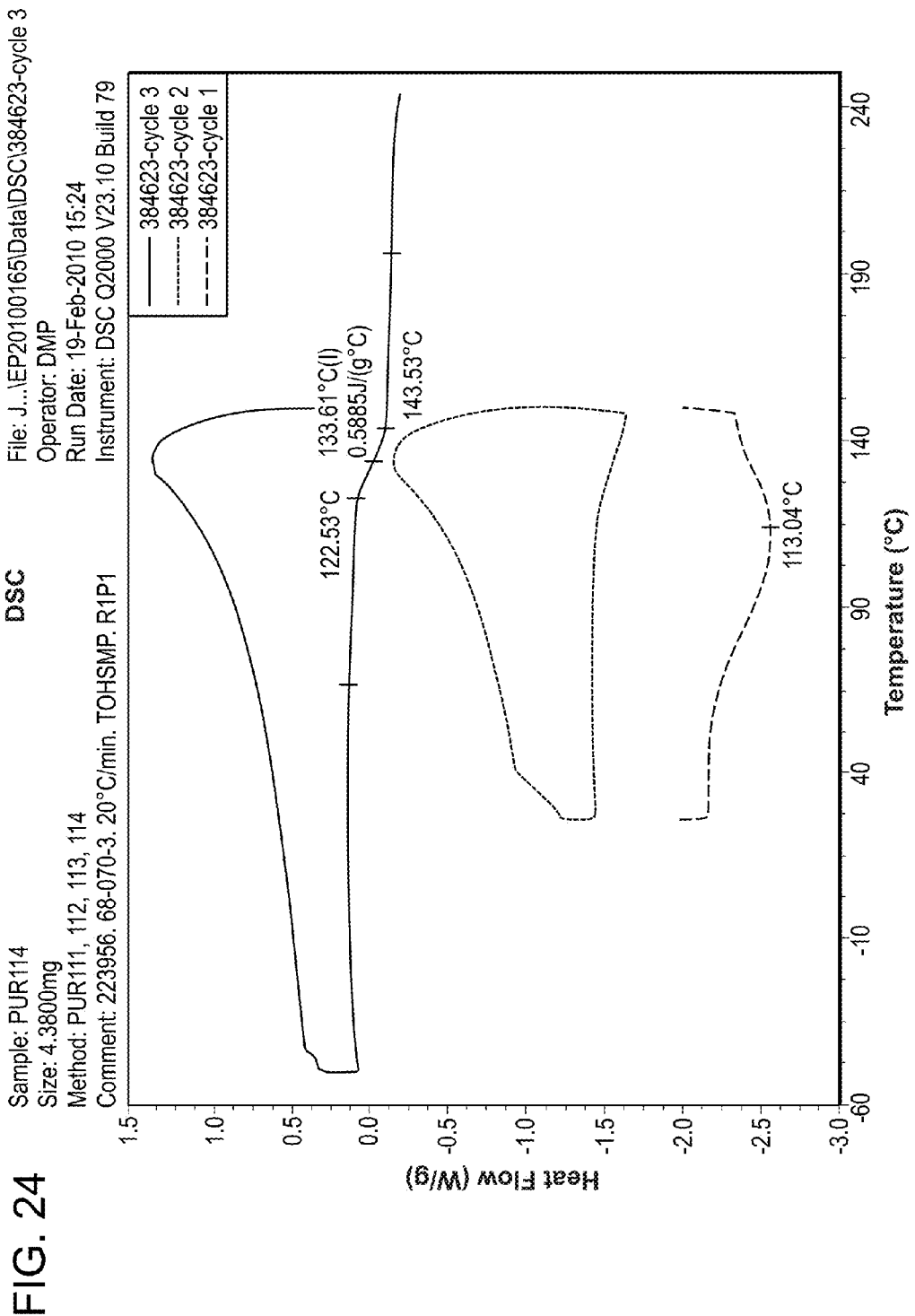
FIG. 24 shows an overlay of temperature cycling DSC thermogram of Formulation XIV. A glass transition temperature of approximately 134° C. was observed via cyclic DSC for the amorphous calcium-rich phase.
Figure 25A:
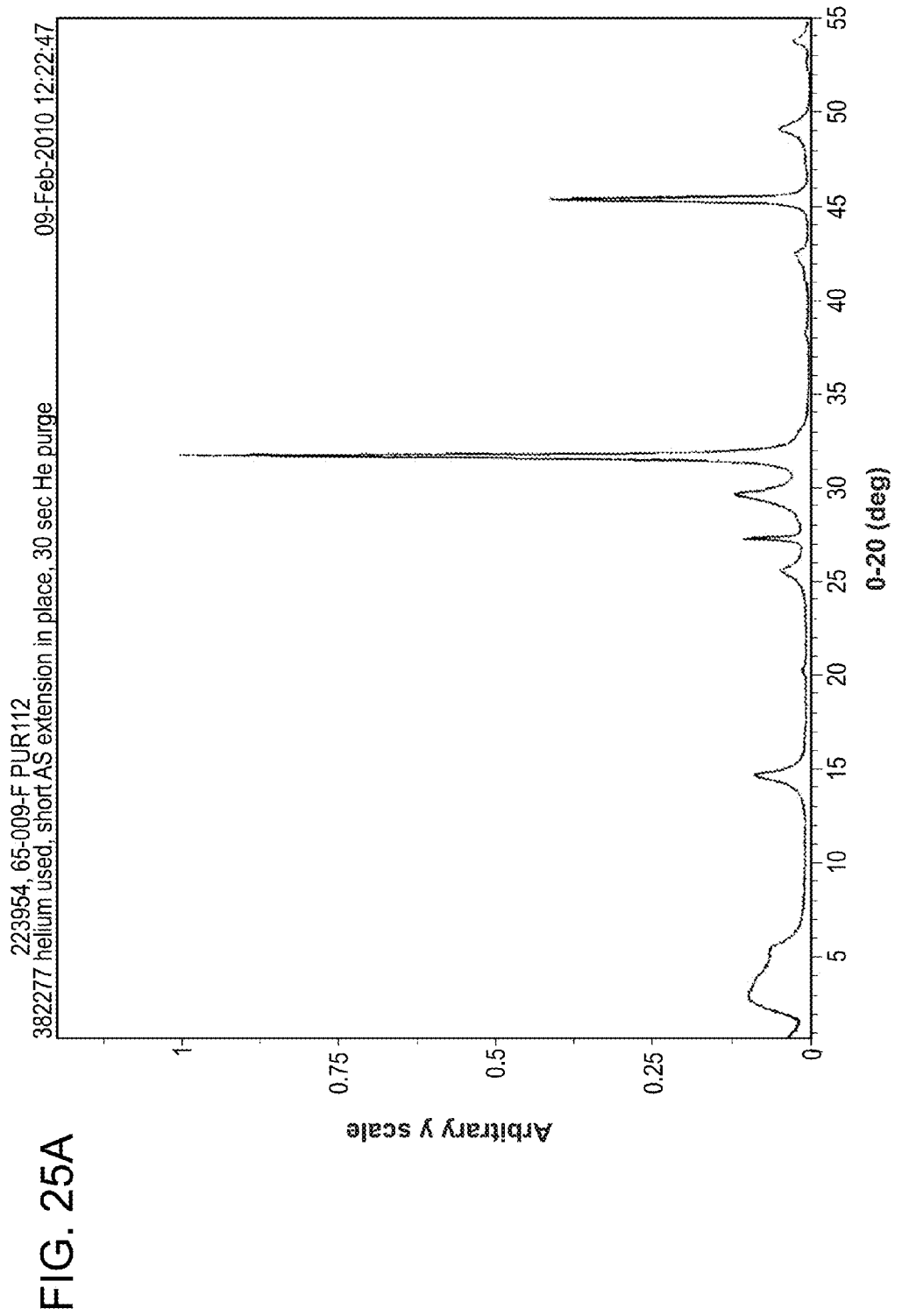
FIG. 25A shows a high resolution XRPD pattern of Formulation III powder. This pattern shows that Formulation III has some degree of crystalline calcium salt content (calcium sulfate) present, in addition to crystalline sodium chloride.
Figure 25B:
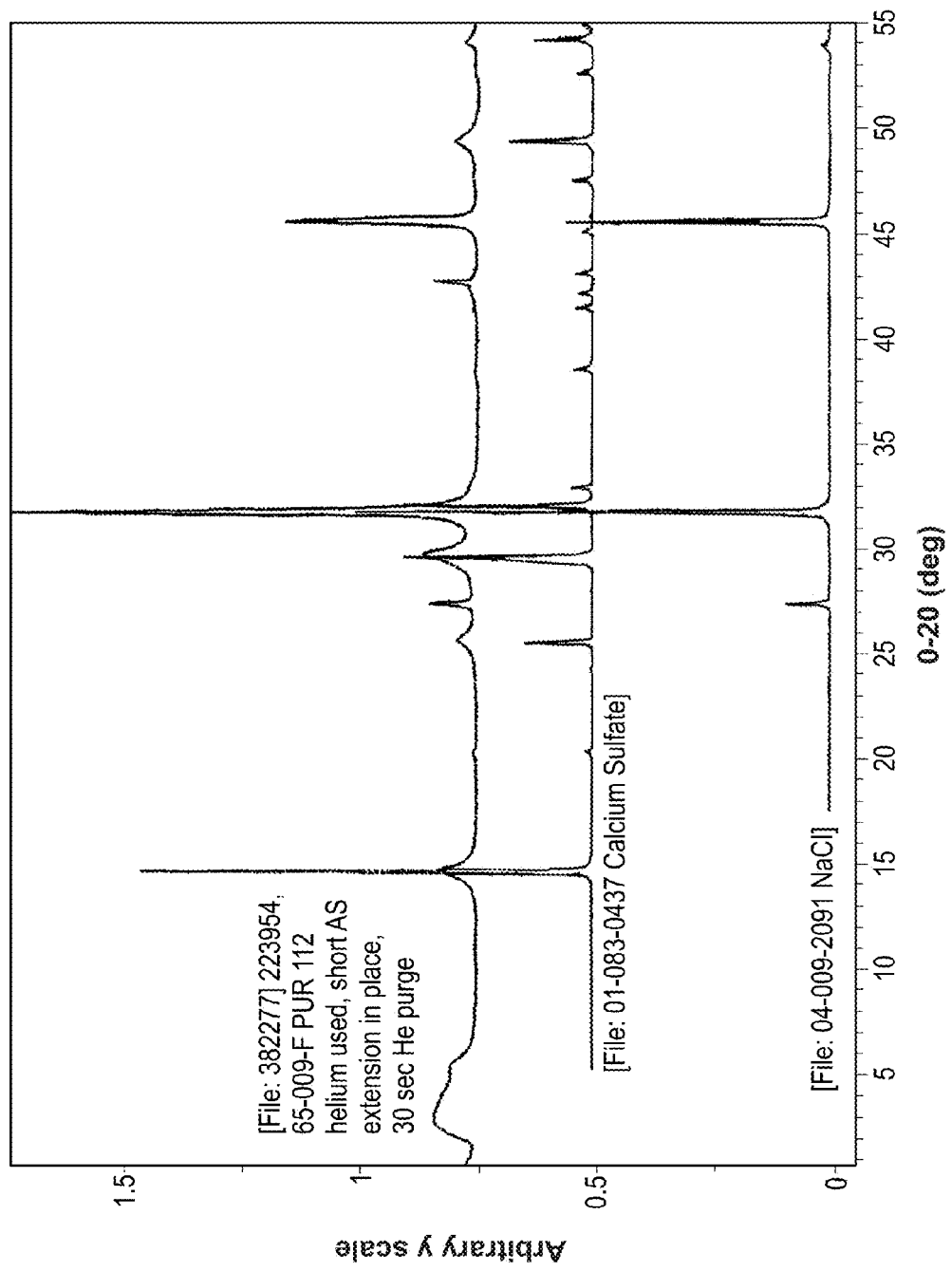
FIG. 25B shows a comparison of XRPD patterns for Formulation III powder with crystalline reflection from NaCl.
Figure 26:
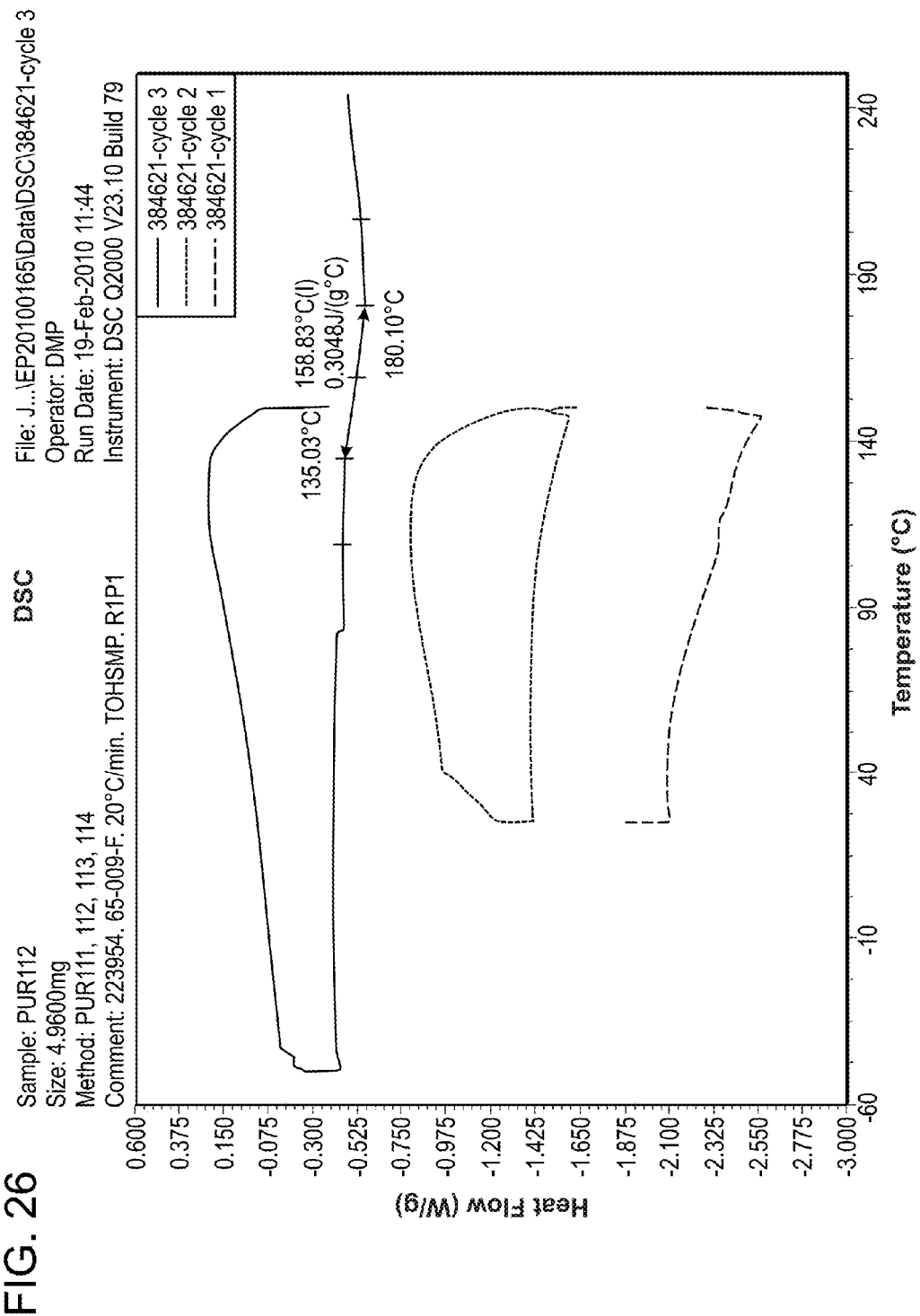
FIG. 26 shows an overlay of temperature cycling DSC thermogram of Formulation III. A glass transition temperature of approximately 159° C. was observed via cyclic DSC for the amorphous calcium-rich phase.
Figure 27C:
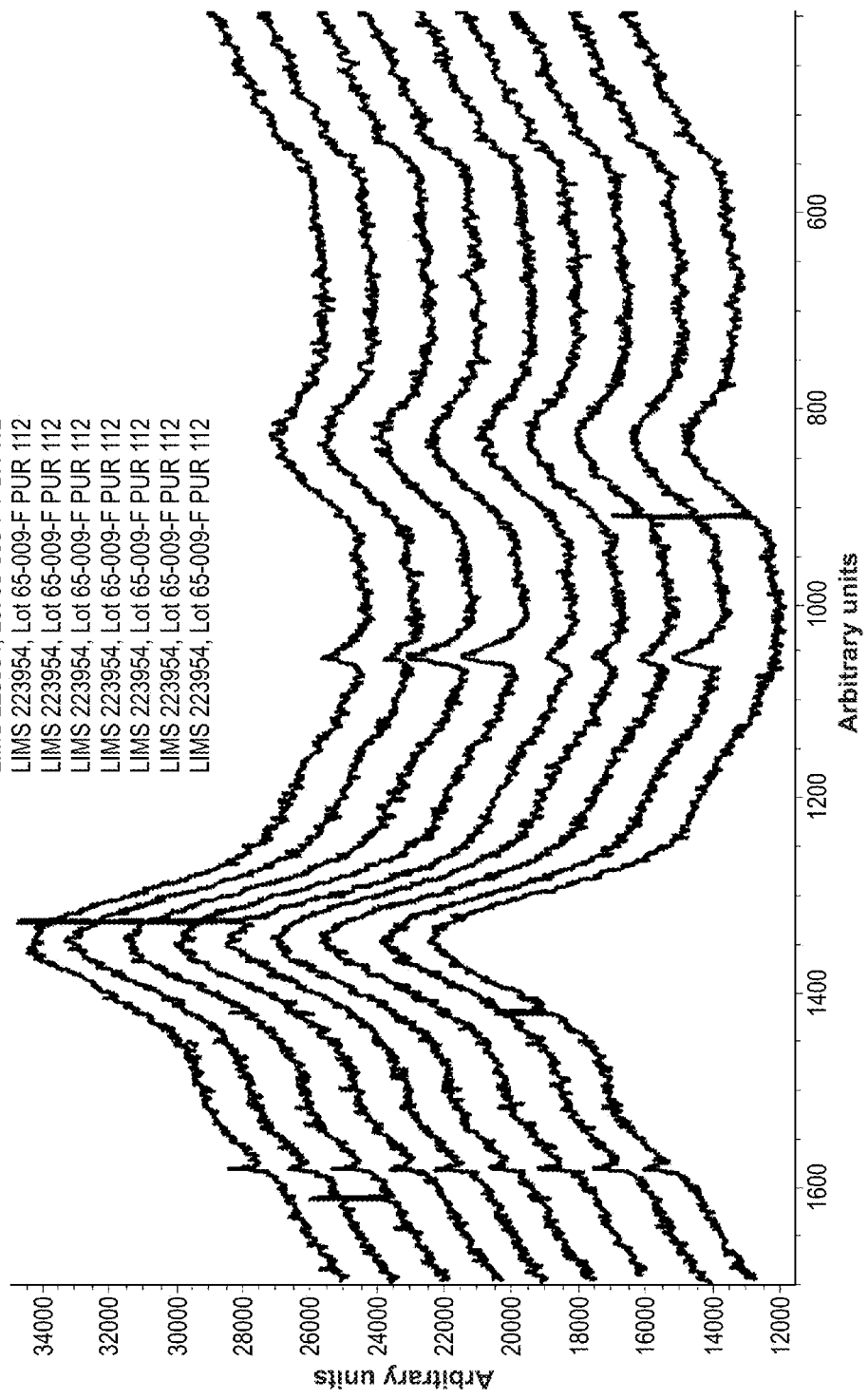
Figure 27F:
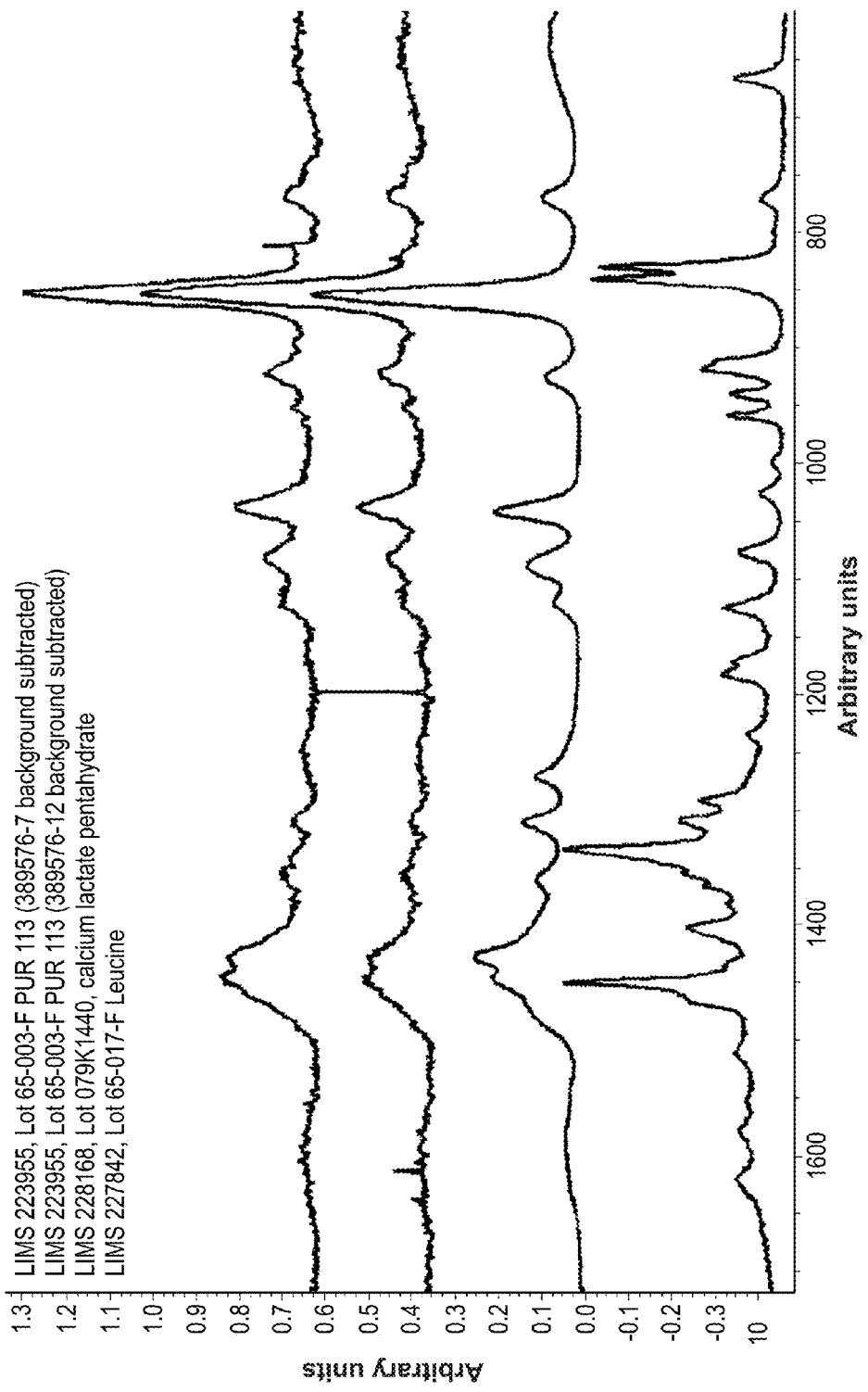
Figure 27H:
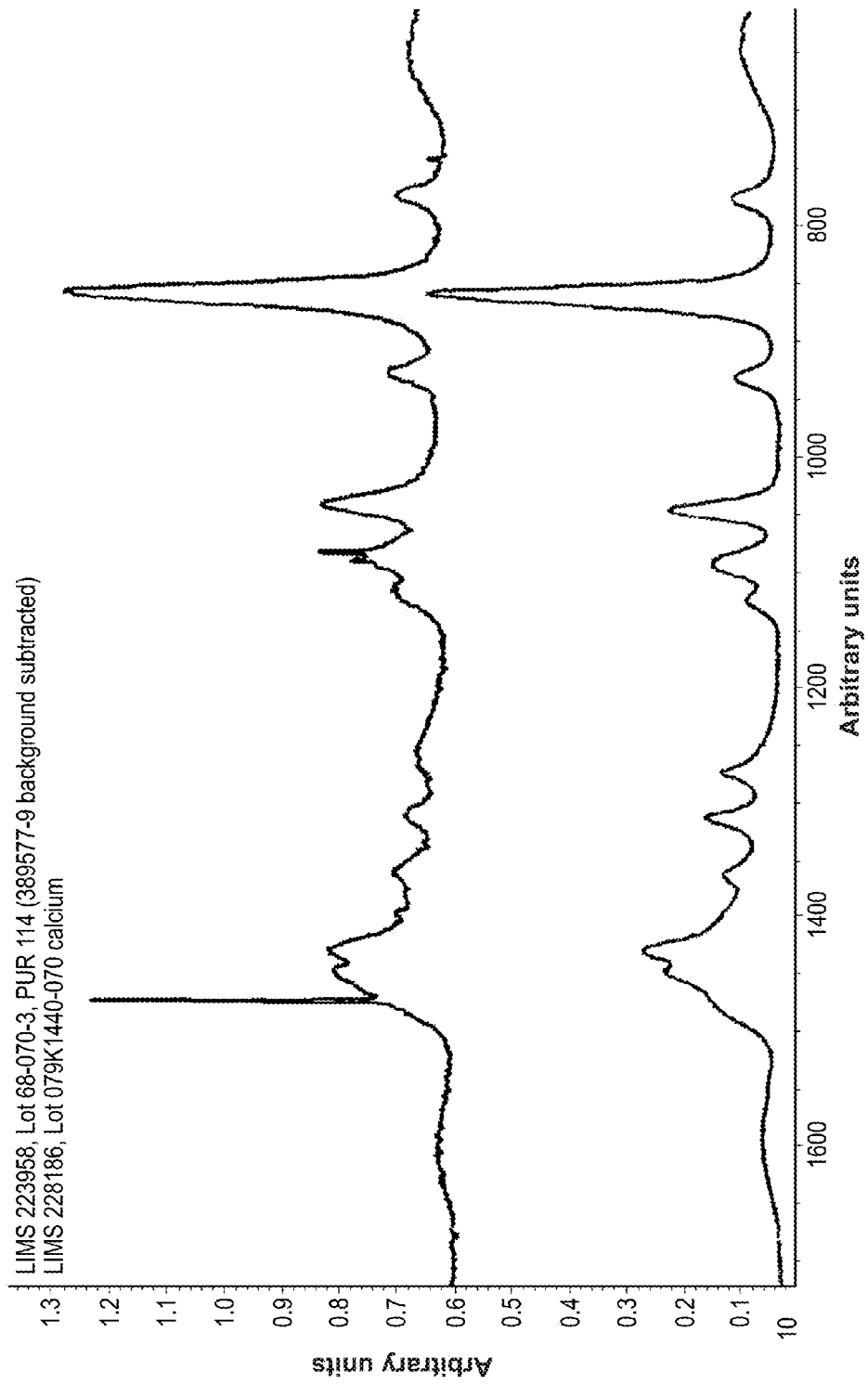

Similar results were seen for powders Formulation II and Formulation XIV. As shown in FIGS. 19 and 20, the Formulation II powder was observed via XRPD to consist of a combination of crystalline sodium chloride and a poorly crystalline or amorphous calcium lactate and potentially calcium chloride-rich phase (as evidenced by a lack of observance of any characteristic peaks for any calcium salt forms in this powder as well as the absence of any characteristic peaks for leucine). As shown in FIG. 21, a glass transition temperature of approximately 144° C. was observed via cyclic DSC for the amorphous calcium-rich phase, indicating that this amorphous phase should be relatively stable to crystalline conversion at standard conditions (25° C., 30% RH). Nearly identical results were seen for the Formulation XIV powder which contained 10% maltodextrin versus 10% leucine (see FIGS. 22 and 23) for XRPD data as well as FIG. 24 which shows a glass transition temperature of approximately 134° C.

In contrast, the Formulation III formulation displayed the presence of some degree of crystalline calcium salt content (calcium sulfate) in addition to crystalline sodium chloride (see FIGS. 25A and 25B). However, this powder still possessed a significant degree of amorphous, calcium-rich phase content, as evidenced by the presence of a glass transition temperature of approximately 159° C. via DSC (see FIG. 26).

B. Surface RAMAN Mapping

Surface Mapping RAMAN experiments were conducted on samples of Formulations I through III and XIV in order to determine the nature of the chemical composition at the surface of the particles comprising these formulations. Raman map spectra were acquired on a Renishaw inVia Ramascope (Gloucestershire, UK) equipped with a Leica DM LM microscope (Wetzlar, Germany). The instrument was calibrated using a silicon wafer standard. The samples were prepared for analysis on an aluminum-coated microscope slide. The excitation wavelength was 785 nm using a high-power near-infrared diode laser source. The data collection for Formulation I, Formulation III and Formulation XIV was a static scan with a 30 second exposure time and 10 accumulations. The data collection for Formulation II was an extended scan with a 60 second exposure time and one accumulation. A Philips ToUcam Pro II camera (model PCVC 840K) (Amsterdam, the Netherlands) was used for image acquisition with a 50× objective. Renishaw WiRE 3.1 (service pack 9) software (Gloucestershire, UK) was used for data collection and processing.

Raman spectra were acquired for six particles from the Formulation I sample, and are shown overlaid in FIG. 27A. Spectra files 389575-1 and 389575-6 are characterized by the presence of weak peaks at approximately 1450, 965 and 850 cm-1. These peaks are discernable as only very weak features in spectra file 389575-6, and are not detected in the remaining spectral data files. In FIG. 27B, spectrum 389575-6 is background subtracted and overlaid with the Raman spectra of calcium citrate tetrahydrate, sodium citrate, and leucine. The sample spectrum exhibits peaks at approximately 1450 and 850 cm-1 which are common to both leucine and the citrate salts. The sample spectrum displays an additional peak at approximately 965 cm-1, which is consistent with the relatively stronger intensity peak in the spectrum of the citrate salts (i.e., calcium citrate tetrahydrate and sodium citrate). The characteristic leucine peak at 1340 cm-1 is not observed in the sample spectra.

Raman spectra were acquired for eight particles from the Formulation III sample, and are shown overlaid in FIG. 27C. All particle spectra are characterized by the presence of a peak at approximately 1060 cm-1. An additional peak at approximately 670 cm-1 is observed in spectral file 388369-4. The 670 cm-1 peak is also observable in spectral data files 388369-1, 3, and 8 after background subtraction (not shown). In FIG. 27D, spectrum 388369-4 is background subtracted and overlaid with the Raman spectra of calcium sulfate, calcium sulfate dihydrate, sodium sulfate anhydrous, and leucine. The background subtracted sample spectrum reveals a possible third peak near 520 cm-1. The peaks at 1060 and 670 cm-1 are present at similar positions to characteristic peaks of the sulfate ions displayed, but do not overlap precisely. The frequencies of the peaks at 1060 and 670 cm-1 in the sample spectrum are consistent with the stretching and bending modes, respectively, of a sulfate ion functional group. Peaks assignable to leucine are not detected in the particle spectra.

Raman spectra were acquired for twelve particles from the Formulation II sample, and are shown overlaid in FIG. 27E. All particle spectra are characterized by the presence of peaks at approximately 1045 and 860 cm-1. Additional peaks can be observed in various spectra at approximately 1450, 1435, 1125, 1095, 930, and 775 cm-1, which generally correlate in relatively intensity with the strong peak at 1045 cm-1. In FIG. 27F, spectra 389576-7 and 389576-12 are background subtracted and overlaid with the Raman spectra of calcium lactate pentahydrate, and leucine. A good correspondence is observed between the sample spectra and calcium lactate pentahydrate spectrum. However, the sample spectra display additional weak peaks at approximately 1345, 1170, 960, 830, and 760 cm-1 which are absent in the spectrum of calcium lactate pentahydrate. Similar peaks are present in the reference spectrum of leucine, although with slightly different relative intensities and frequencies.

Raman spectra were acquired for twelve particles from the Formulation XIV sample, and are shown overlaid in FIG. 27G. All particle spectra are characterized by the presence of a peak at approximately 1045 cm-1. All particle spectra except file 389577-2 also display a peak at approximately 860 cm-1. Additional peaks can be observed in various spectra at approximately 1450, 1435, 1125, 1095, 930, and 775 cm-1, which generally correlate in relatively intensity with the strong peak at 1045 cm-1. In FIG. 27H, spectrum 389577-9 is background subtracted and overlaid with the Raman spectra of calcium lactate pentahydrate. A good correspondence is observed between the sample and calcium lactate pentahydrate spectra. Peaks assigned to maltodextrin (not shown) are not observed in the sample spectra.

Thus, RAMAN surface mapping analysis indicates that the surface composition of each of Formulations I though XIV is dominated by the presence of the various calcium salts (calcium citrate for Formulation I, calcium sulfate for Formulation III and calcium lactate for Formulations II and XIV). For the case of Formulations I through III, this is in contrast to the reported use of leucine as a dispersion-enhancing agent that increases the dispersibility of powders for aerosolization via being concentrated at the surface of the particles comprising said powders. For the formulations disclosed herein, it does not appear that leucine is acting as a dispersibility enhancer in this fashion, as also evidenced by the similar results seen for Formulations II (leucine-containing calcium lactate formulation) and XIV (maltodextrin-containing calcium lactate formulation) with respect to surface content and dispersibility.

EXAMPLE 17

Ion Exchange Reaction for Spray Drying Supersaturated Calcium Citrate and Calcium Sulfate Saturated or super-saturated stocks of aqueous calcium sulfate or calcium citrate were prepared for spray drying using calcium chloride and sodium sulfate or calcium chloride or calcium citrate as starting materials. A range of total solids concentrations from 5 to 30 g/L were prepared both by (i) pre-mixing both salts in water and (ii) keeping the calcium and sodium salt in separate aqueous solutions, with static mixing in-line immediately before spray drying. All of the liquid feed stocks prepared contained saturated or supersaturated calcium sulfate amounts, (where the solubility limit of calcium sulfate in water is 2.98 g/L) and saturated or supersaturated calcium citrate amounts (where the solubility limit of calcium citrate in water is 0.96 g/L). Considering the calcium chloride and sodium sulfate precipitation reaction proceeds to completion ($CaCl_2+Na_2SO_4 \rightarrow CaSO_4+2\ NaCl$), the corresponding final concentrations of calcium sulfate are listed in Table 24. Similar results for the calcium chloride and sodium citrate precipitation reaction ($3CaCl_2+2Na_3C_6H_5O_7 \rightarrow Ca_3(C_6H_5O_7)_2+6NaCl$) are also shown in Table 28.

TABLE 28

Liquid feedstock total solids concentrations and final calcium sulfate or calcium citrate concentrations, where the aqueous solubility limit of calcium sulfate is 2.98 g/L and calcium citrate is 0.96 g/L

| Total solids concentration (g/L) | Final calcium sulfate concentration (g/L) | Final calcium citrate concentration (g/L) |
|---|---|---|
| 5  | 2.7  | 2.9  |
| 10 | 5.4  | 5.9  |
| 15 | 8.1  | 8.8  |
| 20 | 10.8 | 11.7 |
| 30 | 16.1 | 17.6 |

Formulations of 44 weight percent calcium chloride and 56 weight percent sodium sulfate were produced by spray drying utilizing a Mobile Minor spray dryer (Niro, GEA Process Engineering Inc., Columbia, Md.). The liquid feed stocks were prepared at a range of solids concentration from 5-30 g/L. For pre-mixed feeds, sodium salt then calcium salt was dissolved in DI water with constant stirring on a magnetic stirplate. For static mixed feeds, calcium salt was dissolved in DI water, and sodium salt was separately dissolved in DI water with the two solutions maintained in separate vessels with constant agitation. Atomization of the liquid feed was performed using a co-current two-fluid nozzle (Niro, GEA Process Engineering Inc., Columbia, Md.). The liquid feed was fed using gear pumps (Cole-Panner Instrument Company, Vernon Hills, Ill.) either directly into the two-fluid nozzle for pre-mixed feeds or into a static mixer (Charles Ross & Son Company, Hauppauge, N.Y.) immediately before introduction into the two-fluid nozzle for static mixed feeds. Nitrogen was used as the drying gas and dry compressed air as the atomization gas feed to the two-fluid nozzle. The process gas inlet temperature was 240-250° C. and outlet temperature was 94-988° C. with a liquid feedstock rate of 50-70 mL/min. The gas supplying the two-fluid atomizer was approximately 11 kg/hr. The pressure inside the drying chamber was at −2 "WC. Spray dried product was collected from a cyclone and analyzed for volume particle size by laser diffraction using a HELOS with RODOS attachment and for aerosol properties using a collapsed two-stage ACI.

Pre-mixed feeds were assessed for solution stability and clarity. At a total solids concentration of 5 g/L, where the final calcium sulfate concentration would be slightly over the solubility limit of calcium sulfate, the solution stayed clear during the 30 minute duration of mixing and spray drying. As the total solids concentration increased and the final calcium sulfate concentration greatly exceeded the solubility limit, the feed stock became cloudy and precipitation was evident. At 10 g/L the liquid was slightly cloudy, at 20 g/L the liquid was clear for approximately 5-10 minutes before becoming increasingly cloudy over the course of 10 minutes and at 30 g/L the liquid was clear for approximately 2 minutes after mixing, with visible precipitation appearing after approximately 5 minutes.

Figure 28:
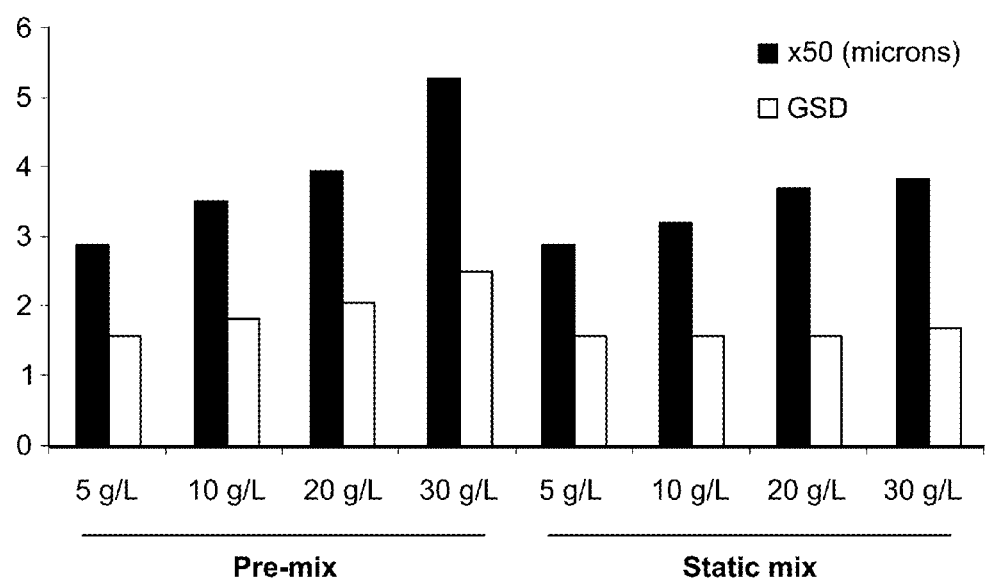
FIG. 28 is a graph showing volume particle size results for Formulation III (calcium sulfate) spray dried powders prepared from p In one aspect, the respirable dry powders and dry particles of the invention may be divalent metal cation (e.g., calcium) dense respirable particles that are small and dispersible. In another aspect, the respirable dry particles may be large or small, e.g., the dry powder has a geometric diameter (VMGD) between 0.5 microns and 30 microns. Optionally, the MMAD of the dry powder may be between 0.5 and 10 microns, more preferably between 1 and 5 microns.
Figure 29:
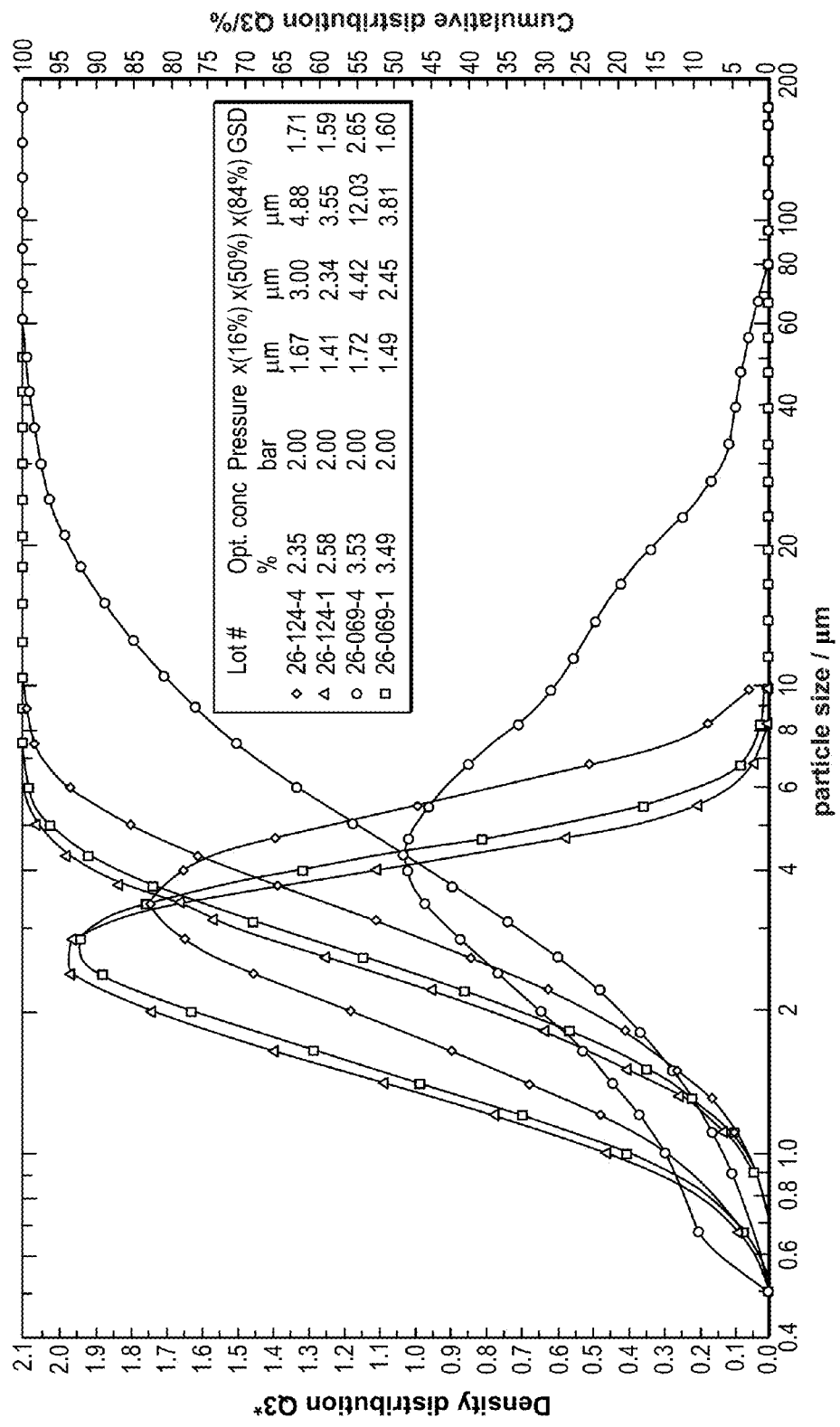

The pre-mixed and static mixed liquid feed stocks were spray dried and the resulting dry powder collected from the cyclone. Results from the HELOS with RODOS are shown in FIG. 28 with representative particle size distributions shown in FIG. 29. While an increase in particle size is expected with increasing feed stock solids concentrations (as seen in the static mixed feeds), the significant particle size increase and broadened particle size distribution in the pre-mixed feeds is undesirable.

Figure 30:
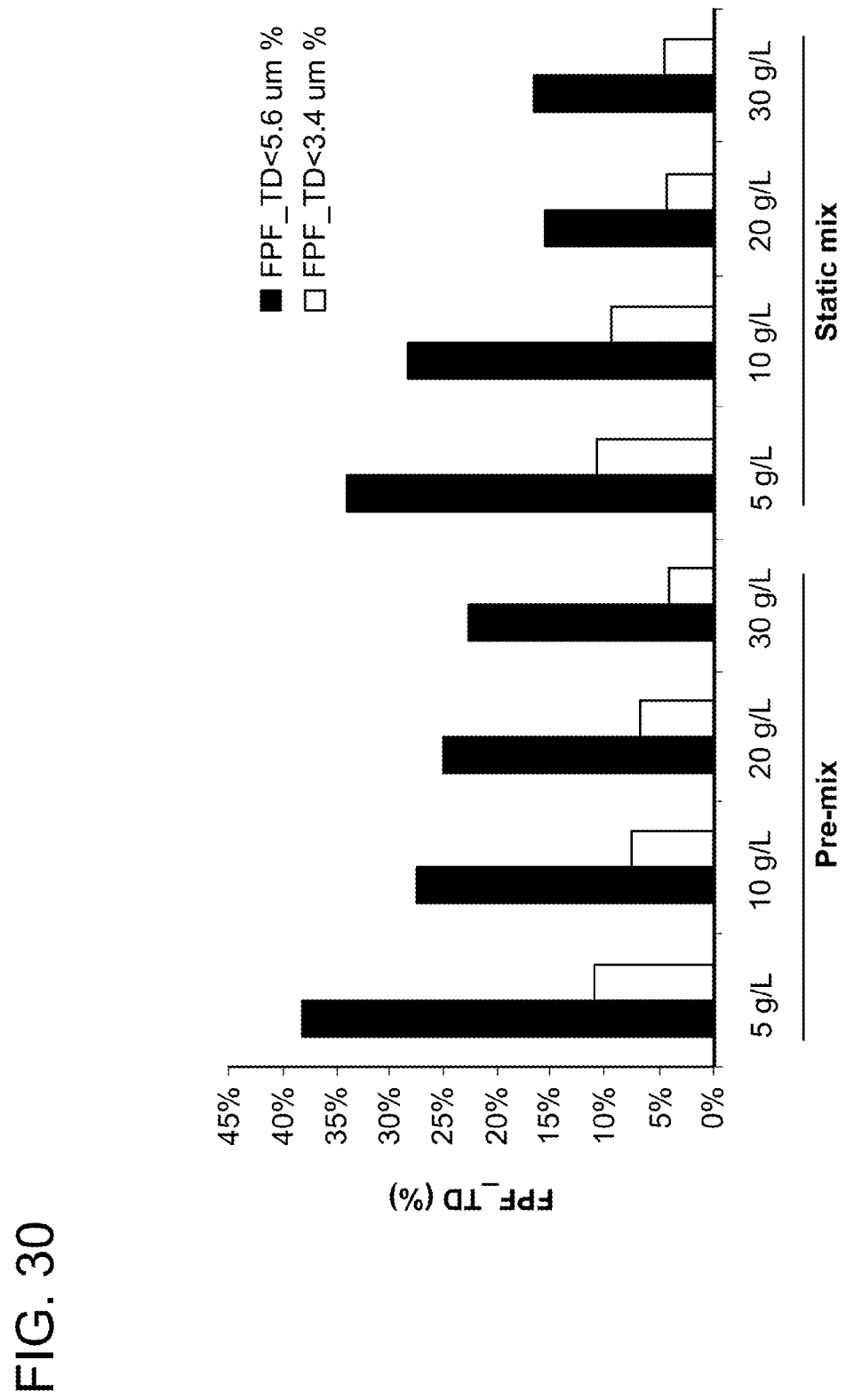
Figure 31A:
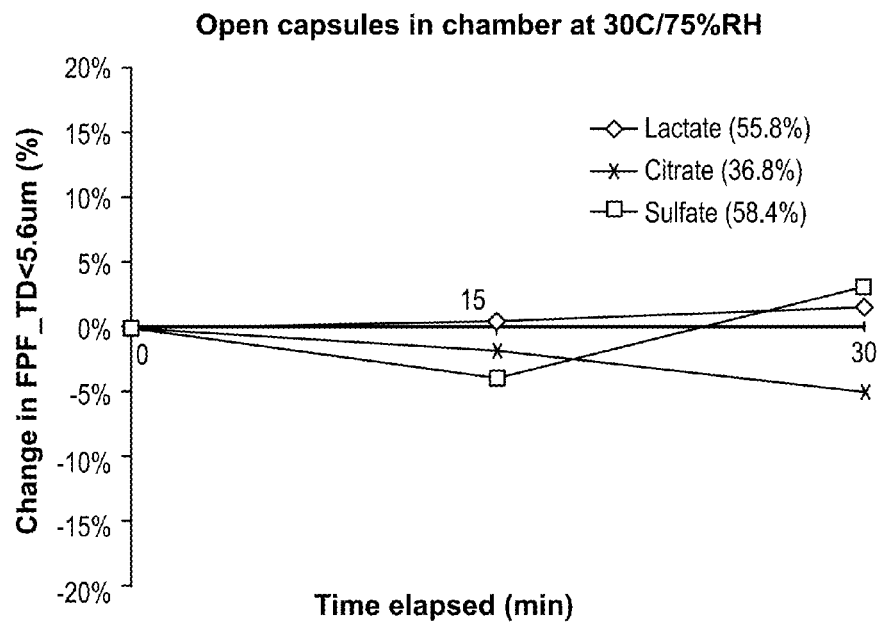
Figure 31B:
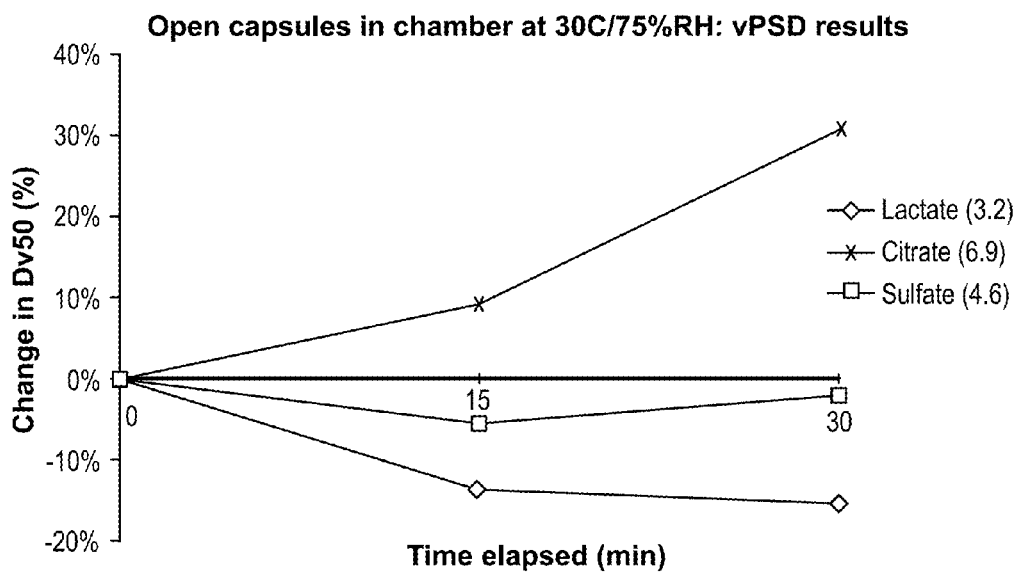
Figure 31C:
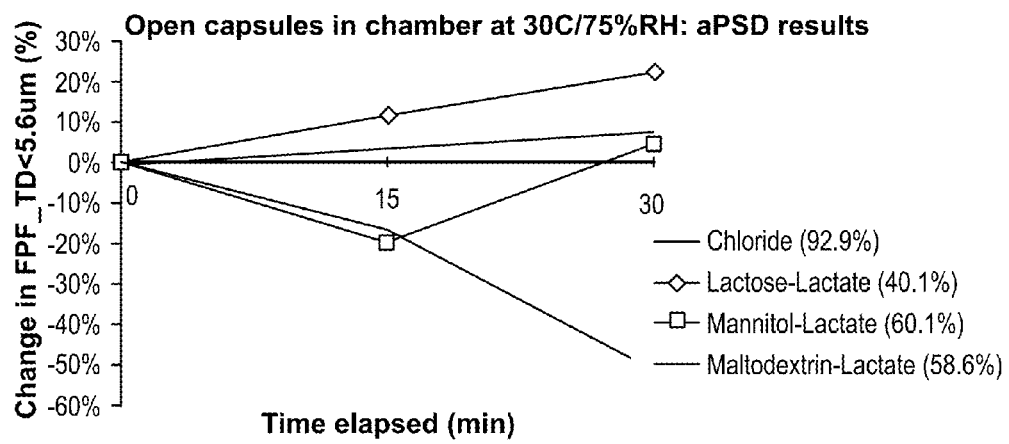
Figure 31D:
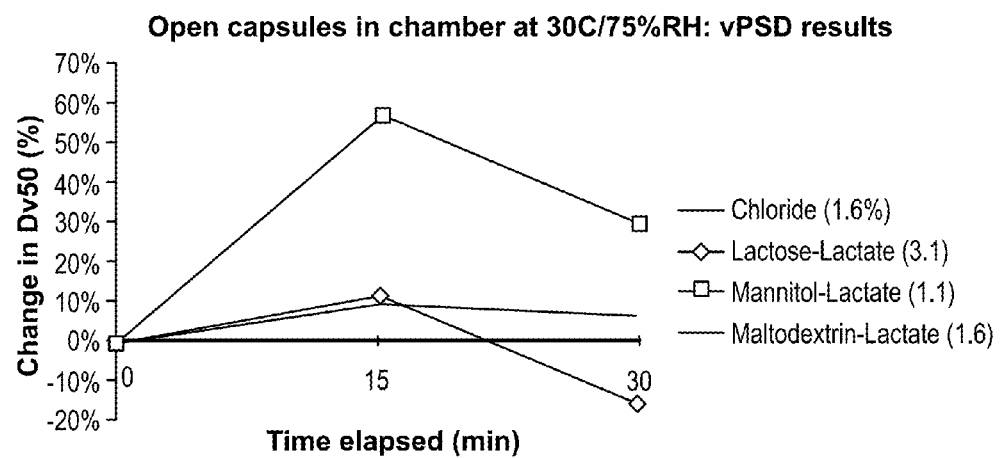

Results for aerosol characterization of the dry powders using the collapsed ACI are shown in FIG. 30.

Unstable solutions with continued precipitation may negatively affect reproducible particle formation during spray drying and also result in a broad particle size distribution. The supersaturated, clear solutions evident for 2-10 minutes for the higher solids concentration suggest that the solutions could be static mixed to achieve a higher spray drying throughput while reproducibly producing a narrow particle size distribution.

Similar results were exemplified for calcium citrate, as demonstrated in Example 1 for the formulation comprising 10.0 weight percent leucine, 35.1 weight percent calcium chloride and 54.9 weight percent sodium citrate (Formulation I-A). The precipitation reaction will result in a formulation comprising 10.0 weight percent leucine, 52.8 weight percent calcium citrate and 37.2 weight percent sodium chloride. At a total solids concentration of 10 g/L, the final calcium citrate concentration would be 5.3 g/L, which exceeds the solubility limit of calcium citrate in water of 0.96 g/L. As can be seen from the properties of the spray dried powder (FIGS. 1A-1E and 2-4), this supersaturated solution resulted in respirable particles with narrow size distribution.

EXAMPLE 18

Small, dispersible particles were made from calcium-containing formulations with and without leucine, as well as magnesium-containing and sodium only formulations.

The following powders were spray dried on the Büchi B-290 using the high performance cyclone with an air feed rate of 30 mm air, aspirator at 90% rate and the small glass collection vessel. The inlet temperature was 220° C. and the outlet temperature was between 96-102° C. The solids concentration was 5 g/L and all were mixed in D.I. water by fully dissolving one component at a time, before adding the next in the order in which they are listed.

18-1) 10.0% lactose, 30.6% magnesium chloride, 59.4% sodium citrate, Ca:Na ratio=1:2
18-2) 63.4% magnesium lactate, 36.6% sodium chloride, Ca:Na ratio=1:2
18-3) 10.0% leucine, 58.4% magnesium lactate, 31.6% sodium chloride, Ca:Na ratio=1:2
18-4) 50.0% leucine, 50% calcium lactate
18-5) 10% leucine, 90% sodium chloride
18-6) 60% leucine, 40% sodium chloride
18-7) 10.0% albuterol, 58.6% calcium lactate, 31.4% sodium chloride
18-8) 90.0% albuterol, 5.9% calcium lactate, 3.1% sodium chloride Characterization results for these powders are shown in Table 29 below. All eight powders exhibited good dispersibility with respect to $\times 50$ 0.5/4 and 1/4 ratios. FPF's<5.6 microns ranged from a low of 18.7% to 75.6%.

TABLE 29

Assorted sodium, calcium and magnesium-based formulations

| Lot | Formulation | Method | x50 (µm) @ 1 bar | GSD @ 1 bar | 1/4 bar | 0.5/4 bar | FPF_TD <3.4 um % | FPF_TD <5.6 um % | % Mass collected | yield % |
|---|---|---|---|---|---|---|---|---|---|---|
| 68.124.1 | lact:MgCl2:Na3Cit 10:30.6:59.4 | Buchi HP | 2.9 | 2.3 | 1.1 | 1.1 | 18.1% | 37.8% | 55.7% | 88.9% |
| 68.129.1 | leucine:MgLact:NaCl 10:58.6:31.4 | Buchi HP | 2.7 | 2.4 | 0.8 | 1.1 | 14.5% | 32.3% | 53.0% | 80.0% |
| 68.129.2 | MgLact:NaCl 63.4:36.6 | Buchi HP | 3.3 | 2.1 | 1.0 | 1.0 | 16.5% | 39.3% | 59.8% | 78.0% |
| 68.125.1 | leu:CaLact 50:50 | Buchi HP | 3.5 | 2.2 | 1.1 | 1.1 | 19.2% | 38.5% | 60.4% | 76.0% |
| 68.124.2 | leu:NaCl 10:90 | Buchi HP | 1.1 | 1.7 | 1.0 | 1.2 | 53.0% | 71.0% | 78.6% | 67.9% |
| 68.124.3 | leu:NaCl 60:40 | Buchi HP | 1.4 | 2.2 | 1.1 | 1.2 | 49.7% | 75.6% | 85.2% | 54.3% |
| 68.125.2 | albuterol:CaLact:NaCl 10:58.6:31.4 | Buchi HP | 2.8 | 2.3 | 0.9 | 1.0 | 16.0% | 38.6% | 60.2% | 81.5% |
| 68.125.3 | albuterol:CaLact:NaCl 90:5.9:3.1 | Buchi HP | 3.5 | 2.3 | 1.0 | 1.1 | 8.9% | 18.7% | 29.1% | 40.5% |

Several additional calcium-free exemplary formulations were produced utilizing various spray-dryer systems (Buchi, Labplant and Niro-based systems) following similar procedures those described above. Selected characterization results for the resultant powders are shown in Table 30 (cells with blank values indicates no value was measured for that powder).

TABLE 30

Non-calcium formulations of small, dispersible powders

| Lot | Formulation | Method | x50 (µm) @ 1 bar | GSD @ 1 bar | 1/4 bar | 0.5/4 bar | water % | FPF_TD <3.4 um % | FPF_TD <5.6 um % | % Mass collected | yield % |
|---|---|---|---|---|---|---|---|---|---|---|---|
| |

Further, several additional examples of compositions containing either no excipients or non-leucine excipients were also produced utilizing various spray-dryer systems (Buchi, Labplant and Niro-based systems) following similar procedures those described above. Selected characterization results for the resultant powders are shown in Table 31 (cells with blank values indicates no value was measured for that powder).

Table 32 contains characterization data for additional leucine and calcium containing small and dispersible powder compositions made via using a Buchi or a Niro spray-drying system per procedures similar to those described above (cells with blank values indicates no value was measured for that powder).

TABLE 31

Non-leucine salt formulations of small, dispersible powders

| Lot | Formulation | Method | x50 (μm) @ 1 bar | GSD @ 1 bar | 1/4 bar | 0.5/4 bar | water % | FPF_TD <3.4 um % | FPF_TD <5.6 um % | % Mass collected | yield % |
|---|---|---|---|---|---|---|---|---|---|---|---|
| | | | | Excipients with lactate | | | | | | | |
| 45.132.1 | leu:mdextrin:CaLact:NaCl 5:5:58.6:31.4 | Buchi HP | 1.5 | 1.9 | 1.0 | 1.0 | | 31.8% | 53.7% | 62.9% | 65.6% |
| 45.137.1 | lact:CaLact:NaCl 10:58.6:31.4 | Buchi HP | 2.7 | 2.0 | 1.0 | 1.0 | 8% | 24.9% | 48.1% | 63.4% | 81.4% |
| 45.137.2 | mannitol:CaLact:NaCl 10:58.6:31.4 | Buchi HP | 1.5 | | | | 6% | 43.6% | 66.6% | 73.1% | 68.6% |
| 45.189.2 | mannitol:CaLact:NaCl 10:58.6:31.4 | Buchi HP | 1.2 | 1.8 | 1.0 | 1.0 | 5% | 44.8% | 66.0% | 71.6% | |
| 45.137.3 | mdextrin:CaLact:NaCl 10:58.6:31.4 | Buchi HP | 1.4 | 1.9 | 1.0 | 1.0 | 6% | 47.5% | 71.3% | 77.6% | 77.7% |
| 45.189.3 | mdextrin:CaLact:NaCl 10:58.6:31.4 | Buchi HP | 1.3 | 1.8 | 1.0 | 1.0 | 7% | 44.8% | 66.6% | 73.2% | |
| 45.137.4 | trehalose:CaLact:NaCl 10:58.6:31.4 | Buchi HP | 1.4 | 1.9 | 1.0 | 1.0 | 4% | 51.3% | 72.8% | 78.2% | 77.2% |
| | | | | Calcium Citrate | | | | | | | |
| 2.26.3 | CaCl2:Na3Cit 39:61 | Labplant | 3.3 | 1.2 | 1.0 | | 11.0% | | | | 22.8% |
| 26.048.2 | CaCl2:Na3Cit2 39:61 | Niro | 7.0 | 2.1 | 1.2 | | | 7.9% | 22.0% | 46.1% | 61.0% |
| 27.03.1 | CaCl2:Na3Cit 39:61 | Labplant | 3.6 | 1.4 | 1.1 | | 9.0% | | | | 25.1% |
| 26.013.3 | CaCl2:Na3Cit 49:51 not to completion | Niro | 3.6 | 2.0 | 1.1 | | | 12.7% | 31.0% | 45.9% | 43.9% |
| 27.183.4 | Ca(OH)2:Cit acid:NaCl 35:61:3.5 | Buchi | 2.6 | 1.8 | 1.0 | | | 9.3% | 17.7% | 21.5% | 23.1% |
| | | | | Calcium Sulfate | | | | | | | |
| 2.26.4 | CaCl2:Na2SO4 44:56 | Labplant | 3.7 | 1.7 | 1.4 | | 5.1% | | | | 12.1% |
| 26.060.1 | CaCl2:Na2SO4 44:56 | Niro | 3.0 | 2.0 | 1.3 | | | 15.3% | 40.2% | 62.9% | 60.8% |
| 26.060.3 | CaCl2:Na2SO4 44:56-static mixed | Niro | 2.6 | 1.6 | 1.2 | | | 17.0% | 42.5% | 58.6% | 31.4% |
| 26.069.1 | CaCl2:NaSO2 44:56 5 g/L | Niro | 2.9 | 1.6 | 1.4 | | | 11.1% | 38.5% | 59.1% | 25.2% |
| 26.069.2 | CaCl2:NaSO2 44:56 10 g/L | Niro | 3.5 | 1.8 | 1.5 | | | 7.6% | 27.7% | 61.1% | 45.6% |
| 26.069.3 | CaCl2:NaSO2 44:56 20 g/L | Niro | 4.0 | 2.1 | 1.4 | | | 6.9% | 25.3% | 62.6% | 37.3% |
| 26.124.1 | CaCl2:Na2SO4, 44:56 5 g/L | Niro | 2.9 | 1.5 | 1.5 | | 6.5% | 11.0% | 34.5% | 53.4% | 22.0% |
| 26.124.2 | CaCl2:Na2SO4, 44:56 10 g/L | Niro | 3.2 | 1.5 | 1.7 | | 7.1% | 9.9% | 28.9% | 45.1% | 35.0% |
| 27.114.5 | CaCl2:Na2SO4 44:56 | Niro | 4.1 | 1.8 | 1.6 | | 6.8% | 5.8% | 22.6% | 50.2% | 52.5% |
| 27.154.1 | CaCl2:Na2SO4 44:56 | Buchi | 3.1 | 1.9 | 1.3 | | | 14.0% | 31.6% | 55.1% | 50.3% |
| 27.114.6 | CaCl2:Na2SO4:Rhod B 44:56:1 | Niro | 3.9 | 1.9 | 1.0 | | 7.2% | 7.4% | 25.5% | 52.4% | 44.2% |
| 27.114.1 | lact:CaCl2:Na2SO4 90:4.4:5.6 | Niro | 3.9 | 2.5 | 1.2 | | 17.9% | 12.0% | 28.5% | 42.5% | 13.3% |
| 27.114.2 | lact:CaCl2:Na2SO4 50:22:28 | Niro | 4.5 | 2.0 | 1.1 | | 12.6% | 10.2% | 29.1% | 44.5% | 58.0% |
| 27.115.3 | CaSO4 100 | Niro | 3.8 | 1.7 | 1.2 | | 14.0% | 15.8% | 38.2% | 57.0% | 47.5% |
| 27.185.2 | Ca(OH)2:Sulf acid:NaCl 41.3:54.6:4.1 | Buchi | 2.5 | 1.8 | 1.3 | | | 17.5% | 45.2% | 65.2% | 44.1% |
| 27.185.3 | Ca(OH)2:Sulf acid 43:57 | Buchi | 2.9 | 2.3 | 1.1 | | | 15.3% | 38.9% | 59.4% | 16.1% |
| 27.183.1 | CaLact:NaCl 96.8:3.2 | Buchi | 3.1 | 2.0 | 1.1 | | | 22.4% | 50.9% | 69.5% | 35.0% |
| 27.115.2 | CaCl2:Na2CO3 51:49 | Niro | 3.9 | 2.1 | 1.4 | | 1.7% | 8.4% | 22.4% | 38.9% | 27.3% |
| 27.184.3 | CaGluc:NaCl 98.3:1.7 | Buchi | 2.9 | 2.0 | 1.0 | | | 13.5% | 26.7% | 48.3% | 47.6% |
| 27.15.2 | MgCl2:Na3Cit, 36:64 | Labplant | 3.1 | 1.4 | 1.0 | | 13.2% | | | | 28.6% |
| 27.33.3 | MgCl2:Na3Cit, 36:64 | Labplant | 4.0 | 2.2 | 1.2 | | 15.7% | 21.4% | 53.7% | 68.2% | 26.2% |
| 27.15.3 | MgCl2:Na2SO4, 40:60 | Labplant | 3.9 | 2.3 | 1.3 | | 11.1% | | | | 31.8% |
| 27.33.9 | MgCl2:Na2CO3, 47:53 | Labplant | 2.7 | 3.7 | 1.4 | | 7.9% | 21.0% | 46.0% | 58.3% | 18.8% |
| 27.15.4 | MgCl2:Na2CO3, 47:53 | Labplant | 2.3 | 1.4 | 1.1 | | 87.4% | | | | 17.6% |
| 68.124.1 | lact:MgCl2:Na3Cit 10:30.6:59.4 | Buchi HP | | | | | | 18.1% | 37.8% | 55.7% | 88.9% |
| 68.129.2 | MgLact:NaCl 63.4:36.6 | Buchi HP | | | | | | 16.5% | 39.3% | 59.8% | 78.0% |

TABLE 32

Leucine and calcium-containing formulations of small, dispersible particles

| Lot | Formulation | Method | x50 (µm) @ 1 bar | GSD @ 1 bar | 1/4 bar | 0.5/4 bar | water % | FPF_TD <3.4 um % | FPF_TD <5.6 um % | % Mass collected | yield % | Tapped density (g/cc) |
|---|---|---|---|---|---|---|---|---|---|---|---|---|
| Chloride | | | | | | | | | | | | |
| 26.010.2 | leu:CaCl2:NaCl 50:29.5:20.5 | Niro | 4.8 | 2.2 | 1.1 | | | 15.8% | 35.9% | 50.8% | 64.1% | |
| 26.041.3 | leu:CaCl2:NaCl 50:29.5:20.5 | Niro | 4.9 | 2.4 | | | | 14.7% | 28.0% | 43.0% | 50.2% | |
| Citrate | | | | | | | | | | | | |
| 26.013.1 | leu:CaCl2:Na3Cit2 50:19.5:30.5 | Niro | 4.2 | 2.1 | 1.6 | | | 16.8% | 35.2% | 53.8% | 56.1% | |
| 26.013.2 | leu:CaCl2:Na3Cit2 10:35.1:54.9 | Niro | 4.8 | 1.8 | 1.3 | | | 20.8% | 39.6% | 52.2% | 57.5% | |
| 26-190-F | Leucine:CaCl2:Na3Cit2 10.0:35.1:54.9 | Niro | 2.6 | 1.9 | 1.2 | 1.2 | | 45.7% | 61.6% | 66.3% | 74.8% | 0.29 |
| Sulfate | | | | | | | | | | | | |
| 26.013.4 | leu:CaCl2:Na2SO4 10:39.6:50.4 | Niro | 3.7 | 2.0 | 1.4 | | | 19.6% | 39.4% | 60.9% | 73.1% | |
| 26.060.2 | leu:CaCl2:Na2SO4 10:39.6:50.4 | Niro | 2.9 | 1.9 | 1.2 | | | 16.2% | 35.2% | 53.2% | 46.5% | 0.18 |
| 26.060.4 | leu:CaCl2:Na2SO4 10:39.6:50.4 | Niro | 2.9 | 1.7 | 1.3 | | | 18.8% | 45.1% | 64.4% | 49.9% | 0.17 |
| 27.154.2 | leu:CaCl2:Na2SO4 10:39.6:50.4 | Buchi | 3.8 | 1.9 | 1.1 | | | 17.2% | 37.5% | 55.5% | 56.1% | 0.30 |
| 65-009-F | Leucine:CaCl2:Na2SO4 10.0:39.6:50.4 | Niro | 2.5 | 2.2 | 1.4 | 1.5 | | 60.1% | 82.7% | 88.6% | 74.2% | 0.34 |
| 26.053.1 | leucine:CaCl2:Na2SO4 50:22:28 | Niro | 4.2 | 2.0 | 1.5 | | 3.3% | 23.0% | 39.6% | 52.0% | 59.6% | |
| 27.114.4 | leu:CaCl2:Na2SO4 50:22:28 | Niro | 4.7 | 1.8 | 1.9 | | 3.8% | 21.2% | 44.6% | 59.6% | 59.6% | |
| 27.155.1 | leu:CaCl2:Na2SO4 50:22:28 | Buchi | 3.7 | 1.9 | 1.2 | | | 15.7% | 42.9% | 68.8% | 47.6% | 0.35 |
| Calcium sulfate | | | | | | | | | | | | |
| 26.019.4 | leu:CaSO4 50:50 | Niro | 4.1 | 2.1 | 1.4 | | | 11.9% | 28.0% | 56.0% | 101.8% | |
| Carbonate | | | | | | | | | | | | |
| 26.019.1 | leu:CaCl2:NaCO3 50:25.5:24.5 | Niro | 3.4 | 1.9 | 1.7 | | | 9.6% | 22.2% | 35.9% | 46.3% | |
| 26.019.2 | leu:CaCl2:NaCO3 10:45.9:44.1 | Niro | 2.7 | 1.8 | 1.4 | | | 10.6% | 23.8% | 37.5% | 51.0% | |
| Lactate | | | | | | | | | | | | |
| 26.041.4 | leu:CaLact:NaCl 50:36.8:13.1 | Niro | 5.0 | 1.9 | | | | 9.7% | 25.9% | 46.6% | 56.5% | |
| 27.183.2 | Leu:CaLact:NaCl 50:48.4:1.6 | Buchi | 3.7 | 1.8 | 1.1 | | | 24.9% | 48.9% | 62.7% | 34.1% | |
| 27.185.1 | Leu:CaLact:NaCl 10:66.6:23.4 | Buchi | 3.0 | 1.9 | 1.0 | | | 26.1% | 53.7% | 70.0% | 44.8% | |
| 45.19.1 | leu:CaLact:NaCl 10:66.6:23.4 | Buchi HP | 3.4 | 2.3 | 0.9 | | 5.2% | 12.8% | 29.1% | 50.3% | 75.6% | 0.74 |
| 45.76.1 | leu:CaLact:NaCl 10:58.6:31.4 | Buchi HP | 3.8 | 2.1 | 1.0 | | 5.0% | 8.6% | 20.9% | 36.6% | 78.5% | |
| 45.78.1 | leu:CaLact:NaCl 10:58.6:31.4 | Buchi HP | 1.5 | 1.9 | 1.1 | | 4.8% | 30.6% | 53.4% | 62.9% | 60.8% | |
| 45.80.1 | leu:CaLact:NaCl 10:58.6:31.4 | Buchi HP | 1.5 | 1.9 | 1.1 | | 4.4% | 30.3% | 53.5% | 63.8% | 71.0% | |
| 45.81.1 | leu:CaLact:NaCl 10:58.6:31.4 | Buchi HP | 2.4 | 2.8 | 1.3 | | 7.2% | 19.3% | 34.1% | 44.3% | 64.6% | |
| 68.70.1 | leu:CaLact:NaCl 10:58.6:31.4 | Buchi HP | 1.5 | 1.9 | 1.0 | | | 42.8% | 63.2% | 67.8% | 73.9% | |
| 65-003-F | Leucine:CaLact:NaCl 10.0:58.6:31.4 | Niro | 1.5 | 2.5 | 1.1 | 1.1 | | 43.4% | 63.5% | 69.7% | 62.9% | 0.69 |
| Gluconate | | | | | | | | | | | | |
| 27.184.1 | Leu:CaGluc:NaCl 50:49.15:0.85 | Buchi | 3.4 | 2.1 | 1.0 | | | 35.0% | 61.4% | 76.3% | 51.9% | |
| 27.184.4 | leu:CaGluc:NaCl 50:42.35:7.65 | Buchi | 3.5 | 2.0 | 1.2 | | | 34.1% | 60.7% | 71.5% | 46.3% | |
| 27.184.2 | Leu:CaGluc:NaCl 10:88.5:1.5 | Buchi | 2.7 | 2.0 | 1.0 | | | 24.9% | 52.2% | 64.2% | 51.0% | |

EXAMPLE 19

Pure calcium chloride was spray dried in the Labplant spray drying system with an inlet temperature of 180° C. The liquid feed consisted of 20 g/L solids concentration of calcium chloride dihydrate in D.I. water. Water condensed in the collection vessel as the calcium chloride deliquesced and no powder could be collected. Pure calcium chloride was deemed too hygroscopic for spray drying from an aqueous solution with high water content in the exhaust drying gas. The liquid feed was then changed to 70% ethanol to reduce humidity in the exhaust gas, keeping the solids concentration at 20 g/L, the inlet temperature at 200° C. and outlet temperature at 69° C. Water still condensed in the collection vessel and the powder looked wet. It was concluded that calcium chloride is too hygroscopic to be spray dried without mixing with other salts or with an excipient to reduce the calcium chloride content in the final powder.

Pure magnesium chloride was spray dried in the Labplant system with an inlet temperature of 195° C. and outlet temperature of 68° C. The liquid feed consisted of 20 g/L solids concentration of magnesium chloride hexahydrate in D.I. water. The dry powder in the collection vessel looked wet and the median particle size measured on the HELOS/RODOS system was 21 microns. The liquid feed was then changed to 70% ethanol to reduce humidity in the exhaust drying gas, keeping the solids concentration at 50 g/L, the inlet temperature at 200° C. and an outlet temperature of 74° C. This magnesium chloride powder did not look wet and had a median volume particle size of 4 microns, but the powder appeared granular and had a fine particle fraction less than 5.6 microns of 19%, indicating that the powder was not sufficiently respirable.

EXAMPLE 20

Large, Porous Particles

TABLE 33

Large Porous Particle formulations

| Formulation | Method | x50 (μm) @ 1 bar | GSD @ 1 bar | 1/4 bar | 0.5/4 bar | Spraytec dV50 (μm) | Spraytec GSD | water % | FPF_TD <3.4 um % | FPF_TD <5.6 um % | % Mass collected | yield % | Tapped density (g/cc) |
|---|---|---|---|---|---|---|---|---|---|---|---|---|---|
| leucine:Cacl2:NaCl 50:29.5:20.5 | Niro | 25.9 | 5.8 | | | | | | 18.2% | 29.0% | 48.6% | 43.2% | |
| leucine:Cacl2:NaCl 50:29.5:20.5 | Niro | 12.2 | 6.3 | | | | | | | | | 35.4% | |
| leu:CaCl2:Na2SO4 90:4.4:5.6 | Niro | 10.0 | 2.4 | | | | | 1.8% | 5.0% | 16.5% | 34.7% | 84.8% | |
| leu:CaLact:NaCl 10:66.6:23.4 | Buchi HP | | | | | 22.4 | 4.4 | | 4.9% | 7.3% | 13.1% | 72.0% | |
| leu:CaCl2:Na2SO4 67.6:30:2.4 | Buchi HP | | | | | 21.2 | 3.0 | | 13.2% | 25.2% | 47.7% | n/a | 0.22 |

EXAMPLE 21

Stability

Dry powders were tested for in-use stability under extreme temperature and humidity conditions (ICH, Climatic Zone XIV), defined as 30° C. and 75% RH. Approximately 25 mg of Formulation I, Formulation II and Formulation III were filled into capsules. The capsules were left opened and then were placed in a stability chamber at the defined conditions for 15 and 30 minutes. The capsules were removed at the appropriate time, closed and tested for aPSD using the collapsed 2-stage ACI and for gPSD using the Malvern Spraytec. Both tests were run at 60 LPM for 2 seconds. Each timepoint was repeated n=2. The results were compared with aPSD/gPSD data from the powder at room temperature and 25-30% RH.

All formulations (Formulation I, Formulation II and Formulation III) showed less than +/−5% change from the fine particle fraction of the total dose (FPFTD) less than 5.6 microns at standard conditions (22° C., 25-30% RH), after a 30 minute exposure to extreme temperature and humidity conditions (30° C., 75% RH). For gPSD, Formulation I showed an increase of approximately 30% after 30 minutes, while Formulation III remained mostly stable and Formulation II had a decrease in Dv50 of approximately 15% after 30 minutes.

While insignificant changes in aerosol properties of the three formulations were seen upon exposure to 30° C., 75% RH for 30 minutes, changes in geometric particle size were more evident (FIGS. 31A and 31 B). Formulation I (calcium citrate) particle size increased by approximately 30%, while Formulation II (calcium lactate) particle size decreased by approximately 15%. Formulation III (calcium sulfate) particle size decreased, but not significantly.

Additional formulations tested were a calcium chloride powder (38.4% leucine, 30.0% calcium chloride, 31.6% sodium chloride) and three calcium lactate powders using different excipients (lactose, mannitol, maltodextrin) matching the Formulation II formulation (10.0% excipient, 58.6% calcium lactate, 31.4% sodium chloride).

After a 30 minute exposure to extreme temperature and humidity conditions (30° C., 75% RH), the maltodextrin (Formulation XIV) and mannitol formulations showed an overall change of less than +/−10% change from the fine particle fraction of the total dose smaller than 5.6 microns at standard conditions (22° C., 25-30% RH). The calcium chloride powder and lactose formulation appeared affected with a decrease of over 50% and an increase of approximately 20%, respectively, in fine particle fraction of the total dose smaller than 5.6 microns. (FIG. 31C) For gPSD, the results were opposite, where the calcium chloride powder and the lactose formulation showed an overall change of less than +/−10% change in $Dv_{50}$ after 30 minutes, while the mannitol formulation had an increase in $Dv_{50}$ of 30%-60% during the test. (FIG. 32D) The maltodextrin formulation was not tested for change in $Dv_{50}$.

EXAMPLE 22

Short-Term Stability at Room Temperature and 30% and 40% RH

Spray dried powders were kept at room temperature at approximately 30% and 40% RH for a period of one week and periodically tested for particle size distribution. Size 3 HPMC capsules (Quali-V, Qualicaps, Whitsett, N.C.) were half filled with each dry powder. One sample was tested immediately in the Spraytec (Malvern Instruments Inc., Westborough, Mass.), a laser diffraction spray particle sizing system where dry powders can be dispersed from an inhaler using the inhaler cell setup. Approximately 16 capsules were filled with each powder. Half of the capsules were kept in the lab at controlled humidity and temperature conditions (~23-28% RH), while the other half were kept in the outside lab at varying temperature and relative humidity (~38-40% RH). At specific time points (t=1 hr, 2 hr, 4 hr, 24 hr, 48 hr, 1 week), one capsule from the environmental controlled room and one from the outside lab were tested on the Spraytec for volume particle size distribution.

Figure 32:
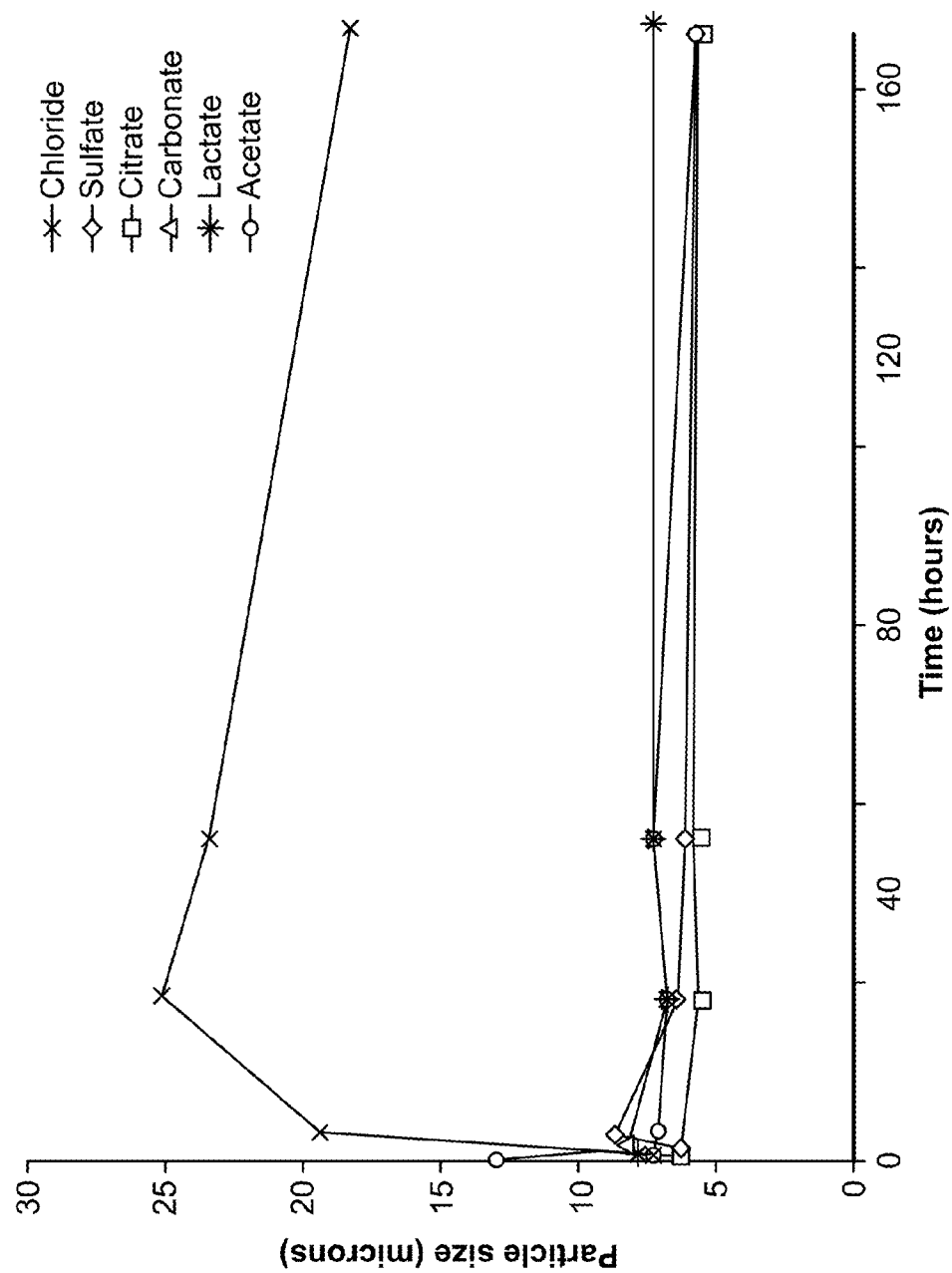
Figure 33:
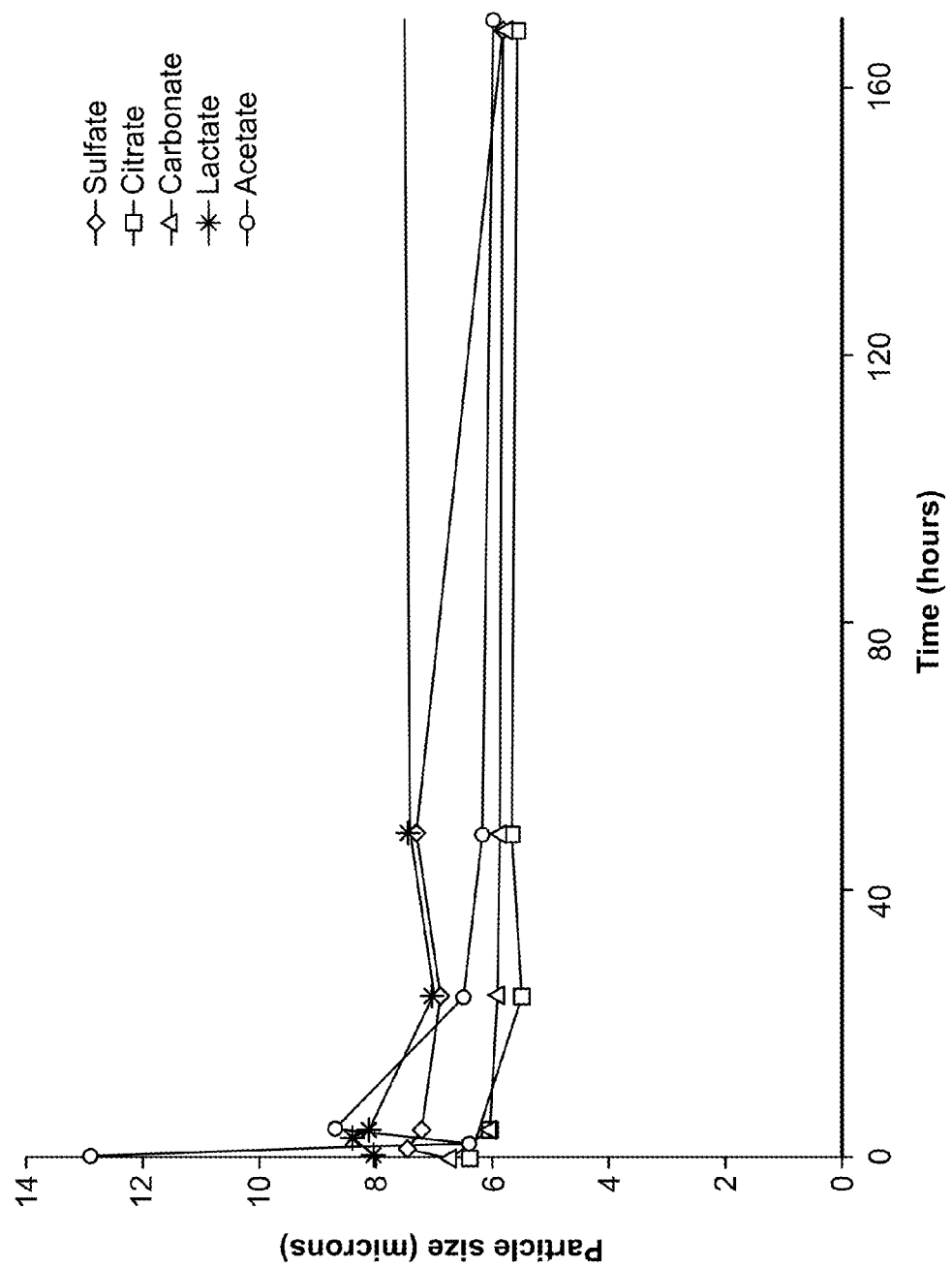

Results for a selection of formulations containing 50% leucine and a combination of calcium chloride and the sodium salt indicated are shown in FIG. 32 and FIG. 33. The formulations containing calcium chloride and sodium chloride showed significant agglomeration after exposure to higher humidity conditions. The acetate formulation had variable results at the initial time points. The sulfate, citrate and carbonate formulations demonstrated good relative stability over the test period.

Dry powder formulations containing calcium chloride and sodium chloride were not stable when held at room temperature and 40% RH after an hour of exposure, while the acetate formulation also showed variable results in particle size. The sulfate and lactate powders increased slightly in size, while carbonate and citrate powders decreased slightly in size. Formulations containing only chloride and those containing acetate were not deemed suitably stable for further study.

EXAMPLE 23

Dry Powder Flow Properties

The flowability of Formulation I, II, III and XIV powders was also assessed using conventional methods in the art for the characterization of powder flowability. The Flowability Index for each powder was determined using a Flodex Powder Flowability Test Instrument (Hanson Research Corp., model 21-101-000). For any given run, the entire sample was loaded using a stainless steel funnel aimed at the center of the trap door hole in the cylinder. Care was taken not to disturb the column of powder in the cylinder. After waiting ~30 sec for the potential formation of flocculi, the trap door was released while causing as little vibration to the apparatus as possible. The test was considered a pass if the powder dropped through the trap door so that the hole was visible looking down through the cylinder from the top and the residue in the cylinder formed an inverted cone; if the hole was not visible or the powder fell straight through the hole without leaving a cone-shaped residue, the test failed. Enough flow discs were tested to find the minimum size hole the powder would pass through, yielding a positive test. The minimum-sized flow disc was tested two additional times to obtain 3 positive tests out of 3 attempts. The flowability index (FI) is reported as this minimum-sized hole diameter.

Bulk and tap densities were determined using a SOTAX Tap Density Tester model TD2. For any given run, the entire sample was introduced to a tared 100-mL graduated cylinder using a stainless steel funnel. The powder mass and initial volume ($V_0$) were recorded and the cylinder was attached to the anvil and run according to the USP I method. For the first pass, the cylinder was tapped using Tap Count 1 (500 taps) and the resulting volume $V_a$ was recorded. For the second pass, Tap Count 2 was used (750 taps) resulting in the new volume $V_{b1}$. If $V_{b1}$>98% of $V_a$, the test was complete, otherwise Tap Count 3 was used (1250 taps) iteratively until $V_{bn}$>98% of $V_{bn-1}$. Calculations were made to determine the powder bulk density ($d_B$), tap density ($d_T$), Hausner Ratio (H) and Compressibility Index (C), the latter two of which are standard measures of powder flowability. "H" is the tap density divided by the bulk density, and "C" is 100*(1−(bulk density divided by the tap density)). Skeletal Density measurement was performed by Micromeritics Analytical Services using an Accupyc II 1340 which used a helium gas displacement technique to determine the volume of the powders. The instrument measured the volume of each sample excluding interstitial voids in bulk powders and any open porosity in the individual particles to which the gas had access. Internal (closed) porosity was still included in the volume. The density was calculated using this measured volume and the sample weight which was determined using a balance. For each sample, the volume was measured 10 times and the skeletal density ($d_S$) was reported as the average of the 10 density calculations with standard deviation.

Results for these density and flowability tests are shown in Tables 34 and 35. All four of the powders tested possess Hausner Ratios and Compressibility Indices that are described in the art as being characteristic of powders with extremely poor flow properties (See, e.g., USP <1174>). It is thus surprising that these powders are highly dispersible and possess good aerosolization properties as described herein.

TABLE 34

Bulk and tap densities and flow properties of Formulation I-IIII and XIV powders.

| Sample | FI (mm) | $d_B$ (g/mL) | $d_T$ (g/mL) | H | C |
|---|---|---|---|---|---|
| Formulation I | 26 | 0.193 | 0.341 | 1.77 | 43.4% |
| Formulation II | 22 | 0.313 | 0.722 | 2.31 | 56.7% |
| Formulation III | 18 | 0.177 | 0.388 | 2.19 | 54.3% |
| Formulation XIV | >34 | 0.429 | 0.751 | 1.75 | 42.9% |

TABLE 35

Skeletal density measurements of powders Formulation I-II and XIV.

| Sample | $d_{S1}$ ± σ (g/mL) | $d_{S2}$ ± σ (g/mL) |
|---|---|---|
| Formulation I | 1.7321 ± 0.0014 | 1.7384 ± 0.0042 |
| Formulation II | 1.6061 ± 0.0007 | 1.6074 ± 0.0004 |

TABLE 35-continued

Skeletal density measurements of
powders Formulation I-II and XIV.

| Sample | $d_{S1} \pm \sigma$ (g/mL) | $d_{S2} \pm \sigma$ (g/mL) |
|---|---|---|
| Formulation III | 2.1243 ± 0.0011 | 2.1244 ± 0.0018 |
| Formulation XIV | 1.6759 ± 0.0005 | 1.6757 ± 0.0005 |

USP <1174> mentioned previously notes that dry powders with a Hausner Ratio greater than 1.35 are poor flowing powders. Flow properties and dispersibility are both negatively effected by particle agglomeration or aggregation. It is therefore unexpected that powders with Hausner Ratios of 1.75 to 2.31 would be highly dispersible

EXAMPLE 24

Water Content and Hygroscopicity

Figure 34:
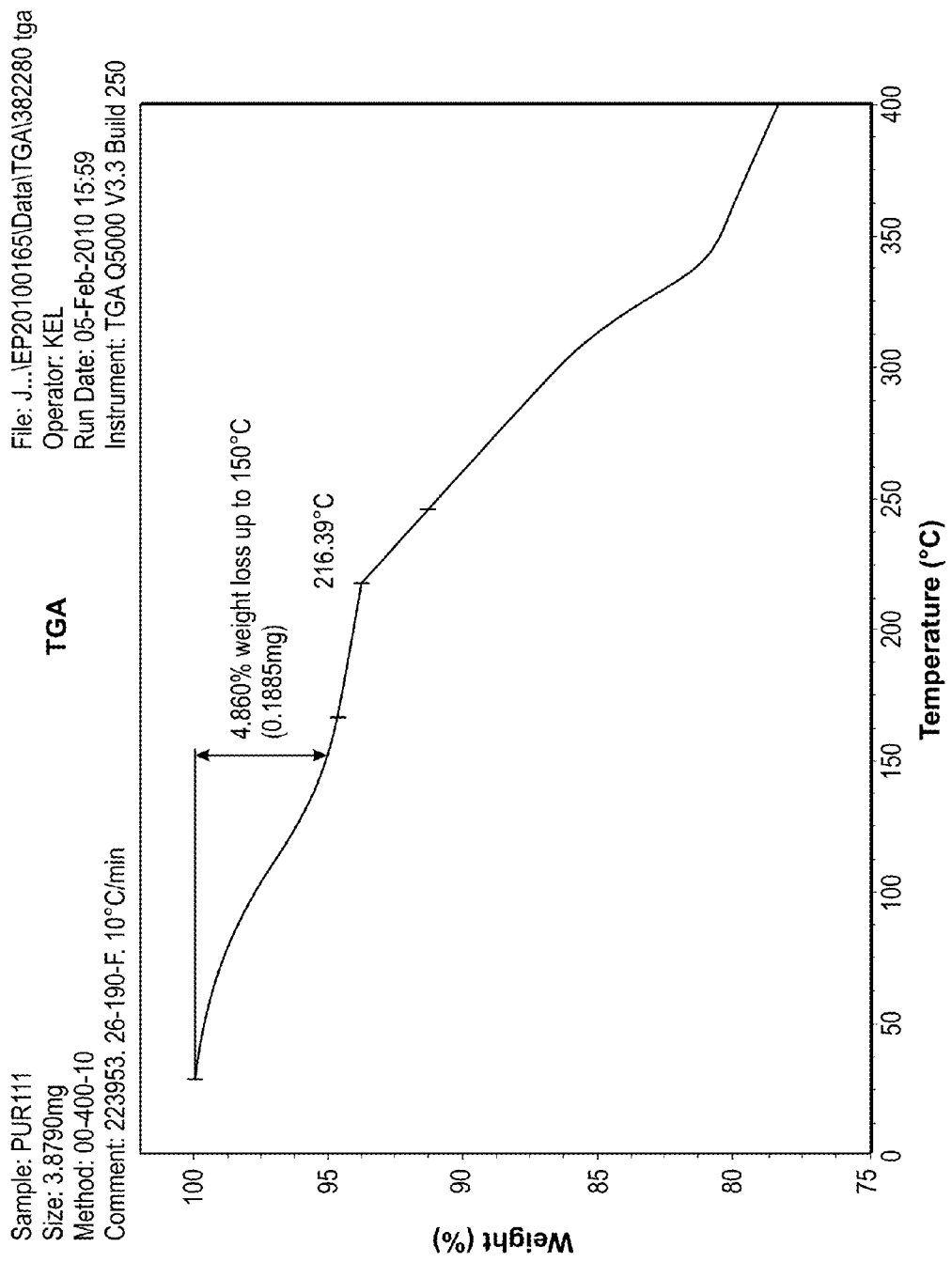

The water content of Formulation I, II, III and XIV powders was determined via both thermogravimetric analysis (TGA) and Karl Fischer analysis. Thermogravimetric analysis (TGA) was performed using a TA Instruments Q5000 IR thermogravimetric analyzer (New Castle, Del.). Sample was placed in an aluminum sample pan and inserted into the TG furnace. The data acquisition and processing parameters are displayed on each thermogram. Nickel and Alumel™ were used as the calibration standards. For TGA, the water content was determined from the loss of mass of the samples upon heating to a temperature of 150° C. (for TGA, since the spray-drying solvent used was 100% water, it was assumed that only water was present as a volatile component in these powders). A representative TGA thermogram for powder Formulation I is shown in FIG. 34 Coulometric Karl Fischer (KF) analysis for water determination was performed using a Mettler Toledo DL39 KF titrator (Greifensee, Switzerland). Sample was placed in the KF titration vessel containing Hydranal-Coulomat AD and mixed for 10 seconds to ensure dissolution. The sample was then titrated by means of a generator electrode which produces iodine by electrochemical oxidation: $2\ I^- \Rightarrow I_2 + 2e$. Generally, one range-finding run and two replicates were obtained to ensure reproducibility. Summary data for powder water contents using these methods are shown in Table 36

TABLE 36

Water content data for FORMUALTIONS I, II,
III and XIV via TGA and Karl fischer

| Powder | Water Content via TGA | Water Content via Karl Fischer |
|---|---|---|
| Formulation I | 4.9% | 3.9% |
| Formulation II | 2.0% | 2.0% |
| Formulation III | 5.1% | 4.6% |
| Formulation XIV | 2.2% | 2.1% |

A dynamic vapor sorption (DVS) step mode experiment was conducted to compare the hygroscopicity and water uptake potential of Formulation I, II, III and XIV powders versus raw calcium chloride dihydrate, as well as a 1:2 calcium chloride: sodium chloride control powder made via spray-drying a formulation containing 38.4% leucine, 30% $CaCl_2$ and 31.6% NaCl (it was determined that 30 wt % was the highest loading level of calcium chloride that could be successfully incorporated into a spray-dried powder without undergoing deliquescence in the collection vehicle immediately after spray-drying). With respect to the DVS operating conditions, the powders were initially equilibrated at 0% RH then exposed to 30% RH for 1 hour followed by exposure to 75% RH for 4 hours. The mass % water uptake for each of the powders is shown in Table 37. As can be seen in Table 37, both raw calcium chloride dihydrate and the control powder were extremely hygroscopic, taking up approximately 14 to 15% water upon exposure to 30% RH for 1 hour and taking up well over 100% their mass in water after exposure to 75% RH. In contrast, the Formulation I, II, III and XIV powders took up less than 2.5% water upon exposure to 30% RH for 1 hour and from 14% to 33% water upon exposure to 75% RH for 4 hours.

TABLE 37

% Change in mass due to water uptake after (i) 30% RH hold
for 1 hour and (ii) 75% RH hold for 4 hours via DVS.

| Powder | % Change in Mass Due to Water Uptake after 30% RH for 1 hr | % Change in Mass Due to Water Uptake after 75% RH for 4 hrs |
|---|---|---|
| $CaCl_2 * 2H_2O$ (raw) | 13.7 | 146 |
| $CaCl_2$-control | 15.3 | 124 |
| Formulation I | 1.68 | 14.7 |
| Formulation II | 1.27 | 28.3 |
| Formulation III | 2.45 | 20.8 |
| Formulation XIV | 1.36 | 32.8 |

EXAMPLE 25

Heat of Solution

Figure 35:
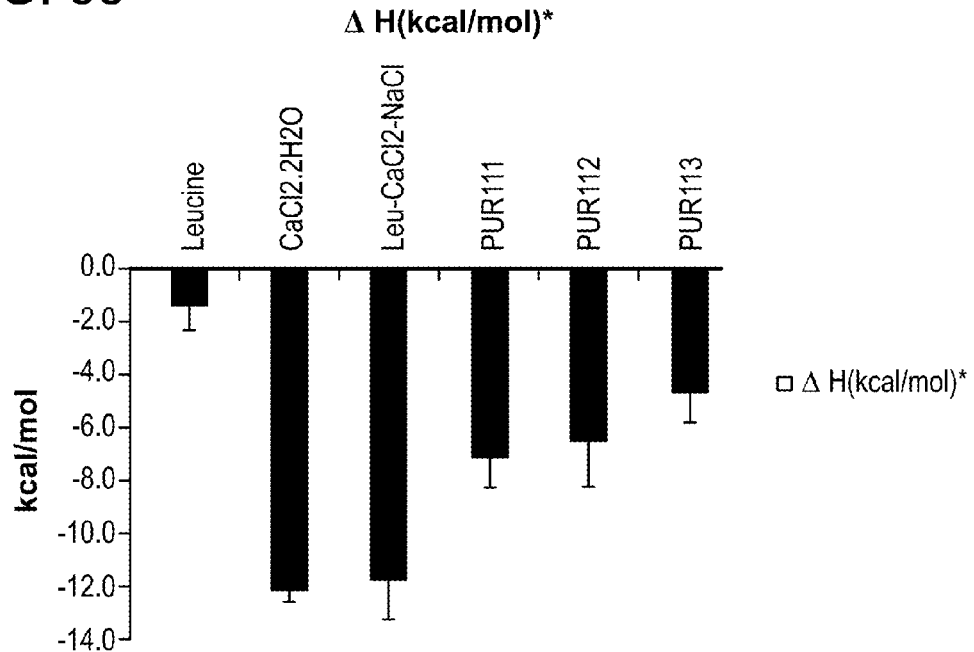

Heats of solution were obtained upon dissolution of samples of Formulations I through III in HBSS buffer in comparison to (i) a control powder comprised of 30% calcium chloride, 31.6% sodium chloride and 38.4% leucine, (ii) raw calcium chloride dihydrate and (iii) raw leucine. As shown in Table 38, masses of Formulation I (PUR111), II (PUR113) and III (PUR112) powder containing equivalent moles of calcium ion were tested for the calcium-containing samples. Results are shown in FIG. 35. As can be seen from the data shown in FIG. 35, Formulations I through III resulted in significantly decreased heats of solution as compared to both raw calcium chloride dihydrate and the control calcium powder. Calcium chloride dihydrate is known to possess a large exothermic heat of solution and to release a significant amount of heat upon contact with water. Under certain circumstances, such as when a large quantity of calcium chloride dihydrate, or other salts that have a large exothermic heat of solution, are rapidly dissolved a large amount of heat is released that can cause burns. Thus, there are safety concerns associated with contacting mucosal surfaces with calcium chloride dihydrate. These safety concerns can be alleviated by producing powders, such as Formulations I through III which do not have large exothermic heats of solution, and thus reduced potential for undesirable exothermic effects.

TABLE 38

Heat of solution data for Formulations I-III, a control powder containing calcium chloride, raw calcium chloride dihydrate and raw leucine.

| | Powder | | | | | | | | | | | |
|---|---|---|---|---|---|---|---|---|---|---|---|---|
| | Leucine | | CaCl•2H2O | | CaCl2-control | | PUR111 | | PUR112 | | PUR113 | |
| | | | | | Lot # | | | | | | | |
| | 65-017-F (-4) | | Spectrum | | 68-113-1 | | 26-190-F | | 65-009-F | | 65-003-F | |
| | Avg. | St. Dev. | Avg. | St. Dev. | Avg. | St. Dev. | Avg. | Avg. | Avg. | St. Dev. | Avg. | St. Dev. |
| g | 0.032 | 0.000 | 0.036 | 0.001 | 0.090 | 0.001 | 0.077 | 0.000 | 0.068 | 0.000 | 0.090 | 0.000 |
| mmol* | 0.244 | 0.001 | 0.242 | 0.000 | 0.242 | 0.000 | 0.242 | 0.000 | 0.243 | 0.000 | 0.242 | 0.000 |
| ΔT (deg. C.) | 0.003 | 0.002 | 0.024 | 0.001 | 0.023 | 0.003 | 0.014 | 0.002 | 0.012 | 0.003 | 0.009 | 0.002 |
| Q (cal) | 0.37 | 0.20 | 2.93 | 0.12 | 2.8 | 0.3 | 1.7 | 0.2 | 1.5 | 0.4 | 1.0 | 0.3 |
| ΔH (kcal/mol)* | −1.5 | 0.8 | −12.1 | 0.4 | −11.7 | 1.4 | −6.9 | 1.0 | −6.2 | 1.6 | −4.3 | 1.1 |
| ΔH (kJ/mol)* | −6 | 4 | −50.6 | 1.6 | −49 | 6 | −29 | 4 | −26 | 7 | −18 | 4 |

*mol Ca for all powders except leucine, which is in mol Leu

EXAMPLE 26

In Vivo Pneumonia Model

Bacteria were prepared by growing cultures on tryptic soy agar (TSA) blood plates overnight at 37° C. plus 5% $CO_2$. Single colonies were resuspended to an $OD_{600}$~0.3 in sterile PBS and subsequently diluted 1:4 in sterile PBS (~$2 \times 10^7$ Colony forming units (CFU)/mL). Mice were infected with 50 μL of bacterial suspension (~$1 \times 10^6$ CFU) by intratracheal instillation while under anesthesia.

C57BL6 mice were exposed to aerosolized liquid formulations in a whole-body exposure system using either a high output nebulizer or Pari LC Sprint nebulizer connected to a pie chamber cage that individually holds up to 11 animals. Mice were treated with dry powder formulations (Table 39) 2 h before infection with *S. pneumoniae*. As a control, animals were exposed to a similar amount of 100% leucine powder. Twenty-four hours after infection mice were euthanized by pentobarbital injection and lungs were collected and homogenized in sterile PBS. Lung homogenate samples were serially diluted in sterile PBS and plated on TSA blood agar plates. CFU were enumerated the following day.

Figure 36:
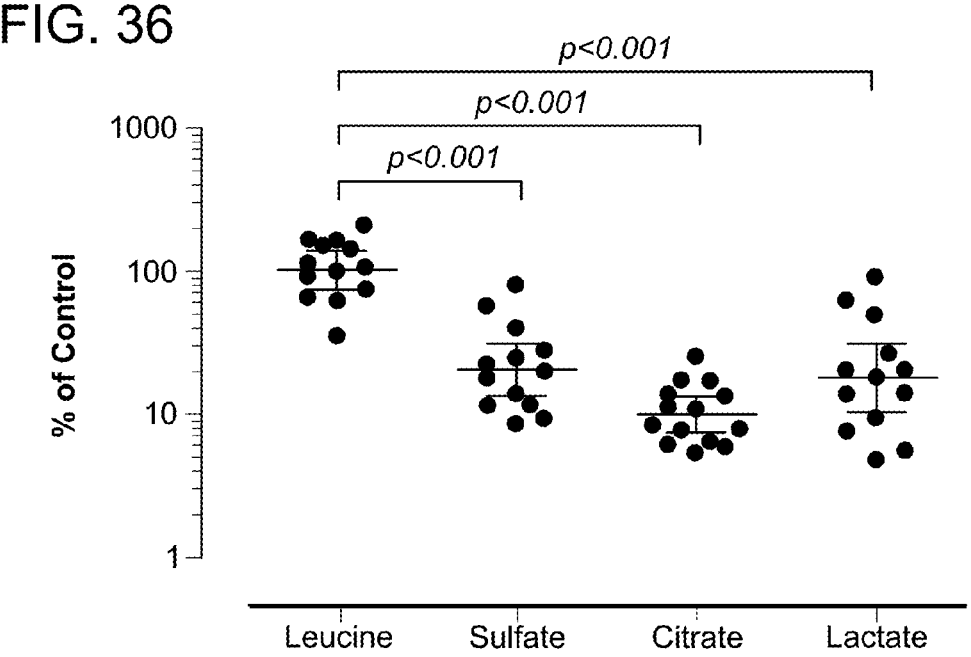

Compared to control animals, calcium dry powder treated animals exhibited reduced bacterial titers 24 hours after infection. Specifically, animals treated with a formulation comprised of calcium sulfate and sodium chloride (Formulation III) exhibited 5-fold lower bacterial titers, animals treated with a formulation comprised of calcium citrate and sodium chloride (Formulation I) exhibited 10.4-fold lower bacterial titers, and animals treated with a formulation comprised of calcium lactate and sodium chloride (Formulation II) exhibited 5.9-fold lower bacterial titers. (FIG. 36)

TABLE 39

Formulations used to evaluate efficacy

| Formulation | Composition | Ca:Na molar ratio |
|---|---|---|
| Formulation I | 10.0% leucine, 35.1% calcium chloride, 54.9% sodium citrate (Active with 12.7% calcium ion) | 1:2 |
| Formulation III | 10.0% leucine, 39.6% calcium chloride, 50.4% sodium sulfate (Active with 14.3% calcium ion) | 1:2 |
| Formulation II | 10.0% leucine, 58.6% calcium lactate, 31.4% sodium chloride (Active with 10.8% calcium ion) | 1:2 |

The data presented herein show that divalent metal cation salt-containing dry powders that are highly dispersible can be manufactured and used to treat bacterial and viral infections.

EXAMPLE 27

3 Month Refrigerated, Standard and Accelerated Conditions Stability Study

A 3 month physical stability study was conducted utilizing representative samples of Formulations I through III filled into size 3 HPMC capsules (Shionogi Qualicaps, Madrid, Spain) and placed at the following conditions (i) 2-8° C. refrigerated storage, (ii) 25° C./60% RH, capsules stored under desiccant and (iii) 40° C./75% RH, capsules stored under desiccant. FPF<5.6 and 3.4 as well as Dv50 (Spraytec) and water content (Karl Fischer) were monitored out to a 3 month timepoint. As shown in Table 40, each of Formulations I through III displayed good stability with respect to the assessed physical properties under each of these conditions.

TABLE 40

3 month stability study results for Formulations I-III.

| | | Formulation I (citrate) | | | | Formulation II (lactate) | | | | Formulation III (sulfate) | | | |
|---|---|---|---|---|---|---|---|---|---|---|---|---|---|
| Condition (° C./% RH) | Time (mo) | FPF <3.4 um | FPF <5.6 um | Spraytec (um) | H2O | FPF <3.4 um | FPF <5.6 um | Spraytec (um) | H2O | FPF <3.4 um | FPF <5.6 um | Spraytec (um) | H2O |
| Time zero | 0 | 50% | 63% | 3.1 | 6% | 42% | 61% | 1.8 | 4% | 55% | 73% | 3.1 | 5% |
| 25 C./ | 1 | 47% | 68% | 1.5 | 7% | 42% | 60% | 2.0 | 4% | 56% | 74% | 3.6 | 6% |
| 60% RH (capsules + desiccant) | 3 | 45% | 68% | 3.5 | 7% | 42% | 61% | 1.2 | 4% | 57% | 73% | 2.4 | 6% |

TABLE 40-continued

| 3 month stability study results for Formulations I-III. | | | | | | | | | | | | | |
|---|---|---|---|---|---|---|---|---|---|---|---|---|---|
| | | Formulation I (citrate) | | | | Formulation II (lactate) | | | | Formulation III (sulfate) | | | |
| Condition (° C./% RH) | Time (mo) | FPF <3.4 um | FPF <5.6 um | Spraytec (um) | H2O | FPF <3.4 um | FPF <5.6 um | Spraytec (um) | H2O | FPF <3.4 um | FPF <5.6 um | Spraytec (um) | H2O |
| 40 C./ | 0.5 | 43% | 66% | 5.3 | 8% | 39% | 58% | 1.8 | 6% | 51% | 67% | 2.9 | 6% |
| 75% RH | 1 | 43% | 65% | 2.0 | 7% | 40% | 58% | 3.0 | 4% | 56% | 70% | 3.9 | 5% |
| (capsules + desiccant) | 3 | 46% | 68% | 3.3 | 7% | 47% | 61% | 1.5 | 4% | 45% | 64% | 2.5 | 5% |
| 2-8 C. | 3 | 46% | 60% | 2.4 | 5% | 43% | 63% | 1.3 | 2% | 56% | 76% | 2.3 | 5% |

The content of each of the patents, patent applications, patent publications and published articles cited in this specification are herein incorporated by reference in their entirety.

The invention claimed is:

1. A respirable dry powder comprising respirable dry particles that comprise a divalent metal cation salt, wherein the divalent metal cation salt provides divalent metal cation in an amount of about 5% or more by weight of the dry particle, and the respirable dry particles that comprise a divalent metal cation salt have a volume median geometric diameter (VMGD) of about 5 microns or less, a tap density of greater than 0.4 g/cubic centimeter (cc) and are further characterized by a capsule emitted powder mass (CEPM) of at least 80% when emitted from a passive dry powder inhaler that has a resistance of about 0.036 sqrt(kPa)/liters per minute (LPM) under the following conditions: an inhalation energy of 1.15 Joules at a flow rate of 30 LPM using a size 3 capsule that contains a total mass of 25 mg, said total mass consisting of the respirable dry particles that comprise a divalent metal cation salt, and wherein the VMGD of the dry particles emitted from the inhaler is 5 microns or less.

2. The respirable dry powder of claim 1, wherein said divalent metal salt is selected from the group consisting of a magnesium salt, and a barium salt.

3. The respirable dry powder of claim 1, wherein the divalent metal cation salt is a calcium salt.

4. The respirable dry powder of claim 3, wherein said calcium salt is selected from the group consisting of calcium citrate and calcium sulfate.

5. The respirable dry powder of claim 1, wherein the divalent metal cation salt is a magnesium salt.

6. The respirable dry powder of claim 1, wherein the respirable dry particles that comprise a divalent metal cation salt further comprise at least one pharmaceutically acceptable excipient.

7. The respirable dry powder of claim 6, wherein the at least one excipient is present in an amount of about ≤50% by weight and comprises leucine.

8. The respirable dry powder of claim 6, wherein the at least one excipient is present in an amount of about ≤50% by weight and comprises maltodextrin or mannitol.

9. The respirable dry powder of claim 1, wherein the respirable dry particles that comprise a divalent metal cation salt further comprises a monovalent salt.

10. The respirable dry powder of claim 9, wherein the monovalent salt is a lithium salt or a potassium salt.

11. The respirable dry powder of claim 9, wherein the monovalent salt is a sodium salt.

12. A method for treating a respiratory disease comprising administering to the respiratory tract of a patient in need thereof an effective amount of a respirable dry powder of claim 1.

13. A method for treating an acute exacerbation of a respiratory disease comprising administering to the respiratory tract of a patient in need thereof an effective amount of a respirable dry powder of claim 1.

* * * * *